(12) United States Patent
Dzierba et al.

(10) Patent No.: US 9,737,542 B2
(45) Date of Patent: Aug. 22, 2017

(54) PYRROLOTRIAZINE KINASE INHIBITORS

(71) Applicant: BRISTOL-MYERS SQUIBB COMPANY, Princeton, NJ (US)

(72) Inventors: Carolyn Diane Dzierba, Middletown, CT (US); Bireshwar Dasgupta, East Hampton, CT (US); John E. Macor, Washington Crossing, PA (US); Joanne J. Bronson, Durham, CT (US); Ramkumar Rajamani, Woodbridge, CT (US); George N. Karageorge, Portland, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/027,585

(22) PCT Filed: Oct. 8, 2014

(86) PCT No.: PCT/US2014/059646
§ 371 (c)(1),
(2) Date: Apr. 6, 2016

(87) PCT Pub. No.: WO2015/054358
PCT Pub. Date: Apr. 16, 2015

(65) Prior Publication Data
US 2016/0243125 A1 Aug. 25, 2016

Related U.S. Application Data

(60) Provisional application No. 61/890,026, filed on Oct. 11, 2013.

(51) Int. Cl.
*A61K 31/53* (2006.01)
*A61K 31/5377* (2006.01)

(52) U.S. Cl.
CPC .......... *A61K 31/53* (2013.01); *A61K 31/5377* (2013.01)

(58) Field of Classification Search
USPC ...................................... 514/247, 248, 291
See application file for complete search history.

(56) References Cited

U.S. PATENT DOCUMENTS

| 2005/0043306 A1* | 2/2005 | Leftheris | C07D 487/04 514/243 |
| 2012/0059162 A1 | 3/2012 | Kusakabe et al. | |

FOREIGN PATENT DOCUMENTS

| WO | WO 02/40486 A2 | 5/2002 |
| WO | WO 03/090912 A1 | 11/2003 |
| WO | WO 2005/037838 A1 | 4/2005 |
| WO | WO2005/066176 A1 | 7/2005 |
| WO | WO2008/057402 A2 | 5/2008 |
| WO | WO 2009/100375 A1 | 8/2009 |
| WO | WO2011/044212 A1 | 4/2011 |
| WO | WO2011/044225 A1 | 4/2011 |
| WO | WO2011044195 A1 | 4/2011 |
| WO | WO 2013/134036 A1 | 9/2013 |
| WO | WO 2013/134219 A1 | 9/2013 |
| WO | WO 2013/134228 A1 | 9/2013 |
| WO | WO 2013/134336 A2 | 9/2013 |
| WO | WO 2014/022167 A1 | 2/2014 |
| WO | WO 2014/130258 A1 | 8/2014 |
| WO | WO 2015/002915 A1 | 1/2015 |
| WO | WO 2015/002926 A1 | 1/2015 |
| WO | WO 2015/006100 A1 | 1/2015 |
| WO | WO2015/026574 A1 | 2/2015 |
| WO | WO 2015/035117 A1 | 3/2015 |
| WO | WO 2015/035167 A1 | 3/2015 |
| WO | WO 2015/038112 A1 | 3/2015 |
| WO | WO 2015/054358 A1 | 4/2015 |
| WO | WO 2015/116060 A1 | 8/2015 |
| WO | WO 2015/116492 A1 | 8/2015 |
| WO | WO 2015/142714 A1 | 9/2015 |
| WO | WO 2015/153720 A1 | 10/2015 |
| WO | WO 2016/022312 A1 | 2/2016 |
| WO | WO 2016/053794 A1 | 4/2016 |
| WO | WO 2016/164295 A2 | 10/2016 |

OTHER PUBLICATIONS

Sorrell; Structure, 24, 40-411, Mar. 1, 2016.*
Guerram; Neurochemistry International, 101 (2016), 1-14.*
Buonanno, A., "The neuregulin signaling pathway and schizophrenia: From genes to synapses and neural circuits", Brain Research Bulletin, vol. 83, pp. 122-131 (2010).
Conner, S.D. et al., "AAK-1 Mediated µ2 Phosphorylation is Stimulated by Assembled Clathrin", Traffic, vol. 4, pp. 885-890 (2003).
Conner, S.D. et al., "Identification of an adaptor-associated kinase, AAK1, as a regulator of clathrin-mediated endocytosis", The Journal of Cell Biology, vol. 156, No. 5, pp. 921-929 (2002).
Greenwood, T.A. et al., "Analysis of 94 Candidate Genes and 12 Endophenotypes for Schizophrenia", Am. J. Psychiatry, vol. 168, No. 9, pp. 930-946 (2011).
Henderson, D.M. et al., "A Novel AAK1 Splice Variant Functions at Multiple Steps of the Endocytic Pathway", Molecular Biology of the Cell, vol. 18, pp. 2698-2706 (2007).
Jaaro-Peled, H. et al., "Review of Pathological Hallmarks of Schizophrenia: Comparison of Genetic Models with Patients and Nongenetic Models", Schizophrenia Bulletin, vol. 36, No. 2, pp. 301-313 (2010).
Jackson, A.P. et al., "Clathrin promotes incorporation of cargo into coated pits by activation of the AP2 adaptor µ2 kinase", The Journal of Cell Biology, vol. 163, No. 2, pp. 231-236 (2003).
Kuai, L. et al., "AAK1 Identified as an Inhibitor of Neuregulin-1/ErbB4-Dependent Neurotrophic Factor Signaling Using Integrative Chemical Genomics and Proteomics", Chemistry & Biology, vol. 18, pp. 891-906 (2011).

(Continued)

*Primary Examiner* — Pancham Bakshi
(74) *Attorney, Agent, or Firm* — Pamela A. Mingo

(57) ABSTRACT

The present disclosure is generally directed to compounds which can inhibit AAK1 (adaptor associated kinase 1), compositions comprising such compounds, and methods for inhibiting AAK1.

7 Claims, 1 Drawing Sheet

(56) References Cited

OTHER PUBLICATIONS

Latourelle, J.C. et al., "Genomewide association study for onset age in Parkinson disease", BMC Medical Genetics, 10:98 (2009).
Motley, A.M. et al., Functional Analysis of AP-2 $\alpha$ and $\mu 2$ Subunits, Molecular Biology of the Cell, vol. 17, pp. 5298-5308 (2006).
Ricotta, D. et al., "Phosphorylation of the AP2 $\mu$ subunit by AAK1 mediates high affinity binding to membrane protein sorting signals", The Journal of Cell Biology, vol. 156, No. 5, pp. 791-795 (2002).
Wen, L. et al., "Neuregulin 1 regulates pyramidal neuron activity via ErbB4 in parvalbumin-positive interneurons", Proc. Natl. Acad. Sci. USA, vol. 107, No. 3, pp. 1211-1216 (2010).

\* cited by examiner

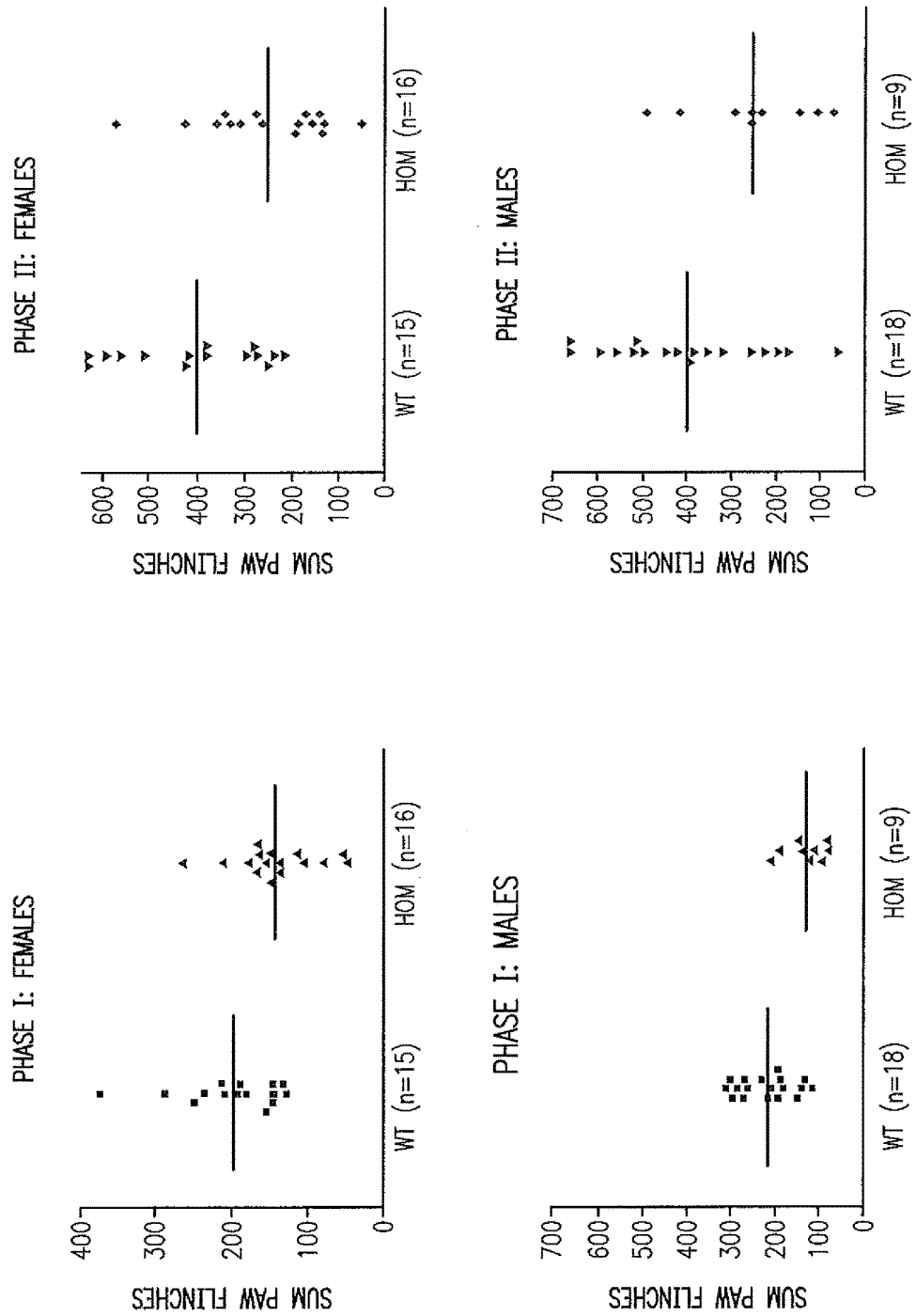

PYRROLOTRIAZINE KINASE INHIBITORS

CROSS-REFERENCE TO RELATED APPLICATIONS

This application claims priority to Provisional U.S. patent application Ser. No. 61/890,026 filed Oct. 11, 2013, hereby incorporated by reference in its entirety.

The present disclosure is generally directed to compounds which can inhibit adaptor associated kinase 1 (AAK1), compositions comprising such compounds, and methods for inhibiting AAK1.

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clatherin coated endocytosis, a process that is important in synaptic vesicle recycling and receptor-mediated endocytosis. AAK1 associates with the AP2 complex, a hetero-tetramer which links receptor cargo to the clatherin coat. The binding of clatherin to AAK1 stimulates AAK1 kinase activity (Conner et. al., *Traffic* 2003, 4, 885-890; Jackson et. al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et. al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et. al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et. al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et. al., *Am. J. Psychiatry* 2011, 168, 930-946). Neuregulin 1 and ErbB4 KO mouse models have shown schizophrenia relevant morphological changes and behavioral phenotypes (Jaaro-Peled et. al., *Schizophrenia Bulletin* 2010, 36, 301-313; Wen et. al., Proc. Natl. Acad. Sci. USA. 2010, 107, 1211-1216). In addition, a single nucleotide polymorphism in an intron of the AAK1 gene has been associated with the age of onset of Parkinson's disease (Latourelle et. al., *BMC Med. Genet.* 2009, 10, 98). These results suggest that inhibition of AAK1 activity may have utility in the treatment of schizophrenia, cognitive deficits in schizophrenia, Parkinson's disease, neuropathic pain, bipolar disorder, and Alzheimer's disease.

In its first aspect the present disclosure provides a method for treating or managing a disease or a disorder mediated by AAK1 activity, the method comprising administering to a patient in need thereof a therapeutically effective amount of a compound of formula (I)

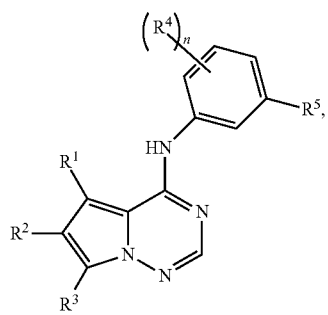

or a pharmaceutically acceptable salt thereof, wherein:

n is 0, 1, or 2;

$R^1$ is selected from hydrogen, $C_1$-$C_3$alkyl, —$CH_2NR^aR^b$, —$C(O)NR^aR^b$, —$CH_2OR^6$, and —$CO_2R^6$;

$R^2$ is selected from hydrogen and —$CO_2R^6$;

$R^3$ is selected from hydrogen and Br;

when n is 1, $R^4$ is selected from halo, haloalkyl, hydroxy$C_1$-$C_3$alkyl, —$OR^6$; or, when n is 2, the two $R^4$ groups are on adjacent carbon atoms, and together with the atoms to which they are attached, form a five-membered ring selected from

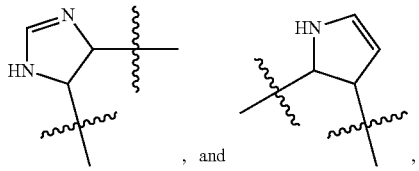 [SMILES: *C1N=CNC1* ; *C1C=CNC1*]

wherein "⸾" indicates the point of attachment to the six-membered aromatic ring;

$R^5$ is selected from $C_2$alkenyl, —$NHC(O)R^7$, —$C(O)NHR^7$,

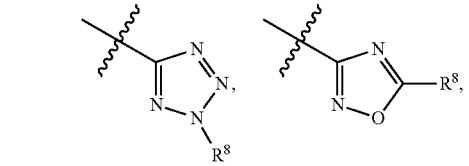

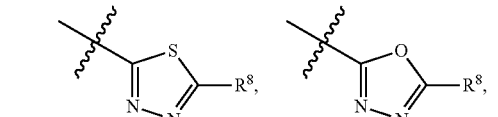

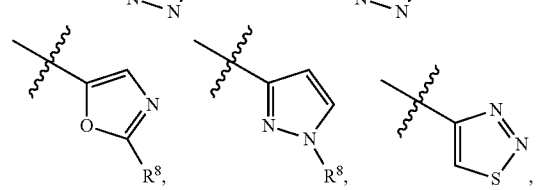

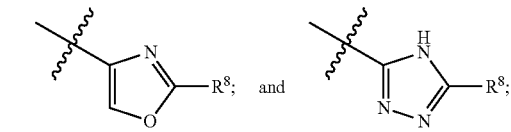

each $R^6$ is independently hydrogen or $C_1$-$C_6$ alkyl;

$R^7$ is selected from $C_1$-$C_6$alkyl, and amino$C_1$-$C_6$alkyl;

$R^8$ is selected from amino$C_1$-$C_6$alkyl, $C_1$-$C_6$alkyl, $C_3$-$C_6$cycloalkyl, halo$C_1$-$C_6$alkyl, hydroxy$C_1$-$C_6$alkyl, and phenyl; and $R^a$ and $R^b$ are independently selected from hydrogen, $C_1$-$C_3$alkoxy$C_1$-$C_3$alkyl, $C_1$-$C_3$alkyl, amino$C_2$-$C_6$alkyl, cyano$C_1$-$C_3$ alkyl, $C_3$-$C_6$cycloalkyl$C_1$-$C_3$ alkyl,

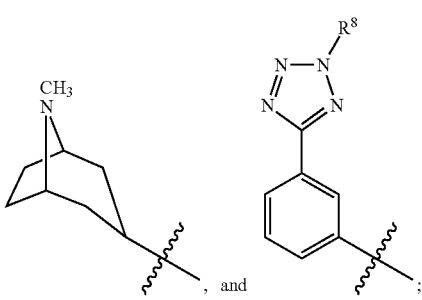

, and or $R^a$ and $R^b$, together with the nitrogen atom to which they are attached, form a ring selected from azetidinyl, morpholinyl, piperazinyl, piperidinyl, pyrrolidinyl,

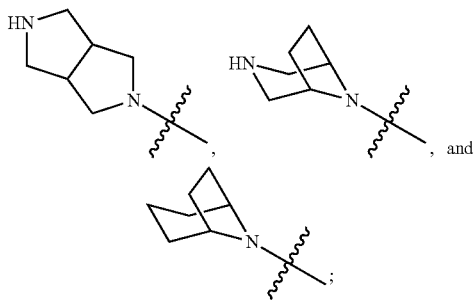

wherein the ring is optionally substituted with one or two substituents independently selected from $C_1$-$C_3$acylamino, $C_1$-$C_3$ alkyl, amino, amino$C_1$-$C_3$alkyl, hydroxy, and methylamino.

In a first embodiment of the first aspect, $R^a$ and $R^b$, together with the nitrogen atom to which they are attached, form a piperidinyl or piperazinyl ring optionally substituted with one or two substituents independently selected from $C_1$-$C_3$acylamino, $C_1$-$C_3$alkyl, amino, amino$C_1$-$C_3$alkyl, hydroxy, and methylamino.

In a second embodiment of the first aspect the present disclosure provides a method for treating or managing a disease or a disorder mediated by AAK1 activity, the method comprising administering to a patient in need thereof a therapeutically effective amount of a compound of formula (I), wherein the disease or disorder is selected from Alzheimer's disease, bipolar disorder, pain, Parkinson's disease, and schizophrenia. In a third embodiment of the first aspect the pain is neuropathic pain. In a fourth embodiment of the first aspect the neuropathic pain is fibromyalgia or peripheral neuropathy.

In a second aspect the present disclosure provides a method of inhibiting adaptor associated kinase 1 (AAK1) activity, comprising contacting AAK1 with a compound of formula (I)

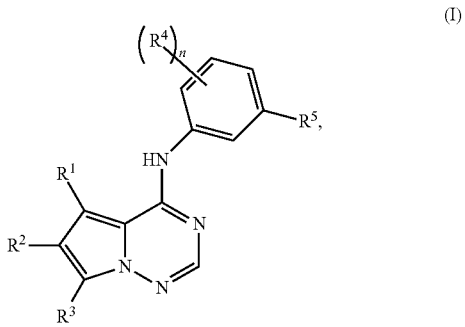

or a pharmaceutically acceptable salt thereof, wherein:

n is 0, 1, or 2;

$R^1$ is selected from hydrogen, $C_1$-$C_3$alkyl, —$CH_2NR^aR^b$, —$C(O)NR^aR^b$, —$CH_2OR^6$, and —$CO_2R^6$;

$R^2$ is selected from hydrogen and —$CO_2R^6$;

$R^3$ is selected from hydrogen and Br;

when n is 1, $R^4$ is selected from halo, haloalkyl, hydroxy$C_1$-$C_3$alkyl, —$OR^6$; or, when n is 2, the two $R^4$ groups are on adjacent carbon atoms, and together with the atoms to which they are attached, form a five-membered ring selected from

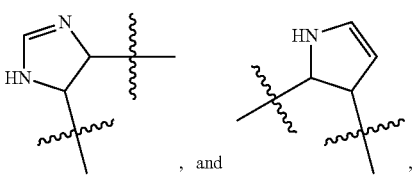 [SMILES: *C1N=CNC1* ; *C1C=CNC1*]

wherein "  " indicates the point of attachment to the six-membered aromatic ring;

$R^5$ is selected from $C_2$alkenyl, —NHC(O)$R^7$, —C(O)NHR$^7$,

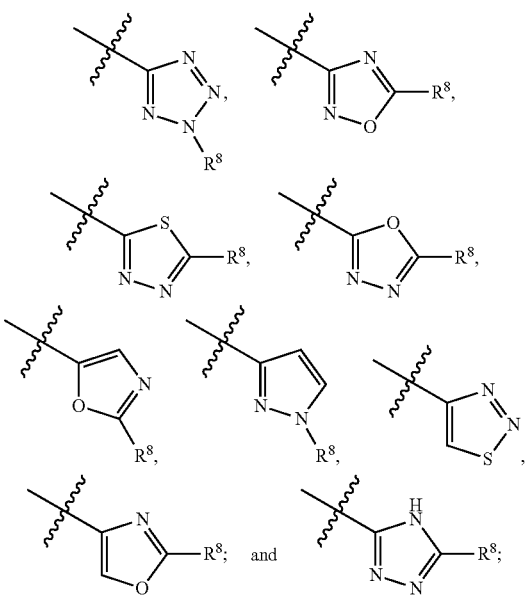

each $R^6$ is independently hydrogen or $C_1$-$C_6$ alkyl;

$R^7$ is selected from $C_1$-$C_6$alkyl, and amino$C_1$-$C_6$alkyl;

$R^8$ is selected from amino$C_1$-$C_6$alkyl, $C_1$-$C_6$alkyl, $C_3$-$C_6$cycloalkyl, halo$C_1$-$C_6$alkyl, hydroxy$C_1$-$C_6$alkyl, and phenyl; and $R^a$ and $R^b$ are independently selected from hydrogen, $C_1$-$C_3$alkoxy$C_1$-$C_3$alkyl, $C_1$-$C_3$alkyl, amino$C_2$-$C_6$ alkyl, cyano$C_1$-$C_3$ alkyl, $C_3$-$C_6$cycloalkyl$C_1$-$C_3$ alkyl,

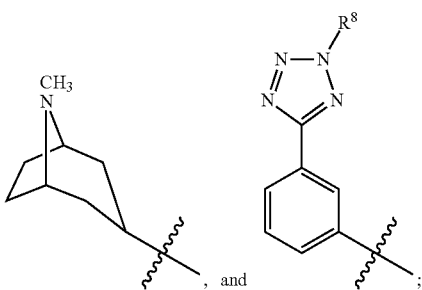

or $R^a$ and $R^b$, together with the nitrogen atom to which they are attached, form a ring selected from azetidinyl, morpholinyl, piperazinyl, piperidinyl, pyrrolidinyl,

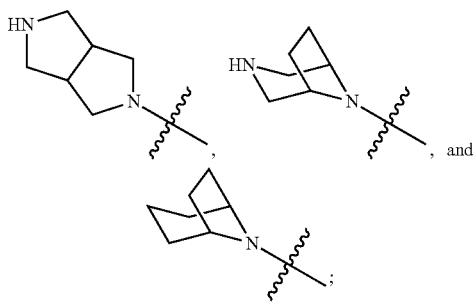

wherein the ring is optionally substituted with one or two substituents independently selected from $C_1$-$C_3$acylamino, $C_1$-$C_3$ alkyl, amino, amino$C_1$-$C_3$ alkyl, hydroxy, and methylamino.

In a first embodiment of the second aspect $R^a$ and $R^b$, together with the nitrogen atom to which they are attached, form a piperidinyl or piperazinyl ring optionally substituted with one or two substituents independently selected from $C_1$-$C_3$ acylamino, $C_1$-$C_3$alkyl, amino, amino$C_1$-$C_3$alkyl, hydroxy, and methylamino.

Other aspects of the present disclosure may include suitable combinations of embodiments disclosed herein.

Yet other aspects and embodiments may be found in the description provided herein.

BRIEF DESCRIPTION OF THE FIGURES

Aspects of the disclosure are illustrated in the FIGURE, which shows results obtained from a formalin pain model using AAK1 homozygous (−/−) knockout mice and their wild-type (+/+) littermates. The AAK1 homozygous (−/−) knockout mice show a clear reduction in both acute and tonic pain response as compared to their wild-type (+/+) littermates.

This disclosure is based, in part, on the discovery that AAK1 knockout mice exhibit a high resistance to pain. That discovery prompted research that ultimately led to the discovery of AAK1 inhibitors, compositions comprising them, and methods of their use.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

As used in the present specification, the following terms have the meanings indicated:

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

In some instances, the number of carbon atoms in any particular group is denoted before the recitation of the group. For example, the term "$C_{1-6}$ alkyl" denotes an alkyl group containing one to six carbon atoms. Where these designations exist they supercede all other definitions contained herein.

The term "acyl," as used herein, refers to —C(O)R, wherein R is an alkyl group.

The term "acylamino," as used herein, refers to —NHR wherein R is an acyl group.

The term "alkenyl," as used herein, refers to The term "alkenyl," as used herein, refers to a straight or branched chain group containing at least one carbon-carbon double bond.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkyl," as used herein, refers to a group derived from a straight or branched chain saturated hydrocarbon.

The term "amino," as used herein, refers to —$NH_2$.

The term "aminoalkyl," as used herein, refers to an alkyl group substituted by one, two, or three amino groups.

The term "cyano," as used herein, refers to —CN.

The term "cyanoalkyl," as used herein, refers to an alkyl group substituted by one, two, or three cyano groups.

The term "cycloalkyl," as used herein, refers to a saturated monocyclic hydrocarbon ring system having zero heteroatoms. Representative examples of cycloalkyl groups include, but are not limited to, cyclopropyl, cyclopentyl, and cyclohexyl.

The term "cycloalkylalkyl," as used herein, refers to an alkyl group substituted with one, two, or three cycloalkyl groups.

The term "halo," as used herein, refers to Br, Cl, F, and/or I.

The term "haloalkyl," as used herein, refers to an alkyl group substituted by one, two, three, or four halogen atoms.

The term "hydroxy," as used herein, refers to —OH.

The term "hydroxyalkyl," as used herein, refers to a hydroxy group attached to the parent molecular moiety through an alkyl group.

The term "methylamino," as used herein, refers to —$NHCH_3$.

Asymmetric centers may exist in the compounds of the present disclosure. It should be understood that the disclosure encompasses all stereochemical isomeric forms, or mixtures thereof, which possess the ability to inhibit AAK1. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, diydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

One embodiment of this disclosure encompasses methods of inhibiting adaptor associated kinase 1 (AAK1), both in vitro and in vivo, which comprise contacting AAK1 with a compound of formula I or a pharmaceutically acceptable salt thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. Unless otherwise indicated, a "therapeutically effective amount" of a compound is an amount sufficient to provide a therapeutic benefit in the treatment or management of a disease or condition, or to delay or minimize one or more symptoms associated with the disease or condition. The term "therapeutically effective amount" can encompass an amount that improves overall therapy, reduces or avoids symptoms or causes of a disease or condition, or enhances the therapeutic efficacy of another therapeutic agent.

The term "therapeutically effective amount," as used herein, refers to an amount of a compound or compounds sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Compounds of the disclosure may be administered in combination with one or more additional therapeutic or prophylactic agents. For example, when used for the treatment of pain, possible additional agents include immunosuppressive agents, anti-inflammatory agents, and/or other agents used in the treatment of pain.

Immunosuppressants suitable for use in the methods and compositions of this disclosure include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples of immunosuppressants include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Other immunosuppressants include inosine monophosphate dehydrogenase inhibitors, such as mycophenolate mofetil (CellCept®) and mycophenolic acid (Myfortic®).

Anti-inflammatory drugs suitable for use in the methods and compositions of this disclosure include those known in the art. Examples include glucocorticoids and NSAIDs. Examples of glucocorticoids include aldosterone, beclometasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Other agents used in the treatment of pain (including but not limited to neuropathic and inflammatory pain) include, but are not limited to, agents such as pregabalin, lidocaine, duloxetine, gabapentin, carbamazepine, capsaicin, and other serotonin/norepinephrine/dopamine reuptake inhibitors, and opiates (such as oxycontin, morphine, and codeine).

In the treatment of pain caused by a known disease or condition, such as diabetes, infection (e.g., herpes zoster or HIV infection), or cancer, compounds of the disclosure may be administered in combination with one or more additional therapeutic or prophylactic agents directed at the underlying disease or condition. For example, when used to treat diabetic neuropathy, compounds of the disclosure may be administered in combination with one or more anti-diabetic agents, anti-hyperglycemic agents, hypolipidemic/lipid lowering agents, anti-obesity agents, anti-hypertensive agents and appetite suppressants. Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, dipeptidyl peptidase IV (DPP4) inhibitors, and sodium-glucose co-transporter 2 (SGLT2) inhibitors (e.g., dapagliflozin, canagliflozin, and LX-4211).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

Unless otherwise indicated, the terms "manage," "managing", and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: RT or rt or r.t. for room temperature or retention time (context will dictate); $t_R$ for retention time; h or hr or hrs for hours; min or mins for minutes; Me for methyl; Et for ethyl; Ph for phenyl; i-Pr or iPr for isopropyl; Ac for acetyl; MeOD for $CD_3OD$; DMSO for dimethylsulfoxide; BOC or Boc for tert-butoxycarbonyl; CDI for (N,N'-carbonyldiimidazole); DIEA or i-$Pr_2$NEt for N,N-diisopropylethylamine; DMF for N,N-dimethylformamide; THF for tetrahydrofuran; TEA or $Et_3N$ for triethylamine; MeOH for methanol; NBS for N-bromosuccinamide; AIBN for azobisisobutyronitrile; EtOH for ethanol; DIC for N,N'-diisopropylcarbodiimide; EtOAc for ethyl acetate; HATU for O-(7-azabenzotriazol-1-yl)-N,N,N',N'-tetramethyluronium hexafluorophosphate; HBTU for O-(benzotriazole-1-yl)-1,1,3,3-tetramethyluronium hexafluorophosphate; DCM for dichloromethane; TFA for trifluoroacetic acid; DCC for N,N'-dicyclohexylcarbodiimide; DMAP for N,N-dimethylaminopyridine; NMP for N-methylpyrrolidinone; and LAH for lithium aluminum hydride.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present disclosure may be prepared using the reactions and techniques described in this section as well as other synthetic methods known to those of ordinary skill in the art. The reactions are performed in solvents appropriate to the reagents and materials employed and suitable for the transformation being affected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Representative schemes for the preparation of intermediates used in the synthesis of compounds of formula (I) are shown below. Intermediate amines 5, 11, and 16 can be prepared by the routes shown in Schemes 1-3.

Intermediates of formula 5 are prepared by the methods outlined in Scheme 1. Treatment of 1 with hydroxylamine hydrochloride in pyridine affords compound 2. Compound 2 can be coupled with an acid chloride 4, either in the presence or absence of a reagent to promote the coupling reaction, in a solvent such as pyridine. If a coupling agent is used, a reagent such as 1,1'-carbonyldiimidazole can be used. Subsequent heating of the reaction mixture at temperatures ranging from 80° C. to 140° C. affords compounds of formula 4. Reduction of the nitro group in 4 is accomplished using standard conditions such as, but not limited to, $H_2$ and Pd/C, zinc with ammonium chloride, or tin chloride, preferably zinc with ammonium chloride, in an appropriate solvent such as methanol or ethanol at temperatures ranging from 0° C. to 100° C. to give compounds of formula 5.

Scheme 1

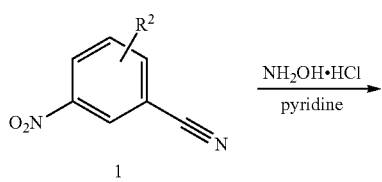

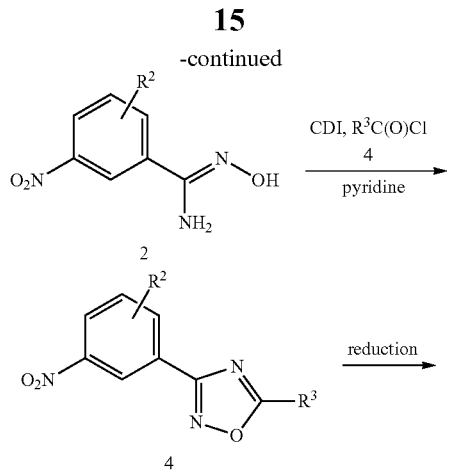

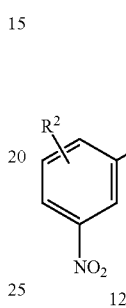

Intermediates of formula 11 are prepared by the methods outlined in Scheme 2. Coupling of acid chloride 6 with acid hydrazides 7 in the presence of a base such as N, N-diisopropylethylamine or triethylamine affords compounds of formula 8. Treatment of compounds of formula 8 with Lawesson's reagent followed by heating at 100° C. furnishes compounds of formula 9. Treatment of compounds of formula 8 with triphenylphoshpine in carbon tetrabromide furnishes compounds of formula 10. Reduction of the nitro group in 9 or 10 as described in Scheme 1 provides compounds of formula 11, where X=S or O, respectively.

Intermediates of formula 16 are prepared by the methods outlined in Scheme 3. Treatment of compound 12 with sodium azide in a solvent such as DMF at temperatures ranging from 100° C. to 150° C. affords compound 13. Treatment of compounds of formula 13 with a base such as potassium carbonate in the presence of an alkylating agent such as an alkyl halide 14 (X=halo or other suitable leaving group) in a solvent such as DMF, THF, acetone, or acetonitrile at temperatures ranging from 80° C. to 150° C. furnishes compounds of formula 15. Reduction of the nitro group in 15 as described in Scheme 1 provides compounds of formula 16.

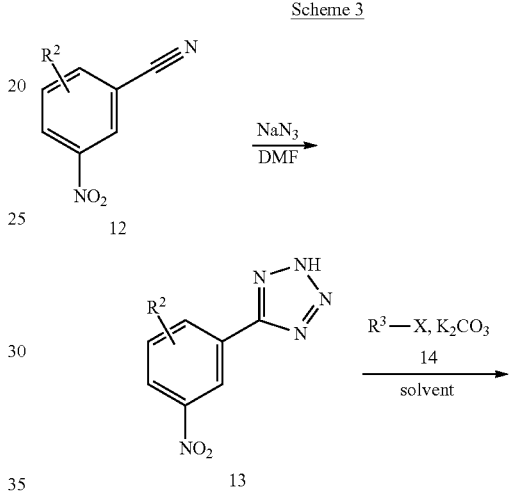

Scheme 3

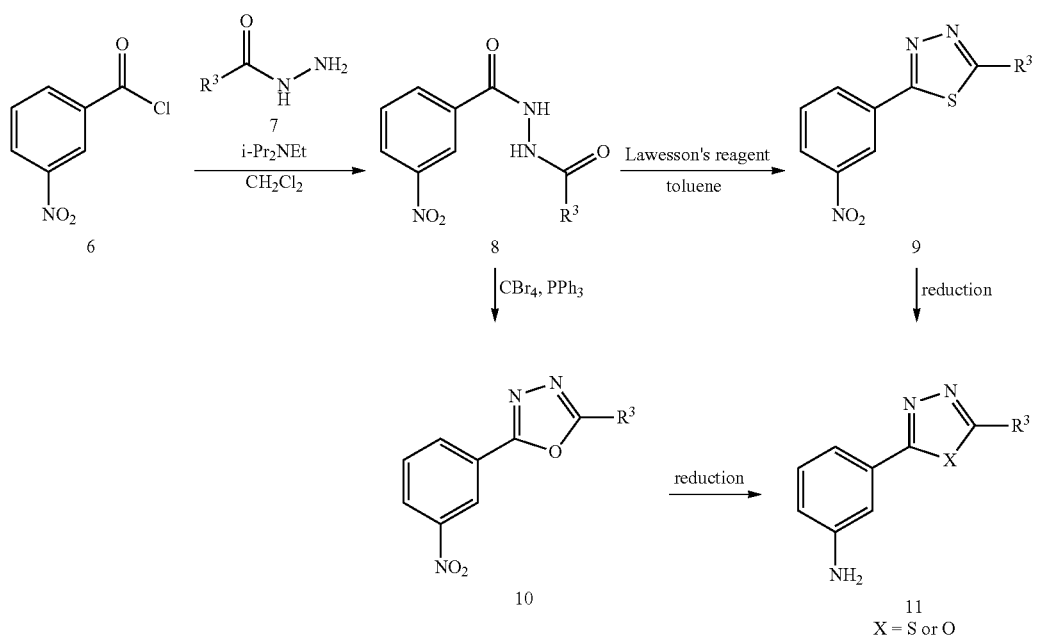

Scheme 2

-continued

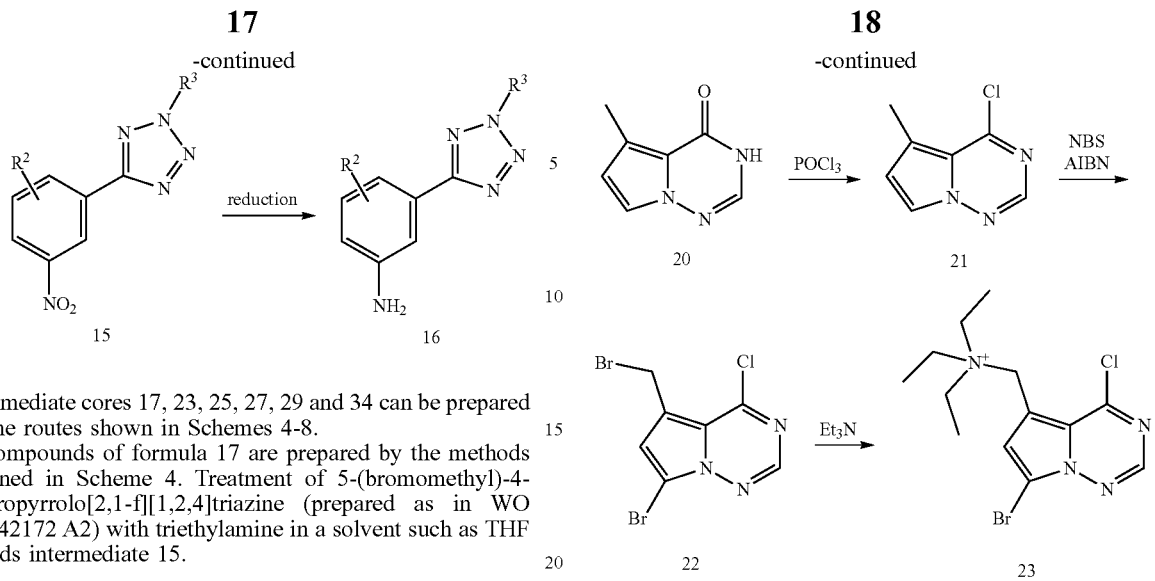

Intermediate cores 17, 23, 25, 27, 29 and 34 can be prepared by the routes shown in Schemes 4-8.

Compounds of formula 17 are prepared by the methods outlined in Scheme 4. Treatment of 5-(bromomethyl)-4-chloropyrrolo[2,1-f][1,2,4]triazine (prepared as in WO 03/042172 A2) with triethylamine in a solvent such as THF affords intermediate 15.

Scheme 4

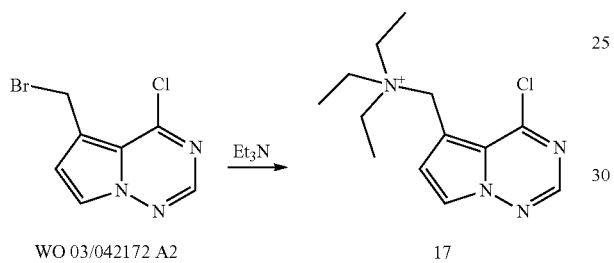

Intermediate 23 is prepared by the methods outlined in Scheme 5. The ester of methyl 5-methyl-4-oxo-3,4-dihydropyrrolo[1,2-f][1,2,4]triazine-6-carboxylate, 18 (prepared as described in WO 2002040486) can be saponified with a base such as LiOH or NaOH in a solvent such as MeOH, THF or water, or a combination thereof to afford 19. Intermediate 19 can be treated with phosphoric acid afford 20. Intermediate 20 can be treated with phosphorous oxychloride to afford aryl chloride 21. Bromination of 21 with NBS and AIBN in a solvent such as CCl$_4$ at elevated temperatures can afford dibromide 22. Treatment of 22 with triethylamine can afford intermediate 23.

Scheme 5

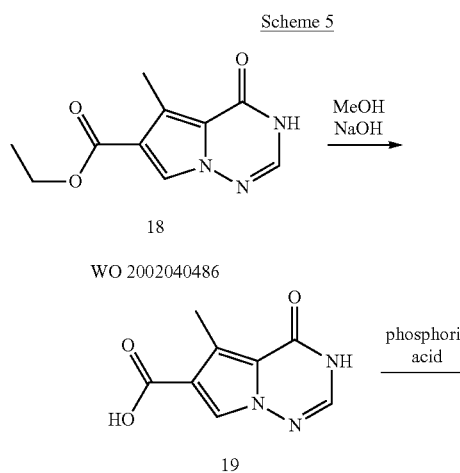

Intermediate 25 is prepared by the methods outlined in Scheme 6. Intermediate 24, prepared as described in S. A. Patil, B. A. Otter and R. S. Klein, *J. Het. Chem.*, 31, 781-786 (1994) can be treated with phosphorous oxychloride to afford intermediate 25.

Scheme 6

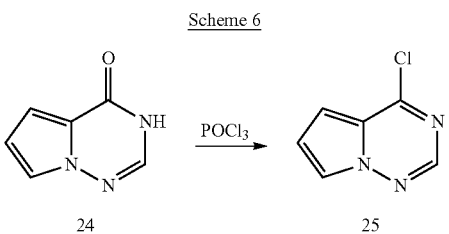

Intermediates 27 and 29 are prepared by the methods outlined in Scheme 7. Intermediate 26, prepared as in U.S. Pat. No. 7,514,435 can be treated with phosphorous oxychloride to afford chloride 27. Intermediate 26 can alternatively be treated with a base such as LiOH or NaOH in a solvent such as MeOH, THF or water, or a combination thereof can afford intermediate 28. Treatment intermediate 28 with phosphorous oxychloride can to afford intermediate 29.

Scheme 7

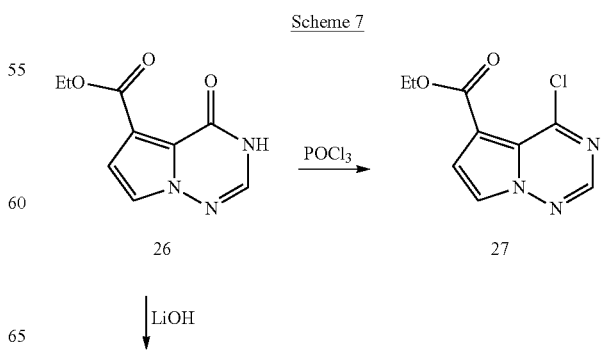

-continued

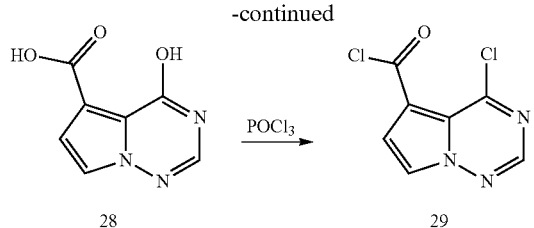

Intermediate 34 is prepared by the methods outlined in Scheme 8. Intermediate 30, prepared as described in WO 2002040486, can be treated with phosphorous oxychloride to afford aryl chloride 32. Bromination of 32 with NBS and AIBN in a solvent such as $CCl_4$ at elevated temperatures can afford dibromide 33. Treatment of 33 with triethylamine can afford intermediate 34.

Scheme 8

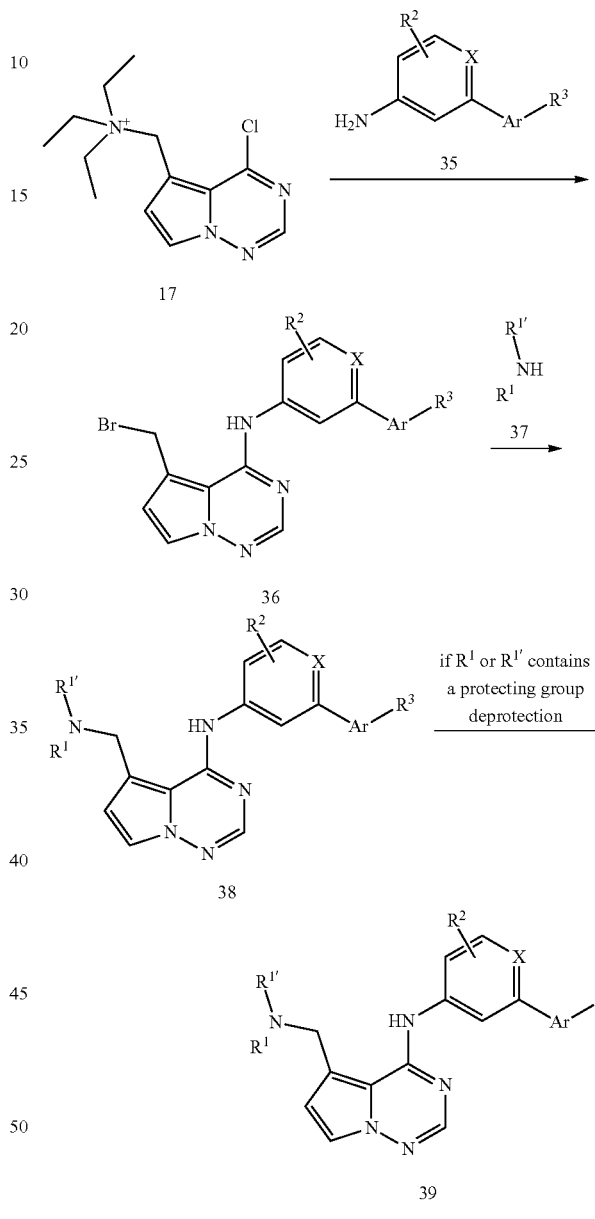

Compounds of the formula 39, 39, 45, 46, 49, 50, 52-55, 61, 63, 64, 66, 67, 71, 72, 75, and 76 can be prepared by the routes shown in Schemes 9-18.

Compounds of formula 38 and 39 are prepared by the methods outlined in Scheme 9. Treatment of 17 with an aniline of the formula 35 in a solvent such as acetonitrile at temperatures ranging from 50° C. to 120° C. furnishes compounds of formula 36. Treatment of 36 with an amine of the formula 37 in the presence of a base such as DIEA or TEA in a solvent such as acetonitrile at temperatures ranging from 50° C. to 120° C. furnishes compounds of formula 38. If $R^1$ or $R^1$ contain an amine group or another functional group that is protected, the protecting group can be removed by treating the substrate with the appropriate reagents as described in *Protective Groups in Organic Synthesis* (Greene, Wuts; 3$^{rd}$ ed., 1999, John Wiley & Sons, Inc.) to provide compounds of formula 39.

Compounds of formula 45 and 46 are prepared by the methods outlined in Scheme 10. Treatment of intermediate 17 with an aniline of the formula 40 in a solvent such as acetonitrile at temperatures ranging from 50° C. to 120° C. furnishes compounds of formula 41. Treatment of 41 with an amine of the formula 37 in the presence of a base such as DIEA or TEA in a solvent such as acetonitrile at temperatures ranging from 50° C. to 120° C. furnishes compounds of formula 42. Compounds of formula 42 can be treated with sodium azide and ammonium chloride in a solvent such as DMF at elevated temperatures to afford compounds of formula 43. The tetrazole of 43 can be alkylated with an alkylhalide 44 (X=halo or other suitable leaving group) to afford compounds of formula 45. If R¹ or R¹ contain an amine group or another functional group that is protected, the protecting group can be removed by treating the substrate with the appropriate reagents as described in *Protective Groups in Organic Synthesis* (Greene, Wuts; 3rd ed., 1999, John Wiley & Sons, Inc.) to provide compounds of formula 46.

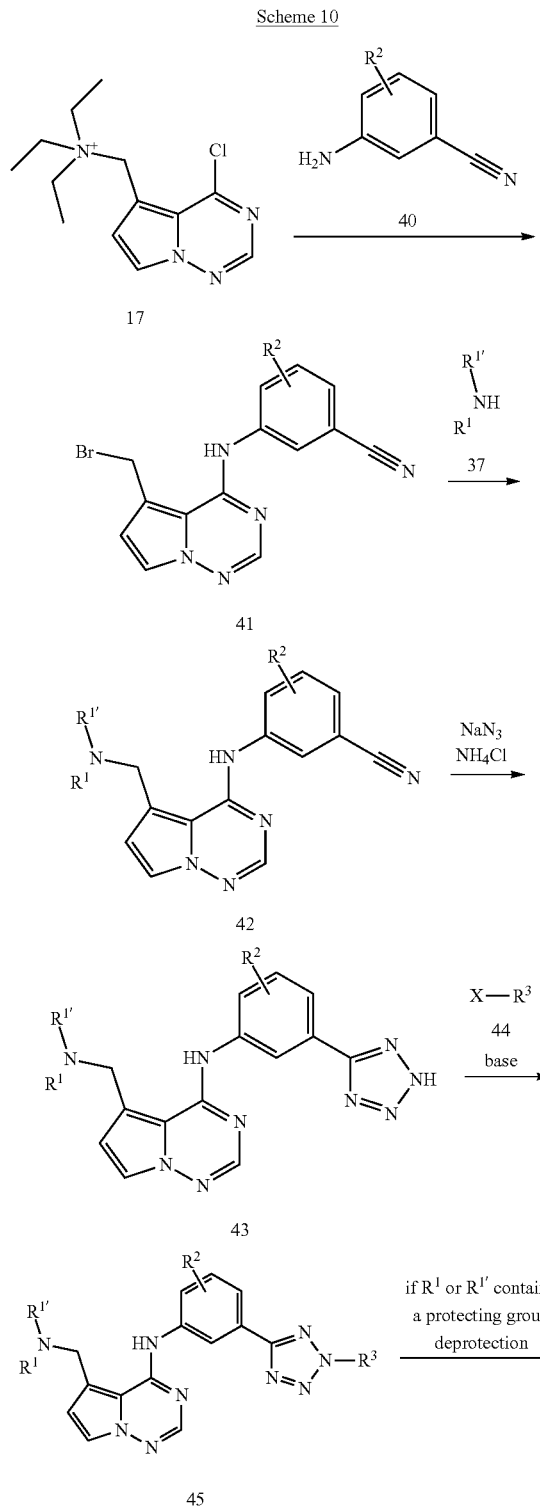

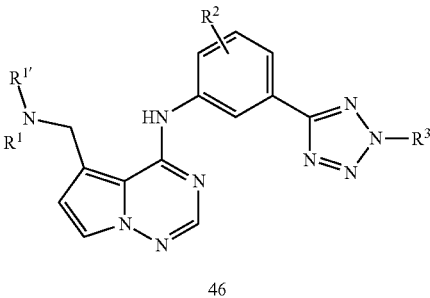

Compounds of formula 49 and 50 are prepared by the methods outlined in Scheme 11. Compounds of formula 42 can be treated with hydroxylamine hydrochloride and as base such as potassium carbonate in a solvent such as EtOH at elevated temperature to afford compounds of formula 47. Compounds of formula 47 can be treated with an acid chloride of the formula 48 and a coupling agent such as DIC in a solvent such as pyridine to afford compounds of formula 49. If R¹ or R¹ contain an amine group or another functional group that is protected, the protecting group can be removed by treating the substrate with the appropriate reagents as described in *Protective Groups in Organic Synthesis* (Greene, Wuts; 3rd ed., 1999, John Wiley & Sons, Inc.) to provide compounds of formula 50.

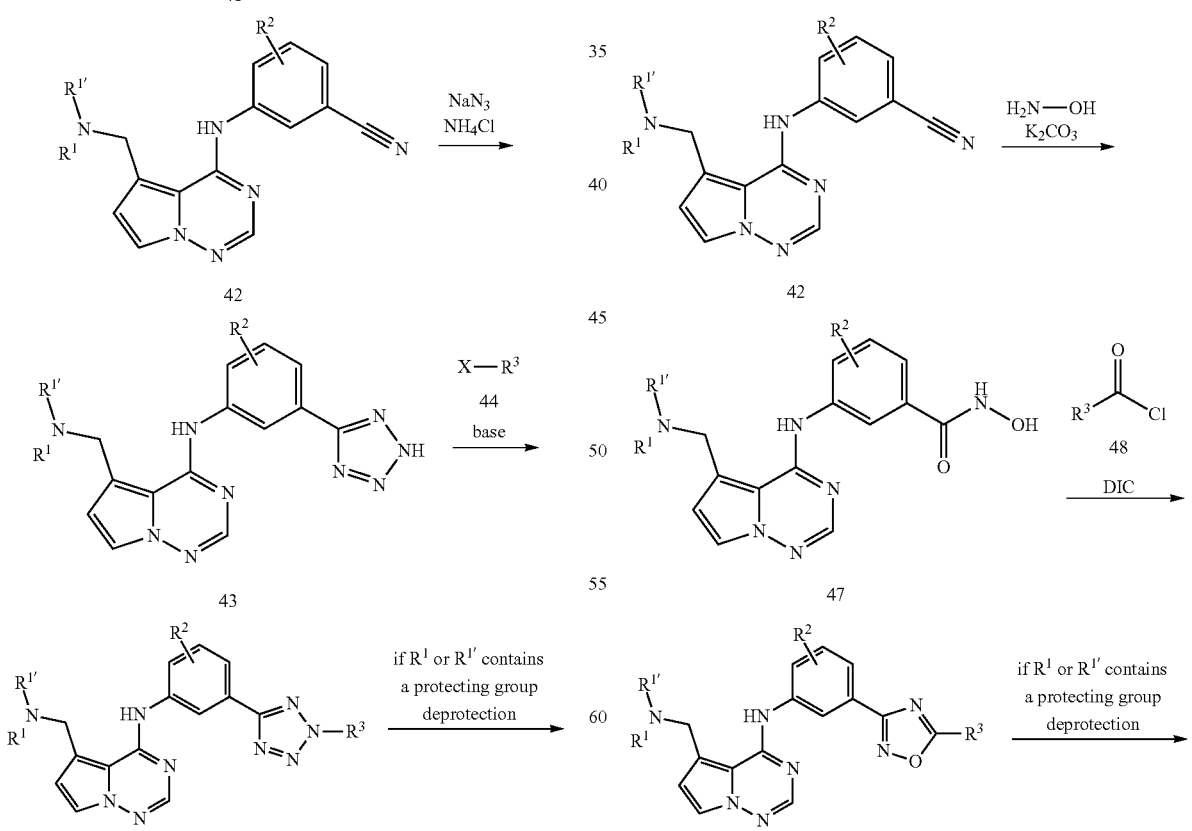

-continued

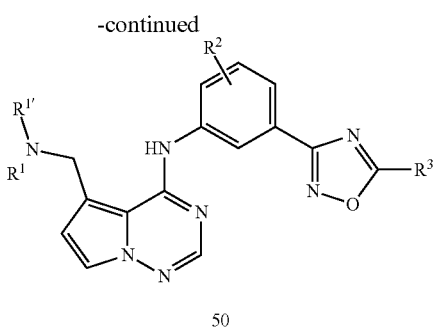

50

Compounds of formula 52-55 are prepared by the methods outlined in Scheme 12. Treatment of intermediate 23 with an aniline of the formula 35 in a solvent such as acetonitrile at temperatures ranging from 50° C. to 120° C. furnishes compounds of formula 51. Treatment of 51 with an amine of the formula 37 in the presence of a base such as DIEA or TEA in a solvent such as acetonitrile at temperatures ranging from 50° C. to 120° C. furnishes compounds of formula 52. Treatment of 52 with palladium on carbon in the presence of hydrogen gas in a solvent such as MeOH can afford compound of the formula 53. If $R^1$ or $R^{1'}$ contain an amine group or another functional group that is protected, the protecting group can be removed by treating the substrate with the appropriate reagents as described in *Protective Groups in Organic Synthesis* (Greene, Wuts; 3$^{rd}$ ed., 1999, John Wiley & Sons, Inc.) to provide compounds of formula 54 or 55.

Scheme 12

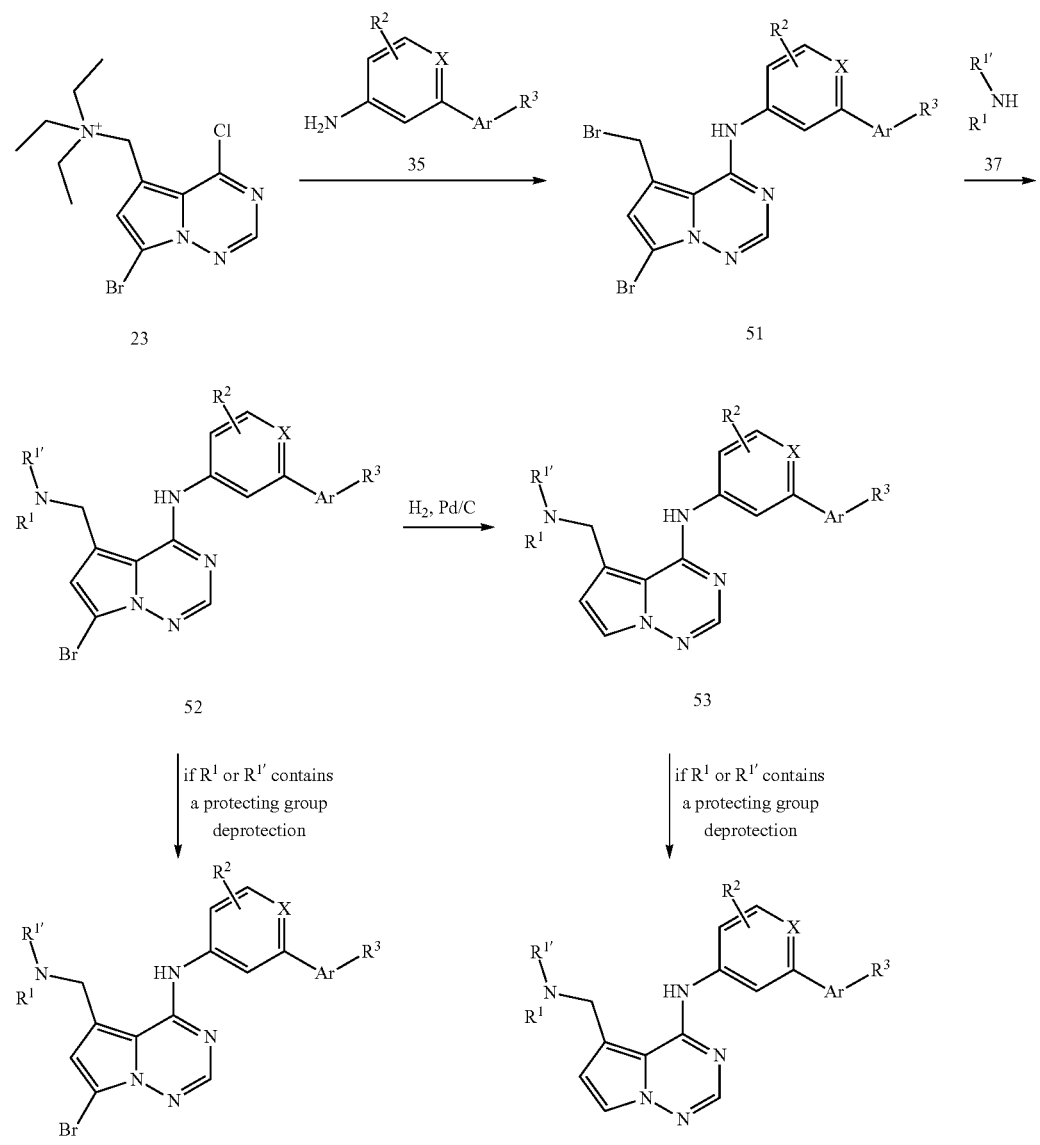

Compounds of formula 56 are prepared by the methods outlined in Scheme 13. Treatment of intermediate 25 with an aniline of the formula 35 in a solvent such as acetonitrile at temperatures ranging from 50° C. to 120° C. furnishes compounds of formula 56.

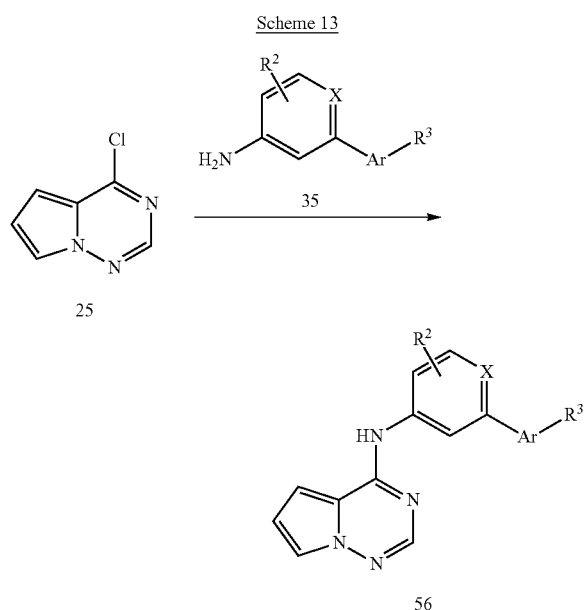

Scheme 13

Compounds of formula 60 are prepared by the methods outlined in Scheme 14. Intermediate 25 can be treated with an aniline of the formula 57 in a solvent such as acetonitrile at temperatures ranging from 50° C. to 120° C. to furnish compounds of formula 58. Intermediate 58 can be treated with sodium azide to form intermediate of formula 59 followed by hydrogenation with palladium on carbon in a solvent such as EtOH or EtOAc to afford compounds of the formula 60.

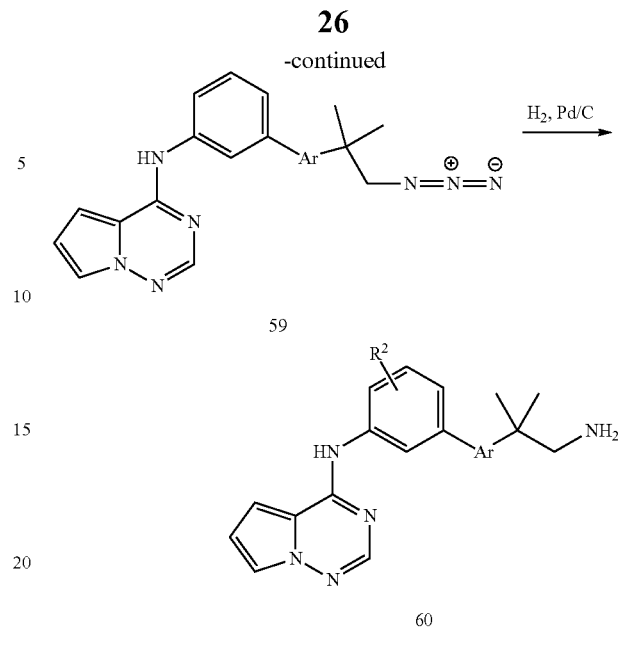

Compounds of formula 61, 63, and 64 are prepared by the methods outlined in Scheme 15. Treatment of intermediate 27 with an aniline of the formula 35 in a solvent such as acetonitrile at temperatures ranging from 50° C. to 120° C. furnishes compounds of formula 61. Treatment of intermediates 61 with a base such as LiOH or NaOH in a solvent such as MeOH, THF or water, or a combination thereof can afford compounds of the formula 62. Treatment of acids 62 with amines such as 37 in the presence of a coupling agent such as HATU or HBTU in a solvent such as DMF or DCM furnishes compounds of formula 63. If $R^1$ or $R^1$ contain an amine group or another functional group that is protected, the protecting group can be removed by treating the substrate with the appropriate reagents as described in *Protective Groups in Organic Synthesis* (Greene, Wuts; 3$^{rd}$ ed., 1999, John Wiley & Sons, Inc.) to provide compounds of formula 64.

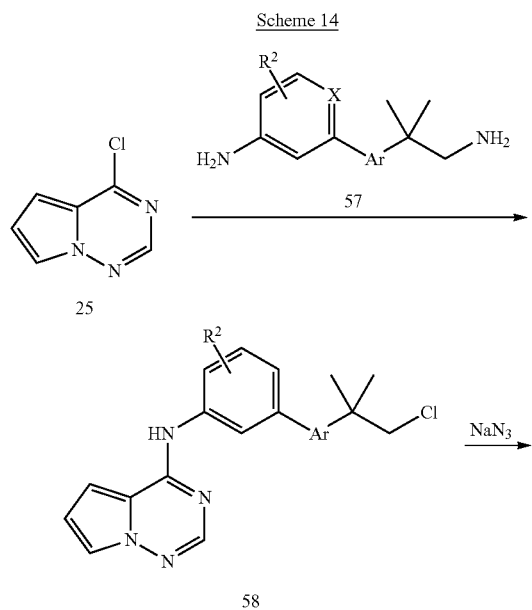

Scheme 14

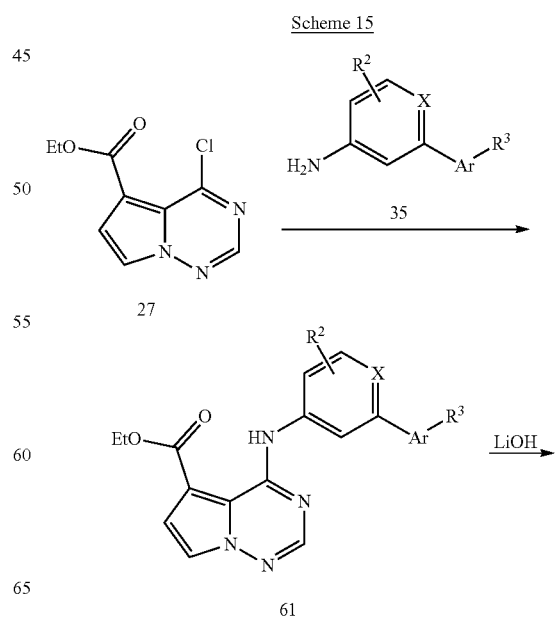

Scheme 15

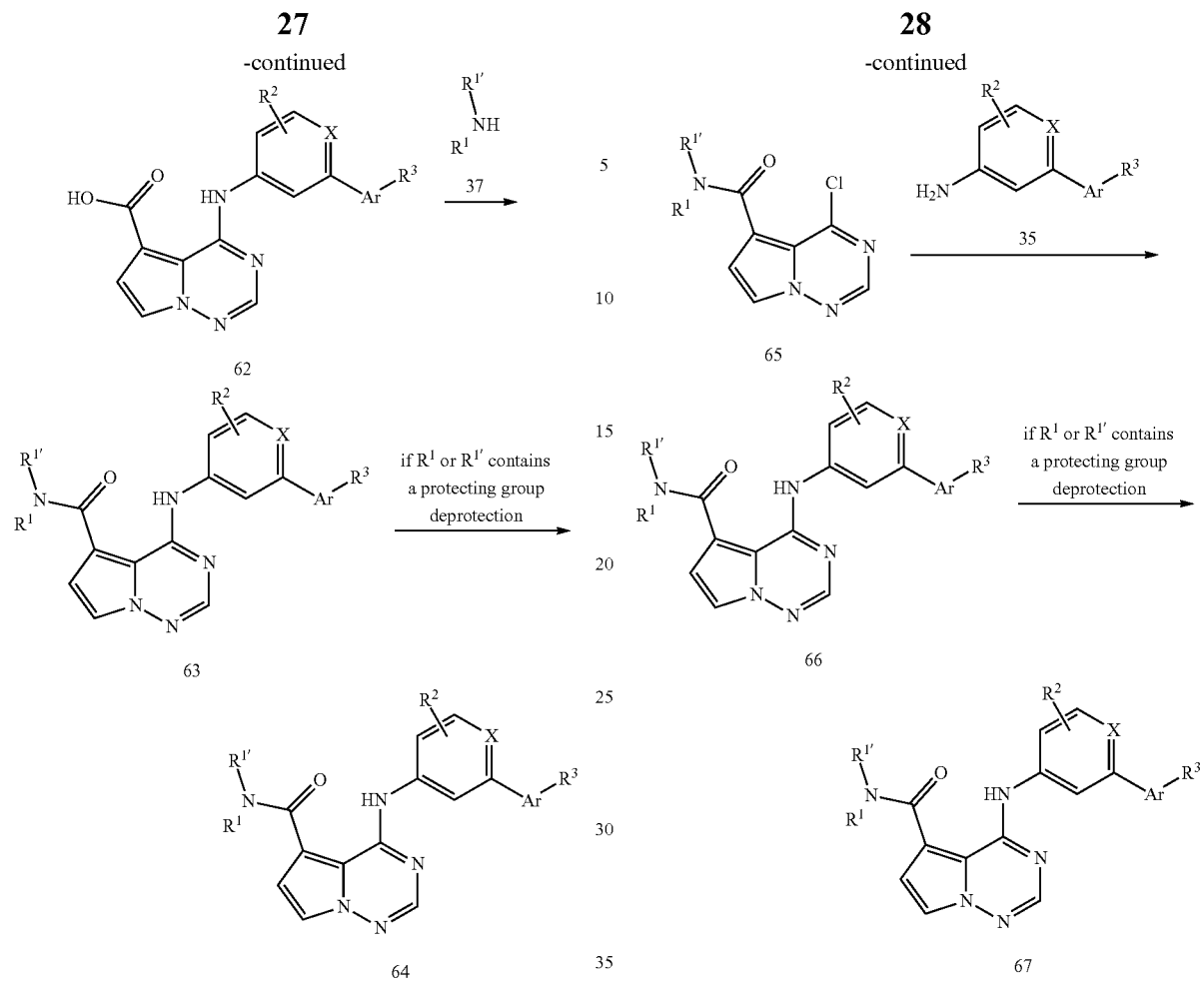

Compounds of formula 66 and 67 are prepared by the methods outlined in Scheme 16. Intermediate 29 can be treated with an amine of the formula 37 in the presence of a base such as DIEA or TEA in a solvent such as acetonitrile at temperatures ranging from 50° C. to 120° C. to furnish compounds of formula 65. Treatment of 65 with an aniline of the formula 35 in a solvent such as acetonitrile at temperatures ranging from 50° C. to 120° C. can furnish compounds of formula 66. If $R^1$ or $R^1$ contain an amine group or another functional group that is protected, the protecting group can be removed by treating the substrate with the appropriate reagents as described in *Protective Groups in Organic Synthesis* (Greene, Wuts; $3^{rd}$ ed., 1999, John Wiley & Sons, Inc.) to provide compounds of formula 67.

Compounds of formula 71 and 72 are prepared by the methods outlined in Scheme 17. Treatment of intermediate 65 with an aniline of the formula 68 in a solvent such as acetonitrile at temperatures ranging from 50° C. to 120° C. can furnish compounds of formula 69. Intermediate 69 can be treated with acids of the formula 70 in the presence of a coupling agent such as DCC or HATU in a solvent such as DMF or DCM to afford compounds of the formula 71. If $R^1$, $R^1$ or $R^3$ contain an amine group or another functional group that is protected, the protecting group can be removed by treating the substrate with the appropriate reagents as described in *Protective Groups in Organic Synthesis* (Greene, Wuts; $3^{rd}$ ed., 1999, John Wiley & Sons, Inc.) to provide compounds of formula 72.

Scheme 16

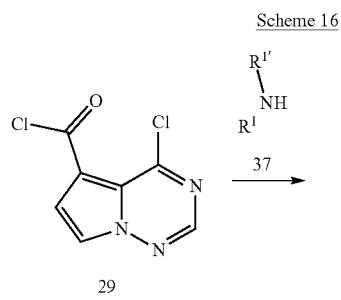

Scheme 17

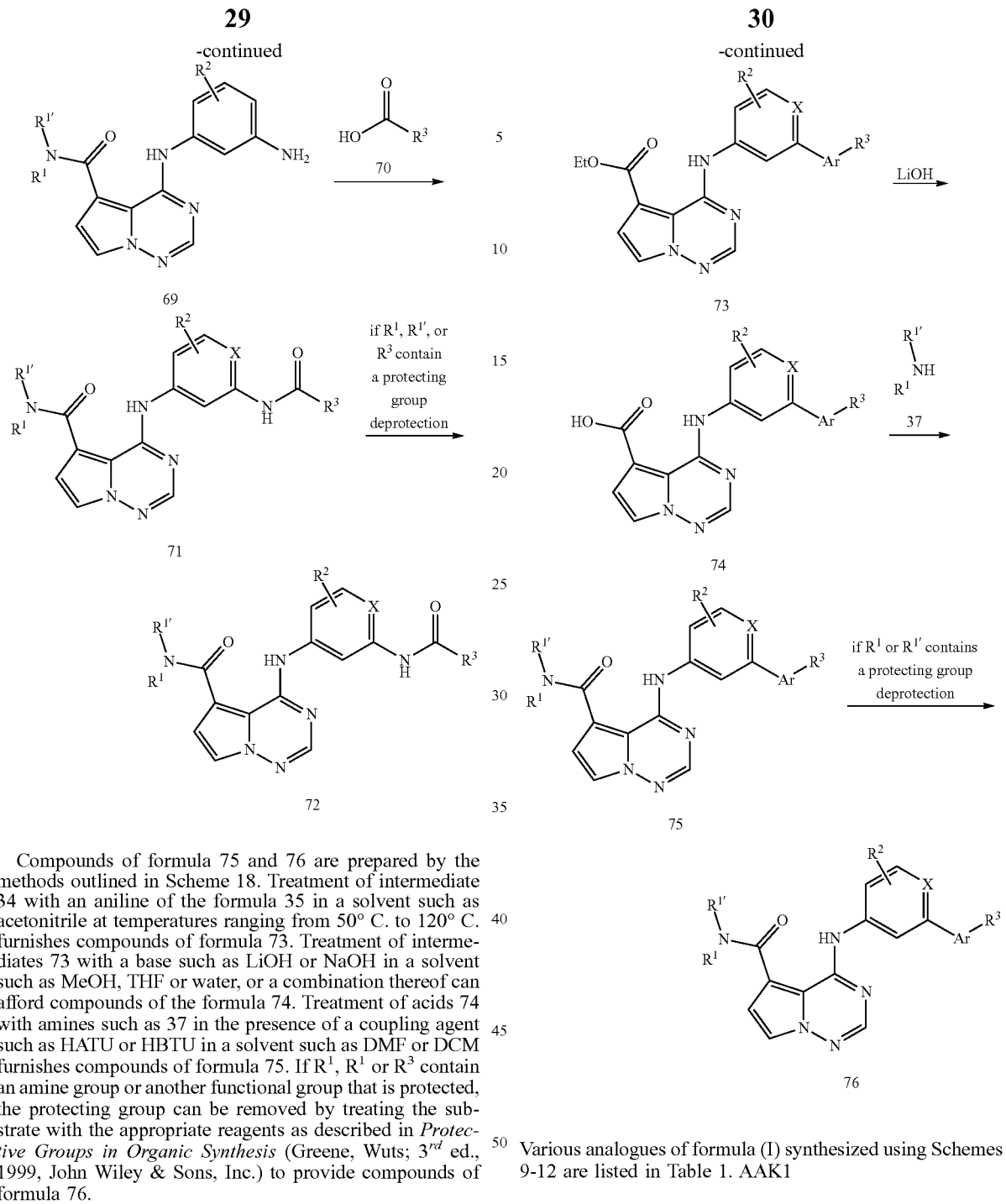

Compounds of formula 75 and 76 are prepared by the methods outlined in Scheme 18. Treatment of intermediate 34 with an aniline of the formula 35 in a solvent such as acetonitrile at temperatures ranging from 50° C. to 120° C. furnishes compounds of formula 73. Treatment of intermediates 73 with a base such as LiOH or NaOH in a solvent such as MeOH, THF or water, or a combination thereof can afford compounds of the formula 74. Treatment of acids 74 with amines such as 37 in the presence of a coupling agent such as HATU or HBTU in a solvent such as DMF or DCM furnishes compounds of formula 75. If $R^1$, $R^{1'}$ or $R^3$ contain an amine group or another functional group that is protected, the protecting group can be removed by treating the substrate with the appropriate reagents as described in *Protective Groups in Organic Synthesis* (Greene, Wuts; 3$^{rd}$ ed., 1999, John Wiley & Sons, Inc.) to provide compounds of formula 76.

Various analogues of formula (I) synthesized using Schemes 9-12 are listed in Table 1. AAK1

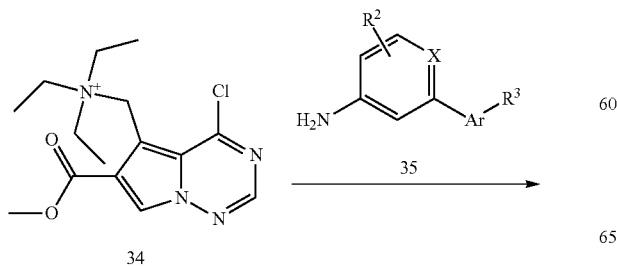

Scheme 18

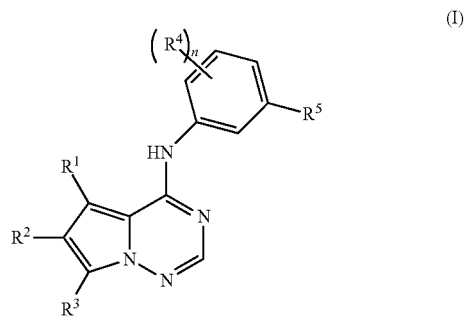

TABLE 1
| Ex. | R¹ | [structure with (R⁴)n, HN, R⁵] | R² | R³ | (M + H)⁺ |
|-----|----|----|----|----|----|
| 1 | 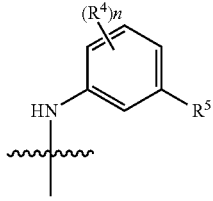 | 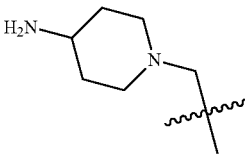 | H | H | 390.2 |
| 2 | 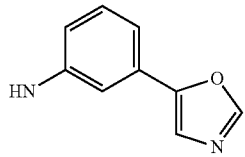 | 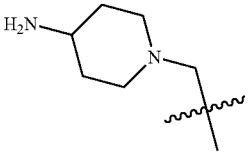 [SMILES: *CN1CCC(N)CC1] | H | H | 433.4 |
| 3 | 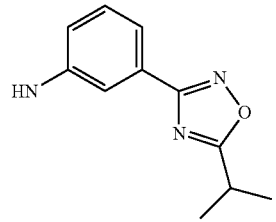 | 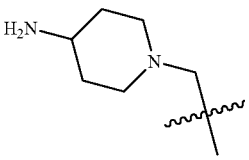 [SMILES: *CN1CCC(N)CC1] | H | H | 449.2 |
| 4 | 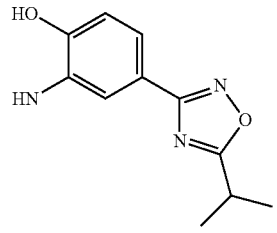 | 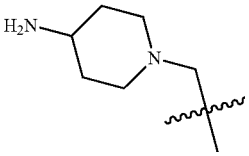 [SMILES: *CN1CCC(N)CC1] | H | H | 349.3 |
| 5 | 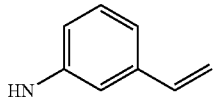 | 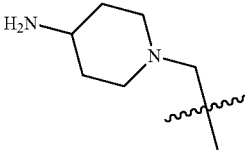 [SMILES: *CN1CCC(N)CC1] | H | H | 447.4 |
| 6 | 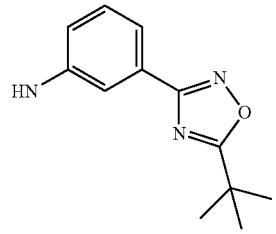 | 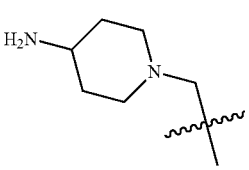 [SMILES: *CN1CCC(N)CC1] | H | H | 461.4 |

TABLE 1-continued
| # | | | | | |
|---|---|---|---|---|---|
| 7 | 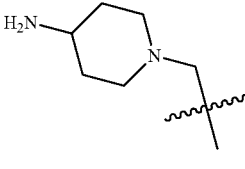 [SMILES: *CN1CCC(N)CC1] | 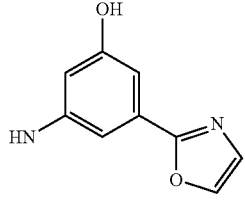 | H | H | 406.3 |
| 8 | 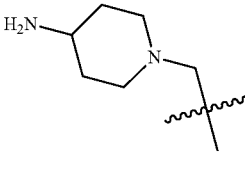 [SMILES: *CN1CCC(N)CC1] | 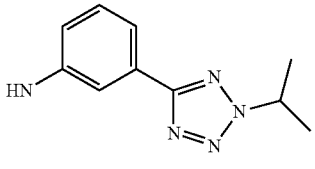 | H | H | 433.4 |
| 9 | 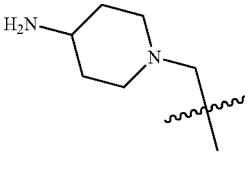 [SMILES: *CN1CCC(N)CC1] | 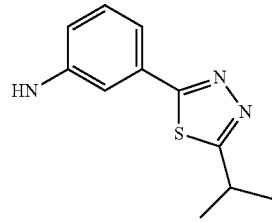 | H | H | 449.3 |
| 10 | 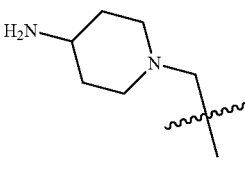 [SMILES: *CN1CCC(N)CC1] | 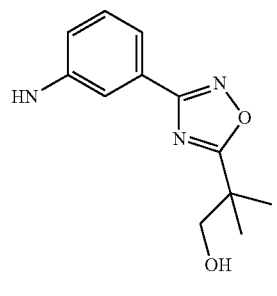 | H | H | 463.4 |
| 11 | 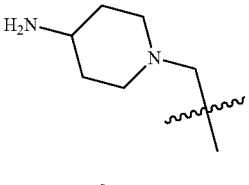 | 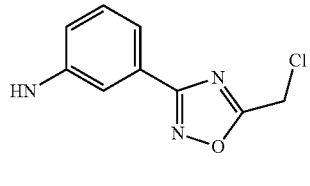 | H | H | 439.1 |
| 12 | 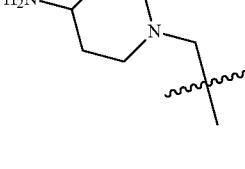 | 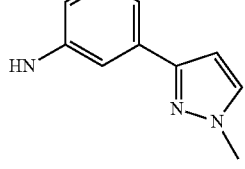 | H | H | 403.3 |
| 13 | 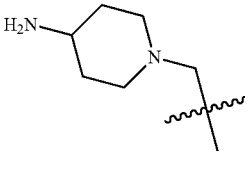 [SMILES: *CN1CCC(N)CC1] |  | H | H | 405.2 |
| 14 | 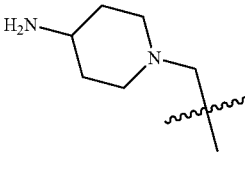 [SMILES: *CN1CCC(N)CC1] | 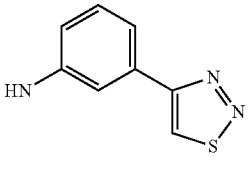 | H | H | 407.2 |

TABLE 1-continued
| | | | | | |
|---|---|---|---|---|---|
| 15 | 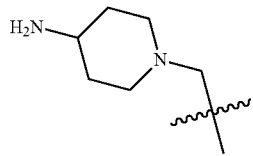 [SMILES: *CN1CCC(N)CC1] | 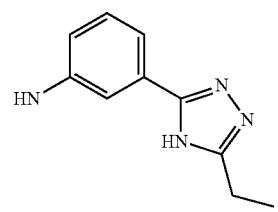 | H | H | 418.3 |
| 16 | 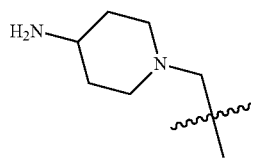 [SMILES: *CN1CCC(N)CC1] | 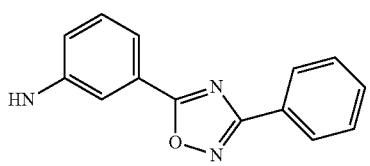 | H | H | 467.2 |
| 17 | 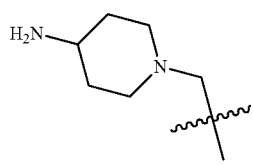 [SMILES: *CN1CCC(N)CC1] | 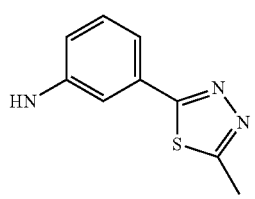 | H | H | 421.3 |
| 18 | 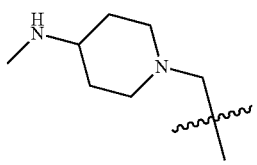 [SMILES: *CN1CCC(NC)CC1] | 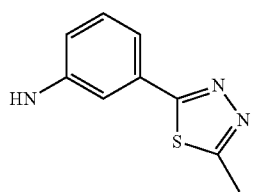 | H | H | 435.3 |
| 19 | 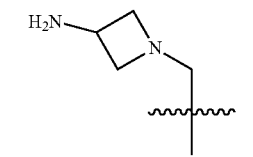 [SMILES: *CN1CC(N)C1] | 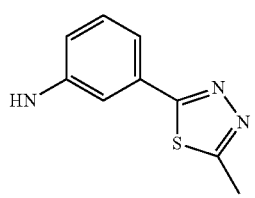 | H | H | 393.3 |
| 20 | 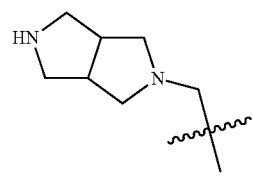 [SMILES: *CN1CC2CNCC2C1] | 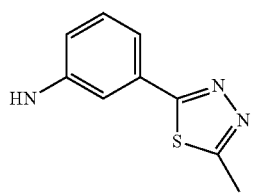 | H | H | 433.2 |
| 21 | 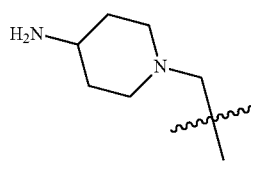 [SMILES: *CN1CCC(N)CC1] | 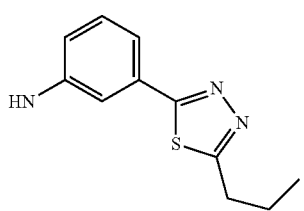 | H | H | 449.3 |

TABLE 1-continued
| | | | | | |
|---|---|---|---|---|---|
| 22 | 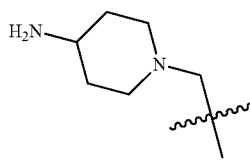 [SMILES: *CN1CCC(N)CC1] | 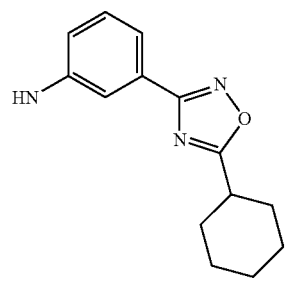 | H | H | 473.3 |
| 23 | 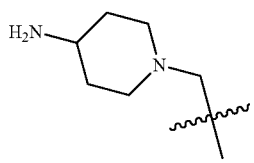 [SMILES: *CN1CCC(N)CC1] | 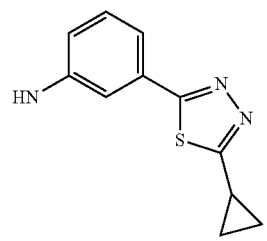 | H | H | 447.3 |
| 24 | 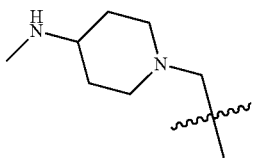 [SMILES: *CN1CCC(NC)CC1] | 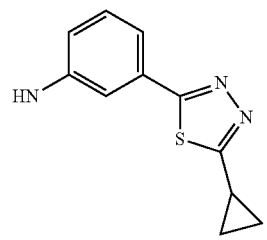 | H | H | 461.3 |
| 25 | 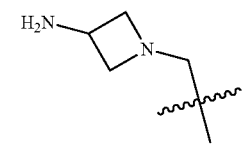 [SMILES: *CN1CC(N)C1] | 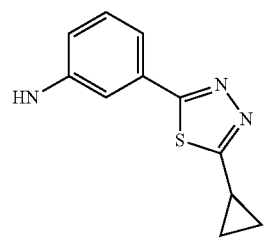 | H | H | 419.2 |
| 26 | 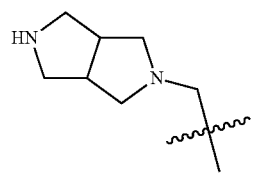 | 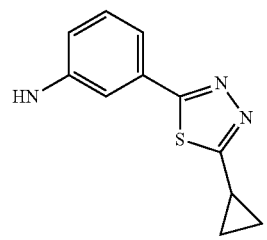 | H | H | 459.2 |
| 27 | 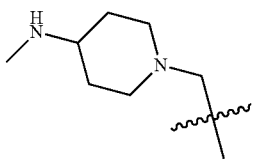 [SMILES: *CN1CCC(NC)CC1] | 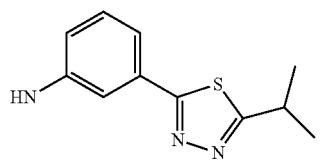 | H | H | 463.3 |
| 28 | 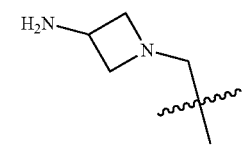 [SMILES: *CN1CC(N)C1] | 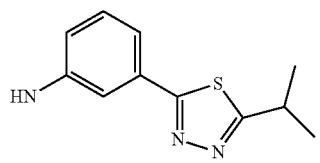 | H | H | 421.3 |

TABLE 1-continued
| | | | | | |
|---|---|---|---|---|---|
| 29 | 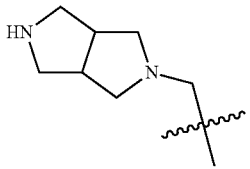 | 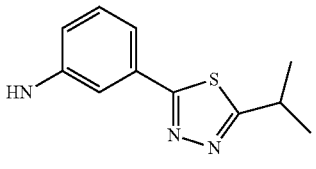 | H | H | 461.3 |
| 30 | 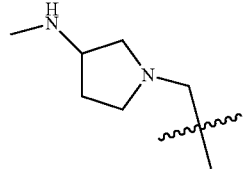 [SMILES: *CN1CCC(NC)C1] | 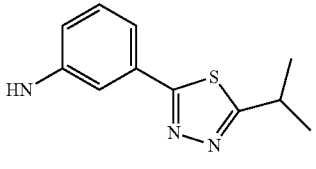 | H | H | 449.3 |
| 31 | 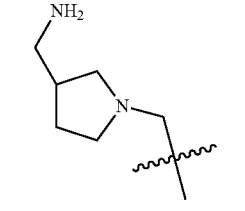 [SMILES: *CN1CCC(CN)C1] | 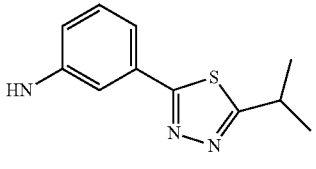 | H | H | 449.3 |
| 32 | 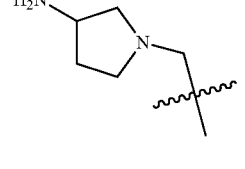 | 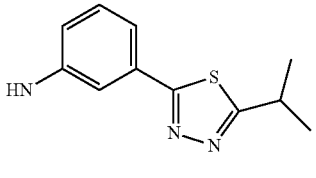 | H | H | 435.3 |
| 33 | 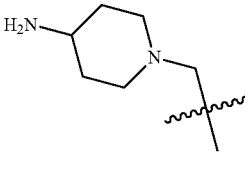 [SMILES: *CN1CCC(N)CC1] | 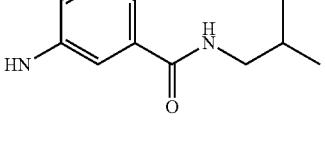 | H | H | 422.4 |
| 34 | 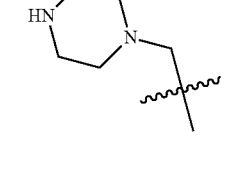 | 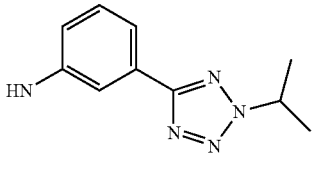 | H | H | 419.3 |
| 35 | 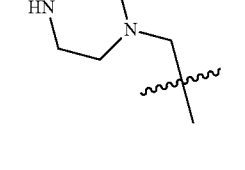 | 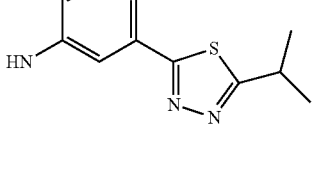 | H | H | 435.2 |
| 36 | 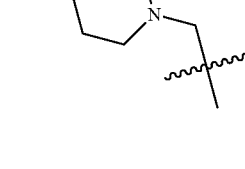 | 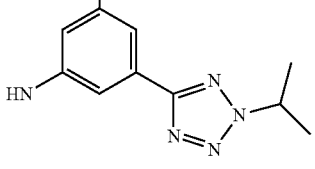 | H | H | 449.3 |

TABLE 1-continued

| # | R1 | R2 | R3 | R4 | MS |
|---|----|----|----|----|-----|
| 37 | 4-amino-piperidinyl-CH2- | 3-amino-5-hydroxyphenyl-(5-isopropyl-1,2,4-oxadiazol-3-yl) | H | H | 449.2 |
| 38 | 4-amino-piperidinyl-CH2- | 3-amino-4-hydroxyphenyl-(2-isopropyl-2H-tetrazol-5-yl) | H | H | 449.3 |
| 39 | 4-methylamino-piperidinyl-CH2- | 3-aminophenyl-(5-isopropyl-1,2,4-oxadiazol-3-yl) | H | H | 447.2 |
| 40 | 4-methylamino-piperidinyl-CH2- | 3-aminophenyl-(5-isopropyl-1,3,4-oxadiazol-2-yl) | H | H | 447.2 |
| 41 | 4-methylamino-piperidinyl-CH2- | 3-aminophenyl-(5-tert-butyl-1,2,4-oxadiazol-3-yl) | H | H | 461.2 |
| 42 | 4-methylamino-piperidinyl-CH2- | 3-aminophenyl-(2-isopropyl-2H-tetrazol-5-yl) | H | H | 447.3 |
| 43 | 4-amino-piperidinyl-CH2- | 3-amino-4-chlorophenyl-(5-isopropyl-1,2,4-oxadiazol-3-yl) | H | H | 467.2 |

TABLE 1-continued

| | | | | | |
|---|---|---|---|---|---|
| 44 | (N-methyl-4-aminopiperidine, N-CH2 linker) | 3-(5-isopropyl-1,2,4-oxadiazol-3-yl)-5-fluoroanilino | H | H | 465.2 |
| 45 | (4-aminopiperidine, N-CH2 linker) | 3-(5-isopropyl-1,2,4-oxadiazol-3-yl)-5-chloroanilino | H | H | 467.2 |
| 46 | (4-aminopiperidine, N-CH2 linker) | 3-(5-isopropyl-1,2,4-oxadiazol-3-yl)-5-fluoroanilino | H | H | 451.3 |
| 47 | (4-aminopiperidine, N-CH2 linker) | 3-(5-cyclopropyl-1,2,4-oxadiazol-3-yl)anilino | H | H | 431.2 |
| 48 | (trans-4-amino-3-hydroxypiperidine, N-CH2 linker) | 3-(5-isopropyl-1,3,4-thiadiazol-2-yl)anilino | H | H | 465.4 |
| 49 | (4-aminopiperidine, N-CH2 linker) | 3-(2-isopropyl-2H-tetrazol-5-yl)-4-fluoroanilino | H | H | 451.3 |
| 50 | (4-aminopiperidine, N-CH2 linker) | 5-(2-isopropyl-2H-tetrazol-5-yl)-2-fluoroanilino | H | H | 451.3 |

TABLE 1-continued

| # | R1 | R2 | R3 | R4 | MS |
|---|---|---|---|---|---|
| 51 | (4-aminopiperidin-1-yl)methyl | 3-fluoro-5-(2-isopropyl-2H-tetrazol-5-yl)phenylamino | H | H | 451.2 |
| 52 | (4-aminopiperidin-1-yl)methyl | 4-fluoro-3-(5-isopropyl-1,2,4-oxadiazol-3-yl)phenylamino | H | H | 451.3 |
| 53 | (4-acetamidopiperidin-1-yl)methyl | 3-(5-isopropyl-1,3,4-thiadiazol-2-yl)phenylamino | H | H | 491.4 |
| 54 | (4-methylpiperazin-1-yl)methyl | 3-(2-isopropyl-2H-tetrazol-5-yl)phenylamino | H | H | 433.2 |
| 55 | (4-methylpiperazin-1-yl)methyl | 3-(5-isopropyl-1,3,4-thiadiazol-2-yl)phenylamino | H | H | 449.2 |
| 56 | morpholinomethyl | 3-(5-isopropyl-1,3,4-thiadiazol-2-yl)phenylamino | H | H | 436.1 |
| 57 | morpholinomethyl | 3-(2-isopropyl-2H-tetrazol-5-yl)phenylamino | H | H | 420.2 |
| 58 | (8-methyl-8-azabicyclo[3.2.1]octan-3-ylamino)methyl | 3-(2-isopropyl-2H-tetrazol-5-yl)phenylamino | H | H | 473.4 |

TABLE 1-continued

| # | R1 | R2 | R3 | R4 | MS |
|---|---|---|---|---|---|
| 59 | 3-hydroxyquinuclidine | 3-(2-isopropyl-2H-tetrazol-5-yl)phenylamino | H | H | 460.4 |
| 60 | 3-methyl-3,8-diazabicyclo[3.2.1]octan-8-ylmethyl | 3-(2-isopropyl-2H-tetrazol-5-yl)phenylamino | H | H | 459.4 |
| 61 | [3-(2-isopropyl-2H-tetrazol-5-yl)phenylamino]methyl | 3-(2-isopropyl-2H-tetrazol-5-yl)phenylamino | H | H | 536.3 |
| 62 | (4-aminopiperidin-1-yl)methyl | 3-(2-isopropyl-2H-tetrazol-5-yl)-5-isopropoxyphenylamino | H | H | 491.2 |
| 63 | methylaminomethyl | 3-(2-isopropyl-2H-tetrazol-5-yl)phenylamino | H | H | 364.2 |
| 64 | (3-cyanoazetidin-1-yl)methyl | 3-(2-isopropyl-2H-tetrazol-5-yl)phenylamino | H | H | 415.1 |
| 65 | (4-cyanopiperidin-1-yl)methyl | 3-(2-isopropyl-2H-tetrazol-5-yl)phenylamino | H | H | 433.3 |
| 66 | (cyanomethylamino)methyl | 3-(2-isopropyl-2H-tetrazol-5-yl)phenylamino | H | H | 359.2 |

TABLE 1-continued

| # | (col2) | (col3) | | | MS |
|---|---|---|---|---|---|
| 67 | 4-aminopiperidine-N-CH2- | 3-(NHC(O)CH(NH2)CH2CH(CH3)2)-phenyl-NH- | H | H | 451.3 |
| 68 | 4-aminopiperidine-N-CH2- | 3-(furan-2-yl)phenyl-NH- | H | Br | 468.2 |
| 69 | H2N-CH2CH2CH2-NH-CH2- | 3-(5-isopropyl-1,3,4-thiadiazol-2-yl)phenyl-NH- | H | H | 423.3 |
| 70 | H2N-CH2-CH(CH3)-CH2-NH-CH2- | 3-(5-isopropyl-1,3,4-thiadiazol-2-yl)phenyl-NH- | H | H | 437.3 |
| 71 | 3-(aminomethyl)piperidine-N-CH2- | 3-(5-isopropyl-1,3,4-thiadiazol-2-yl)phenyl-NH- | H | H | 436.4 |
| 72 | 4-aminopiperidine-N-CH2- | 3-(difluoromethyl)-5-(2-isopropyl-2H-tetrazol-5-yl)phenyl-NH- | H | H | 483.4 |
| 73 | 4-aminopiperidine-N-CH2- | 3-(5-cyclopentyl-1,2,4-oxadiazol-3-yl)phenyl-NH- | H | H | 459.3 |

TABLE 1-continued

| Example | Structure 1 | Structure 2 | R¹ | R² | R³ | (M + H)⁺ |
|---|---|---|---|---|---|---|
| 74 | 4-amino-piperidinyl-CH(CH₃)- | 5-(2-isopropyl-2H-tetrazol-5-yl)-1H-indol-7-yl-amino | | H | H | 472.3 |
| 75 | 4-amino-piperidinyl-CH(CH₃)- | 4-(2-isopropyl-2H-tetrazol-5-yl)-1H-benzimidazol-6-yl-amino | | H | H | 472.3 |

Structure: HN-phenyl(R⁴)ₙ-R⁵

| Example | Structure | R¹ | R² | R³ | (M + H)⁺ |
|---|---|---|---|---|---|
| 76 | 3-(2-isopropyl-2H-tetrazol-5-yl)phenylamino | H | H | H | 321.2 |
| 77 | 3-(5-isopropyl-1,2,4-oxadiazol-3-yl)phenylamino | H | H | H | 321.0 |
| 78 | 3-[5-(1-chloro-2-methylpropan-2-yl)-1,2,4-oxadiazol-3-yl]phenylamino | H | H | H | 369.0 |
| 79 | 3-(5-isopropyl-1,3,4-thiadiazol-2-yl)phenylamino | H | H | H | 337.0 |
| 80 | 3-(5-isopropyl-1,3,4-oxadiazol-2-yl)phenylamino | H | H | H | 321.0 |

TABLE 1-continued
| | | | | | |
|---|---|---|---|---|---|
| 81 | 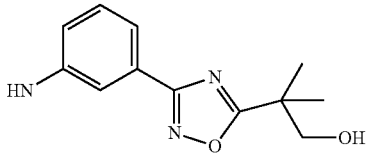 | H | H | H | 351.0 |
| 82 | 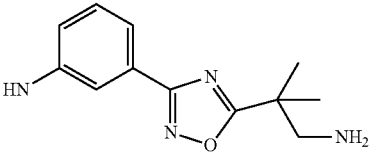 | H | H | H | 351.1 |
| 83 | 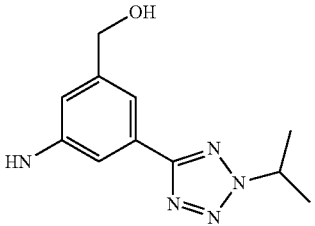 | H | H | H | 351.0 |
| 84 | 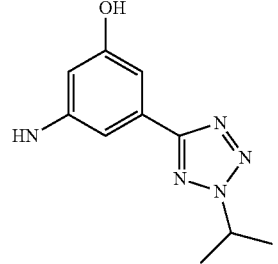 | H | H | H | 337.1 |
| 85 | 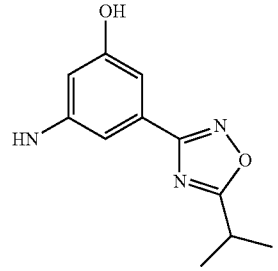 | H | H | H | 337.1 |
| 86 | 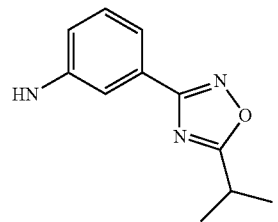 | Me | H | H | 335.3 |
| 87 | 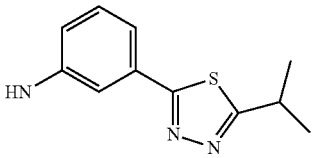 | Me | H | H | 351.2 |

TABLE 1-continued

| | | | | | |
|---|---|---|---|---|---|
| 88 | 3-(2-isopropyl-2H-tetrazol-5-yl)aniline structure | Me | H | H | 335.3 |
| 89 | 2-(3-(3-aminophenyl)-1,2,4-oxadiazol-5-yl)-2-methylpropan-1-ol structure | Me | H | H | 365.2 |
| 90 | 3-(5-(1-chloro-2-methylpropan-2-yl)-1,2,4-oxadiazol-3-yl)aniline structure | Me | H | H | 383.2 |
| 91 | 2-(3-(3-aminophenyl)-1,2,4-oxadiazol-5-yl)-2-methylpropan-1-amine structure | Me | H | H | 364.2 |
| 92 | 3-(5-isopropyl-1,2,4-oxadiazol-3-yl)-5-methoxyaniline structure | Me | H | H | 365.2 |
| 93 | 3-amino-5-(5-isopropyl-1,2,4-oxadiazol-3-yl)phenol structure | Me | H | H | 351.1 |

TABLE 1-continued

| | | | | | |
|---|---|---|---|---|---|
| 94 | 3-(5-isopropyl-1,3,4-thiadiazol-2-yl)aniline (HN-phenyl-thiadiazole-iPr) | CO$_2$Et | H | H | 409.0 |
| 95 | 3-hydroxy-5-(2-isopropyl-2H-tetrazol-5-yl)aniline (OH, HN-phenyl-tetrazole-iPr) | CO$_2$Et | H | H | 409.0 |
| 96 | 3-(2-isopropyl-2H-tetrazol-5-yl)aniline (HN-phenyl-tetrazole-iPr) | CO$_2$Et | H | H | 393.2 |
| 97 | 3-(5-isopropyl-1,2,4-oxadiazol-3-yl)aniline (HN-phenyl-oxadiazole-iPr) | CO$_2$Et | H | H | 393.2 |
| 98 | 3-(2-isopropyl-2H-tetrazol-5-yl)aniline (HN-phenyl-tetrazole-iPr) | CH$_2$OH | H | H | 351.2 |
| 99 | 3-(2-isopropyl-2H-tetrazol-5-yl)aniline (HN-phenyl-tetrazole-iPr) | CH$_2$NH$_2$ | H | H | 350.2 |
| 100 | 3-(2-isopropyl-2H-tetrazol-5-yl)aniline (HN-phenyl-tetrazole-iPr) | CH$_2$OMe | H | H | 365.2 |
| 101 | 3-(2-isopropyl-2H-tetrazol-5-yl)aniline (HN-phenyl-tetrazole-iPr) | CONMe$_2$ | H | H | 392.3 |

TABLE 1-continued

| | | | | | |
|---|---|---|---|---|---|
| 102 | 3-(2-isopropyl-tetrazol-5-yl)aniline | CH$_2$NMe$_2$ | H | H | 378.2 |
| 103 | 3-(2-isopropyl-tetrazol-5-yl)aniline | CONHMe | H | H | 378.2 |
| 104 | 3-(2-isopropyl-tetrazol-5-yl)aniline | CONHEt | H | H | 392.1 |
| 105 | 3-(2-isopropyl-tetrazol-5-yl)aniline | CONHCH$_2$cycPr | H | H | 418.1 |
| 106 | 3-(2-isopropyl-tetrazol-5-yl)aniline | CONHiPr | H | H | 406.1 |
| 107 | 3-(2-isopropyl-tetrazol-5-yl)aniline | CONHCH$_2$CN | H | H | 403.1 |
| 108 | 3-(2-isopropyl-tetrazol-5-yl)aniline | CONHCH$_2$CH$_2$OMe | H | H | 422.1 |
| 109 | 3-(2-isopropyl-tetrazol-5-yl)aniline | 4-amino-piperidinyl carbonyl | H | H | 447.2 |
| 110 | 3-amino-(leucinamido)aniline | 4-amino-piperidinyl carbonyl | H | H | 465.3 |

TABLE 1-continued

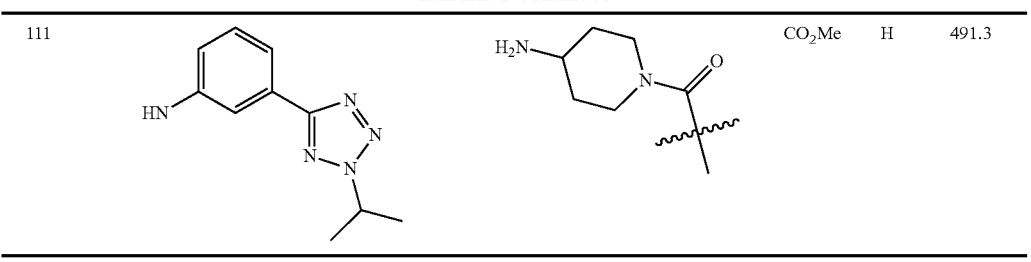

| 111 | | | CO₂Me | H | 491.3 |

DESCRIPTION OF THE SPECIFIC EMBODIMENTS

In the following examples, proton NMR spectra were recorded on either a Bruker 400 or 500 MHz NMR spectrometer. Chemical shifts are reported in δ values relative to tetramethylsilane. Liquid chromatography (LC)/mass spectra were run on a Shimadzu LC coupled to a Waters Micromass ZQ. HPLC retention times were obtained using at least one of the following methods:

Method A:
Waters analytical C18 sunfire column (4.6×150 mm, 3.5 µm); mobile phase: A=H₂O with 0.1% TFA, B=acetonitrile with 0.1% TFA; 1-15 min, 10% B→95% B; 15-18 min, 95% B; flow rate=1 mL/min; λ=254 nm; run time=18 min.

Method B:
Waters analytical phenyl Xbridge column (4.6×150 mm, 3.5 µm), mobile phase: A=H₂O with 0.1% TFA, B=acetonitrile with 0.1% TFA, 1-15 min, 10% B→95% B; 15-18 min, 95% B; flow rate=1 mL/min; λ=254 nm; run time=18 min.

Method C:
Waters analytical YMC C18 S5 column (4.6×50 mm, 3.5 µm), mobile phase: A=10% MeOH—90% H₂O—0.2% H₃PO₄, B=90% MeOH—10% H₂O—0.2% H₃PO₄, 1-19 min, 0% B→100% B; 19-20 min, 100% B; flow rate=4 mL/min; λ=254 nm; run time=20 min.

Method D:
Waters analytical YMC C18 S5 column (4.6×50 mm, 3.5 µm), mobile phase: A=10% MeOH—90% H₂O—0.2% H₃PO₄, B=90% MeOH—10% H₂O—0.2% H₃PO₄, 1-30 min, 0% B→100% B; flow rate=2.5 mL/min; λ=254 nm; run time=30 min.

Method E:
Waters analytical C18 sunfire column (4.6×150 mm, 3.5 µm); mobile phase: A=H₂O with 0.1% TFA, B=acetonitrile with 0.1% TFA; 1-20 min, 10% B→95% B; 20-23 min, 95% B; flow rate=1 mL/min; λ=254 nm; run time=23 min.

Method F:
Waters analytical phenyl Xbridge column (4.6×150 mm, 3.5 µm), mobile phase: A=H₂O with 0.1% TFA, B=acetonitrile with 0.1% TFA, 1-20 min, 10% B→95% B; 20-23 min, 95% B; flow rate=1 mL/min; λ=254 nm; run time=23 min.

Method G:
Waters analytical YMC C18 S5 column (4.6×50 mm, 3.5 µm), mobile phase: A=10% MeOH—90% H₂O—0.2% H₃PO₄, B=90% MeOH—10% H₂O—0.2% H₃PO₄, 1-17 min, 0% B→100% B; flow rate=4 mL/min; λ=254 nm; run time=17 min.

Method H:
Waters analytical C18 sunfire column (4.6×150 mm, 3.5 µm); mobile phase: A=H₂O with 0.1% TFA, B=acetonitrile with 0.1% TFA; 1-27 min, 10% B→95% B; 27-30 min, 95% B; flow rate=1 mL/min; λ=254 nm; run time=30 min.

Method I:
Waters analytical phenyl Xbridge column (4.6×150 mm, 3.5 µm), mobile phase: A=H₂O with 0.1% TFA, B=acetonitrile with 0.1% TFA, 1-27 min, 10% B→95% B; 27-30 min, 95% B; flow rate=1 mL/min; λ=254 nm; run time=30 min.

Experimental procedures for the preparation of intermediates used in the synthesis of final products (compounds of formula (I)) are shown below. The procedures below are representative procedures. One skilled in the art will appreciate that analogs with other alkyl or aryl groups at R² and R³ (Schemes 1-4) may be prepared in a similar fashion.

3-(5-Isopropyl-1,2,4-oxadiazol-3-yl)aniline

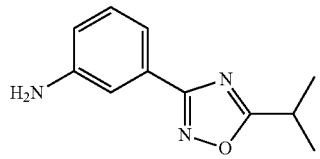

Part A. (Z)—N'-hydroxy-3-nitrobenzimidamide

To a solution of hydroxylamine hydrochloride (62.2 g, 894 mmol) in pyridine (200 mL) at 0° C. was added 3-nitrobenzonitrile (22.08 g, 149 mmol). The reaction mixture was allowed to warm up to room temperature and was stirred overnight. The reaction mixture was diluted with ethyl acetate (1000 mL) and was washed with satd. Aq. NH₄Cl, satd. aq. NaHCO₃ and water. The organic layer was dried over MgSO₄ and concentrated to obtain crude (Z)—N'-hydroxy-3-nitrobenzimidamide (32 g, 81% yield). The product was used without further purification. LCMS (ESI) m/e 182 [(M+H)⁺, calcd for C₇H₈N₃O₃ 182.1].

Part B.
5-Isopropyl-3-(3-nitrophenyl)-1,2,4-oxadiazole

To a solution of isobutyryl chloride (4.13 g, 38.8 mmol) in dry pyridine (50 mL) at room temperature under nitrogen was added CDI (6.28 g, 38.8 mmol). The reaction mixture was stirred for 15 minutes and (Z)—N'-hydroxy-3-nitrobenzimidamide (5.4 g, 29.8 mmol) was added. The reaction mixture was heated in an oil bath at 110° C. for 4 hours. The mixture was concentrated to remove the pyridine. The residue was redissolved in ethyl acetate and was washed with water, brine, dried over MgSO₄, filtered, and concentrated. The residue was purified by column chromatography on silica gel (0%→60% ethyl acetate in hexanes) to afford 5-isopropyl-3-(3-nitrophenyl)-1,2,4-oxadiazole (4.91 g, 71% yield) as reddish oil: LCMS (ESI) m/e 234 [(M+H)+, calcd for $C_{11}H_{12}N_3O_3$ 234.1].

Part C. 3-(5-Isopropyl-1,2,4-oxadiazol-3-yl)aniline

To a solution of 5-isopropyl-3-(3-nitrophenyl)-1,2,4-oxadiazole (4.91 g, 21.05 mmol) in absolute ethanol (50 mL) at room temperature was added ammonium chloride (13.51 g, 253 mmol). To the stirred suspension was added zinc dust (19.27 g, 295 mmol). The reaction mixture was stirred overnight at room temperature. No reaction was observed. The reaction mixture was then heated at reflux for 6 hours. Complete consumption of starting material was observed by LC-MS. The reaction mixture was filtered through a pad of Celite and the filtrate was concentrated. The residue was dissolved in ethyl acetate (600 mL). The organic layer was washed with water, brine and dried over $MgSO_4$, filtered and concentrated to afford 3-(5-isopropyl-1,2,4-oxadiazol-3-yl)aniline (3.69 g, 86% yield). The product was used without further purification. LCMS (ESI) m/e 204 [(M+H)+, calcd for $C_{11}H_{12}N_3O_3$ 204.1].

3-(5-Isopropyl-1,3,4-thiadiazol-2-yl)aniline

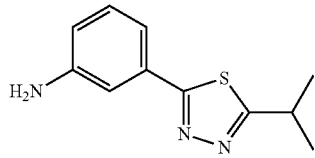

Part A. N'-Isobutyryl-3-nitrobenzohydrazide

To a solution of isobutyric acid hydrazide (1.101 g, 10.78 mmol) in dichloromethane (80 mL) containing N,N-diisopropylethylamine (1.882 mL, 10.78 mmol) at room temperature under nitrogen was added 3-nitrobenzoyl chloride (2.00 g, 10.78 mmol). The reaction mixture was stirred for 30 minutes at room temperature. The product crashed out as a white solid. The reaction mixture was filtered through a Buchner funnel and the solid was washed with cold hexanes then dried under high vacuum overnight to afford N'-isobutyryl-3-nitrobenzohydrazide (2.09 g, 77% yield). LCMS (ESI) m/e 252 [(M+H)+, calcd for $C_{11}H_{14}N_3O_4$ 252.1].

Part B.
2-Isopropyl-5-(3-nitrophenyl)-1,3,4-thiadiazole

To a solution of N'-isobutyryl-3-nitrobenzohydrazide (3.9 g, 15.52 mmol) in dry toluene (120 mL) at room temperature under nitrogen was added Lawesson's reagent (11.30 g, 27.9 mmol). The reaction mixture was heated at 100° C. overnight. Complete consumption of starting material was observed. The residue was purified by column chromatography on silica gel (0%→100% ethyl acetate in hexanes) to afford 2-isopropyl-5-(3-nitrophenyl)-1,3,4-thiadiazole (2.92 g, 75% yield). LCMS (ESI) m/e 250 [(M+H)+, calcd for $C_{11}H_{13}N_3O_2S$ 250.1].

Part C. 3-(5-Isopropyl-1,3,4-thiadiazol-2-yl)aniline

To a solution of the 2-isopropyl-5-(3-nitrophenyl)-1,3,4-thiadiazole (2.92 g, 11.71 mmol) in absolute ethanol (200 mL) at room temperature was added ammonium chloride (7.52 g, 141 mmol). To the stirred suspension mixture was added zinc dust (10.72 g, 164 mmol). The reaction mixture was stirred overnight at room temperature. No reaction was observed. The reaction mixture was then heated to reflux for 6 hours. Complete consumption of starting material was observed by LC-MS. The reaction mixture was filtered through a pad of Celite and the filtrate was concentrated. The residue was dissolved in ethyl acetate (600 mL). The organic layer was washed with water, brine, dried over $MgSO_4$, filtered and concentrated to afford 3-(5-isopropyl-1,3,4-thiadiazol-2-yl)aniline (2.39 g, 93% yield). The product was used without further purification. LCMS (ESI) m/e 220 [(M+H)+, calcd for $C_{11}H_{14}N_3S$ 220.1].

3-(5-isopropyl-1,3,4-oxadiazol-2-yl)aniline

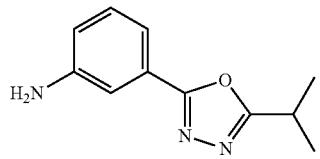

Part A.
2-Isopropyl-5-(3-nitrophenyl)-1,3,4-oxadiazole

To a solution of N'-isobutyryl-3-nitrobenzohydrazide (1.354 g, 5.39 mmol), prepared as above, in dichloromethane (60 ml) at 0° C. under nitrogen was added carbon tetrabromide (3.57 g, 10.78 mmol) followed by triphenylphosphine (2.83 g, 10.78 mmol). The reaction mixture was warmed to room temperature and stirred overnight. The reaction mixture was poured into a separatory funnel containing diethyl ether (100 mL) and 1M $KHSO_4$ (50 mL). The ether layer was separated, washed with NaHCO3 (1×50 mL) brine (1×50 mL), dried (MgSO4), filtered and concentrated under reduced pressure. The residue was purified via silica gel chromatography (10-50% ethyl acetate in hexanes) to afford 2-isopropyl-5-(3-nitrophenyl)-1,3,4-oxadiazole (1.03 g, 4.11 mmol, 76% yield) as a colorless solid. LCMS (ESI) m/e 234.2 [(M+H)+, calcd for C11H12N3O3 234.1].

Part B

To a solution of 2-isopropyl-5-(3-nitrophenyl)-1,3,4-oxadiazole (1.03 g, 4.11 mmol) in ethanol (50 ml) was added zinc dust (3.84 g, 58.7 mmol) and ammonium chloride (2.7 g, 50.5 mmol). The mixture was then stirred under nitrogen overnight. The reaction mixture was cooled to room temperature, diluted with EtOAc (200 mL) and filtered through a pad of Celite. The filtrate was concentrated under reduced pressure to obtain 3-(5-isopropyl-1,3,4-oxadiazol-2-yl)aniline (0.95 g, 3.74 mmol, 91% yield) a pale yellow oil. The material was carried on without further purification. LCMS (ESI) m/e 204.2 [(M+H)+, calcd for C11H14N3O 204.1].

3-(2-Isopropyl-2H-tetrazol-5-yl)aniline

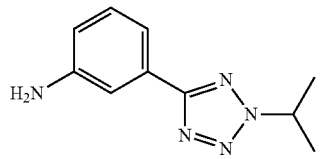

Part A. 5-(3-Nitrophenyl)-2H-tetrazole

A mixture of 3-nitrobenzonitrile (2.00 g, 13.50 mmol), sodium azide (5.27 g, 81 mmol) and ammonia hydrochloride (4.33 g, 81 mmol) in DMF (30 mL) was heated at reflux for 16 h. The mixture was cooled and then poured into (200 mL) 1N HCl and diluted with water (100 mL). The precipitate that formed was collected to afford 5-(3-nitrophenyl)-2H-tetrazole (2.5 g, 97% yield) as a colorless solid, which was used directly in the next step.

Part B. 2-Isopropyl-5-(3-nitrophenyl)-2H-tetrazole

A mixture of 5-(3-nitrophenyl)-2H-tetrazole (200 mg, 1.046 mmol), 2-iodopropane (0.125 mL, 1.256 mmol) and potassium carbonate (318 mg, 2.302 mmol) in DMF (20 mL) was heated to 100° C. in a sealed tube for 12 h. The mixture was transferred to a reparatory funnel containing ethyl acetate. The organic layer was washed with brine, dried over $Na_2SO_4$, filtered, and concentrated to afford 2-isopropyl-5-(3-nitrophenyl)-2H-tetrazole (200 mg, 82% yield) as a yellow solid. LCMS (ESI) m/e 234.2 [(M+H)$^+$, calcd for $C_{10}H_{12}N_5O_2$ 234.1].

Part C. 3-(2-Isopropyl-2H-tetrazol-5-yl)aniline

To a mixture of 2-isopropyl-5-(3-nitrophenyl)-2H-tetrazole (200 mg, 0.858 mmol) and ammonium chloride (550 mg, 10.29 mmol) in ethanol (10 mL) was added zinc dust (785 mg, 12.01 mmol). The mixture was heated at reflux for 3 h. The mixture was filtered through a pad of Celite. The filtrate was concentrated and redissolved in ethyl acetate. The organic layer was washed with water, brine, dried over $Na_2SO_4$, filtered, and concentrated to afford 3-(2-isopropyl-2H-tetrazol-5-yl)aniline (170 mg, 98% yield) as a brown oil, which was used without further purification. LCMS (ESI) m/e 204.3 [(M+H)$^+$, calcd for $C_{10}H_{14}N_5$ 204.1].

Experimental procedures for the preparation of final products (compounds of formula (I) are described below.

Example 1

5-((4-aminopiperidin-1-yl)methyl)-N-(3-(oxazol-5-yl)phenyl)pyrrolo[2,1-f][1,2,4]triazin-4-amine

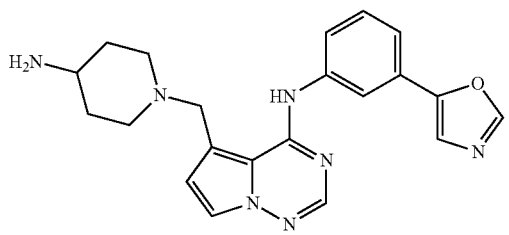 [SMILES: NC1CCN(Cc2ccn3ncnc(Nc4cccc(-c5cnco5)c4)c23)CC1]

Part A. N-((4-chloropyrrolo[2,1-f][1,2,4]triazin-5-yl)methyl)-N,N-diethylethanaminium To a solution of 5-(bromomethyl)-4-chloropyrrolo[1,2-f][1,2,4]triazine (9.8 g, 39.8 mmol) (prepared as in WO 03/042172 A2) in dry THF (200 mL) at room temperature under nitrogen was added triethylamine (12.75 mL, 91 mmol) and the reaction mixture was stirred overnight. The light brown solid was collected by vacuum filtration and was washed with cold THF. The solid was dried under vacuum to obtain N-((4-chloropyrrolo[1,2-f][1,2,4]triazin-5-yl)methyl)-N,N-diethylethanaminium (5.012 g, 18.72 mmol, 47% yield) as a tan solid. The material carried on without further purification (stored under nitrogen in a dry dessicator until needed). LCMS (ESI) m/e 267.2 [(M)$^+$, calcd for $C_{13}H_{20}ClN_4$ 267.1]. $^1$H NMR (400 MHz, DMSO-d$_6$) δ 8.58 (s, 1H), 8.44 (d, J=2.8 Hz, 1H), 7.34 (d, J=2.8 Hz, 1H), 4.89 (s, 2H), 3.34 (d, J=7.3 Hz, 6H), 1.31 (t, J=7.1 Hz, 9H).

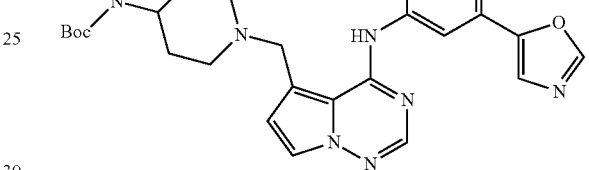

Part B. tert-butyl (1-((4-((3-(oxazol-5-yl)phenyl)amino)pyrrolo[2,1-f][1,2,4]triazin-5-yl)methyl)piperidin-4-yl)carbamate To a solution of N-((4-chloropyrrolo[1,2-f][1,2,4]triazin-5-yl)methyl)-N,N-diethylethanaminium, bromide salt (0.1 g, 0.288 mmol) in dry acetonitrile (4 mL) in a microwave tube flushed with nitrogen was added 3-(oxazol-5-yl)aniline (0.046 g, 0.288 mmol). The reaction tube was capped and heated in a microwave at 75° C. for 30 min. To the reaction mixture was added 4-(N—BOC amino)-piperidine (0.058 g, 0.288 mmol) and DIEA (0.126 mL, 0.719 mmol). The reaction tube was capped again and heated in a microwave at 75° C. for 30 min. The reaction mixture was concentrated under reduced pressure. The residue was purified by silica gel chromatography (dichloromethane:ethyl acetate containing 0.5% TEA). Obtained tert-butyl 1-((4-(3-(oxazol-5-yl)phenylamino)pyrrolo[1,2-f][1,2,4]triazin-5-yl)methyl)piperidin-4-ylcarbamate (0.099 g, 0.202 mmol, 70% yield) as a yellow solid. LCMS (ESI) m/e 490.2 [(M+H)$^+$, calcd for $C_{26}H_{32}N_7O_3$ 490.3].

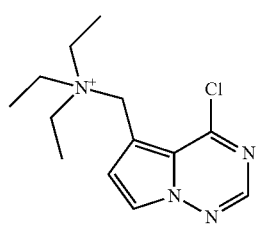

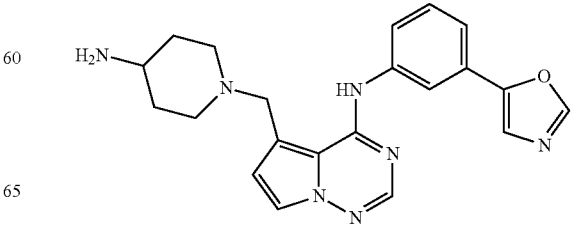

Part C. 5-((4-aminopiperidin-1-yl)methyl)-N-(3-(oxazol-5-yl)phenyl)pyrrolo[2,1-f][1,2,4]triazin-4-amine To a solution of tert-butyl 1-((4-(3-(oxazol-5-yl)phenylamino)pyrrolo[1,2-f][1,2,4]triazin-5-yl)methyl)piperidin-4-ylcarbamate (0.099 g, 0.202 mmol) in dry CH$_2$Cl$_2$ (20 mL) at room temperature was added TFA (0.156 mL, 2.022 mmol). The reaction mixture was stirred overnight. The reaction mixture was concentrated under reduced pressure. The residue was redissolved in MeOH (2 mL) and purified by reverse phase preparative HPLC (30×100 mm Xterra column and 10-100% B, 18 minute gradient, 20 minute run; Solvent A: 90% water, 10% Methanol, 0.1% TFA: Solvent B: 10% Water, 90% Methanol, 0.1% TFA)). Obtained 5-((4-aminopiperidin-1-yl)methyl)-N-(3-(oxazol-5-yl)phenyl)pyrrolo[1,2-f][1,2,4]triazin-4-amine, TFA (0.0538 g, 0.105 mmol, 52% yield) as a colorless solid. LCMS (ESI) m/e 390.2 [(M+H)$^+$, calcd for C$_{21}$H$_{24}$N$_7$O 390.2]. $^1$H NMR (400 MHz, MeOD) 8.26 (s, 1H), 7.70-7.46 (m, 6H), 7.28-7.15 (m, 1H), 6.70 (d, J=3.0 Hz, 1H), 4.55 (s, 2H), 3.68 (d, J=9.1 Hz, 2H), 3.43 (t, J=11.5 Hz, 1H), 3.22-2.98 (m, 2H), 2.24 (d, J=12.6 Hz, 2H), 1.76 (br. s, 2H); HPLC retention time (method C): t$_R$=2.28 min.

Example 2

5-((4-aminopiperidin-1-yl)methyl)-N-(3-(5-isopropyl-1,2,4-oxadiazol-3-yl)phenyl)pyrrolo[2,1-f][1,2,4]triazin-4-amine

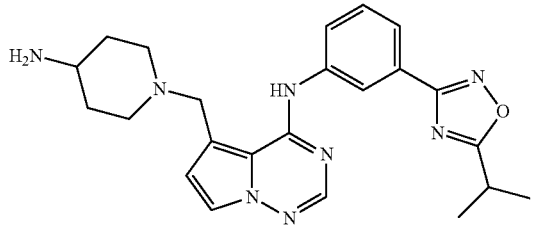 [SMILES: CC(C)c1nc(-c2cccc(Nc3ncnn4ccc(CN5CCC(N)CC5)c34)c2)no1]

Prepared as in Example 1, Parts B and C using 3-(5-isopropyl-1,2,4-oxadiazol-3-yl)aniline (0.117 g, 0.575 mmol) to afford 5-((4-aminopiperidin-1-yl)methyl)-N-(3-(5-isopropyl-1,2,4-oxadiazol-3-yl)phenyl)pyrrolo[1,2-f][1,2,4]triazin-4-amine, HCl (0.1344 g, 0.281 mmol, 49% yield for 2 steps) as a reddish oil. LCMS (ESI) m/e 433.4 [(M+H)$^+$, calcd for C$_{28}$H$_{29}$N$_8$O 433.3]. $^1$H NMR (400 MHz, MeOD) δ 7.95-7.88 (m, 1H), 7.87 (d, J=1.5 Hz, 1H), 7.60 (t, J=7.9 Hz, 1H), 7.53 (s, 1H), 7.50 (d, J=3.0 Hz, 1H), 7.39 (d, J=8.1 Hz, 1H), 6.71 (d, J=2.8 Hz, 1H), 4.59 (s, 2H), 3.68 (br. s, 2H), 3.45 (br. s, 1H), 3.35-3.29 (m, 1H), 3.15 (d, J=3.0 Hz, 2H), 2.26 (d, J=12.3 Hz, 2H), 1.80 (br. s, 2H), 1.42 (d, J=7.1 Hz, 6H); HPLC retention time (method C): t$_R$=5.90 min.

Example 3

2-((5-((4-aminopiperidin-1-yl)methyl)pyrrolo[2,1-f][1,2,4]triazin-4-yl)amino)-4-(5-isopropyl-1,2,4-oxadiazol-3-yl)phenol

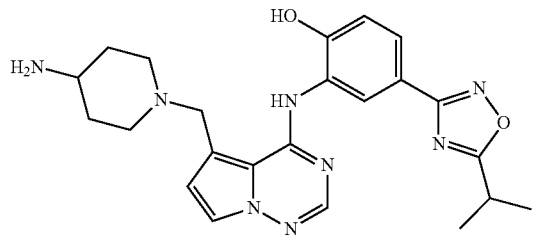 [SMILES: CC(C)c1nc(-c2ccc(O)c(Nc3ncnn4ccc(CN5CCC(N)CC5)c34)c2)no1]

Prepared as in Example 1, Parts B and C using 2-amino-4-(5-isopropyl-1,2,4-oxadiazol-3-yl)phenol (0.246 g, 1.122 mmol) to afford 2-(5-((4-aminopiperidin-1-yl)methyl)pyrrolo[1,2-f][1,2,4]triazin-4-ylamino)-4-(5-isopropyl-1,2,4-oxadiazol-3-yl)phenol, TFA (0.0532 g, 0.078 mmol, 25% yield for 2 steps) as a pale yellow oil. LCMS (ESI) m/e 449.2 [(M+H)$^+$, calcd for C$_{23}$H$_{29}$N$_8$O$_2$ 449.2]. $^1$H NMR (400 MHz, MeOD) δ ppm 7.89 (d, J=1.76 Hz, 1H), 7.83 (dd, J=8.44, 2.14 Hz, 1H), 7.57 (s, 1H), 7.54 (d, J=2.77 Hz, 1H), 7.13 (d, J=8.31 Hz, 1H), 6.69 (d, J=2.77 Hz, 1H), 4.44 (s, 2H), 3.96 (s, 1H), 3.59 (d, J=10.58 Hz, 2H), 3.34-3.46 (m, 1H), 2.91-3.09 (m, 2H), 2.18 (d, J=12.34 Hz, 2H), 1.80 (d, J=13.35 Hz, 2H), 1.42 (d, J=7.05 Hz, 6H); HPLC retention time (method C): t$_R$=5.70 min.

Example 4

5-((4-aminopiperidin-1-yl)methyl)-N-(3-vinylphenyl)pyrrolo[2,1-f][1,2,4]triazin-4-amine

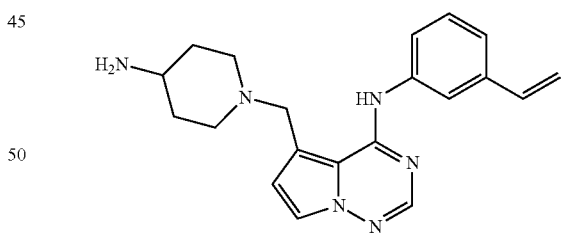

Prepared as in Example 1, Parts B and C using 3-vinylaniline (0.134 g, 1.122 mmol) to afford 5-((4-aminopiperidin-1-yl)methyl)-N-(3-vinylphenyl)pyrrolo[1,2-f][1,2,4]triazin-4-amine, 2 TFA (0.143 g, 0.245 mmol, 22% yield for 2 steps) as a pale brown solid. LCMS (ESI) m/e 349.3 [(M+H)$^+$, calcd for C$_{20}$H$_{25}$N$_6$ 349.2]. $^1$H NMR (400 MHz, MeOD) δ 7.57-7.51 (m, 2H), 7.45 (s, 1H), 7.40-7.35 (m, 1H), 7.32 (s, 1H), 7.16 (s, 1H), 6.83-6.69 (m, 2H), 5.83 (dd, J=17.6, 0.5 Hz, 1H), 5.29 (d, J=11.3 Hz, 1H), 4.51 (s, 2H), 3.63 (d, J=9.6 Hz, 2H), 3.42 (t, J=10.7 Hz, 1H), 3.07 (br. s, 2H), 2.23 (d, J=12.3 Hz, 2H), 1.76 (br. s, 2H); HPLC retention time (method C): t$_R$=3.19 min.

Example 5

5-((4-aminopiperidin-1-yl)methyl)-N-(3-(5-(tert-butyl)-1,2,4-oxadiazol-3-yl)phenyl)pyrrolo[2,1-f][1,2,4]triazin-4-amine

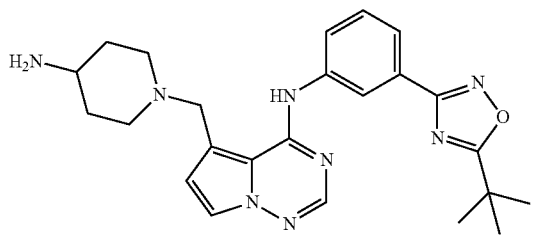 [SMILES: CC(C)(C)c1nc(-c2cccc(Nc3ncnn4ccc(CN5CCC(N)CC5)c34)c2)no1]

Prepared as in Example 1, Parts B and C using 3-(5-tert-butyl-1,2,4-oxadiazol-3-yl)aniline (0.110 g, 0.505 mmol) to afford 5-((4-aminopiperidin-1-yl)methyl)-N-(3-(5-tert-butyl-1,2,4-oxadiazol-3-yl)phenyl)pyrrolo[1,2-f][1,2,4]triazin-4-amine, HCl (0.103 g, 0.210 mmol, 42% yield for 2 steps) as a pale brown oil. LCMS (ESI) m/e 447.4 [(M+H)+, calcd for $C_{24}H_{31}N_8O$ 447.3]. $^1$H NMR (400 MHz, MeOD) δ 7.95-7.89 (m, 1H), 7.87 (d, J=1.5 Hz, 1H), 7.60 (t, J=7.8 Hz, 1H), 7.54-7.51 (m, 1H), 7.51-7.48 (m, 1H), 7.39 (d, J=7.8 Hz, 1H), 6.70 (d, J=2.8 Hz, 1H), 4.58 (s, 2H), 3.68 (br. s, 2H), 3.44 (br. s, 1H), 3.14 (br. s, 2H), 2.25 (d, J=12.8 Hz, 2H), 1.79 (br. s, 2H), 1.47 (s, 9H); HPLC retention time (method C): $t_R$=6.96 min.

Example 6

5-((4-aminopiperidin-1-yl)methyl)-N-(3-(5-(tert-pentyl)-1,2,4-oxadiazol-3-yl)phenyl)pyrrolo[2,1-f][1,2,4]triazin-4-amine

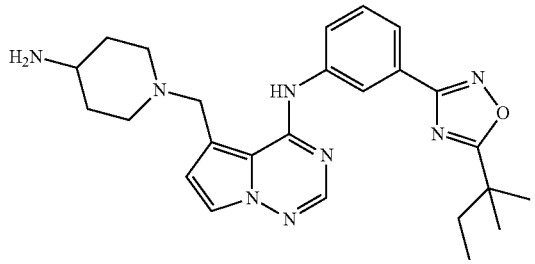 [SMILES: CCC(C)(C)c1nc(-c2cccc(Nc3ncnn4ccc(CN5CCC(N)CC5)c34)c2)no1]

Prepared as in Example 1, Parts B and C using 3-(5-tert-pentyl-1,2,4-oxadiazol-3-yl)aniline (0.133 g, 0.575 mmol) to afford 5-((4-aminopiperidin-1-yl)methyl)-N-(3-(5-tert-pentyl-1,2,4-oxadiazol-3-yl)phenyl)pyrrolo[1,2-f][1,2,4]triazin-4-amine, HCl (0.142 g, 0.280 mmol, 49% yield for 2 steps) as a off-white solid. LCMS (ESI) m/e 461.4 [(M+H)+, calcd for $C_{25}H_{33}N_8O$ 461.3]. $^1$H NMR (400 MHz, MeOD) δ 7.92 (dd, J=7.9, 1.1 Hz, 1H), 7.89 (s, 1H), 7.60 (t, J=7.8 Hz, 1H), 7.53 (s, 1H), 7.51 (d, J=3.0 Hz, 1H), 7.40 (d, J=7.8 Hz, 1H), 6.71 (d, J=2.8 Hz, 1H), 4.60 (s, 2H), 3.69 (m, 2H), 3.45 (m, 1H), 3.16 (m, 2H), 2.27 (m, 2H), 1.83 (q, J=7.6 Hz, 2H), 1.82 (m, 2H), 1.44 (s, 6H), 0.84 (t, J=7.6 Hz, 3H); HPLC retention time (method C): $t_R$=7.98 min.

Example 7

3-((5-((4-aminopiperidin-1-yl)methyl)pyrrolo[2,1-f][1,2,4]triazin-4-yl)amino)-5-(oxazol-2-yl)phenol

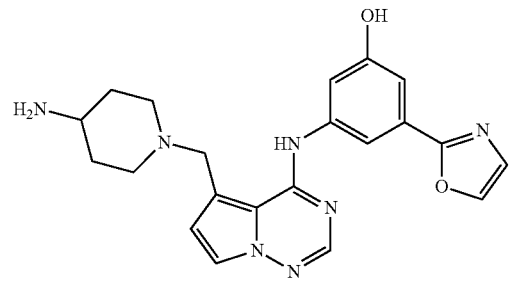 [SMILES: NC1CCN(Cc2ccn3ncnc(Nc4cc(O)cc(-c5ncco5)c4)c23)CC1]

Prepared as in Example 1, Parts B and C using 3-amino-5-(oxazol-2-yl)phenol (62 mg, 0.352 mmol) to afford 3-(5-((4-aminopiperidin-1-yl)methyl)pyrrolo[1,2-f][1,2,4]triazin-4-ylamino)-5-(oxazol-2-yl)phenol, bis-HCl salt (14 mg, 0.028 mmol, 7% yield for 2 steps) as a yellow solid. LCMS (ESI) m/e 406.3 [(M+H)+, calcd for $C_{21}H_{24}N_7O_2$ 406.2]. $^1$H NMR (400 MHz, MeOD) δ ppm 7.96 (d, J=0.76 Hz, 1H), 7.83 (s, 1H), 7.80 (t, J=1.64 Hz, 1H), 7.50 (d, J=2.52 Hz, 1H), 7.46 (t, J=2.14 Hz, 1H), 7.27 (d, J=0.76 Hz, 1H), 7.21 (dd, J=2.27, 1.51 Hz, 1H), 6.60 (d, J=2.52 Hz, 1H), 3.81 (s, 2H), 3.08-3.18 (m, 2H), 2.76-2.93 (m, 1H), 2.13-2.29 (m, 2H), 1.90-2.00 (m, 2H), 1.55-1.69 (m, 2H); HPLC retention time (method D): $t_R$=4.52 min.

Example 8

5-((4-aminopiperidin-1-yl)methyl)-N-(3-(2-isopropyl-2H-tetrazol-5-yl)phenyl)pyrrolo[2,1-f][1,2,4]triazin-4-amine

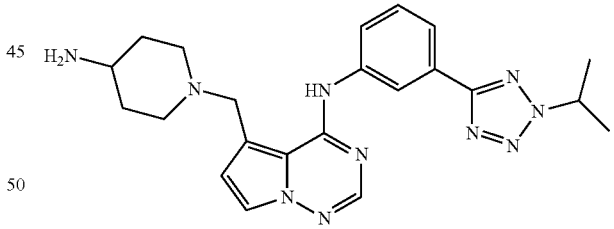

Prepared as in Example 1, Parts B and C using 3-(2-isopropyl-2H-tetrazol-5-yl)aniline (3.0 g, 8.63 mmol) to afford 5-((4-aminopiperidin-1-yl)methyl)-N-(3-(2-isopropyl-2H-tetrazol-5-yl)phenyl)pyrrolo[1,2-f][1,2,4]triazin-4-amine, 2 HCl (1.37 g, 2.68 mmol, 31% yield for 2 steps) as a pale yellow solid. LCMS (ESI) m/e 433.4 [(M+H)+, calcd for $C_{22}H_{29}N_{10}$ 433.3]. $^1$H NMR (400 MHz, MeOD) δ ppm 8.01 (d, J=7.81 Hz, 1H), 7.95 (s, 1H), 7.65 (t, J=7.81 Hz, 1H), 7.53-7.59 (m, 2H), 7.40 (d, J=8.06 Hz, 1H), 6.78 (d, J=2.77 Hz, 1H), 5.12-5.24 (m, 1H), 4.61 (s, 2H), 3.71 (d, J=11.33 Hz, 2H), 3.40-3.52 (m, 1H), 3.11-3.25 (m, 2H), 2.26 (d, J=12.34 Hz, 2H), 1.74-1.89 (m, 2H), 1.68 (d, J=6.55 Hz, 6H); HPLC retention time (method E): $t_R$=4.04 min; HPLC retention time (method F): $t_R$=5.18 min.

Example 9

5-((4-aminopiperidin-1-yl)methyl)-N-(3-(5-isopropyl-1,3,4-thiadiazol-2-yl)phenyl)pyrrolo[2,1-f][1,2,4]triazin-4-amine

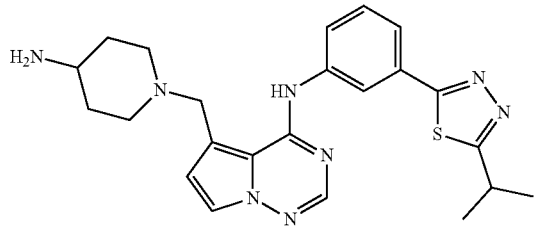 [SMILES: CC(C)c1nnc(-c2cccc(Nc3ncnn4ccc(CN5CCC(N)CC5)c34)c2)s1]

Prepared as in Example 1, Parts B and C using 3-(5-isopropyl-1,3,4-thiadiazol-2-yl)aniline (40 mg, 0.182 mmol) to afford 5-((4-aminopiperidin-1-yl)methyl)-N-(3-(5-isopropyl-1,3,4-thiadiazol-2-yl)phenyl)pyrrolo[1,2-f][1,2,4]triazin-4-amine, HCl (54.2 mg, 0.111 mmol, 7% yield for 2 steps). as a pale yellow solid. LCMS (ESI) m/e 449.3 [(M+H)+, calcd for $C_{23}H_{29}N_8S$ 449.2]. $^1$H NMR (400 MHz, MeOD) δ ppm 8.39 (d, J=1.76 Hz, 1H), 8.06 (s, 1H), 7.89 (s, 1H), 7.62-7.69 (m, 1H), 7.50-7.58 (m, 2H), 6.63 (d, J=2.52 Hz, 1H), 3.86 (s, 2H), 3.51 (dt, J=13.79, 6.83 Hz, 1H), 3.20 (d, J=12.09 Hz, 2H), 2.98-3.13 (m, 1H), 2.20-2.34 (m, 2H), 1.97-2.08 (m, 2H), 1.64-1.79 (m, 2H), 1.49 (s, 3H), 1.47 (s, 3H); HPLC retention time (method D): $t_R$=7.51 min.

Example 10

2-(3-(3-((5-((4-aminopiperidin-1-yl)methyl)pyrrolo[2,1-f][1,2,4]triazin-4-yl)amino)phenyl)-1,2,4-oxadiazol-5-yl)-2-methylpropan-1-ol

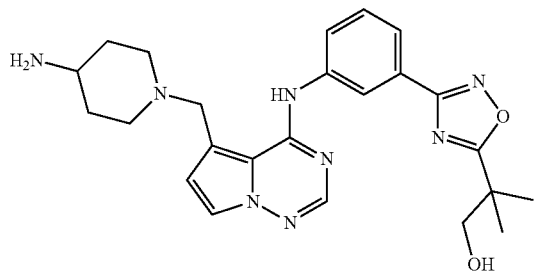 [SMILES: CC(C)(CO)c1nc(-c2cccc(Nc3ncnn4ccc(CN5CCC(N)CC5)c34)c2)no1]

Prepared as in Example 1, Parts B and C using 2-(3-(3-aminophenyl)-1,2,4-oxadiazol-5-yl)-2-methylpropan-1-ol (0.134 g, 0.575 mmol) to afford 2-(3-(3-(5-((4-aminopiperidin-1-yl)methyl)pyrrolo[1,2-f][1,2,4]triazin-4-ylamino)phenyl)-1,2,4-oxadiazol-5-yl)-2-methylpropan-1-ol, HCl (0.130 g, 0.258 mmol, 41% yield for 2 steps) as an off-white solid. LCMS (ESI) m/e 463.4 [(M+H)+, calcd for $C_{24}H_{31}N_8O_2$ 463.3]. $^1$H NMR (400 MHz, MeOD) δ 7.92 (dt, J=7.7, 1.2 Hz, 1H), 7.88 (t, J=1.6 Hz, 1H), 7.66-7.56 (m, 1H), 7.54-7.48 (m, 2H), 7.39 (dd, J=7.9, 0.9 Hz, 1H), 6.70 (d, J=3.0 Hz, 1H), 4.57 (s, 2H), 3.76 (s, 2H), 3.69 (d, J=10.1 Hz, 2H), 3.52-3.36 (m, 1H), 3.22-3.00 (m, 1H), 2.25 (d, J=12.8 Hz, 2H), 1.87-1.67 (m, 2H), 1.44 (s, 6H); HPLC retention time (method C): $t_R$=5.02 min.

Example 11

5-((4-aminopiperidin-1-yl)methyl)-N-(3-(5-(chloromethyl)-1,2,4-oxadiazol-3-yl)phenyl)pyrrolo[2,1-f][1,2,4]triazin-4-amine

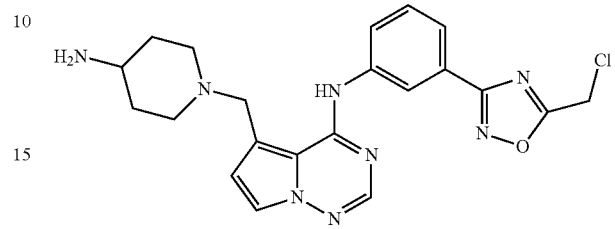

Prepared as in Example 1, Parts B and C using 3-(5-(chloromethyl)-1,2,4-oxadiazol-3-yl)aniline (0.060 g, 0.288 mmol) to afford 5-((4-aminopiperidin-1-yl)methyl)-N-(3-(5-(chloromethyl)-1,2,4-oxadiazol-3-yl)phenyl)pyrrolo[1,2-f][1,2,4]triazin-4-amine, TFA (0.0155 g, 0.027 mmol, 10% yield for 2 steps) as a colorless oil. LCMS (ESI) m/e 439.1 [(M+H)+, calcd for $C_{21}H_{24}ClN_8O$ 439.2]. $^1$H NMR (400 MHz, MeOD) δ 7.98-7.88 (m, 2H), 7.62 (t, J=7.8 Hz, 1H), 7.57-7.48 (m, 2H), 7.44 (d, J=7.8 Hz, 1H), 6.68 (d, J=2.8 Hz, 1H), 4.94 (s, 2H), 4.51 (s, 2H), 3.66 (d, J=11.1 Hz, 2H), 3.46-3.35 (m, 1H), 3.14-3.02 (m, 2H), 2.30-2.11 (m, 2H), 1.83-1.69 (m, 2H); HPLC retention time (method G): $t_R$=4.11 min.

Example 12

5-((4-aminopiperidin-1-yl)methyl)-N-(3-(1-methyl-1H-pyrazol-3-yl)phenyl)pyrrolo[2,1-f][1,2,4]triazin-4-amine

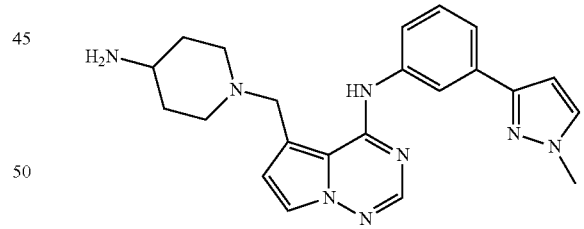

Prepared as in Example 1, Parts B and C using 3-(1-methyl-1H-pyrazol-3-yl)aniline (0.050 g, 0.288 mmol) to afford 5-((4-aminopiperidin-1-yl)methyl)-N-(3-(1-methyl-1H-pyrazol-3-yl)phenyl)pyrrolo[1,2-f][1,2,4]triazin-4-amine, TFA (0.0726 g, 0.139 mmol, 49% yield for 2 steps) as a colorless oil. LCMS (ESI) m/e 403.3 [(M+H)+, calcd for $C_{22}H_{27}N_8$ 403.2]. $^1$H NMR (400 MHz, MeOD) δ 7.66 (dt, J=7.9, 1.2 Hz, 1H), 7.63 (d, J=2.3 Hz, 2H), 7.56-7.48 (m, 3H), 7.19 (dd, J=7.8, 1.0 Hz, 1H), 6.71 (d, J=2.8 Hz, 1H), 6.67 (d, J=2.3 Hz, 1H), 4.48 (s, 2H), 3.93 (s, 3H), 3.64 (d, J=9.6 Hz, 2H), 3.42 (t, J=11.0 Hz, 1H), 3.13-2.98 (m, 2H), 2.24 (d, J=12.6 Hz, 2H), 1.86-1.67 (m, 2H); HPLC retention time (method G): $t_R$=2.82 min.

Example 13

5-((4-aminopiperidin-1-yl)methyl)-N-(3-(5-methyl-1,2,4-oxadiazol-3-yl)phenyl)pyrrolo[2,1-f][1,2,4]triazin-4-amine

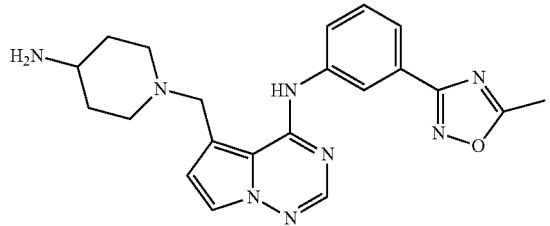 [SMILES: Cc1nc(-c2cccc(Nc3ncnn4ccc(CN5CCC(N)CC5)c34)c2)no1]

Prepared as in Example 1, Parts B and C using 3-(5-methyl-1,2,4-oxadiazol-3-yl)aniline (0.065 g, 0.373 mmol) to afford 5-((4-aminopiperidin-1-yl)methyl)-N-(3-(5-methyl-1,2,4-oxadiazol-3-yl)phenyl)pyrrolo[1,2-f][1,2,4]triazin-4-amine, TFA (0.041 g, 0.078 mmol, 27% yield for 2 steps) as a colorless oil. LCMS (ESI) m/e 405.2 [(M+H)$^+$, calcd for $C_{21}H_{25}N_8O$ 405.2]. $^1$H NMR (400 MHz, MeOD) δ 7.90 (dd, J=7.8, 1.0 Hz, 1H), 7.85 (s, 1H), 7.60 (t, J=7.9 Hz, 1H), 7.52 (s, 1H), 7.50 (d, J=3.0 Hz, 1H), 7.40 (dd, J=8.1, 1.0 Hz, 1H), 6.69 (d, J=2.8 Hz, 1H), 4.54 (s, 2H), 3.67 (d, J=11.3 Hz, 2H), 3.43 (t, J=11.3 Hz, 1H), 3.21-3.00 (m, 2H), 2.65 (s, 3H), 2.24 (d, J=13.3 Hz, 2H), 1.87-1.68 (m, 2H); HPLC retention time (method $t_R$=2.98 min.

Example 14

N-(3-(1,2,3-thiadiazol-4-yl)phenyl)-5-((4-aminopiperidin-1-yl)methyl)pyrrolo[2,1-f][1,2,4]triazin-4-amine

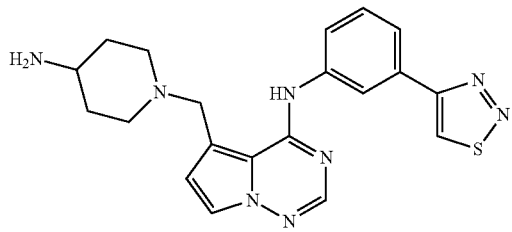 [SMILES: NC1CCN(Cc2ccn3ncnc(Nc4cccc(-c5csnn5)c4)c23)CC1]

Prepared as in Example 1, Parts B and C using 3-(1,2,3-thiadiazol-4-yl)aniline (0.066 g, 0.373 mmol) to afford N-(3-(1,2,3-thiadiazol-4-yl)phenyl)-5-((4-aminopiperidin-1-yl)methyl)pyrrolo[1,2-f][1,2,4]triazin-4-amine, TFA (0.0244 g, 0.046 mmol, 16% yield for 2 steps) as a colorless oil. LCMS (ESI) m/e 407.2 [(M+H)$^+$, calcd for $C_{20}H_{23}N_8S$ 407.2]. $^1$H NMR (400 MHz, MeOD) δ 9.32 (s, 1H), 8.01 (t, J=1.6 Hz, 1H), 7.97-7.91 (m, 1H), 7.63 (t, J=7.8 Hz, 1H), 7.55 (s, 1H), 7.52 (d, J=2.8 Hz, 1H), 7.35 (dd, J=7.8, 1.0 Hz, 1H), 6.69 (d, J=2.8 Hz, 1H), 4.50 (s, 2H), 3.66 (d, J=11.3 Hz, 2H), 3.49-3.36 (m, 1H), 3.15-2.99 (m, 2H), 2.23 (d, J=12.8 Hz, 2H), 1.87-1.71 (m, 2H); HPLC retention time (method G): $t_R$=2.66 min.

Example 15

5-((4-aminopiperidin-1-yl)methyl)-N-(3-(5-ethyl-4H-1,2,4-triazol-3-yl)phenyl)pyrrolo[2,1-f][1,2,4]triazin-4-amine

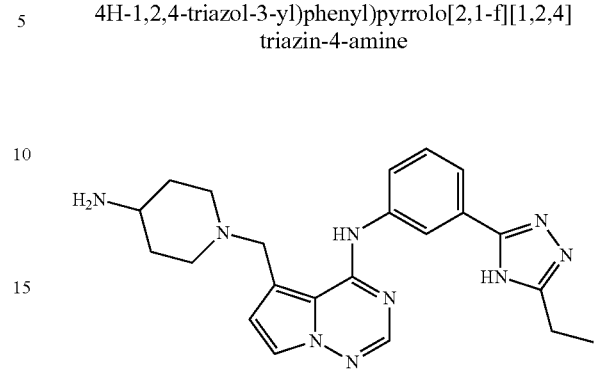

Prepared as in Example 1, Parts B and C using 3-(5-ethyl-4H-1,2,4-triazol-3-yl)aniline (0.070 g, 0.373 mmol) to afford 5-((4-aminopiperidin-1-yl)methyl)-N-(3-(5-ethyl-4H-1,2,4-triazol-3-yl)phenyl)pyrrolo[1,2-f][1,2,4]triazin-4-amine, TFA (0.0278 g, 0.051 mmol, 18% yield for 2 steps) as a colorless oil. LCMS (ESI) m/e 418.3 [(M+H)$^+$, calcd for $C_{22}H_{28}N_9$ 418.3]. $^1$H NMR (400 MHz, MeOD) δ 7.87 (dt, J=7.8, 1.3 Hz, 1H), 7.81 (t, J=1.6 Hz, 1H), 7.60 (t, J=7.9 Hz, 1H), 7.53 (s, 1H), 7.51 (d, J=2.8 Hz, 1H), 7.34 (dd, J=7.9, 1.1 Hz, 1H), 6.69 (d, J=2.8 Hz, 1H), 4.52 (s, 2H), 3.66 (d, J=10.8 Hz, 2H), 3.43 (t, J=11.6 Hz, 1H), 3.19-3.00 (m, 2H), 2.93 (q, J=7.8 Hz, 2H), 2.24 (d, J=12.8 Hz, 2H), 1.86-1.71 (m, 2H), 1.39 (t, J=7.7 Hz, 3H); HPLC retention time (method G): $t_R$=2.43 min.

Example 16

5-((4-aminopiperidin-1-yl)methyl)-N-(3-(3-phenyl-1,2,4-oxadiazol-5-yl)phenyl)pyrrolo[2,1-f][1,2,4]triazin-4-amine

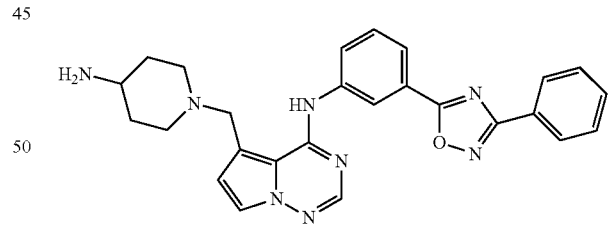

Prepared as in Example 1, Parts B and C using 3-(3-phenyl-1,2,4-oxadiazol-5-yl)aniline (0.088 g, 0.373 mmol) to afford 5-((4-aminopiperidin-1-yl)methyl)-N-(3-(3-phenyl-1,2,4-oxadiazol-5-yl)phenyl)pyrrolo[1,2-f][1,2,4]triazin-4-amine, TFA (0.0482 g, 0.082 mmol, 29% yield for 2 steps) as a colorless oil. LCMS (ESI) m/e 467.2 [(M+H)$^+$, calcd for $C_{26}H_{27}N_8O$ 467.2]. $^1$H NMR (400 MHz, MeOD) δ 8.15-8.09 (m, 2H), 8.08-8.03 (m, 2H), 7.76-7.65 (m, 1H), 7.58-7.48 (m, 6H), 6.70 (d, J=2.8 Hz, 1H), 4.59 (s, 2H), 3.70 (d, J=10.1 Hz, 2H), 3.51-3.36 (m, 1H), 3.13 (d, J=13.8 Hz, 2H), 2.25 (d, J=12.6 Hz, 2H), 1.88-1.71 (m, 2H); HPLC retention time (method G): $t_R$=7.20 min.

Example 17

5-((4-aminopiperidin-1-yl)methyl)-N-(3-(5-methyl-1,3,4-thiadiazol-2-yl)phenyl)pyrrolo[2,1-f][1,2,4]triazin-4-amine

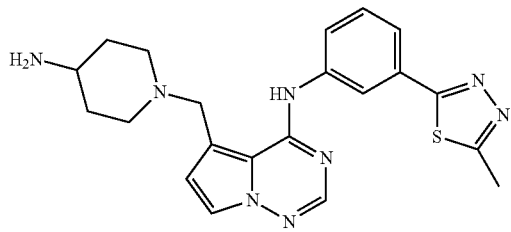 [SMILES: Cc1nnc(-c2cccc(Nc3ncnn4ccc(CN5CCC(N)CC5)c34)c2)s1]

Prepared as in Example 1, Parts B and C using 3-(3-(5-methyl-1,3,4-thiadiazol-2-yl)aniline (0.055 g, 0.288 mmol) to afford 5-((4-aminopiperidin-1-yl)methyl)-N-(3-(5-methyl-1,3,4-thiadiazol-2-yl)phenyl)pyrrolo[1,2-f][1,2,4]triazin-4-amine, TFA (0.027 g, 0.049 mmol, 17% yield for 2 steps) as a colorless oil. LCMS (ESI) m/e 421.3 [(M+H)$^+$, calcd for $C_{21}H_{25}N_8S$ 421.2]. $^1$H NMR (400 MHz, MeOD) δ 7.83 (s, 1H), 7.75-7.69 (m, 1H), 7.60 (t, J=7.8 Hz, 1H), 7.54 (s, 1H), 7.50 (d, J=2.8 Hz, 1H), 7.41 (d, J=8.1 Hz, 1H), 6.68 (d, J=2.8 Hz, 1H), 4.52 (s, 2H), 3.66 (d, J=11.8 Hz, 2H), 3.43 (t, J=11.3 Hz, 1H), 3.18-3.02 (m, 2H), 2.81 (s, 3H), 2.24 (d, J=13.3 Hz, 2H), 1.79 (d, J=11.3 Hz, 2H); HPLC retention time (method C): $t_R$=3.85 min.

Example 18

N-(3-(5-methyl-1,3,4-thiadiazol-2-yl)phenyl)-5-((4-(methylamino)piperidin-1-yl)methyl)pyrrolo[2,1-f][1,2,4]triazin-4-amine

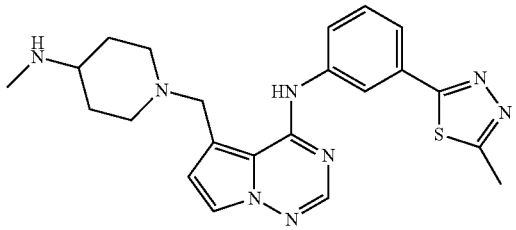 [SMILES: CNC1CCN(Cc2ccn3ncnc(Nc4cccc(-c5nnc(C)s5)c4)c23)CC1]

Prepared as in Example 1 using 3-(5-methyl-1,3,4-thiadiazol-2-yl)aniline (0.055 g, 0.288 mmol) and tert-butyl methyl(piperidin-4-yl)carbamate (0.062 g, 0.288 mmol) to afford N-(3-(5-methyl-1,3,4-thiadiazol-2-yl)phenyl)-5-((4-(methylamino)piperidin-1-yl)methyl)pyrrolo[1,2-f][1,2,4]triazin-4-amine, TFA (0.006 g, 0.011 mmol, 4% yield for 2 steps) as a colorless oil. LCMS (ESI) m/e 435.3 [(M+H)$^+$, calcd for $C_{22}H_{27}N_8S$ 435.2]. $^1$H NMR (400 MHz, MeOD) δ 7.98 (s, 1H), 7.72-7.67 (m, 1H), 7.66-7.56 (m, 3H), 7.53 (d, J=2.8 Hz, 1H), 6.68 (d, J=2.8 Hz, 1H), 4.34 (s, 2H), 3.58 (d, J=12.3 Hz, 2H), 3.35-3.31 (m, 1H), 2.90-2.83 (m, 2H), 2.81 (s, 3H), 2.69 (s, 3H), 2.29 (d, J=12.8 Hz, 2H), 1.88-1.66 (m, 2H); HPLC retention time (method C): $t_R$=4.18 min.

Example 19

5-((3-aminoazetidin-1-yl)methyl)-N-(3-(5-methyl-1,3,4-thiadiazol-2-yl)phenyl)pyrrolo[2,1-f][1,2,4]triazin-4-amine

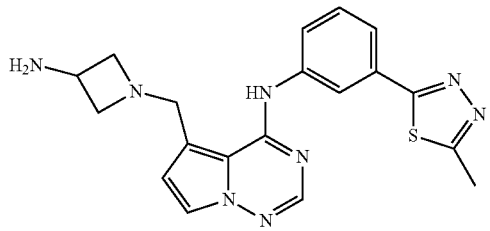 [SMILES: Cc1nnc(-c2cccc(Nc3ncnn4ccc(CN5CC(N)C5)c34)c2)s1]

Prepared as in Example 1, Parts B and C using 3-(5-methyl-1,3,4-thiadiazol-2-yl)aniline (0.055 g, 0.288 mmol) and tert-butyl azetidin-3-ylcarbamate (0.050 g, 0.288 mmol) to afford 5-((3-aminoazetidin-1-yl)methyl)-N-(3-(5-methyl-1,3,4-thiadiazol-2-yl)phenyl)pyrrolo[1,2-f][1,2,4]triazin-4-amine, TFA (0.012 g, 0.023 mmol, 8% yield for 2 steps) as a colorless oil. LCMS (ESI) m/e 393.3 [(M+H)$^+$, calcd for $C_{19}H_{21}N_8S$ 393.2]. $^1$H NMR (400 MHz, MeOD) δ 8.04 (s, 1H), 7.70 (dt, J=7.3, 1.6 Hz, 1H), 7.66 (s, 1H), 7.63-7.54 (m, 2H), 7.52 (d, J=2.8 Hz, 1H), 6.71 (d, J=2.8 Hz, 1H), 4.49 (s, 2H), 4.34-4.19 (m, 3H), 3.96 (d, J=3.3 Hz, 2H), 2.81 (s, 3H); HPLC retention time (method C): $t_R$=4.90 min.

Example 20

5-((hexahydropyrrolo[3,4-c]pyrrol-2(1H)-yl)methyl)-N-(3-(5-methyl-1,3,4-thiadiazol-2-yl)phenyl)pyrrolo[2,1-f][1,2,4]triazin-4-amine

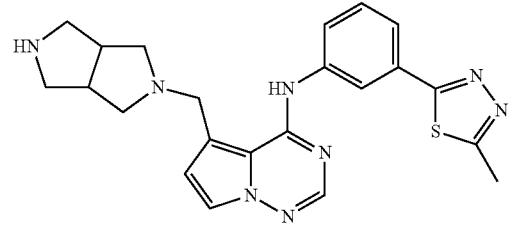 [SMILES: Cc1nnc(-c2cccc(Nc3ncnn4ccc(CN5CC6CNCC6C5)c34)c2)s1]

Prepared as in Example 1, Parts B and C using 3-(5-methyl-1,3,4-thiadiazol-2-yl)aniline (0.055 g, 0.288 mmol) and tert-butyl hexahydropyrrolo[3,4-c]pyrrole-2(1H)-carboxylate (0.061 g, 0.288 mmol) to afford 5-((hexahydropyrrolo[3,4-c]pyrrol-2(1H)-yl)methyl)-N-(3-(5-methyl-1,3,4-thiadiazol-2-yl)phenyl)pyrrolo[1,2-f][1,2,4]triazin-4-amine, TFA (0.0092 g, 0.016 mmol, 6% yield for 2 steps) as a colorless oil. LCMS (ESI) m/e 433.2 [(M+H)$^+$, calcd for $C_{22}H_{25}N_8S$ 433.2]. $^1$H NMR (400 MHz, MeOD) δ 7.90 (s, 1H), 7.69 (dt, J=7.6, 1.4 Hz, 1H), 7.61 (s, 1H), 7.60-7.55 (m, 1H), 7.55-7.50 (m, 2H), 6.68 (d, J=2.8 Hz, 1H), 4.50 (s, 2H), 3.74-3.61 (m, 2H), 3.51-3.41 (m, 2H), 3.35-3.30 (m, 4H), 3.08 (d, J=5.5 Hz, 2H), 2.81 (s, 3H); HPLC retention time (method C): $t_R$=4.52 min.

Example 21

5-((4-aminopiperidin-1-yl)methyl)-N-(3-(5-propyl-1,3,4-thiadiazol-2-yl)phenyl)pyrrolo[2,1-f][1,2,4]triazin-4-amine

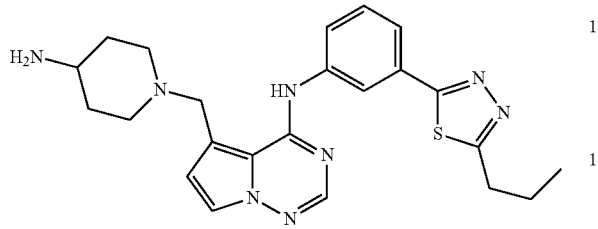

Prepared as in Example 1, Parts B and C using 3-(5-propyl-1,3,4-thiadiazol-2-yl)aniline (0.063 g, 0.288 mmol) and tert-butyl piperidin-4-ylcarbamate (0.058 g, 0.288 mmol) to afford 5-((4-aminopiperidin-1-yl)methyl)-N-(3-(5-propyl-1,3,4-thiadiazol-2-yl)phenyl)pyrrolo[1,2-f][1,2,4]triazin-4-amine, TFA (0.007 g, 0.012 mmol, 4% yield for 2 steps) as a colorless oil. LCMS (ESI) m/e 449.3 [(M+H)$^+$, calcd for $C_{23}H_{29}N_8S$ 449.2 $^1$H NMR (400 MHz, MeOD) δ 7.98 (s, 1H), 7.74-7.68 (m, 1H), 7.63 (s, 1H), 7.61-7.56 (m, 2H), 7.52 (d, J=2.8 Hz, 1H), 6.67 (d, J=2.8 Hz, 1H), 4.35 (s, 2H), 3.56 (d, J=12.1 Hz, 2H), 3.44-3.33 (m, 1H), 3.14 (t, J=7.4 Hz, 2H), 2.96-2.83 (m, 2H), 2.21 (d, J=13.1 Hz, 2H), 1.94-1.82 (m, 2H), 1.79 (d, J=12.8 Hz, 2H), 1.05 (t, J=7.3 Hz, 3H); HPLC retention time (method C): $t_R$=6.14 min.

Example 22

5-((4-aminopiperidin-1-yl)methyl)-N-(3-(5-cyclohexyl-1,2,4-oxadiazol-3-yl)phenyl)pyrrolo[2,1-f][1,2,4]triazin-4-amine

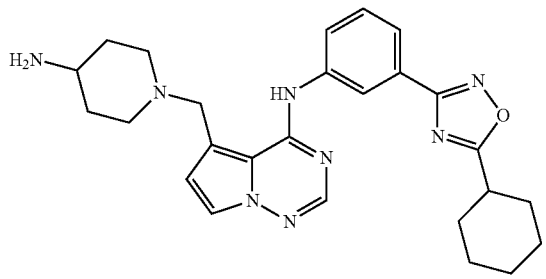 [SMILES: NC1CCN(Cc2ccn3ncnc(Nc4cccc(-c5noc(C6CCCCC6)n5)c4)c23)CC1]

Prepared as in Example 1, Parts B and C using 3-(5-cyclohexyl-1,2,4-oxadiazol-3-yl)aniline (0.070 g, 0.288 mmol) and tert-butyl piperidin-4-ylcarbamate (0.058 g, 0.288 mmol) to afford 5-((4-aminopiperidin-1-yl)methyl)-N-(3-(5-cyclohexyl-1,2,4-oxadiazol-3-yl)phenyl)pyrrolo[1,2-f][1,2,4]triazin-4-amine, TFA (0.079 g, 0.133 mmol, 46% yield for 2 steps) as a pale brown oil. LCMS (ESI) m/e 473.3 [(M+H)$^+$, calcd for $C_{26}H_{33}N_8O$ 473.2]. $^1$H NMR (400 MHz, MeOD) δ 7.95-7.88 (m, 1H), 7.87 (d, J=1.8 Hz, 1H), 7.52 (s, 1H), 7.50 (d, J=2.8 Hz, 1H), 7.40 (dd, J=8.1, 1.0 Hz, 1H), 6.69 (d, J=2.8 Hz, 1H), 4.56 (s, 2H), 3.67 (d, J=10.1 Hz, 2H), 3.43 (t, J=10.6 Hz, 1H), 3.20-3.00 (m, 3H), 2.32-2.19 (m, 2H), 2.16-2.05 (m, 2H), 1.90-1.60 (m, 7H), 1.54-1.24 (m, 3H); HPLC retention time (method C): $t_R$=9.07 min.

Example 23

5-((4-aminopiperidin-1-yl)methyl)-N-(3-(5-cyclopropyl-1,3,4-thiadiazol-2-yl)phenyl)pyrrolo[2,1-f][1,2,4]triazin-4-amine

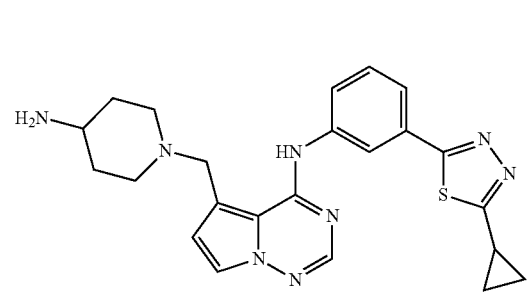 [SMILES: NC1CCN(Cc2ccn3ncnc(Nc4cccc(-c5nnc(C6CC6)s5)c4)c23)CC1]

Prepared as in Example 1, Parts B and C using 3-(5-cyclopropyl-1,3,4-thiadiazol-2-yl)aniline (0.062 g, 0.288 mmol) and tert-butyl piperidin-4-ylcarbamate (0.058 g, 0.288 mmol) to afford 5-((4-aminopiperidin-1-yl)methyl)-N-(3-(5-cyclopropyl-1,3,4-thiadiazol-2-yl)phenyl)pyrrolo[1,2-f][1,2,4]triazin-4-amine, TFA (0.030 g, 0.053 mmol, 19% yield for 2 steps) as a colorless oil. LCMS (ESI) m/e 447.3 [(M+H)$^+$, calcd for $C_{23}H_{27}N_8S$ 447.2]. $^1$H NMR (400 MHz, MeOD) δ 7.81 (d, J=1.5 Hz, 1H), 7.69 (dt, J=7.9, 1.2 Hz, 1H), 7.58 (t, J=7.9 Hz, 1H), 7.54 (s, 1H), 7.50 (d, J=2.8 Hz, 1H), 7.41 (d, J=8.1 Hz, 1H), 6.68 (d, J=2.8 Hz, 1H), 4.51 (s, 2H), 3.72-3.58 (m, 2H), 3.43 (t, J=11.8 Hz, 1H), 3.16-2.99 (m, 2H), 2.50 (tt, J=8.3, 4.8 Hz, 1H), 2.24 (d, J=13.6 Hz, 2H), 1.79 (d, J=10.3 Hz, 2H), 1.35-1.28 (m, 2H), 1.17-1.10 (m, 2H); HPLC retention time (method C): $t_R$=5.49 min.

Example 24

N-(3-(5-cyclopropyl-1,3,4-thiadiazol-2-yl)phenyl)-5-((4-(methylamino)piperidin-1-yl)methyl)pyrrolo[2,1-f][1,2,4]triazin-4-amine

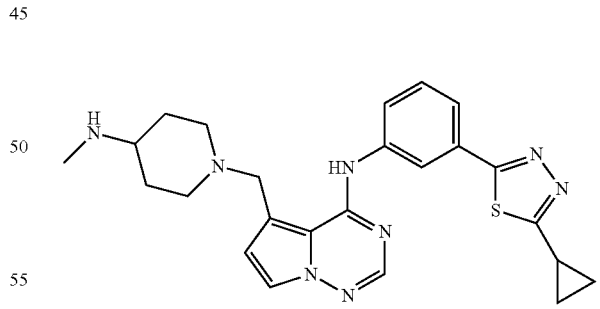

Prepared as in Example 1, Parts B and C using 3-(5-cyclopropyl-1,3,4-thiadiazol-2-yl)aniline (0.062 g, 0.288 mmol) and tert-butyl methyl(piperidin-4-yl)carbamate (0.062 g, 0.288 mmol) to afford N-(3-(5-cyclopropyl-1,3,4-thiadiazol-2-yl)phenyl)-5-((4-(methylamino)piperidin-1-yl)methyl)pyrrolo[1,2-f][1,2,4]triazin-4-amine, TFA (0.0247 g, 0.043 mmol, 15% yield for 2 steps) as a colorless oil. LCMS (ESI) m/e 461.3 [(M+H)$^+$, calcd for $C_{24}H_{29}N_8S$ 461.2]. $^1$H NMR (400 MHz, MeOD) δ 7.80 (t, J=1.8 Hz, 1H), 7.73-7.69 (m, 1H), 7.59 (t, J=7.9 Hz, 1H), 7.54 (s, 1H), 7.51 (d, J=2.8

Hz, 1H), 7.44-7.36 (m, 1H), 6.69 (d, J=2.8 Hz, 1H), 4.53 (s, 2H), 3.69 (d, J=12.6 Hz, 2H), 3.41-3.31 (m, 1H), 3.13-3.01 (m, 2H), 2.67 (s, 3H), 2.50 (tt, J=8.3, 4.8 Hz, 1H), 2.33 (d, J=13.1 Hz, 2H), 1.86-1.70 (m, 2H), 1.35-1.28 (m, 2H), 1.16-1.10 (m, 2H); HPLC retention time (method C): $t_R$=5.71 min.

Example 25

5-((3-aminoazetidin-1-yl)methyl)-N-(3-(5-cyclopropyl-1,3,4-thiadiazol-2-yl)phenyl)pyrrolo[2,1-f][1,2,4]triazin-4-amine

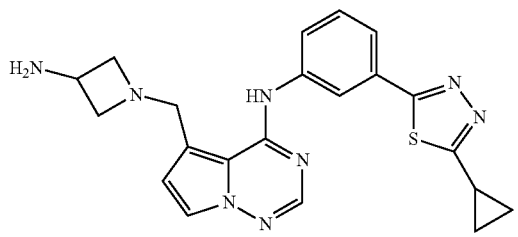 [SMILES: NC1CN(Cc2ccn3ncnc(Nc4cccc(-c5nnc(C6CC6)s5)c4)c23)C1]

Prepared as in Example 1, Parts B and C using 3-(5-cyclopropyl-1,3,4-thiadiazol-2-yl)aniline (0.062 g, 0.288 mmol) and tert-butyl azetidin-3-ylcarbamate (0.050 g, 0.288 mmol) to afford 5-((3-aminoazetidin-1-yl)methyl)-N-(3-(5-cyclopropyl-1,3,4-thiadiazol-2-yl)phenyl)pyrrolo[1,2-f][1,2,4]triazin-4-amine, TFA (0.009 g, 0.017 mmol, 6% yield for 2 steps) as a colorless oil. LCMS (ESI) m/e 419.2 [(M+H)$^+$, calcd for $C_{21}H_{23}N_8S$ 419.2]. $^1$H NMR (400 MHz, MeOD) δ 8.01 (s, 1H), 7.70-7.66 (m, 1H), 7.65 (s, 1H), 7.62-7.54 (m, 2H), 7.52 (d, J=2.8 Hz, 1H), 6.71 (d, J=2.5 Hz, 1H), 4.49 (s, 2H), 4.34-4.22 (m, 3H), 4.01-3.92 (m, 2H), 2.51 (tt, J=8.3, 4.9 Hz, 1H), 1.36-1.28 (m, 2H), 1.18-1.09 (m, 2H); HPLC retention time (method C): $t_R$=6.90 min.

Example 26

N-(3-(5-cyclopropyl-1,3,4-thiadiazol-2-yl)phenyl)-5-((hexahydropyrrolo[3,4-c]pyrrol-2(1H)-yl)methyl)pyrrolo[2,1-f][1,2,4]triazin-4-amine

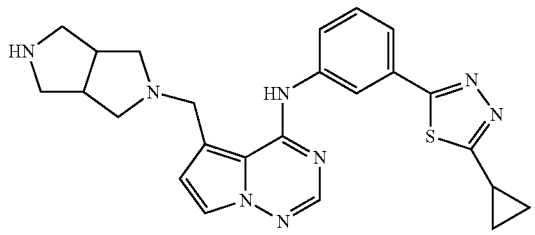 [SMILES: c1cc(Nc2ncnn3ccc(CN4CC5CNCC5C4)c23)cc(-c2nnc(C3CC3)s2)c1]

Prepared as in Example 1, Parts B and C using 3-(5-cyclopropyl-1,3,4-thiadiazol-2-yl)aniline (0.062 g, 0.288 mmol) and tert-butyl hexahydropyrrolo[3,4-c]pyrrole-2 (1H)-carboxylate (0.061 g, 0.288 mmol) to afford N-(3-(5-cyclopropyl-1,3,4-thiadiazol-2-yl)phenyl)-5-((hexahydropyrrolo[3,4-c]pyrrol-2(1H)-yl)methyl)pyrrolo[1,2-f][1,2,4]triazin-4-amine, TFA (0.027 g, 0.046 mmol, 16% yield for 2 steps) as an off-white solid. LCMS (ESI) m/e 459.2 [(M+H)$^+$, calcd for $C_{24}H_{27}N_8S$ 459.2]. $^1$H NMR (400 MHz, MeOD) δ 7.80 (t, J=1.8 Hz, 1H), 7.73-7.65 (m, 1H), 7.60-7.56 (m, 1H), 7.55 (s, 1H), 7.50 (d, J=2.8 Hz, 1H), 7.42-7.37 (m, 1H), 6.69 (d, J=2.8 Hz, 1H), 4.61 (s, 2H), 3.82-3.69 (m, 2H), 3.52-3.40 (m, 2H), 3.38-3.31 (m, 4H), 3.25-3.15 (m, 2H), 2.50 (tt, J=8.3, 4.9 Hz, 1H), 1.35-1.27 (m, 2H), 1.17-1.09 (m, 2H); HPLC retention time (method C): $t_R$=6.31 min.

Example 27

N-(3-(5-isopropyl-1,3,4-thiadiazol-2-yl)phenyl)-5-((4-(methylamino)piperidin-1-yl)methyl)pyrrolo[2,1-f][1,2,4]triazin-4-amine

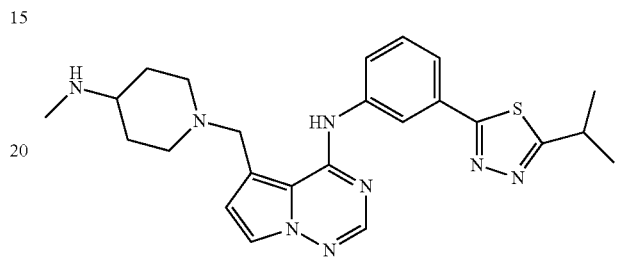

Prepared as in Example 1, Parts B and C using 3-(5-isopropyl-1,3,4-thiadiazol-2-yl)aniline (0.063 g, 0.288 mmol) and tert-butyl methyl(piperidin-4-yl)carbamate (0.062 g, 0.288 mmol) to afford N-(3-(5-isopropyl-1,3,4-thiadiazol-2-yl)phenyl)-5-((4-(methylamino)piperidin-1-yl)methyl)pyrrolo[1,2-f][1,2,4]triazin-4-amine, TFA (0.0051 g, 8.67 μmol, 3% yield for 2 steps) as a colorless oil. LCMS (ESI) m/e 463.3 [(M+H)$^+$, calcd for $C_{24}H_{31}N_8S$ 463.2]. $^1$H NMR (400 MHz, MeOD) δ 7.97 (s, 1H), 7.77-7.68 (m, 1H), 7.63 (s, 1H), 7.60 (br. s, 1H), 7.59 (br. s, 1H), 7.53 (d, J=2.5 Hz, 1H), 6.68 (d, J=2.8 Hz, 1H), 4.36 (s, 2H), 3.60 (d, J=12.3 Hz, 2H), 3.51 (dt, J=13.8, 6.9 Hz, 1H), 3.35-3.31 (m, 1H), 2.87 (br. s, 2H), 2.69 (s, 3H), 2.30 (t, J=6.0 Hz, 2H), 1.77 (d, J=13.1 Hz, 2H), 1.47 (d, J=6.8 Hz, 6H); HPLC retention time (method C): $t_R$=8.19 min.

Example 28

5-((3-aminoazetidin-1-yl)methyl)-N-(3-(5-isopropyl-1,3,4-thiadiazol-2-yl)phenyl)pyrrolo[2,1-f][1,2,4]triazin-4-amine

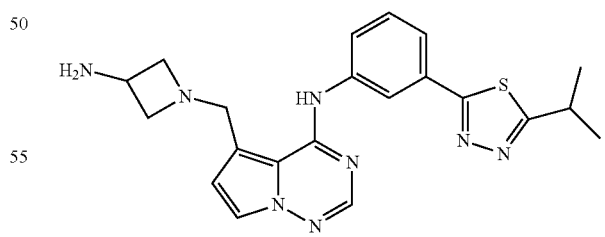

Prepared as in Example 1, Parts B and C using 3-(5-isopropyl-1,3,4-thiadiazol-2-yl)aniline (0.063 g, 0.288 mmol) and tert-butyl azetidin-3-ylcarbamate (0.050 g, 0.288 mmol) to afford 5-((3-aminoazetidin-1-yl)methyl)-N-(3-(5-isopropyl-1,3,4-thiadiazol-2-yl)phenyl)pyrrolo[1,2-f][1,2,4]triazin-4-amine, TFA (0.009 g, 0.016 mmol, 6% yield for 2 steps) as a colorless oil. LCMS (ESI) m/e 421.3 [(M+H)$^+$, calcd for $C_{21}H_{25}N_8S$ 421.2]. $^1$H NMR (400 MHz, MeOD)

δ 8.15 (s, 1H), 7.74-7.67 (m, 3H), 7.60-7.54 (m, 1H), 7.53 (d, J=2.8 Hz, 1H), 6.70 (d, J=2.8 Hz, 1H), 4.38 (s, 2H), 4.26 (q, J=7.1 Hz, 1H), 4.21-4.11 (m, 2H), 3.81 (d, J=7.8 Hz, 2H), 3.51 (quin, J=6.9 Hz, 1H), 1.47 (d, J=6.8 Hz, 6H); HPLC retention time (method C): $t_R$=7.36 min.

Example 29

5-((hexahydropyrrolo[3,4-c]pyrrol-2(1H)-yl)methyl)-N-(3-(5-isopropyl-1,3,4-thiadiazol-2-yl)phenyl)pyrrolo[2,1-f][1,2,4]triazin-4-amine

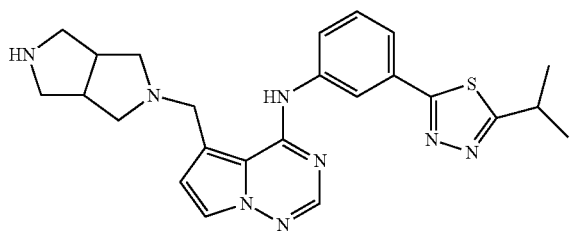 [SMILES: CC(C)c1nnc(-c2cccc(Nc3ncnn4ccc(CN5CC6CNCC6C5)c34)c2)s1]

Prepared as in Example 1, Parts B and C using 3-(5-isopropyl-1,3,4-thiadiazol-2-yl)aniline (0.063 g, 0.288 mmol) and tert-butyl hexahydropyrrolo[3,4-c]pyrrole-2(1H)-carboxylate (0.061 g, 0.288 mmol) to afford 5-((hexahydropyrrolo[3,4-c]pyrrol-2(1H)-yl)methyl)-N-(3-(5-isopropyl-1,3,4-thiadiazol-2-yl)phenyl)pyrrolo[1,2-f][1,2,4]triazin-4-amine, TFA (0.0111 g, 0.019 mmol, 7% yield for 2 steps) as a colorless oil. LCMS (ESI) m/e 461.3 [(M+H)$^+$, calcd for $C_{24}H_{29}N_8S$ 461.2]. $^1$H NMR (400 MHz, MeOD) δ 7.88 (s, 1H), 7.76-7.69 (m, 1H), 7.62-7.55 (m, 2H), 7.51 (d, J=2.8 Hz, 1H), 7.48 (d, J=8.1 Hz, 1H), 6.69 (d, J=2.8 Hz, 1H), 4.56 (s, 2H), 3.77-3.66 (m, 2H), 3.56-3.41 (m, 3H), 3.37-3.31 (m, 4H), 3.16 (d, J=7.1 Hz, 2H), 1.47 (d, J=7.1 Hz, 6H); HPLC retention time (method C): $t_R$=6.84 min.

Example 30

N-(3-(5-isopropyl-1,3,4-thiadiazol-2-yl)phenyl)-5-((3-(methylamino)pyrrolidin-1-yl)methyl)pyrrolo[2,1-f][1,2,4]triazin-4-amine

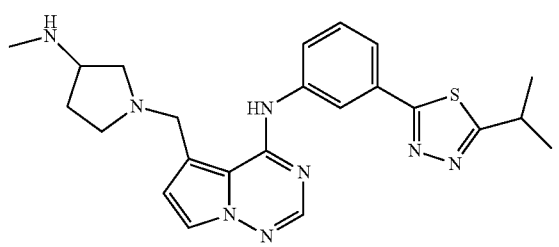 [SMILES: CNC1CCN(Cc2ccn3ncnc(Nc4cccc(-c5nnc(C(C)C)s5)c4)c23)C1]

Prepared as in Example 1, Parts B and C using 3-(5-isopropyl-1,3,4-thiadiazol-2-yl)aniline (0.063 g, 0.288 mmol) and tert-butyl methyl(pyrrolidin-3-yl)carbamate (0.058 g, 0.288 mmol) to afford N-(3-(5-isopropyl-1,3,4-thiadiazol-2-yl)phenyl)-5-((3-(methylamino)pyrrolidin-1-yl)methyl)pyrrolo[1,2-f][1,2,4]triazin-4-amine, TFA (0.0137 g, 0.024 mmol, 8% yield for 2 steps) as a colorless oil. LCMS (ESI) m/e 449.3 [(M+H)$^+$, calcd for $C_{23}H_{29}N_8S$ 449.2]. $^1$H NMR (400 MHz, MeOD) δ 8.07-7.96 (m, 1H), 7.77-7.73 (m, 1H), 7.72 (s, 1H), 7.70-7.65 (m, 1H), 7.59-7.55 (m, 1H), 7.53 (d, J=2.8 Hz, 1H), 6.70 (d, J=2.5 Hz, 1H), 4.47-4.30 (m, 2H), 4.09-3.96 (m, 1H), 3.71 (dd, J=11.8, 8.1 Hz, 1H), 3.57-3.44 (m, 1H), 3.40-3.31 (m, 1H), 3.24-3.15 (m, 1H), 3.07 (dd, J=11.7, 6.9 Hz, 1H), 2.73 (s, 3H), 2.62-2.46 (m, 1H), 2.23-2.07 (m, 1H), 1.47 (d, J=6.8 Hz, 6H); HPLC retention time (method C): $t_R$=8.31 min.

Example 31

5-((3-(aminomethyl)pyrrolidin-1-yl)methyl)-N-(3-(5-isopropyl-1,3,4-thiadiazol-2-yl)phenyl)pyrrolo[2,1-f][1,2,4]triazin-4-amine

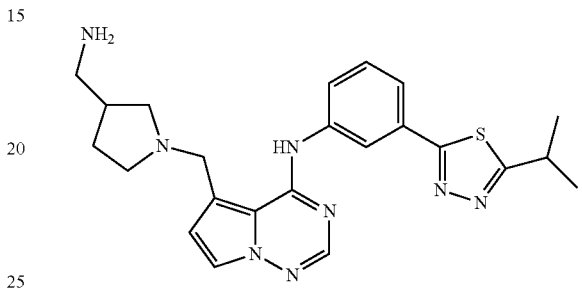

Prepared as in Example 1, Parts B and C using 3-(5-isopropyl-1,3,4-thiadiazol-2-yl)aniline (0.063 g, 0.288 mmol) and tert-butyl pyrrolidin-3-ylmethylcarbamate (0.058 g, 0.288 mmol) to afford 5-((3-(aminomethyl)pyrrolidin-1-yl)methyl)-N-(3-(5-isopropyl-1,3,4-thiadiazol-2-yl)phenyl)pyrrolo[1,2-f][1,2,4]triazin-4-amine, TFA (0.0178 g, 0.031 mmol, 11% yield for 2 steps) as a colorless oil. LCMS (ESI) m/e 449.3 [(M+H)$^+$, calcd for $C_{23}H_{29}N_8S$ 449.2]. $^1$H NMR (400 MHz, MeOD) δ 7.77 (d, J=1.5 Hz, 1H), 7.74-7.70 (m, 1H), 7.58 (t, J=7.9 Hz, 1H), 7.49 (s, 1H), 7.47 (d, J=2.8 Hz, 1H), 7.37-7.29 (m, 1H), 6.68 (d, J=2.8 Hz, 1H), 4.66 (s, 2H), 3.76-3.61 (m, 1H), 3.58-3.43 (m, 3H), 3.23-3.13 (m, 1H), 3.13-2.96 (m, 2H), 2.82-2.69 (m, 1H), 2.41-2.30 (m, 1H), 1.94-1.81 (m, 1H), 1.47 (d, J=7.1 Hz, 6H); HPLC retention time (method C): $t_R$=5.38 min.

Example 32

5-((3-aminopyrrolidin-1-yl)methyl)-N-(3-(5-isopropyl-1,3,4-thiadiazol-2-yl)phenyl)pyrrolo[2,1-f][1,2,4]triazin-4-amine

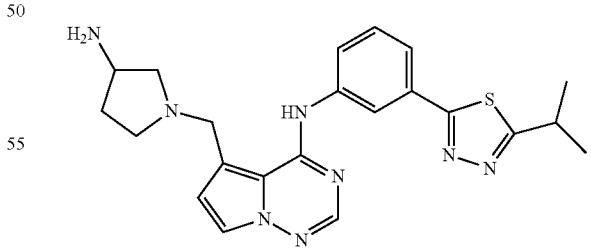

Prepared as in Example 1, Parts B and C using 3-(5-isopropyl-1,3,4-thiadiazol-2-yl)aniline (0.063 g, 0.288 mmol) and tert-butyl pyrrolidin-3-ylcarbamate (0.054 g, 0.288 mmol) to afford 5-((3-aminopyrrolidin-1-yl)methyl)-N-(3-(5-isopropyl-1,3,4-thiadiazol-2-yl)phenyl)pyrrolo[1,2-f][1,2,4]triazin-4-amine, TFA (0.0216 g, 0.039 mmol, 13% yield for 2 steps) as a colorless oil. LCMS (ESI) m/e 435.3

[(M+H)+, calcd for C22H27N8S 435.2]. 1H NMR (400 MHz, MeOD) δ 7.91 (s, 1H), 7.71 (dt, J=6.6, 2.0 Hz, 1H), 7.63 (s, 1H), 7.61-7.55 (m, 2H), 7.53 (d, J=2.8 Hz, 1H), 6.71 (d, J=2.8 Hz, 1H), 4.53 (s, 2H), 4.14-4.02 (m, 1H), 3.79-3.78 (m, 1H), 3.79 (dd, J=12.2, 8.2 Hz, 1H), 3.57-3.32 (m, 2H), 3.22-3.12 (m, 1H), 2.61-2.47 (m, 1H), 2.21-2.07 (m, 1H), 1.47 (d, J=7.1 Hz, 6H); HPLC retention time (method C): $t_R$=7.33 min.

Example 33

3-((5-((4-aminopiperidin-1-yl)methyl)pyrrolo[2,1-f][1,2,4]triazin-4-yl)amino)-N-isobutylbenzamide

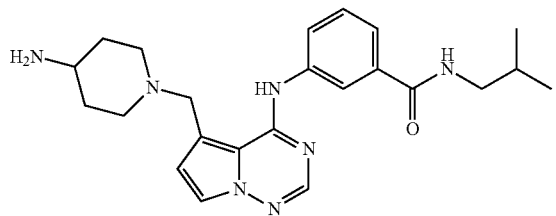 [SMILES: CC(C)CNC(=O)c1cccc(Nc2ncnn3ccc(CN4CCC(N)CC4)c23)c1]

Prepared as in Example 1, Parts B and C using 3-amino-N-isobutylbenzamide (41.5 mg, 0.216 mmol) (0.063 g, 0.288 mmol) and tert-butyl piperidin-4-ylcarbamate (43.2 mg, 0.216 mmol) to afford 3-(5-((4-aminopiperidin-1-yl)methyl)pyrrolo[1,2-f][1,2,4]triazin-4-ylamino)-N-isobutylbenzamide, 2 TFA (101 mg, 0.152 mmol, 71% yield for 2 steps) as a colorless semi-solid. LCMS (ESI) m/e 422.4 [(M+H)+, calcd for C23H32N7O 422.2]. 1H NMR (400 MHz, MeOD) δ ppm 7.68-7.72 (m, 1H), 7.64-7.68 (m, 1H), 7.59 (s, 1H), 7.54-7.57 (m, 2H), 7.51 (d, J=2.77 Hz, 1H), 6.66 (d, J=2.77 Hz, 1H), 4.35 (s, 2H), 3.56 (d, J=12.59 Hz, 2H), 3.38 (t, J=11.71 Hz, 1H), 3.21 (d, J=7.05 Hz, 2H), 2.90 (t, J=12.21 Hz, 2H), 2.20 (d, J=13.09 Hz, 2H), 1.87-1.99 (m, J=13.58, 6.74, 6.74, 6.74, 6.74 Hz, 1H), 1.76 (q, J=12.51 Hz, 2H), 0.96 (d, J=6.55 Hz, 6H); HPLC retention time (method A): $t_R$=4.00 min; HPLC retention time (method B): $t_R$=4.70 min.

Example 34

N-(3-(2-isopropyl-2H-tetrazol-5-yl)phenyl)-5-(piperazin-1-ylmethyl)pyrrolo[2,1-f][1,2,4]triazin-4-amine

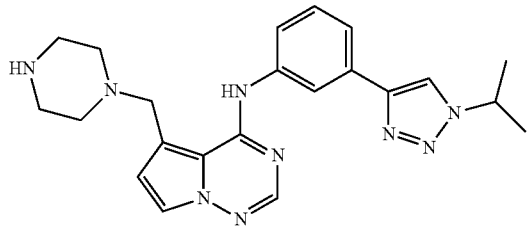 [SMILES: CC(C)n1cc(-c2cccc(Nc3ncnn4ccc(CN5CCNCC5)c34)c2)nn1]

Prepared as in Example 1, Parts B and C using 3-(2-isopropyl-2H-tetrazol-5-yl)aniline (0.169 g, 0.831 mmol) and tert-butyl piperazine-1-carboxylate (0.155 g, 0.831 mmol) to afford N-(3-(2-isopropyl-2H-tetrazol-5-yl)phenyl)-5-(piperazin-1-ylmethyl)pyrrolo[1,2-f][1,2,4]triazin-4-amine, 2 TFA (0.055 g, 0.084 mmol, 10% yield for 2 steps) as a brown oil. LCMS (ESI) m/e 419.3 [(M+H)+, calcd for C21H27N10 419.2]. 1H NMR (400 MHz, MeOD) δ 8.32-8.24 (m, 1H), 7.99 (dt, J=7.8, 1.3 Hz, 1H), 7.89 (ddd, J=8.1, 2.2, 1.0 Hz, 1H), 7.86 (s, 1H), 7.67-7.58 (m, 2H), 6.75 (d, J=2.8 Hz, 1H), 5.16 (spt, J=6.7 Hz, 1H), 4.07 (s, 2H), 3.34-3.25 (m, 4H), 3.07-2.95 (m, 4H), 1.68 (d, J=6.5 Hz, 6H); HPLC retention time (method C): $t_R$=8.22 min.

Example 35

N-(3-(5-isopropyl-1,3,4-thiadiazol-2-yl)phenyl)-5-(piperazin-1-ylmethyl)pyrrolo[2,1-f][1,2,4]triazin-4-amine

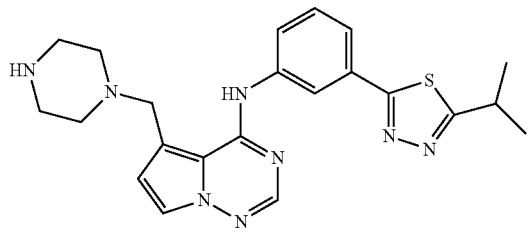 [SMILES: CC(C)c1nnc(-c2cccc(Nc3ncnn4ccc(CN5CCNCC5)c34)c2)s1]

Prepared as in Example 1, Parts B and C using 3-(5-isopropyl-1,3,4-thiadiazol-2-yl)aniline (0.182 g, 0.828 mmol) and tert-butyl piperazine-1-carboxylate (0.154 g, 0.828 mmol) to afford N-(3-(5-isopropyl-1,3,4-thiadiazol-2-yl)phenyl)-5-(piperazin-1-ylmethyl)pyrrolo[1,2-f][1,2,4]triazin-4-amine, 2 TFA (0.0384 g, 0.057 mmol, 9% yield for 2 steps) as a colorless oil. LCMS (ESI) m/e 435.2 [(M+H)+, calcd for C22H27N8S 435.2]. 1H NMR (400 MHz, CHLOROFORM-d) δ 8.13 (ddd, J=8.0, 2.1, 1.0 Hz, 1H), 8.04 (t, J=1.8 Hz, 1H), 7.87 (s, 1H), 7.51-7.35 (m, 3H), 6.53 (d, J=2.8 Hz, 1H), 3.85 (s, 2H), 3.50-3.30 (m, 5H), 2.90 (br. s, 4H), 1.41 (d, J=6.8 Hz, 6H); HPLC retention time (method C): $t_R$=9.16 min.

Example 36

3-((5-((4-aminopiperidin-1-yl)methyl)pyrrolo[2,1-f][1,2,4]triazin-4-yl)amino)-5-(2-isopropyl-2H-tetrazol-5-yl)phenol

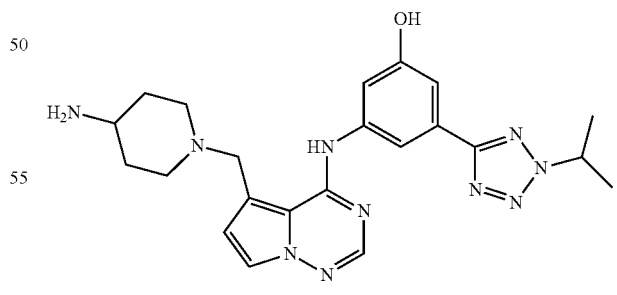

Prepared as in Example 1, Parts B and C using 3-amino-5-(2-isopropyl-2H-tetrazol-5-yl)phenol (0.177 g, 0.805 mmol) and tert-butyl piperidin-4-ylcarbamate (0.161 g, 0.805 mmol) to afford 3-(5-((4-aminopiperidin-1-yl)methyl)pyrrolo[1,2-f][1,2,4]triazin-4-ylamino)-5-(2-isopropyl-2H-tetrazol-5-yl)phenol, 2 TFA (0.167 g, 0.242 mmol, 34% yield for 2 steps) as an off-white solid. LCMS (ESI) m/e 449.3 [(M+H)⁺, calcd for $C_{22}H_{29}N_{10}O$ 449.2]. ¹H NMR (400 MHz, MeOD) δ 7.54 (s, 1H), 7.50 (d, J=2.8 Hz, 1H), 7.44-7.38 (m, 2H), 6.85 (t, J=1.9 Hz, 1H), 6.67 (d, J=2.8 Hz, 1H), 5.15 (spt, J=6.7 Hz, 1H), 4.47 (s, 2H), 3.64 (d, J=10.6 Hz, 2H), 3.42 (t, J=11.3 Hz, 1H), 3.06 (br. s, 2H), 2.24 (d, J=13.3 Hz, 2H), 1.89-1.71 (m, 2H), 1.67 (d, J=6.8 Hz, 6H); HPLC retention time (method D): $t_R$=5.33 min.

Example 37

3-((5-((4-aminopiperidin-1-yl)methyl)pyrrolo[2,1-f][1,2,4]triazin-4-yl)amino)-5-(5-isopropyl-1,2,4-oxadiazol-3-yl)phenol

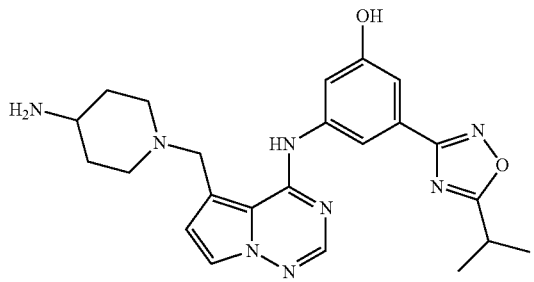

Prepared as in Example 1, Parts B and C using 3-amino-5-(5-isopropyl-1,2,4-oxadiazol-3-yl)phenol (0.177 g, 0.805 mmol) and tert-butyl piperidin-4-ylcarbamate (0.161 g, 0.805 mmol) to afford 3-(5-((4-aminopiperidin-1-yl)methyl)pyrrolo[1,2-f][1,2,4]triazin-4-ylamino)-5-(5-isopropyl-1,2,4-oxadiazol-3-yl)phenol, 2 TFA (0.1507 g, 0.221 mmol, 30% yield for 2 steps) as an off-white solid. LCMS (ESI) m/e 449.2 [(M+H)⁺, calcd for $C_{23}H_{29}N_{8}O_2$ 449.2]. ¹H NMR (400 MHz, MeOD) δ 7.93 (s, 1H), 7.52 (s, 1H), 7.48 (d, J=2.8 Hz, 1H), 7.39-7.28 (m, 2H), 6.86 (s, 1H), 6.68 (d, J=2.8 Hz, 1H), 4.54 (s, 2H), 3.66 (br. s, 2H), 3.45 (br. s, 1H), 3.13 (br. s, 2H), 2.26 (d, J=12.6 Hz, 2H), 1.81 (br. s, 2H), 1.42 (d, J=7.1 Hz, 6H); HPLC retention time (method D): $t_R$=6.92 min.

Example 38

2-((5-((4-aminopiperidin-1-yl)methyl)pyrrolo[2,1-f][1,2,4]triazin-4-yl)amino)-4-(2-isopropyl-2H-tetrazol-5-yl)phenol

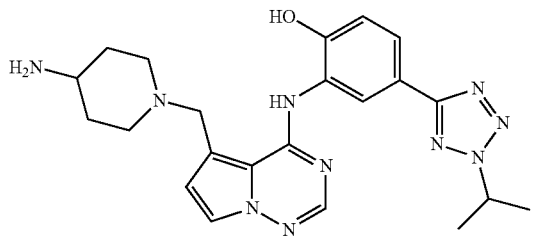 [SMILES: CC(C)n1nnc(-c2ccc(O)c(Nc3ncnn4ccc(CN5CCC(N)CC5)c34)c2)n1]

Prepared as in Example 1, Parts B and C using 2-amino-4-(2-isopropyl-2H-tetrazol-5-yl)phenol (100 mg, 0.456 mmol) and 4-(N-Boc amino)-piperidine (91 mg, 0.456 mmol) to afford 2-(5-((4-aminopiperidin-1-yl)methyl)pyrrolo[1,2-f][1,2,4]triazin-4-ylamino)-4-(2-isopropyl-2H-tetrazol-5-yl)phenol, 2 HCl (85 mg, 0.161 mmol, 35% yield for 2 steps) as a yellow solid. LCMS (ESI) m/e 449.3 [(M+H)⁺, calcd for $C_{22}H_{29}N_{10}O$ 449.2]. ¹H NMR (400 MHz, MeOD) δ 7.96 (br. s, 1H), 7.90 (dd, J=8.4, 1.9 Hz, 1H), 7.62 (br. s, 2H), 7.18 (d, J=8.3 Hz, 1H), 6.81 (d, J=2.3 Hz, 1H), 5.14 (dquin, J=13.5, 6.8 Hz, 1H), 4.57 (s, 2H), 3.63 (br. s, 2H), 3.46 (br. s, 1H), 3.24-3.04 (m, 2H), 2.23 (d, J=13.6 Hz, 2H), 1.93 (br. s, 2H), 1.66 (d, J=6.8 Hz, 6H); HPLC retention time (method D): $t_R$=6.92 min.

Example 39

N-(3-(5-isopropyl-1,2,4-oxadiazol-3-yl)phenyl)-5-((4-(methylamino)piperidin-1-yl)methyl)pyrrolo[2,1-f][1,2,4]triazin-4-amine

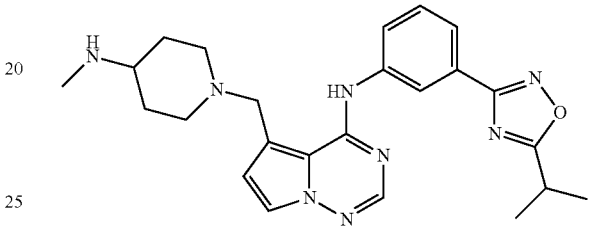

Prepared as in Example 1, Parts B and C using 3-(5-isopropyl-1,2,4-oxadiazol-3-yl)aniline (0.123 g, 0.604 mmol) and tert-butyl methyl(piperidin-4-yl)carbamate (0.129 g, 0.604 mmol) to afford N-(3-(5-isopropyl-1,2,4-oxadiazol-3-yl)phenyl)-5-((4-(methylamino)piperidin-1-yl)methyl)pyrrolo[1,2-f][1,2,4]triazin-4-amine, 2 TFA (0.0384 g, 0.056 mmol, 9% yield for 2 steps) as a colorless oil. LCMS (ESI) m/e 447.2 [(M+H)⁺, calcd for $C_{24}H_{31}N_{8}O$ 447.3]. ¹H NMR (400 MHz, MeOD) δ 7.95-7.90 (m, 1H), 7.88 (t, J=1.6 Hz, 1H), 7.61 (t, J=7.8 Hz, 1H), 7.53 (s, 1H), 7.52 (d, J=2.8 Hz, 1H), 7.44-7.37 (m, 1H), 6.69 (d, J=3.0 Hz, 1H), 4.53 (s, 2H), 3.69 (d, J=11.6 Hz, 2H), 3.38-3.31 (m, 2H), 3.15-2.98 (m, 2H), 2.65 (s, 3H), 2.32 (d, J=13.1 Hz, 2H), 1.74 (br. s, 2H), 1.43 (d, J=7.1 Hz, 6H); HPLC retention time (method C): $t_R$=6.02 min.

Example 40

N-(3-(5-isopropyl-1,3,4-oxadiazol-2-yl)phenyl)-5-((4-(methylamino)piperidin-1-yl)methyl)pyrrolo[2,1-f][1,2,4]triazin-4-amine

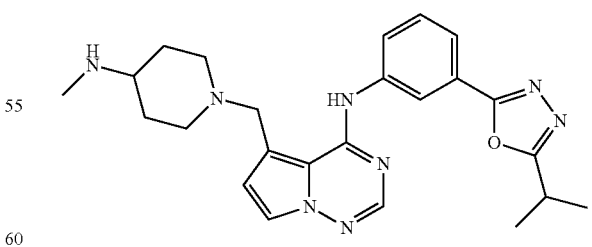

Prepared as in Example 1, Parts B and C using 3-(5-isopropyl-1,3,4-oxadiazol-2-yl)aniline (0.123 g, 0.604 mmol) and tert-butyl methyl(piperidin-4-yl)carbamate (0.129 g, 0.604 mmol) to afford N-(3-(5-isopropyl-1,3,4-oxadiazol-2-yl)phenyl)-5-((4-(methylamino)piperidin-1-yl)methyl)pyrrolo[1,2-f][1,2,4]triazin-4-amine, 2 TFA (0.043 g, 0.063 mmol, 10% yield for 2 steps) as a pale yellow solid. LCMS (ESI) m/e 447.2 [(M+H)+, calcd for C24H31N8O 447.3]. 1H NMR (400 MHz, MeOD) δ 7.90-7.81 (m, 2H), 7.64 (t, J=7.9 Hz, 1H), 7.55 (s, 1H), 7.51 (d, J=2.8 Hz, 1H), 7.47 (d, J=8.1 Hz, 1H), 6.69 (d, J=2.8 Hz, 1H), 4.54 (s, 2H), 3.70 (d, J=12.3 Hz, 2H), 3.42-3.31 (m, 2H), 3.09 (d, J=13.3 Hz, 2H), 2.67 (s, 3H), 2.33 (d, J=12.8 Hz, 2H), 1.79 (br. s, 2H), 1.44 (d, J=7.1 Hz, 6H); HPLC retention time (method C): $t_R$=5.21 min.

Example 41

N-(3-(5-(tert-butyl)-1,2,4-oxadiazol-3-yl)phenyl)-5-((4-(methylamino)piperidin-1-yl)methyl)pyrrolo[2,1-f][1,2,4]triazin-4-amine

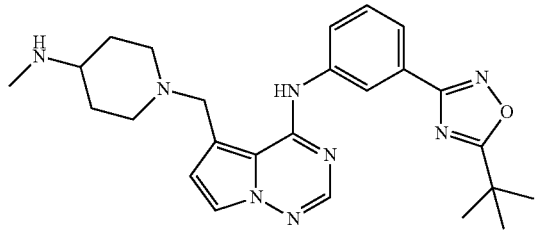 [SMILES: CNC1CCN(Cc2ccn3ncnc(Nc4cccc(-c5noc(C(C)(C)C)n5)c4)c23)CC1]

Prepared as in Example 1, Parts B and C using 3-(5-tert-butyl-1,2,4-oxadiazol-3-yl)aniline (0.131 g, 0.604 mmol) and tert-butyl methyl(piperidin-4-yl)carbamate (0.129 g, 0.604 mmol) to afford N-(3-(5-tert-butyl-1,2,4-oxadiazol-3-yl)phenyl)-5-((4-(methylamino)piperidin-1-yl)methyl)pyrrolo[1,2-f][1,2,4]triazin-4-amine, 2 TFA (0.0147 g, 0.021 mmol, 4% yield for 2 steps) as a pale yellow solid.

LCMS (ESI) m/e 461.2 [(M+H)+, calcd for C25H33N8O 461.3]. 1H NMR (400 MHz, MeOD) δ 7.97-7.86 (m, 2H), 7.64-7.58 (m, 1H), 7.57 (s, 1H), 7.52 (d, J=2.8 Hz, 1H), 7.50-7.44 (m, 1H), 6.68 (d, J=2.8 Hz, 1H), 4.47 (s, 2H), 3.65 (d, J=12.3 Hz, 2H), 3.38-3.31 (m, 1H), 2.99 (t, J=11.8 Hz, 2H), 2.65 (s, 3H), 2.30 (d, J=13.6 Hz, 2H), 1.73 (d, J=10.6 Hz, 2H), 1.48 (s, 9H); HPLC retention time (method C): $t_R$=7.34 min.

Example 42

N-(3-(2-isopropyl-2H-tetrazol-5-yl)phenyl)-5-((4-(methylamino)piperidin-1-yl)methyl)pyrrolo[2,1-f][1,2,4]triazin-4-amine

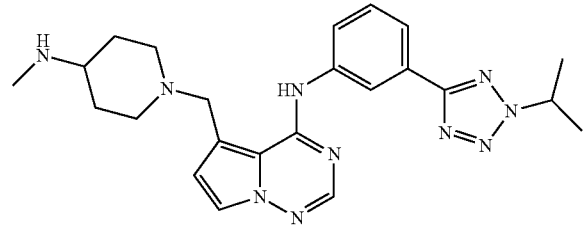 [SMILES: CNC1CCN(Cc2ccn3ncnc(Nc4cccc(-c5nnn(C(C)C)n5)c4)c23)CC1]

Prepared as in Example 1, Parts B and C using 3-(2-isopropyl-2H-tetrazol-5-yl)aniline (0.123 g, 0.604 mmol) and tert-butyl methyl(piperidin-4-yl)carbamate (0.129 g, 0.604 mmol) to afford N-(3-(2-isopropyl-2H-tetrazol-5-yl)phenyl)-5-((4-(methylamino)piperidin-1-yl)methyl)pyrrolo[1,2-f][1,2,4]triazin-4-amine, 2 TFA (0.0761 g, 0.111 mmol, 23% yield for 2 steps) as a pale oil. LCMS (ESI) m/e 447.3 [(M+H)+, calcd for C23H31N10 447.3]. 1H NMR (400 MHz, MeOD) δ 8.01-7.92 (m, 2H), 7.61 (t, J=8.1 Hz, 1H), 7.57 (s, 1H), 7.52 (d, J=2.8 Hz, 1H), 7.43 (dd, J=7.9, 0.9 Hz, 1H), 6.69 (d, J=2.8 Hz, 1H), 5.17 (spt, J=6.7 Hz, 1H), 4.48 (s, 2H), 3.66 (d, J=12.1 Hz, 2H), 3.40-3.33 (m, 1H), 3.07-2.94 (m, 2H), 2.66 (s, 3H), 2.32 (d, J=13.1 Hz, 2H), 1.84-1.73 (m, 2H), 1.71-1.63 (m, 6H); HPLC retention time (method C): $t_R$=5.36 min.

Example 43

5-((4-aminopiperidin-1-yl)methyl)-N-(2-chloro-5-(5-isopropyl-1,2,4-oxadiazol-3-yl)phenyl)pyrrolo[2,1-f][1,2,4]triazin-4-amine

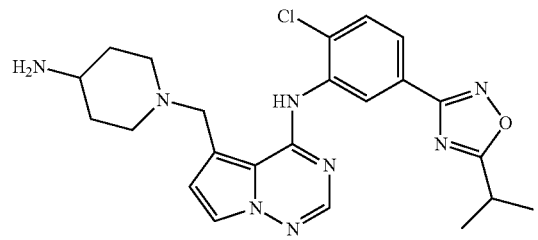 [SMILES: CC(C)c1nc(-c2ccc(Cl)c(Nc3ncnn4ccc(CN5CCC(N)CC5)c34)c2)no1]

Prepared as in Example 1, Parts B and C using 2-chloro-5-(5-isopropyl-1,2,4-oxadiazol-3-yl)aniline (0.137 g, 0.575 mmol) and tert-butyl piperidin-4-ylcarbamate (0.115 g, 0.575 mmol) to afford 5-((4-aminopiperidin-1-yl)methyl)-N-(2-chloro-5-(5-isopropyl-1,2,4-oxadiazol-3-yl)phenyl)pyrrolo[1,2-f][1,2,4]triazin-4-amine, 2 TFA (0.008 g, 10.72 μmol, 2% yield for 2 steps) as a colorless oil. LCMS (ESI) m/e 467.2 [(M+H)+, calcd for C23H28ClN8O 467.2]. 1H NMR (400 MHz, MeOD) δ 7.90-7.84 (m, 2H), 7.70 (d, J=9.1 Hz, 1H), 7.52-7.49 (m, 1H), 7.48 (s, 1H), 6.69 (d, J=2.8 Hz, 1H), 4.65 (s, 2H), 3.85-3.66 (m, 2H), 3.46-3.43 (m, 2H), 3.20 (d, J=11.1 Hz, 2H), 2.23 (d, J=11.6 Hz, 2H), 1.88-1.66 (m, 2H), 1.42 (d, J=7.1 Hz, 6H); HPLC retention time (method C): $t_R$=5.68 min.

Example 44

N-(3-fluoro-5-(5-isopropyl-1,2,4-oxadiazol-3-yl)phenyl)-5-((4-(methylamino)piperidin-1-yl)methyl)pyrrolo[2,1-f][1,2,4]triazin-4-amine

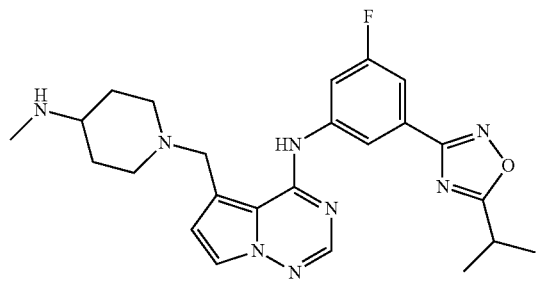 [SMILES: CNC1CCN(Cc2ccn3ncnc(Nc4cc(F)cc(-c5noc(C(C)C)n5)c4)c23)CC1]

Prepared as in Example 1, Parts B and C using 3-fluoro-5-(5-isopropyl-1,2,4-oxadiazol-3-yl)aniline (0.134 g, 0.604 mmol) and tert-butyl methyl(piperidin-4-yl)carbamate (0.129 g, 0.604 mmol) to afford N-(3-fluoro-5-(5-isopropyl-1,2,4-oxadiazol-3-yl)phenyl)-5-((4-(methylamino)piperidin-1-yl)methyl)pyrrolo[1,2-f][1,2,4]triazin-4-amine, 2 TFA (0.006 g, 7.92 μmol, 2% yield for 2 steps) as a colorless oil. LCMS (ESI) m/e 465.2 [(M+H)$^+$, calcd for $C_{24}H_{30}FN_8O$ 465.3]. $^1$H NMR (400 MHz, MeOD) δ 7.72 (s, 1H), 7.62 (s, 1H), 7.60-7.55 (m, 1H), 7.51 (d, J=2.8 Hz, 1H), 7.42 (d, J=9.8 Hz, 1H), 6.68 (d, J=2.8 Hz, 1H), 4.46 (s, 2H), 3.65 (d, J=13.3 Hz, 2H), 3.37-3.30 (m, 2H), 3.01-2.89 (m, 2H), 2.66 (s, 3H), 2.30 (d, J=12.8 Hz, 2H), 1.75 (d, J=11.3 Hz, 2H), 1.43 (d, J=6.8 Hz, 6H); HPLC retention time (method C): $t_R$=7.40 min.

Example 45

5-((4-aminopiperidin-1-yl)methyl)-N-(3-chloro-5-(5-isopropyl-1,2,4-oxadiazol-3-yl)phenyl)pyrrolo[2,1-f][1,2,4]triazin-4-amine

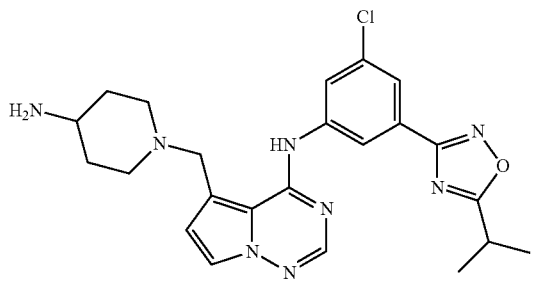 [SMILES: CC(C)c1nc(-c2cc(Cl)cc(Nc3ncnn4ccc(CN5CCC(N)CC5)c34)c2)no1]

Prepared as in Example 1, Parts B and C using 3-chloro-5-(5-isopropyl-1,2,4-oxadiazol-3-yl)aniline (0.137 g, 0.575 mmol) and tert-butyl piperidin-4-ylcarbamate (0.115 g, 0.575 mmol) to afford 5-((4-aminopiperidin-1-yl)methyl)-N-(3-chloro-5-(5-isopropyl-1,2,4-oxadiazol-3-yl)phenyl)pyrrolo[1,2-f][1,2,4]triazin-4-amine, 2 TFA (0.0411 g, 0.058 mmol, 10% yield for 2 steps) as a colorless oil. LCMS (ESI) m/e 467.2 [(M+H)$^+$, calcd for $C_{23}H_{28}ClN_8O$ 467.3]. $^1$H NMR (400 MHz, MeOD) δ 7.86 (dd, J=2.0, 1.5 Hz, 1H), 7.75 (t, J=1.6 Hz, 1H), 7.52 (s, 1H), 7.48 (d, J=3.0 Hz, 1H), 7.44 (s, 1H), 6.69 (d, J=2.8 Hz, 1H), 4.61 (s, 2H), 3.70 (br. s, 2H), 3.52-3.38 (m, 1H), 3.36-3.31 (m, 1H), 3.23-3.07 (m, 2H), 2.25 (d, J=12.8 Hz, 2H), 1.78 (br. s, 2H), 1.48-1.39 (m, 6H); HPLC retention time (method C): $t_R$=8.25 min.

Example 46

5-((4-aminopiperidin-1-yl)methyl)-N-(3-fluoro-5-(5-isopropyl-1,2,4-oxadiazol-3-yl)phenyl)pyrrolo[1,2-f][1,2,4]triazin-4-amine

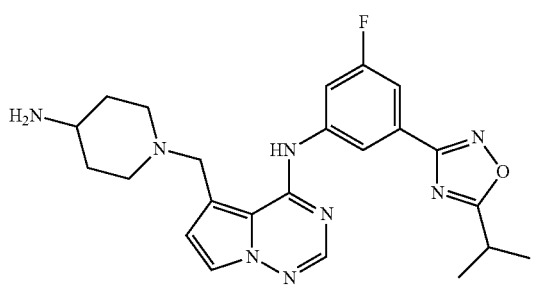

Prepared as in Example 1, Parts B and C using 3-fluoro-5-(5-isopropyl-1,2,4-oxadiazol-3-yl)aniline (0.134 g, 0.604 mmol) and tert-butyl piperidin-4-ylcarbamate (0.121 g, 0.604 mmol) to afford 5-((4-aminopiperidin-1-yl)methyl)-N-(3-fluoro-5-(5-isopropyl-1,2,4-oxadiazol-3-yl)phenyl)pyrrolo[1,2-f][1,2,4]triazin-4-amine, 2 TFA (0.0614 g, 0.088 mmol, 15% yield for 2 steps) as a pale yellow oil. LCMS (ESI) m/e 451.3 [(M+H)$^+$, calcd for $C_{23}H_{28}FN_8O$ 451.2]. $^1$H NMR (400 MHz, MeOD) δ 7.66 (d, J=1.3 Hz, 1H), 7.62-7.55 (m, 1H), 7.53 (s, 1H), 7.49 (d, J=2.8 Hz, 1H), 7.21 (d, J=9.6 Hz, 1H), 6.69 (d, J=2.8 Hz, 1H), 4.60 (s, 2H), 3.69 (br. s, 2H), 3.51-3.39 (m, 1H), 3.36-3.30 (m, 1H), 3.13 (d, J=15.1 Hz, 2H), 2.25 (d, J=13.1 Hz, 2H), 1.80 (br. s, 2H), 1.43 (d, J=7.1 Hz, 6H); HPLC retention time (method C): $t_R$=7.03 min.

Example 47

5-((4-aminopiperidin-1-yl)methyl)-N-(3-(5-cyclopropyl-1,2,4-oxadiazol-3-yl)phenyl)pyrrolo[2,1-f][1,2,4]triazin-4-amine

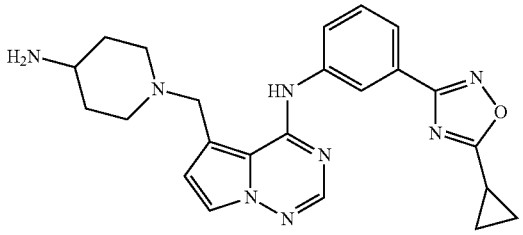 [SMILES: NC1CCN(Cc2ccn3ncnc(Nc4cccc(-c5noc(C6CC6)n5)c4)c23)CC1]

Prepared as in Example 1, Parts B and C using 3-(5-cyclopropyl-1,2,4-oxadiazol-3-yl)aniline (0.083 g, 0.411 mmol) and tert-butyl piperidin-4-ylcarbamate (0.082 g, 0.411 mmol) to afford 5-((4-aminopiperidin-1-yl)methyl)-N-(3-(5-cyclopropyl-1,2,4-oxadiazol-3-yl)phenyl)pyrrolo[1,2-f][1,2,4]triazin-4-amine, 2 TFA (0.0301 g, 0.045 mmol, 12 yield for 2 steps) as a colorless oil. LCMS (ESI) m/e 431.2 [(M+H)$^+$, calcd for $C_{23}H_{27}N_8O$ 431.2]. $^1$H NMR (400 MHz, MeOD) δ 7.91-7.85 (m, 1H), 7.82 (s, 1H), 7.59 (t, J=7.9 Hz, 1H), 7.52 (s, 1H), 7.50 (d, J=2.8 Hz, 1H), 7.39 (dd, J=7.9, 0.9 Hz, 1H), 6.68 (d, J=2.8 Hz, 1H), 4.53 (s, 2H), 3.66 (d, J=11.1 Hz, 2H), 3.42 (t, J=11.1 Hz, 1H), 3.10 (br. s, 2H), 2.32 (tt, J=8.1, 5.0 Hz, 1H), 2.23 (d, J=13.1 Hz, 2H), 1.76 (br. s, 2H), 1.34-1.26 (m, 2H), 1.25-1.19 (m, 2H); HPLC retention time (method C): $t_R$=5.48 min.

Example 48

(3R,4R)-4-amino-1-((4-((3-(5-isopropyl-1,3,4-thiadiazol-2-yl)phenyl)amino)pyrrolo[2,1-f][1,2,4]triazin-5-yl)methyl)piperidin-3-ol

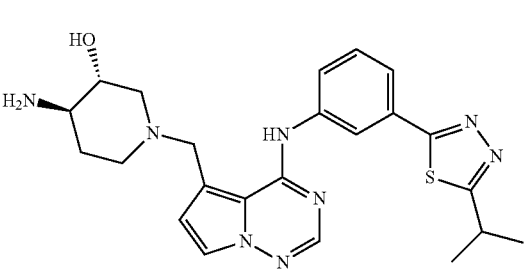

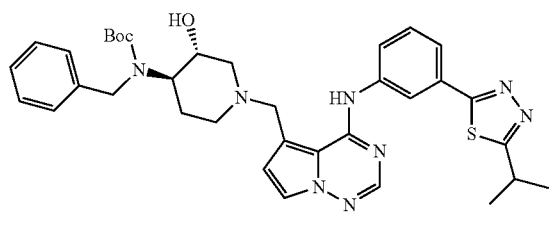 [SMILES: CC(C)c1nnc(-c2cccc(Nc3ncnn4ccc(CN5CC[C@@H](NCc6ccccc6)[C@H](O)C5)c34)c2)s1]

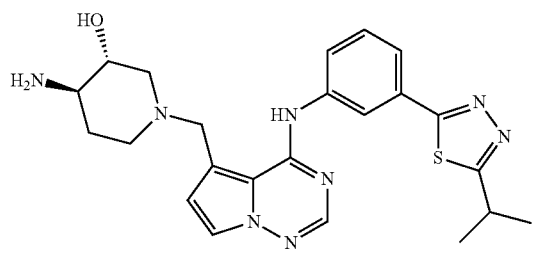 [SMILES: CC(C)c1nnc(-c2cccc(Nc3ncnn4ccc(CN5CC[C@@H](N)[C@H](O)C5)c34)c2)s1]

Part A: tert-butyl benzyl((3R,4R)-3-hydroxy-1-((4-((3-(5-isopropyl-1,3,4-thiadiazol-2-yl)phenyl)amino)pyrrolo[2,1-f][1,2,4]triazin-5-yl)methyl)piperidin-4-yl)carbamate Prepared as in Example 1, Parts B and C using 3-(5-isopropyl-1,3,4-thiadiazol-2-yl)aniline (126 mg, 0.575 mmol) and tert-butyl benzyl((3R,4R)-3-hydroxypiperidin-4-yl)carbamate (176 mg, 0.575 mmol) to afford tert-butyl benzyl((3R,4R)-3-hydroxy-1-((4-(3-(5-isopropyl-1,3,4-thiadiazol-2-yl)phenylamino)pyrrolo[1,2-f][1,2,4]triazin-5-yl)methyl)piperidin-4-yl)carbamate (0.221 g, 0.304 mmol, 53 yield) as a colorless oil. LCMS (ESI) m/e 655.4 [(M+H)$^+$, calcd for $C_{35}H_{43}N_8O_3S$ 655.3]. $^1$H NMR (400 MHz, CHLOROFORM-d) δ ppm 11.72 (br. s, 1H), 8.27 (s, 1H), 7.95 (s, 1H), 7.60 (d, J=7.81 Hz, 1H), 7.40-7.48 (m, 2H), 7.06-7.13 (m, 3H), 6.91-7.01 (m, 2H), 6.48 (d, J=2.52 Hz, 1H), 4.18-4.31 (m, 1H), 3.98-4.07 (m, 1H), 3.70-3.86 (m, 3H), 3.50 (spt, J=6.92 Hz, 1H), 3.30-3.39 (m, 1H), 3.06-3.15 (m, 1H), 2.68 (br. s, 1H), 2.04-2.18 (m, 2H), 1.68-1.81 (m, 2H), 1.48 (d, J=6.80 Hz, 6H), 1.38 (br. s, 9H).

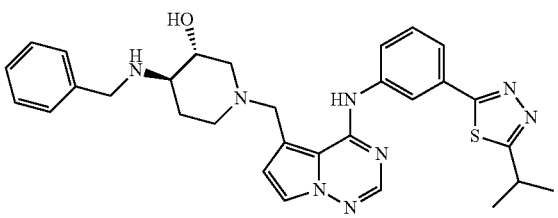

Part B: (3R,4R)-4-(benzylamino)-1-((4-((3-(5-isopropyl-1,3,4-thiadiazol-2-yl)phenyl)amino)pyrrolo[2,1-f][1,2,4]triazin-5-yl)methyl)piperidin-3-ol A solution of tert-butyl benzyl((3R,4R)-3-hydroxy-1-((4-((3-(5-isopropyl-1,3,4-thiadiazol-2-yl)phenylamino)pyrrolo[1,2-f][1,2,4]triazin-5-yl)methyl)piperidin-4-yl)carbamate (221 mg, 0.337 mmol) and trifluoroacetic acid (5 mL, 64.9 mmol) in 1,2-dichloroethane (10 mL) was stirred at room temperature for 5 h. The reaction mixture was concentrated under reduced pressure and carried on without purification. LCMS (ESI) m/e 555.5 [(M+H)$^+$, calcd for $C_{30}H_{35}N_8OS$ 555.3].

Part C: (3R,4R)-4-amino-1-((4-((3-(5-isopropyl-1,3,4-thiadiazol-2-yl)phenyl)amino)pyrrolo[2,1-f][1,2,4]triazin-5-yl)methyl)piperidin-3-ol A solution of (3R,4R)-4-(benzylamino)-1-((4-(3-(5-isopropyl-1,3,4-thiadiazol-2-yl)phenylamino)pyrrolo[1,2-f][1,2,4]triazin-5-yl)methyl)piperidin-3-ol, 2 TFA (240 mg, 0.307 mmol) was added to the Parr flask. Pd/C (163 mg, 0.153 mmol) and EtOH (3.0 mL) were added and the mixture was shaken under 60 psi hydrogen overnight. The mixture was filtered through Celite and washed with ethanol. The filtrate was concentrated under reduced pressure and purified by reverse phase HPLC (15%-80% MeOH/H2O/0.1% TFA). The fractions were concentrated and the residue was passed through a SCX column to free base, eluting with 2N ammonium in MeOH. The solution was concentrated under reduced pressure to remove the solvent and excess ammonia. To the residue was added 2N HCl in diethyl ether (3 mL) and the mixture was stirred for 5 min. The cloudy solution was concentrated under reduced pressure to obtain (3R,4R)-4-amino-1-((4-((3-(5-isopropyl-1,3,4-thiadiazol-2-yl)phenylamino)pyrrolo[1,2-f][1,2,4]triazin-5-yl)methyl)piperidin-3-ol, 2 HCl (35 mg, 0.063 mmol, 21% yield for 2 steps) as a pale yellow solid. LCMS (ESI) m/e 465.4 [(M+H)$^+$, calcd for $C_{23}H_{29}N_8OS$ 465.2].

$^1$H NMR (400 MHz, MeOD) δ 7.94 (br. s, 1H), 7.85 (d, J=6.3 Hz, 1H), 7.65 (br. s, 3H), 7.50 (br. s, 1H), 6.84 (br. s, 1H), 4.63 (br. s, 2H), 3.94-3.78 (m, 1H), 3.71-3.41 (m, 4H), 3.21-2.85 (m, 2H), 2.39-2.14 (m, 1H), 1.95-1.79 (m, 1H), 1.47 (d, J=6.8 Hz, 6H); HPLC retention time (method H): $t_R$=6.49 min; HPLC retention time (method I): $t_R$=7.38 min.

Example 49

5-((4-aminopiperidin-1-yl)methyl)-N-(4-fluoro-3-(2-isopropyl-2H-tetrazol-5-yl)phenyl)pyrrolo[2,1-f][1,2,4]triazin-4-amine

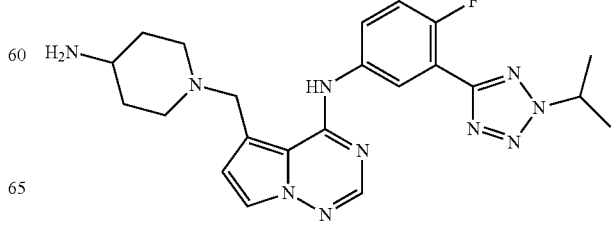

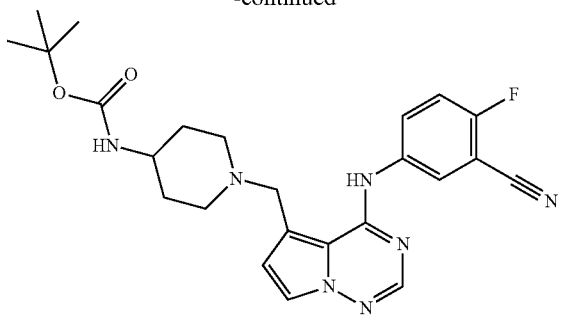

Part A. tert-butyl (1-((4-((3-cyano-4-fluorophenyl)amino)pyrrolo[2,1-f][1,2,4]triazin-5-yl)methyl)piperidin-4-yl)carbamate Prepared as in Example 1, Parts B and C using 5-amino-2-fluorobenzonitrile (98 mg, 0.719 mmol) and tert-butyl piperidin-4-ylcarbamate (144 mg, 0.719 mmol) to afford tert-butyl 1-((4-(3-cyano-4-fluorophenylamino)pyrrolo[1,2-f][1,2,4]triazin-5-yl)methyl)piperidin-4-ylcarbamate (146 mg, 0.282 mmol, 39% yield) as a colorless solid. LCMS (ESI) m/e 466.4 [(M+H)$^+$, calcd for $C_{24}H_{29}FN_7O_2$ 466.2].

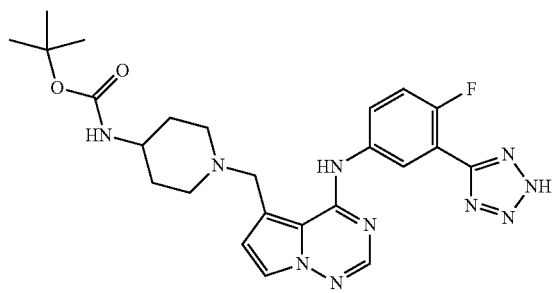 [SMILES: CC(C)(C)OC(=O)NC1CCN(Cc2ccn3ncnc(Nc4ccc(F)c(-c5nn[nH]n5)c4)c23)CC1]

Part B. tert-butyl (1-((4-((4-fluoro-3-(2H-tetrazol-5-yl)phenyl)amino)pyrrolo[2,1-f][1,2,4]triazin-5-yl)methyl)piperidin-4-yl)carbamate To a solution of tert-butyl 1-((4-(3-cyano-4-fluorophenylamino)pyrrolo[1,2-f][1,2,4]triazin-5-yl)methyl)piperidin-4-ylcarbamate (146 mg, 0.314 mmol) in DMF (928 µL) was added sodium azide (122 mg, 1.882 mmol) and ammonia hydrochloride (101 mg, 1.882 mmol). The solution was heated to 100° C. for 12 h. The solution was cooled to room temperature and quenched with water (2 mL). The solution was extracted with ethyl acetate (3×10 mL). The combined organics were washed with brine (1×10 mL), dried (MgSO4), filtered and concentrated under reduced pressure. The material was carried on without further purification assuming quantitative yield. Obtained tert-butyl 1-((4-(4-fluoro-3-(2H-tetrazol-5-yl)phenylamino)pyrrolo[1,2,4]triazin-5-yl)methyl)piperidin-4-ylcarbamate (159 mg, 0.314 mmol, quantitative crude yield) as a yellow oil. (ESI) m/e 509.3 [(M+H)$^+$, calcd for $C_{24}H_{30}FN_{10}O_2$ 509.3].

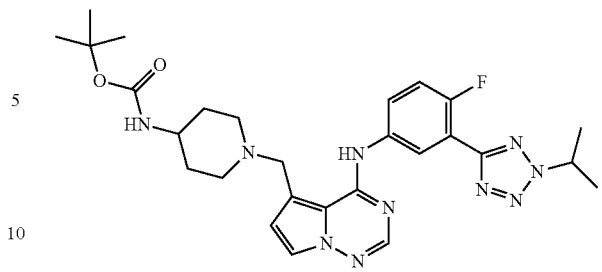

Part C. tert-butyl (1-((4-((4-fluoro-3-(2-isopropyl-2H-tetrazol-5-yl)phenyl)amino)pyrrolo[2,1-f][1,2,4]triazin-5-yl)methyl)piperidin-4-yl)carbamate To tert-butyl 1-((4-(4-fluoro-3-(2H-tetrazol-5-yl)phenylamino)pyrrolo[1,2-f][1,2,4]triazin-5-yl)methyl)piperidin-4-ylcarbamate (0.160 g, 0.314 mmol) and potassium carbonate (0.087 g, 0.628 mmol) in DMF (3.14 mL) was added 2-iodopropane (0.038 mL, 0.377 mmol). The solution was heated to 90° for 12 h. The solution was cooled to room temperature and diluted with water (5 mL). The solution was extracted with ethyl acetate (3×10 mL). The combined organics were washed with brine (1×10 mL), dried (MgSO4), filtered, and concentrated under reduced pressure. The material was carried on without further purification and assuming quantitative yield. Obtained tert-butyl 1-((4-(4-fluoro-3-(2-isopropyl-2H-tetrazol-5-yl)phenylamino)pyrrolo[1,2-f][1,2,4]triazin-5-yl)methyl)piperidin-4-ylcarbamate (0.173 g, 0.314 mmol, quantitative crude yield) as a yellow oil. (ESI) m/e 551.3 [(M+H)$^+$, calcd for $C_{27}H_{36}FN_{10}O_2$ 551.3].

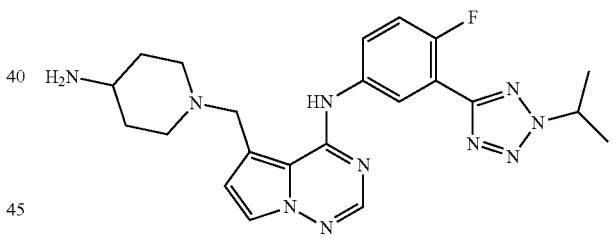

Part D. 5-((4-aminopiperidin-1-yl)methyl)-N-(4-fluoro-3-(2-isopropyl-2H-tetrazol-5-yl)phenyl)pyrrolo[2,1-f][1,2,4]triazin-4-amine A solution of tert-butyl 1-((4-(4-fluoro-3-(2-isopropyl-2H-tetrazol-5-yl)phenylamino)pyrrolo[1,2-f][1,2,4]triazin-5-yl)methyl)piperidin-4-ylcarbamate (173 mg, 0.314 mmol) and trifluoroacetic acid (2419 µL, 31.4 mmol) in DCM (3140 µL) was stirred at room temperature for 2 h. The reaction mixture was concentrated under reduced pressure and the crude material was purified by reverse phase HPLC (10%-40% MeOH/H$_2$O/0.1% TFA). The desired fractions were combined and concentrated. The residue was diluted with methanol and eluted through a Stratera CSX ion exchange column. Eluted free base with 2N ammonium in methanol and concentrated. The residue was diluted with methanol (4 mL) and 2M HCl in diethyl ether (3 mL) added. The solution and stirred at room temperature for 30 min then concentrated. Obtained 5-((4-aminopiperidin-1-yl)

methyl)-N-(4-fluoro-3-(2-isopropyl-2H-tetrazol-5-yl)phenyl)pyrrolo[1,2-f][1,2,4]triazin-4-amine, 2 HCl (67 mg, 0.125 mmol, 40% yield for 3 steps) as a pale yellow amorphous solid. LCMS (ESI) m/e 451.3 [(M+H)$^+$, calcd for $C_{22}H_{28}FN_{10}$ 451.3]. $^1$H NMR (400 MHz, MeOD) δ ppm 8.30 (br. s, 1H), 7.84-8.03 (m, 2H), 7.50-7.84 (m, 2H), 7.19 (br. s, 1H), 5.20 (ddd, J=12.28, 5.98, 5.67 Hz, 1H), 4.90 (br. s, 2H), 3.77 (br. s, 2H), 3.35-3.61 (m, 3H), 2.20-2.40 (m, 2H), 1.99-2.17 (m, 2H), 1.68 (d, J=6.30 Hz, 6H); HPLC retention time (method E): $t_R$=4.64 min; HPLC retention time (method F): $t_R$=5.84 min.

Example 50

5-((4-aminopiperidin-1-yl)methyl)-N-(2-fluoro-5-(2-isopropyl-2H-tetrazol-5-yl)phenyl)pyrrolo[2,1-f][1,2,4]triazin-4-amine

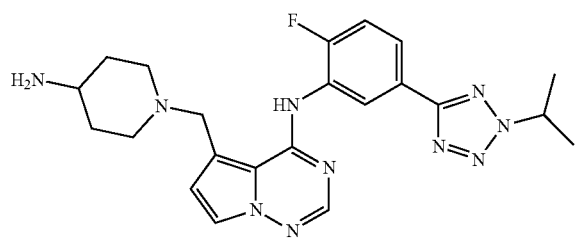 [SMILES: CC(C)n1nnc(-c2ccc(F)c(Nc3ncnn4ccc(CN5CCC(N)CC5)c34)c2)n1]

Prepared as in example 49 to give 5-((4-aminopiperidin-1-yl)methyl)-N-(2-fluoro-5-(2-isopropyl-2H-tetrazol-5-yl)phenyl)pyrrolo[1,2-f][1,2,4]triazin-4-amine, 2 HCl (145 mg, 0.271 mmol) as a pale yellow solid. LCMS (ESI) m/e 451.3 [(M+H)$^+$, calcd for $C_{22}H_{28}FN_{10}$ 451.3]. $^1$H NMR (400 MHz, MeOD) δ 8.24-7.98 (m, 2H), 7.67 (d, J=6.5 Hz, 2H), 7.47 (t, J=9.2 Hz, 1H), 6.92 (br. s, 1H), 5.16 (dt, J=13.3, 6.6 Hz, 1H), 4.77 (br. s, 2H), 3.75 (br. s, 2H), 3.64-3.33 (m, 3H), 2.35-2.21 (m, 2H), 1.94 (br. s, 2H), 1.67 (d, J=6.5 Hz, 6H); HPLC retention time (method E): $t_R$=4.64 min; HPLC retention time (method F): $t_R$=5.85 min.

Example 51

5-((4-aminopiperidin-1-yl)methyl)-N-(3-fluoro-5-(2-isopropyl-2H-tetrazol-5-yl)phenyl)pyrrolo[2,1-f][1,2,4]triazin-4-amine

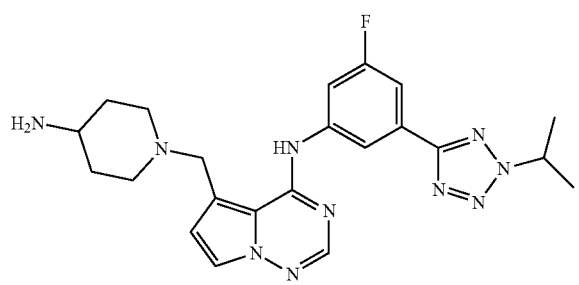 [SMILES: CC(C)n1nnc(-c2cc(F)cc(Nc3ncnn4ccc(CN5CCC(N)CC5)c34)c2)n1]

Prepared as in example 49 to give 5-((4-aminopiperidin-1-yl)methyl)-N-(3-fluoro-5-(2-isopropyl-2H-tetrazol-5-yl)phenyl)pyrrolo[2,1-f][1,2,4]triazin-4-amine, 2 HCl (125 mg, 0.175 mmol) as an off-white solid. LCMS (ESI) m/e 451.2 [(M+H)$^+$, calcd for $C_{22}H_{28}FN_{10}$ 451.3]. $^1$H NMR (400 MHz, MeOD) δ 7.72 (s, 1H), 7.65-7.59 (m, 1H), 7.53 (s, 1H), 7.48 (d, J=2.8 Hz, 1H), 7.15 (d, J=9.6 Hz, 1H), 6.70 (d, J=2.8 Hz, 1H), 5.23-5.10 (m, 1H), 4.63 (s, 2H), 3.72 (br. s, 2H), 3.47 (d, J=2.0 Hz, 1H), 3.17 (d, J=7.8 Hz, 2H), 2.27 (d, J=12.3 Hz, 2H), 1.94-1.75 (m, 2H), 1.67 (d, J=6.5 Hz, 6H); HPLC retention time (method D): $t_R$=8.19 min.

Example 52

5-((4-aminopiperidin-1-yl)methyl)-N-(2-fluoro-5-(5-isopropyl-1,2,4-oxadiazol-3-yl)phenyl)pyrrolo[2,1-f][1,2,4]triazin-4-amine

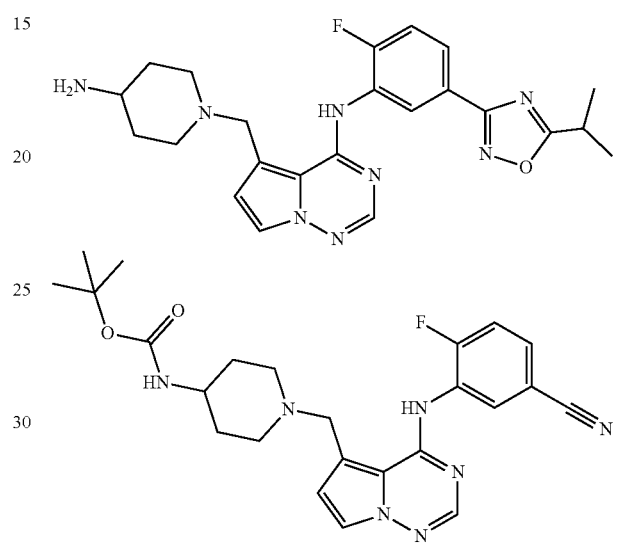

Part A. tert-butyl (1-((4-((5-cyano-2-fluorophenyl)amino)pyrrolo[2,1-f][1,2,4]triazin-5-yl)methyl)piperidin-4-yl)carbamate Prepared as in Example 1, Parts B and C using 3-amino-4-fluorobenzonitrile (136.9 mg, 0.977 mmol) and tert-butyl piperidin-4-ylcarbamate (201.8 mg, 1.01 mmol) to afford tert-butyl 1-((4-(5-cyano-2-fluorophenylamino)pyrrolo[1,2-f][1,2,4]triazin-5-yl)methyl)piperidin-4-ylcarbamate (62 mg, 0.133 mmol, 15% crude yield) as a pale pink solid. LCMS (ESI) m/e 466.4 [(M+H)$^+$, calcd for $C_{24}H_{29}FN_7O_2$ 466.2].

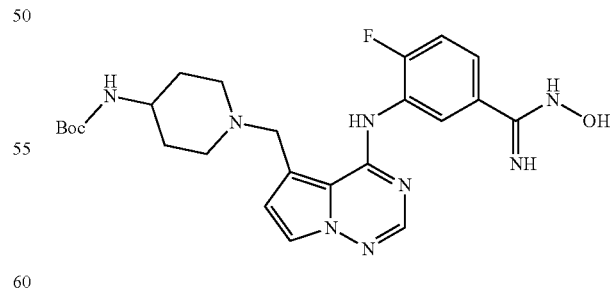

Part B. tert-butyl (1-((4-((2-fluoro-5-(N-hydroxycarbamimidoyl)phenyl)amino)pyrrolo[2,1-f][1,2,4]triazin-5-yl)methyl)piperidin-4-yl)carbamate A solution of tert-butyl 1-((4-(5-cyano-2-fluorophenylamino)pyrrolo[1,2-f][1,2,4]triazin-5-yl)methyl)piperidin-4-ylcarbamate (75 mg, 0.161 mmol), hydroxylamine hydrochloride (33.6 mg, 0.483 mmol) and potassium carbonate (89 mg, 0.644 mmol) in EtOH (3.2 mL) was heated to reflux for 12 h. The reaction mixture was cooled to room temperature and quenched with water (5 mL). The solution was extracted with ethyl acetate (3×10 mL). The combined organics were washed with brine (1×10 mL), dried (MgSO$_4$), filtered, and concentrated under reduced pressure. The material was carried on without further purification and assuming quantitative yield. Obtained 3-(5-((4-aminopiperidin-1-yl)methyl)pyrrolo[1,2-f][1,2,4]triazin-4-ylamino)-4-fluoro-N-hydroxybenzimidamide (0.162 mmol, quantitative crude yield) as yellow solid. LCMS (ESI) m/e 499.4 [(M+H)$^+$, calcd for C$_{24}$H$_{32}$FN$_8$O$_3$ 499.3].

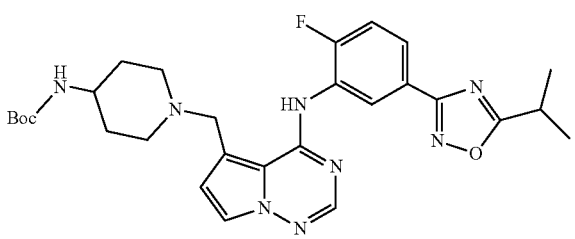 [SMILES: CC(C)c1nc(-c2ccc(F)c(Nc3ncnn4ccc(CN5CCC(NC(=O)OC(C)(C)C)CC5)c34)c2)no1]

Part C. tert-butyl (1-((4-((2-fluoro-5-(5-isopropyl-1,2,4-oxadiazol-3-yl)phenyl)amino)pyrrolo[2,1-f][1,2,4]triazin-5-yl)methyl)piperidin-4-yl)carbamate To a solution of DIC (51.2 mg, 0.316 mmol) in dry pyridine (717 μL) at room temperature under nitrogen was added isobutyryl chloride (33.3 μL, 0.316 mmol). The reaction mixture was stirred at room temperature for 15 min. This was slowly added to a solution of tert-butyl 1-((4-(2-fluoro-5-(N-hydroxycarbamimidoyl)phenylamino)pyrrolo[1,2-f][1,2,4]triazin-5-yl)methyl)piperidin-4-ylcarbamate (143 mg, 0.287 mmol) in dry pyridine (717 μL). The reaction mixture was stirred at room temperature for 1 h, then was heated in an oil bath at 90° C. for 12 h. The reaction mixture was cooled to room temperature and extracted with ethyl acetate (3×10 mL). The combined organics were washed with brine (1×10 mL), dried (MgSO4), filtered, and concentrated under reduced pressure. The crude material was purified by reverse phase HPLC (10%-70% MeOH/H$_2$O/0.1% TFA). Obtained tert-butyl 1-((4-(2-fluoro-5-(5-isopropyl-1,2,4-oxadiazol-3-yl)phenylamino)pyrrolo[1,2-f][1,2,4]triazin-5-yl)methyl)piperidin-4-ylcarbamate (15 mg, 0.027 mmol, 9% yield for 2 steps) as a brown oil. LCMS (ESI) m/e 551.4 [(M+H)$^+$, calcd for C$_{28}$H$_{36}$FN$_8$O$_3$ 551.3].

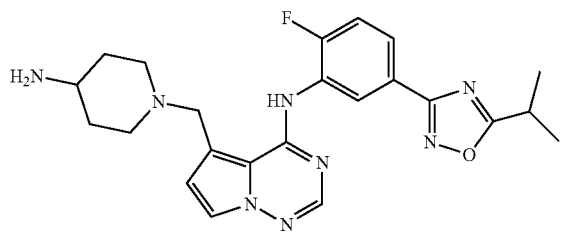 [SMILES: CC(C)c1nc(-c2ccc(F)c(Nc3ncnn4ccc(CN5CCC(N)CC5)c34)c2)no1]

Part D. 5-((4-aminopiperidin-1-yl)methyl)-N-(2-fluoro-5-(5-isopropyl-1,2,4-oxadiazol-3-yl)phenyl)pyrrolo[2,1-f][1,2,4]triazin-4-amine A solution of tert-butyl 1-((4-(2-fluoro-5-(5-isopropyl-1,2,4-oxadiazol-3-yl)phenylamino)pyrrolo[1,2-f][1,2,4]triazin-5-yl)methyl)piperidin-4-ylcarbamate (15 mg, 0.027 mmol) in hydrogen chloride (2M in diethyl ether) (681 μL, 1.362 mmol) was stirred at room temperature for 12 h. The reaction mixture was concentrated and purified by reverse phase HPLC (10%-70% MeOH/H2O/0.1% TFA). Obtained 5-((4-aminopiperidin-1-yl)methyl)-N-(2-fluoro-5-(5-isopropyl-1,2,4-oxadiazol-3-yl)phenyl)pyrrolo[1,2-f][1,2,4]triazin-4-amine, 2 TFA (15 mg, 0.022 mmol, 80% yield) as a yellow oil. LCMS (ESI) m/e 451.3 [(M+H)$^+$, calcd for C$_{23}$H$_{28}$FN$_8$O 451.2]. $^1$H NMR (400 MHz, MeOD) δ ppm 7.96 (dd, J=7.81, 2.27 Hz, 1H), 7.91 (ddd, J=8.56, 4.78, 2.27 Hz, 1H), 7.52 (s, 1H), 7.50 (d, J=3.02 Hz, 1H), 7.40 (dd, J=10.20, 8.69 Hz, 1H), 6.69 (d, J=2.77 Hz, 1H), 4.60 (s, 2H), 3.69 (d, J=9.82 Hz, 2H), 3.38-3.52 (m, 1H), 3.30-3.37 (m, 1H), 3.07-3.24 (m, 2H), 2.24 (d, J=12.84 Hz, 2H), 1.82 (d, J=10.58 Hz, 2H), 1.42 (d, J=6.80 Hz, 6H); HPLC retention time (method A): t$_R$=5.58 min; HPLC retention time (method B): t$_R$=6.63 min.

Example 53

N-(1-((4-((3-(5-isopropyl-1,3,4-thiadiazol-2-yl)phenyl)amino)pyrrolo[2,1-f][1,2,4]triazin-5-yl)methyl)piperidin-4-yl)acetamide

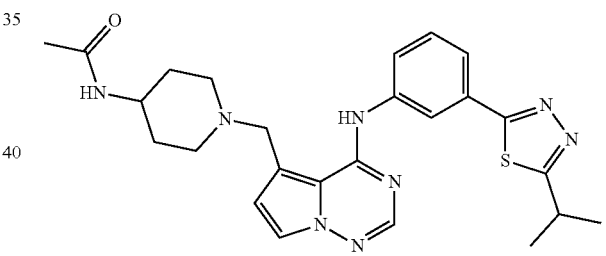

Prepared as in Example 1, Part B using 3-(5-isopropyl-1,3,4-thiadiazol-2-yl)aniline (47.3 mg, 0.216 mmol) and N-(piperidin-4-yl)acetamide (30.7 mg, 0.216 mmol) to afford N-(1-((4-(3-(5-isopropyl-1,3,4-thiadiazol-2-yl)phenylamino)pyrrolo[1,2-f][1,2,4]triazin-5-yl)methyl)piperidin-4-yl)acetamide, TFA (0.038 g, 0.074 mmol, 34% yield) as a colorless solid. LCMS (ESI) m/e 491.4 [(M+H)$^+$, calcd for C$_{25}$H$_{31}$N$_8$OS 491.2]. $^1$H NMR (400 MHz, CHLOROFORM-d) δ ppm 12.51 (br. s, 1H), 8.35 (t, J=1.76 Hz, 1H), 8.29-8.34 (m, 1H), 7.91 (s, 1H), 7.50 (t, J=7.93 Hz, 1H), 7.46 (d, J=2.52 Hz, 1H), 7.37 (d, J=7.81 Hz, 1H), 7.23 (br. s, 1H), 6.51 (d, J=2.52 Hz, 1H), 4.11-4.21 (m, 1H), 3.75 (s, 2H), 3.39-3.51 (m, J=7.05, 6.90, 6.90, 6.90, 6.90, 6.90 Hz, 1H), 3.17 (d, J=11.58 Hz, 2H), 2.20-2.27 (m, 2H), 2.19 (s, 3H), 1.90-2.06 (m, 4H), 1.47 (d, J=7.05 Hz, 6H); HPLC retention time (method A): t$_R$=5.81 min; HPLC retention time (method B): t$_R$=6.61 min.

Example 54

N-(3-(2-isopropyl-2H-tetrazol-5-yl)phenyl)-5-((4-methylpiperazin-1-yl)methyl)pyrrolo[2,1-f][1,2,4]triazin-4-amine

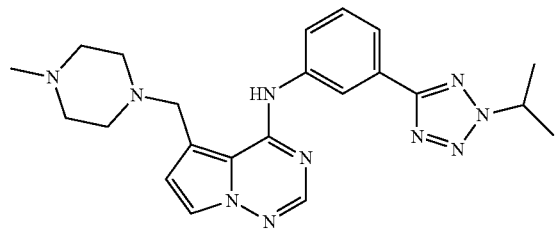 [SMILES: CC(C)n1nnc(-c2cccc(Nc3ncnn4ccc(CN5CCN(C)CC5)c34)c2)n1]

Prepared as in Example 1, Part B using 3-(2-isopropyl-2H-tetrazol-5-yl)aniline (0.164 g, 0.805 mmol) and 1-methylpiperazine (0.081 g, 0.805 mmol) to afford N-(3-(2-isopropyl-2H-tetrazol-5-yl)phenyl)-5-((4-methylpiperazin-1-yl)methyl)pyrrolo[1,2-f][1,2,4]triazin-4-amine, HCl (0.2778 g, 0.586 mmol, 73% yield) as a brown oil. LCMS (ESI) m/e 433.2 [(M+H)$^+$, calcd for $C_{22}H_{29}N_{10}$ 433.3].

$^1$H NMR (400 MHz, MeOD) δ 8.24 (t, J=1.8 Hz, 1H), 7.98 (dd, J=7.9, 1.1 Hz, 1H), 7.90-7.85 (m, 1H), 7.84 (s, 1H), 7.67-7.63 (m, 1H), 7.63-7.58 (m, 1H), 6.76 (d, J=2.8 Hz, 1H), 5.19-5.09 (m, 4H), 4.06 (s, 2H), 3.58-3.33 (m, 4H), 3.29 (dt, J=3.3, 1.6 Hz, 1H), 2.96 (s, 3H), 1.67 (d, J=6.5 Hz, 6H); HPLC retention time (method C): $t_R$=8.31 min.

Example 55

N-(3-(5-isopropyl-1,3,4-thiadiazol-2-yl)phenyl)-5-((4-methylpiperazin-1-yl)methyl)pyrrolo[2,1-f][1,2,4]triazin-4-amine

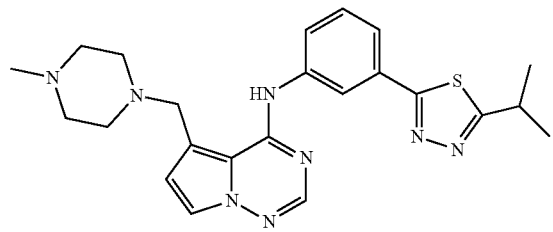 [SMILES: CC(C)c1nnc(-c2cccc(Nc3ncnn4ccc(CN5CCN(C)CC5)c34)c2)s1]

Prepared as in Example 1, Part B using 3-(5-isopropyl-1,3,4-thiadiazol-2-yl)aniline (0.180 g, 0.820 mmol) and 1-methylpiperazine (0.082 g, 0.820 mmol) to afford N-(3-(5-isopropyl-1,3,4-thiadiazol-2-yl)phenyl)-5-((4-methylpiperazin-1-yl)methyl)pyrrolo[1,2-f][1,2,4]triazin-4-amine, HCl (0.225 g, 0.459 mmol, 56% yield) as a yellow solid. LCMS (ESI) m/e 449.2 [(M+H)$^+$, calcd for $C_{23}H_{29}N_8S$ 449.2]. $^1$H NMR (400 MHz, MeOD) δ 8.20 (t, J=1.8 Hz, 1H), 7.83 (s, 1H), 7.81 (ddd, J=8.1, 2.2, 1.0 Hz, 1H), 7.76-7.72 (m, 1H), 7.65 (d, J=2.5 Hz, 1H), 7.63-7.56 (m, 1H), 6.77 (d, J=2.5 Hz, 1H), 5.35-5.20 (m, 4H), 4.10 (s, 2H), 3.54-3.34 (m, 4H), 3.29 (dt, J=3.3, 1.6 Hz, 1H), 2.97 (s, 3H), 1.45 (d, J=7.1 Hz, 6H); HPLC retention time (method C): $t_R$=9.47 min.

Example 56

N-(3-(5-isopropyl-1,3,4-thiadiazol-2-yl)phenyl)-5-(morpholinomethyl)pyrrolo[2,1-f][1,2,4]triazin-4-amine

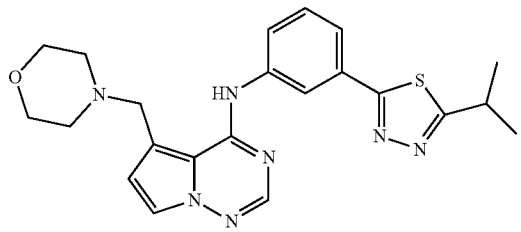 [SMILES: CC(C)c1nnc(-c2cccc(Nc3ncnn4ccc(CN5CCOCC5)c34)c2)s1]

Prepared as in Example 1, Part B using 3-(5-isopropyl-1,3,4-thiadiazol-2-yl)aniline (0.182 g, 0.828 mmol) and morpholine (0.072 mL, 0.828 mmol) to afford N-(3-(5-isopropyl-1,3,4-thiadiazol-2-yl)phenyl)-5-(morpholinomethyl)pyrrolo[1,2-f][1,2,4]triazin-4-amine, HCl (0.132 g, 0.273 mmol, 33% yield) as a yellow solid. LCMS (ESI) m/e 436.1 [(M+H)$^+$, calcd for $C_{22}H_{26}N_7OS$ 436.2]. $^1$H NMR (400 MHz, MeOD) δ 7.83-7.79 (m, 1H), 7.74 (dt, J=8.1, 1.1 Hz, 1H), 7.58 (t, J=7.8 Hz, 1H), 7.53 (s, 1H), 7.49 (d, J=2.8 Hz, 1H), 7.37 (dt, J=8.0, 0.9 Hz, 1H), 6.69 (d, J=2.8 Hz, 1H), 5.08 (br. s, 4H), 4.57 (s, 2H), 4.15-3.87 (m, 2H), 3.52-3.41 (m, 1H), 3.23-3.05 (m, 2H), 1.44 (d, J=6.8 Hz, 6H); HPLC retention time (method C): $t_R$=8.36 min.

Example 57

N-(3-(2-isopropyl-2H-tetrazol-5-yl)phenyl)-5-(morpholinomethyl)pyrrolo[2,1-f][1,2,4]triazin-4-amine

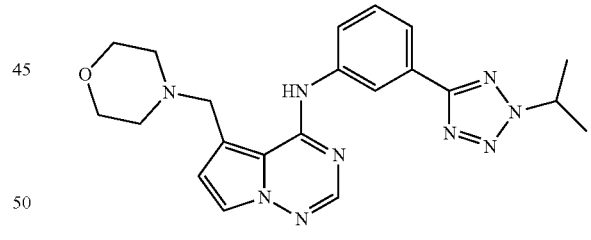

Prepared as in Example 1, Part B using 3-(2-isopropyl-2H-tetrazol-5-yl)aniline (0.164 g, 0.805 mmol) and morpholine (0.070 mL, 0.805 mmol) to afford N-(3-(2-isopropyl-2H-tetrazol-5-yl)phenyl)-5-(morpholinomethyl)pyrrolo[1,2-f][1,2,4]triazin-4-amine, HCl (0.1889 g, 0.406 mmol, 50% yield) as a yellow oil. LCMS (ESI) m/e 420.2 [(M+H)$^+$, calcd for $C_{21}H_{26}N_9O$ 420.2]. $^1$H NMR (400 MHz, MeOD) δ 7.99-7.92 (m, 2H), 7.66-7.57 (m, 1H), 7.54 (s, 1H), 7.50 (d, J=2.8 Hz, 1H), 7.39-7.33 (m, 1H), 6.70 (d, J=2.8 Hz, 1H), 5.21-5.00 (m, 5H), 4.55 (s, 2H), 4.13-3.90 (m, 2H), 3.73-3.54 (m, 2H), 3.52-3.35 (m, 2H), 3.23-3.02 (m, 2H), 1.66 (d, J=6.8 Hz, 6H); HPLC retention time (method C): $t_R$=8.13 min.

Example 58

N-(3-(2-isopropyl-2H-tetrazol-5-yl)phenyl)-5-((8-methyl-8-azabicyclo[3.2.1]octan-3-ylamino)methyl)pyrrolo[1,2-f][1,2,4]triazin-4-amine

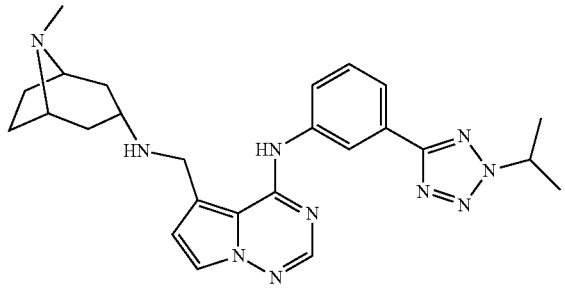 [SMILES: CC(C)n1nnc(-c2cccc(Nc3ncnn4ccc(CNC5CC6CCC(C5)N6C)c34)c2)n1]

Prepared as in Example 1, Part B using 3-(2-isopropyl-2H-tetrazol-5-yl)aniline (0.152 g, 0.747 mmol) and 8-methyl-8-azabicyclo[3.2.1]octan-3-amine (0.209 g, 1.494 mmol) to afford N-(3-(2-isopropyl-2H-tetrazol-5-yl)phenyl)-5-((8-methyl-8-azabicyclo[3.2.1]octan-3-ylamino)methyl)pyrrolo[1,2-f][1,2,4]triazin-4-amine (0.028 g, 0.056 mmol, 8% yield) as a colorless solid. LCMS (ESI) m/e 473.4 [(M+H)+, calcd for $C_{25}H_{33}N_{10}$ 473.3]. $^1$H NMR (400 MHz, CHLOROFORM-d) δ 8.24 (t, J=1.8 Hz, 1H), 8.12-8.07 (m, 1H), 7.96 (s, 1H), 7.86 (dt, J=7.7, 1.2 Hz, 1H), 7.49 (t, J=7.9 Hz, 1H), 7.45 (d, J=2.5 Hz, 1H), 6.51 (d, J=2.5 Hz, 1H), 5.09 (spt, J=6.7 Hz, 1H), 4.11 (br. s, 2H), 3.51 (br. s, 2H), 3.17 (d, J=6.8 Hz, 1H), 2.67 (dd, J=9.7, 4.4 Hz, 2H), 2.50 (s, 3H), 2.28-2.17 (m, 3H), 2.11-2.02 (m, 2H), 1.92 (d, J=15.1 Hz, 2H), 1.69 (d, J=6.5 Hz, 6H).

Example 59

(1R,5S)-8-((4-((3-(2-isopropyl-2H-tetrazol-5-yl)phenyl)amino)pyrrolo[2,1-f][1,2,4]triazin-5-yl)methyl)-8-azabicyclo[3.2.1]octan-3-ol

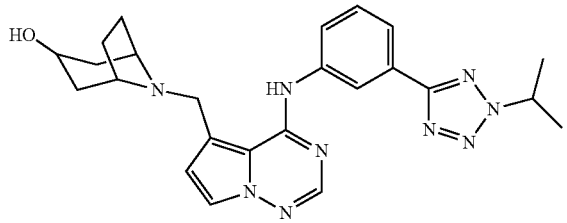 [SMILES: CC(C)n1nnc(-c2cccc(Nc3ncnn4ccc(CN5C6CCC5CC(O)C6)c34)c2)n1]

Prepared as in Example 1, Part B using 3-(2-isopropyl-2H-tetrazol-5-yl)aniline (0.152 g, 0.747 mmol) and 8-azabicyclo[3.2.1]octan-3-ol (0.095 g, 0.747 mmol) to afford 8-((4-(3-(2-isopropyl-2H-tetrazol-5-yl)phenylamino)pyrrolo[1,2-f][1,2,4]triazin-5-yl)methyl)-8-azabicyclo[3.2.1]octan-3-ol (0.057 g, 0.123 mmol, 16% yield) as a colorless solid. LCMS (ESI) m/e 460.4 [(M+H)+, calcd for $C_{24}H_{30}N_9O$ 460.3]. $^1$H NMR (400 MHz, CHLOROFORM-d) δ 8.14 (br. s, 1H), 8.03-7.83 (m, 3H), 7.49 (t, J=7.9 Hz, 1H), 7.46-7.43 (m, 1H), 6.46 (br. s, 1H), 5.08 (quin, J=6.7 Hz, 1H), 4.22 (t, J=4.8 Hz, 1H), 3.74 (br. s, 2H), 3.34 (br. s, 2H), 2.32-2.15 (m, 4H), 2.13-2.02 (m, 2H), 1.82 (d, J=13.3 Hz, 2H), 1.71-1.64 (m, 6H).

Example 60

N-(3-(2-isopropyl-2H-tetrazol-5-yl)phenyl)-5-(((1R,5S)-3-methyl-3,8-diazabicyclo[3.2.1]octan-8-yl)methyl)pyrrolo[2,1-f][1,2,4]triazin-4-amine

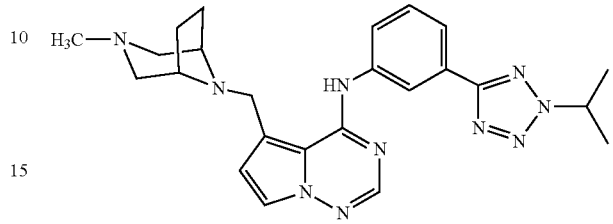

Prepared as in Example 1, Part B using 3-(2-isopropyl-2H-tetrazol-5-yl)aniline (0.152 g, 0.747 mmol) and 3-methyl-3,8-diazabicyclo[3.2.1]octane (0.094 g, 0.747 mmol) to afford N-(3-(2-isopropyl-2H-tetrazol-5-yl)phenyl)-5-(((1R,5S)-3-methyl-3,8-diazabicyclo[3.2.1]octan-8-yl)methyl)pyrrolo[2,1-f][1,2,4]triazin-4-amine (0.062 g, 0.134 mmol, 18% yield) as a colorless solid. LCMS (ESI) m/e 459.4 [(M+H)+, calcd for $C_{24}H_{31}N_{10}$ 459.3]. $^1$H NMR (400 MHz, CHLOROFORM-d) δ 8.39 (br. s, 1H), 8.02-7.89 (m, 3H), 7.51 (t, J=7.8 Hz, 1H), 7.46 (d, J=2.5 Hz, 1H), 6.47 (br. s, 1H), 5.09 (spt, J=6.7 Hz, 1H), 3.76 (br. s, 2H), 3.29 (br. s, 2H), 2.66 (d, J=9.8 Hz, 2H), 2.43 (d, J=10.3 Hz, 2H), 2.21 (s, 3H), 2.07-1.98 (m, 2H), 1.89 (d, J=6.8 Hz, 2H), 1.69 (d, J=6.8 Hz, 6H).

Example 61

N-(3-(2-isopropyl-2H-tetrazol-5-yl)phenyl)-5-(((3-(2-isopropyl-2H-tetrazol-5-yl)phenyl)amino)methyl)pyrrolo[2,1-f][1,2,4]triazin-4-amine

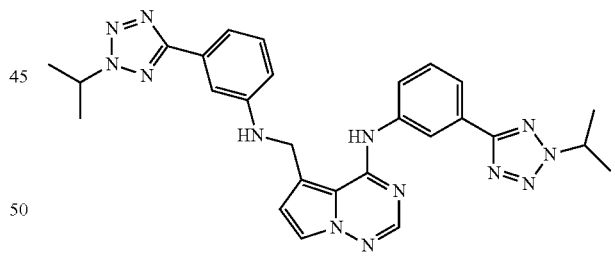

Prepared as in Example 1, Part B using 3-(2-isopropyl-2H-tetrazol-5-yl)aniline (0.152 g, 0.747 mmol) to afford N-(3-(2-isopropyl-2H-tetrazol-5-yl)phenyl)-5-(((3-(2-isopropyl-2H-tetrazol-5-yl)phenyl)amino)methyl)pyrrolo[2,1-f][1,2,4]triazin-4-amine (0.060 g, 0.108 mmol, 14% yield) as a colorless solid. LCMS (ESI) m/e 536.3 [(M+H)+, calcd for $C_{27}H_{30}N_{13}$ 536.3]. $^1$H NMR (400 MHz, CHLOROFORM-d) δ 10.52 (s, 1H), 8.38 (t, J=1.8 Hz, 1H), 8.02 (s, 1H), 7.80-7.72 (m, 3H), 7.61-7.53 (m, 1H), 7.50 (d, J=2.5 Hz, 1H), 7.43 (t, J=7.8 Hz, 1H), 7.30 (t, J=7.9 Hz, 1H), 7.13-7.06 (m, 1H), 6.62 (d, J=2.5 Hz, 1H), 5.13-5.04 (m, 1H), 5.04-4.95 (m, 1H), 4.61 (d, J=5.8 Hz, 2H), 4.44 (t, J=5.9 Hz, 1H), 1.67 (d, J=6.8 Hz, 6H), 1.61 (d, J=6.5 Hz, 6H).

Example 62

5-((4-aminopiperidin-1-yl)methyl)-N-(3-isopropoxy-5-(2-isopropyl-2H-tetrazol-5-yl)phenyl)pyrrolo[2,1-f][1,2,4]triazin-4-amine

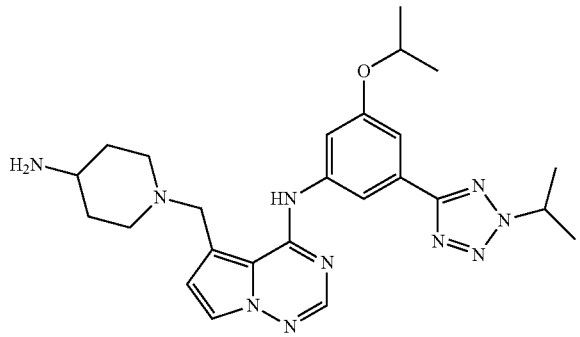 [SMILES: CC(C)Oc1cc(Nc2ncnn3ccc(CN4CCC(N)CC4)c23)cc(-c2nnn(C(C)C)n2)c1]

Prepared as in Example 1, Parts B and C using 3-isopropoxy-5-(2-isopropyl-2H-tetrazol-5-yl)aniline (0.180 g, 0.690 mmol) and tert-butyl piperidin-4-ylcarbamate (0.138 g, 0.690 mmol) to afford 5-((4-aminopiperidin-1-yl)methyl)-N-(3-isopropoxy-5-(2-isopropyl-2H-tetrazol-5-yl)phenyl) pyrrolo[1,2-f][1,2,4]triazin-4-amine, 2 TFA (0.1755 g, 0.234 mmol, 35% yield for 2 steps) as a colorless solid.

LCMS (ESI) m/e 491.2 [(M+H)$^+$, calcd for $C_{25}H_{35}N_{10}O$ 491.3]. $^1$H NMR (400 MHz, MeOD) δ 7.53 (s, 1H), 7.49 (d, J=2.8 Hz, 1H), 7.48-7.46 (m, 2H), 6.93 (t, J=1.8 Hz, 1H), 6.70 (d, J=2.8 Hz, 1H), 5.21-5.10 (m, 1H), 4.72 (dquin, J=12.1, 6.0 Hz, 1H), 4.57 (s, 2H), 3.68 (br. s, 2H), 3.53-3.36 (m, 1H), 3.14 (br. s, 2H), 2.26 (d, J=12.6 Hz, 2H), 1.92-1.74 (m, 2H), 1.67 (d, J=6.8 Hz, 6H), 1.37 (d, J=6.0 Hz, 6H); HPLC retention time (method C): $t_R$=11.19 min.

Example 63

N-(3-(2-isopropyl-2H-tetrazol-5-yl)phenyl)-5-((methylamino)methyl)pyrrolo[2,1-f][1,2,4]triazin-4-amine

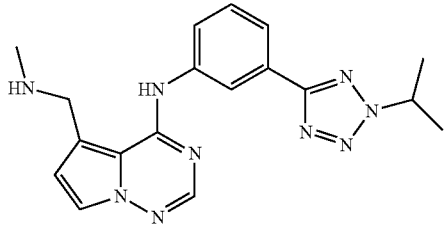 [SMILES: CNCc1ccn2ncnc(Nc3cccc(-c4nnn(C(C)C)n4)c3)c12]

Prepared as in Example 1, Part B using 3-(2-isopropyl-2H-tetrazol-5-yl)aniline (0.126 g, 0.618 mmol) and methanamine (0.309 mL, 0.618 mmol) to afford N-(3-(2-isopropyl-2H-tetrazol-5-yl)phenyl)-5-((methylamino)methyl) pyrrolo[1,2-f][1,2,4]triazin-4-amine, TFA (0.116 g, 0.238 mmol, 39% yield) as a brown oil. LCMS (ESI) m/e 364.2 [(M+H)$^+$, calcd for $C_{18}H_{22}N_9$ 364.3]. $^1$H NMR (400 MHz, MeOD) 7.95-7.89 (m, 2H), 7.61-7.53 (m, 1H), 7.50 (s, 1H), 7.47 (d, J=2.8 Hz, 1H), 7.32 (dt, J=7.6, 1.3 Hz, 1H), 6.69 (d, J=2.8 Hz, 1H), 5.15 (spt, J=6.7 Hz, 1H), 4.47 (s, 2H), 2.75 (s, 3H), 1.67 (d, J=6.5 Hz, 6H); HPLC retention time (method C): $t_R$=7.15 min.

Example 64

1-((4-((3-(2-isopropyl-2H-tetrazol-5-yl)phenyl) amino)pyrrolo[2,1-f][1,2,4]triazin-5-yl)methyl)azetidine-3-carbonitrile Prepared as in Example 1, Part B using 3-(2-isopropyl-2H-tetrazol-5-yl)aniline (0.133 g, 0.656 mmol) and azetidine-3-carbonitrile, HCl (0.078 g, 0.656 mmol) to afford 1-((4-(3-(2-isopropyl-2H-tetrazol-5-yl)phenylamino)pyrrolo[1,2-f][1,2,4]triazin-5-yl)methyl)azetidine-3-carbonitrile, TFA (0.1558 g, 0.289 mmol, 44% yield) as a brown oil. LCMS (ESI) m/e 415.1 [(M+H)$^+$, calcd for $C_{21}H_{23}N_{10}$ 415.2]. $^1$H NMR (400 MHz, MeOD) δ 8.08 (d, J=1.8 Hz, 1H), 8.00 (dt, J=7.7, 1.3 Hz, 1H), 7.65-7.57 (m, 3H), 7.53-7.45 (m, 1H), 6.78 (d, J=2.8 Hz, 1H), 5.16 (spt, J=6.5 Hz, 1H), 4.57 (s, 2H), 4.25 (d, J=7.1 Hz, 4H), 3.87 (quin, J=7.8 Hz, 1H), 1.66 (d, J=6.5 Hz, 6H); HPLC retention time (method C): $t_R$=10.05 min.

Example 65

1-((4-((3-(2-isopropyl-2H-tetrazol-5-yl)phenyl) amino)pyrrolo[2,1-f][1,2,4]triazin-5-yl)methyl)piperidine-4-carbonitrile Prepared as in Example 1, Part B using 3-(2-isopropyl-2H-tetrazol-5-yl)aniline (0.117 g, 0.575 mmol) and piperidine-4-carbonitrile (0.063 g, 0.575 mmol) to afford 1-((4-(3-(2-isopropyl-2H-tetrazol-5-yl)phenylamino)pyrrolo[1,2-f][1,2,4]triazin-5-yl)methyl)piperidine-4-carbonitrile, TFA (0.0352 g, 0.062 mmol, 11% yield) as a pale brown solid. LCMS (ESI) m/e 443.3 [(M+H)$^+$, calcd for $C_{23}H_{27}N_{10}$ 443.2]. $^1$H NMR (400 MHz, MeOD) δ 7.98 (d, J=8.1 Hz, 1H), 7.92 (d, J=1.8 Hz, 1H), 7.62 (t, J=7.8 Hz, 1H), 7.53 (s, 1H), 7.50 (d, J=2.8 Hz, 1H), 7.36 (dd, J=7.9, 1.1 Hz, 1H), 6.68 (d, J=2.8 Hz, 1H), 5.16 (spt, J=6.7 Hz, 1H), 4.50 (br. s, 2H), 3.53 (br. s, 2H), 3.04 (br. s, 3H), 2.42-1.78 (m, 4H), 1.67 (d, J=6.8 Hz, 6H); HPLC retention time (method C): $t_R$=9.18 min.

Example 66

2-(((4-((3-(2-isopropyl-2H-tetrazol-5-yl)phenyl)amino)pyrrolo[2,1-f][1,2,4]triazin-5-yl)methyl)amino)acetonitrile

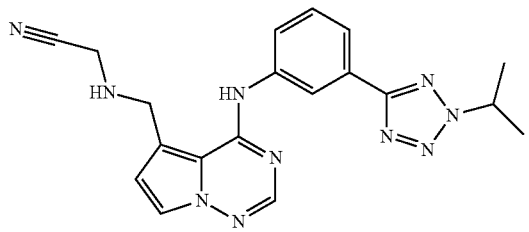 [SMILES: CC(C)n1nnc(-c2cccc(Nc3ncnn4ccc(CNCC#N)c34)c2)n1]

Prepared as in Example 1, Part B using 3-(2-isopropyl-2H-tetrazol-5-yl)aniline (0.114 g, 0.560 mmol) and 2-aminoacetonitrile (0.031 g, 0.560 mmol) to afford 2-((4-(3-(2-isopropyl-2H-tetrazol-5-yl)phenylamino)pyrrolo[1,2-f][1,2,4]triazin-5-yl)methylamino)acetonitrile, TFA (0.0116 g, 0.022 mmol, 4% yield) as an off-white solid. LCMS (ESI) m/e 389.2 [(M+H)+, calcd for $C_{19}H_{21}N_{10}$ 389.3]. 1H NMR (400 MHz, CHLOROFORM-d) δ 8.26 (br. s, 1H), 7.95-7.78 (m, 3H), 7.56 (s, 1H), 7.45 (t, J=6.9 Hz, 1H), 6.77 (br. s, 1H), 5.15-5.01 (m, 1H), 4.39 (br. s, 2H), 3.99 (br. s, 2H), 1.71 (d, J=6.8 Hz, 6H); HPLC retention time (method C): $t_R$=11.29 min.

Example 67

(R)-2-amino-N-(3-((5-((4-aminopiperidin-1-yl)methyl)pyrrolo[2,1-f][1,2,4]triazin-4-yl)amino)phenyl)-4-methylpentanamide

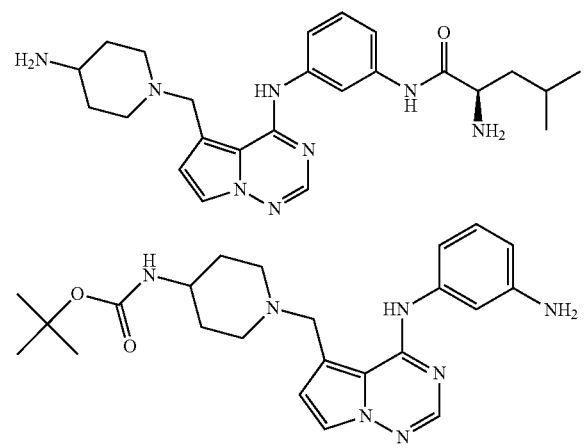

Part A: tert-butyl (1-((4-((3-aminophenyl)amino)pyrrolo[2,1-f][1,2,4]triazin-5-yl)methyl)piperidin-4-yl)carbamate Prepared as in Example 1, Part B using benzene-1,3-diamine (31.1 mg, 0.288 mmol) (0.114 g, 0.560 mmol) and tert-butyl piperidin-4-ylcarbamate (57.6 mg, 0.288 mmol) to afford tert-butyl 1-((4-(3-aminophenylamino)pyrrolo[1,2-f][1,2,4]triazin-5-yl)methyl)piperidin-4-ylcarbamate (30 mg, 0.065 mmol, 23% yield) as a brown oil. LCMS (ESI) m/e 438.2 [(M+H)+, calcd for $C_{23}H_{32}N_7O$ 438.3].

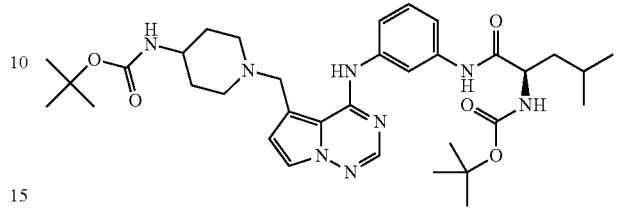

Part B: (R)-tert-butyl (1-((4-((3-(2-(tert-butylcarbomoylamino)-4-methylpentanamido)phenyl)amino)pyrrolo[2,1-f][1,2,4]triazin-5-yl)methyl)piperidin-4-yl)carbamate A solution of (R)-2-(tert-butoxycarbonylamino)-4-methylpentanoic acid (17.44 mg, 0.075 mmol), DCC (15.56 mg, 0.075 mmol) and DMAP (0.838 mg, 6.86 μmol) in DCM (686 μL) was stirred for 5 min. To this was added tert-butyl 1-((4-(3-aminophenylamino)pyrrolo[1,2-f][1,2,4]triazin-5-yl)methyl)piperidin-4-ylcarbamate (30 mg, 0.069 mmol) and DMAP (0.838 mg, 6.86 μmol). Continued stirring at room temperature overnight. The reaction mixture was concentrated under reduced pressure and purified by reverse phase HPLC (20%-100% MeOH/$H_2O$/0.1% TFA). Obtained (R)-tert-butyl (1-((4-((3-(2-(tert-butylcarbomoylamino)-4-methylpentanamido)phenyl)amino)pyrrolo[2,1-f][1,2,4]triazin-5-yl)methyl)piperidin-4-yl)carbamate (10 mg, 0.014 mmol, 21% yield) as a brown oil as well (R)-tert-butyl 1-(3-(5-((4-aminopiperidin-1-yl)methyl)pyrrolo[1,2-f][1,2,4]triazin-4-ylamino)phenylamino)-4-methyl-1-oxopentan-2-ylcarbamate (5 mg, 9.08 μmol, 13% yield) as a brown oil. Combined the two in the next step (Boc deprotection).

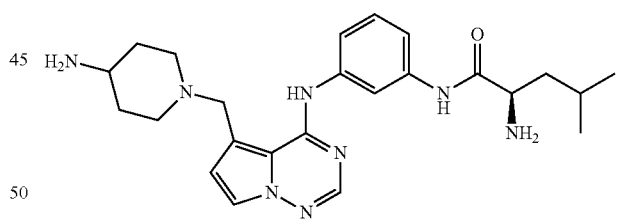

Part C: (R)-2-amino-N-(3-((5-((4-aminopiperidin-1-yl)methyl)pyrrolo[2,1-f][1,2,4]triazin-4-yl)amino)phenyl)-4-methylpentanamide A solution of (R)-tert-butyl (1-((4-((3-(2-(tert-butylcarbomoylamino)-4-methylpentanamido)phenyl)amino)pyrrolo[2,1-f][1,2,4]triazin-5-yl)methyl)piperidin-4-yl)carbamate (10 mg, 0.014 mmol) and (R)-tert-butyl 1-(3-(5-((4-aminopiperidin-1-yl)methyl)pyrrolo[1,2-f][1,2,4]triazin-4-ylamino)phenylamino)-4-methyl-1-oxopentan-2-ylcarbamate (5 mg, 9.08 μmol) in hydrogen chloride (2M in diethyl ether) (1152 μL, 2.305 mmol) was stirred at room temperature for 2 h. The reaction mixture was concentrated under reduced pressure and purified by reverse phase HPLC (10%-80% MeOH/H₂O/0.1% TFA). Obtained (R)-2-amino-N-(3-(5-((4-aminopiperidin-1-yl)methyl)pyrrolo[1,2-f][1,2,4]triazin-4-ylamino)phenyl)-4-methylpentanamide, 2 TFA (2 mg, 2.80 µmol, 12% yield) as a pale brown oil.

LCMS (ESI) m/e 451.3 [(M+H)⁺, calcd for $C_{24}H_{35}N_8O$ 451.3]. ¹H NMR (400 MHz, MeOD) δ ppm 7.96 (s, 1H), 7.51 (s, 1H), 7.49 (d, J=2.8 Hz, 1H), 7.44 (t, J=7.9 Hz, 1H), 7.03 (br. s, 1H), 6.98 (d, J=8.1 Hz, 2H), 6.66 (d, J=2.8 Hz, 1H), 4.48 (s, 2H), 3.86-3.95 (m, 1H), 3.55-3.65 (m, 3H), 3.01-3.14 (m, 2H), 2.06-2.18 (m, 2H), 1.47-1.90 (m, 4H), 1.09-1.21 (m, 1H), 0.88-1.03 (m, 6H); HPLC retention time (method E): $t_R$=5.21 min; HPLC retention time (method F): $t_R$=5.86 min.

Example 68

5-((4-aminopiperidin-1-yl)methyl)-7-bromo-N-(3-(oxazol-5-yl)phenyl)pyrrolo[2,1-f][1,2,4]triazin-4-amine

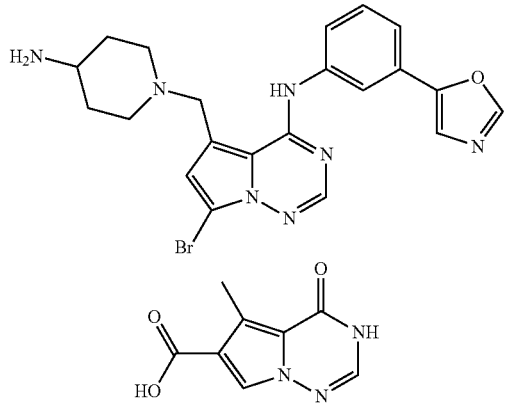

Part A: 5-methyl-4-oxo-3,4-dihydropyrrolo[2,1-f][1,2,4]triazine-6-carboxylic acid To a solution of the methyl 5-methyl-4-oxo-3,4-dihydropyrrolo[1,2-f][1,2,4]triazine-6-carboxylate (19 g, 92 mmol) in MeOH (300 mL) at room temperature was added sodium hydroxide (275 mL, 275 mmol). The reaction mixture was heated to reflux overnight. The reaction mixture was concentrated under reduced pressure to remove most of the methanol. The solution was acidified with conc. HCl to pH 6 and extracted with ethyl acetate (4×500 mL). The combined organic layers were washed with water (1×50 mL), brine (1×50 mL), dried (MgSO₄), filtered and concentrated under reduced pressure to obtain 5-methyl-4-oxo-3,4-dihydropyrrolo[1,2-f][1,2,4]triazine-6-carboxylic acid (16.98 g, 88 mmol, 96% yield). Product was carried on without further purification. LCMS (ESI) m/e 194.2 [(M+H)⁺, calcd for $C_8H_8N_3O_3$ 194.1].

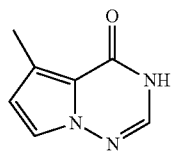

Part B:
5-methylpyrrolo[2,1-f][1,2,4]triazin-4(3H)-one

A mixture of 5-methyl-4-oxo-3,4-dihydropyrrolo[1,2-f][1,2,4]triazine-6-carboxylic acid (16.91 g, 88 mmol) and phosphoric acid (101 g, 875 mmol) (85% wt in water) was heated in a round bottom flask at 110° C. for 18 h. Addition of phosphoric acid was done slowly as some frothing was observed. The reaction mixture was allowed to cool to room temperature and poured into ice water. The mixture was filtered through a Buchner funnel to collect the solid residue. The residue was washed with cold water to remove excess acid. The filtrate still had some product, so was extracted with ethyl acetate (3×300 mL). The combined organic layers were washed with water (3×100 mL), brine (3×100 mL), and dried (MgSO4). The solution was concentrated to obtain brown solid. The two batches of solid were combined to obtain 5-methylpyrrolo[1,2-f][1,2,4]triazin-4(3H)-one (11.02 g, 73.9 mmol, 84% yield) as brown solid. The product was carried on without further purification. LCMS (ESI) m/e 150.2 [(M+H)⁺, calcd for $C_7H_8N_3O$ 150.1].

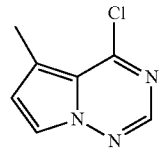

Part C:
4-chloro-5-methylpyrrolo[2,1-f][1,2,4]triazine

To a solution of 5-methylpyrrolo[1,2-f][1,2,4]triazin-4(3H)-one (10.91 g, 73.1 mmol) in dry toluene (200 mL) at room temperature under nitrogen was added POCl₃ (8.59 mL, 92 mmol) and DIEA (10.09 mL, 57.8 mmol). The reaction mixture was heated to reflux for 5 h. The reaction mixture was concentrated under reduced pressure and the residue was dissolved in dichloromethane. The organics was washed with saturated aqueous sodium bicarbonate (2×100 mL), dried (MgSO₄) and concentrated under reduced pressure. The residue was purified via silica gel chromatography (dichloromethane) to obtain 4-chloro-5-methylpyrrolo[1,2-f][1,2,4]triazine (8.7 g, 51.9 mmol, 71% yield) as yellow solid. LCMS (ESI) m/e 168.3 [(M+H)⁺, calcd for $C_7H_7ClN_3$ 168.1].

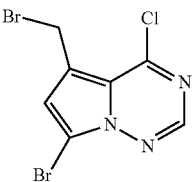

Part D: 7-bromo-5-(bromomethyl)-4-chloropyrrolo[2,1-f][1,2,4]triazine

To a solution of the 4-chloro-5-methylpyrrolo[1,2-f][1,2,4]triazine (8.7 g, 51.9 mmol) in dry CCl₄ (300 mL) under nitrogen atmosphere at room temperature was added NBS (10.16 g, 57.1 mmol) and AIBN (0.852 g, 5.19 mmol). The reaction mixture was heated to reflux for 110 min. The solution was cooled to room temperature, poured into a separatory funnel then washed with cold saturated NaHCO$_3$ solution aqueous (1×150 mL). The organic layer was separated and washed with brine (1×150 mL) and dried (MgSO$_4$). The solution was concentrated under reduced pressure to obtain 7-bromo-5-(bromomethyl)-4-chloropyrrolo[1,2-f][1,2,4]triazine (12 g, 36.9 mmol, 71% yield). The product was carried on without further purification. LCMS (ESI) m/e 324.0, 325.0 Br pattern [(M+H)$^+$, calcd for C$_7$H$_5$Br$_2$ClN$_3$ 323.9].

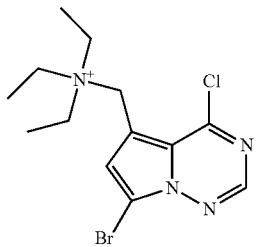 [SMILES: CC[N+](CC)(CC)Cc1cc(Br)n2ncnc(Cl)c12]

Part E: N-((7-bromo-4-chloropyrrolo[2,1-f][1,2,4]triazin-5-yl)methyl)-N,N-diethylethanaminium To a solution of 7-bromo-5-(bromomethyl)-4-chloropyrrolo[1,2-f][1,2,4]triazine (12 g, 36.9 mmol) in dry THF (200 mL) at room temperature under nitrogen was added TEA (12.85 mL, 92 mmol). The reaction mixture was stirred overnight. A light brown solid crashed out of the reaction mixture. The light brown solid was collected by vacuum filtration and washed with cold THF to obtain N-((7-bromo-4-chloropyrrolo[1,2-f][1,2,4]triazin-5-yl)methyl)-N,N-diethylethanaminium, bromate salt (13.2 g, 27.8 mmol, 75% yield). Solid was dried under vacuum and used as such without further purification. The material was stored under nitrogen in a dry dessicator until needed. LCMS (ESI) m/e 345.2, 347.2 Br pattern [(M)$^+$, calcd for C$_{13}$H$_{19}$BrClN$_4$ 345.1].

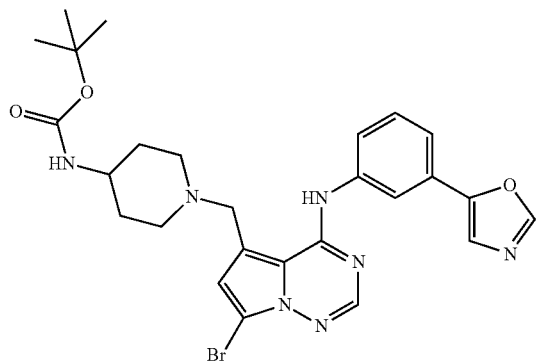 [SMILES: CC(C)(C)OC(=O)NC1CCN(Cc2cc(Br)n3ncnc(Nc4cccc(-c5cnco5)c4)c23)CC1]

Part F: tert-butyl (1-((7-bromo-4-((3-(oxazol-5-yl)phenyl)amino)pyrrolo[2,1-f][1,2,4]triazin-5-yl)methyl)piperidin-4-yl)carbamate To a solution of N-((7-bromo-4-chloropyrrolo[1,2-f][1,2,4]triazin-5-yl)methyl)-N,N-diethylethanaminium (0.5 g, 1.442 mmol) in dry acetonitrile (10 mL) in a microwave tube flushed with nitrogen was added 3-(oxazol-5-yl)aniline (0.231 g, 1.442 mmol). The reaction tube was capped and heated in the microwave at 75° C. for 30 min. To the reaction mixture was added tert-butyl piperidin-4-ylcarbamate (0.289 g, 1.442 mmol) and DIEA (0.252 mL, 1.442 mmol). The reaction tube was capped again and heated in a microwave at 75° C. for 30 min. The reaction mixture was concentrated under reduced pressure and purified by silica gel chromatography (dichloromethane/ethyl acetate/0.5% TEA) to obtain tert-butyl 1-((7-bromo-4-(3-(oxazol-5-yl)phenylamino)pyrrolo[1,2-f][1,2,4]triazin-5-yl)methyl)piperidin-4-ylcarbamate (0.398 g, 0.700 mmol, 49% yield). LCMS (ESI) m/e 568.2, 570.2 Br pattern [(M+H)$^+$, calcd for C$_{26}$H$_{31}$BrN$_7$O$_3$ 568.2].

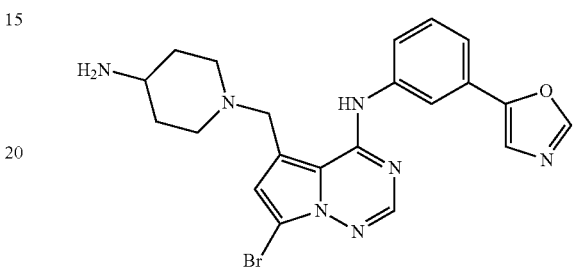

Part G: 5-((4-aminopiperidin-1-yl)methyl)-7-bromo-N-(3-(oxazol-5-yl)phenyl)pyrrolo[2,1-f][1,2,4]triazin-4-amine To a solution of tert-butyl 1-((7-bromo-4-(3-(oxazol-5-yl)phenylamino)pyrrolo[1,2-f][1,2,4]triazin-5-yl)methyl)piperidin-4-ylcarbamate (1.1 g, 1.935 mmol) in dry acetonitrile (10 mL) at room temperature was added TFA (1.491 mL, 19.35 mmol). The reaction mixture was stirred for 4 h. The reaction mixture was concentrated under reduced pressure and the residue redissolved in MeOH (2 mL) and purified by reverse phase preparative HPLC (water/Methanol/0.1% TFA) to obtain 5-((4-aminopiperidin-1-yl)methyl)-7-bromo-N-(3-(oxazol-5-yl)phenyl)pyrrolo[2,1-f][1,2,4]triazin-4-amine, TFA (0.542 g, 0.903 mmol, 47% yield) as an off-white solid. LCMS (ESI) m/e 468.2, 470.2 Br pattern [(M+H)$^+$, calcd for C$_{21}$H$_{23}$BrN$_7$O 468.2]. $^1$H NMR (400 MHz, CHLOROFORM-d) δ 7.95 (s, 1H), 7.90 (d, J=2.3 Hz, 2H), 7.42-7.30 (m, 3H), 7.26 (s, 1H), 6.51 (s, 1H), 3.74 (br. s, 2H), 3.14-2.95 (m, 3H), 2.22 (br. s, 2H), 1.96 (d, J=12.3 Hz, 2H), 1.70-1.51 (m, 2H); HPLC retention time (method C): t$_R$=4.90 min.

Example 69

N1-((4-((3-(5-isopropyl-1,3,4-thiadiazol-2-yl)phenyl)amino)pyrrolo[2,1-f][1,2,4]triazin-5-yl)methyl)propane-1,3-diamine

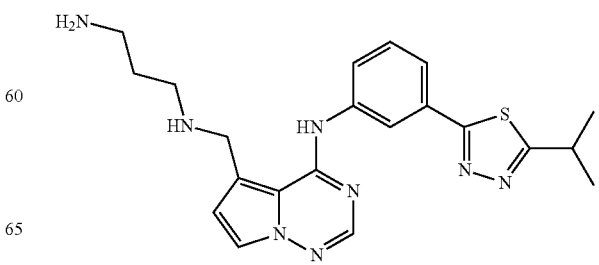

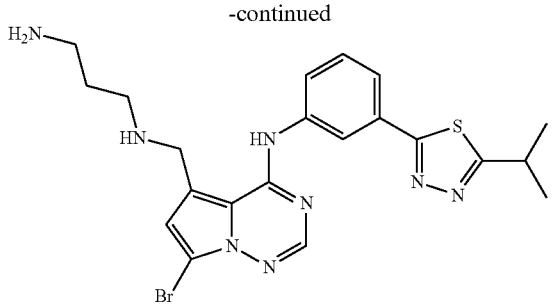

Part A: N1-((7-bromo-4-((3-(5-isopropyl-1,3,4-thiadiazol-2-yl)phenyl)amino)pyrrolo[2,1-f][1,2,4]triazin-5-yl)methyl)propane-1,3-diamine Prepared as in Example 68 using 3-(5-isopropyl-1,3,4-thiadiazol-2-yl)aniline (0.057 g, 0.258 mmol) and tert-butyl N-(3-aminopropyl)carbamate (0.045 mL, 0.258 mmol) in Part F to afford N1-((7-bromo-4-(3-(5-isopropyl-1,3,4-thiadiazol-2-yl)phenylamino)pyrrolo[1,2-f][1,2,4]triazin-5-yl)methyl)propane-1,3-diamine, TFA (0.075 g, 0.119 mmol) as an off-white solid after Boc deprotection. LCMS (ESI) m/e 501.2, 503.2 Br pattern [(M+H)$^+$, calcd for $C_{21}H_{26}BrN_8S$ 501.1]. $^1$H NMR (400 MHz, MeOD) δ 7.76 (s, 1H), 7.73-7.66 (m, 1H), 7.60-7.52 (m, 2H), 7.32 (d, J=7.8 Hz, 1H), 6.77 (s, 1H), 4.50 (s, 2H), 3.50 (spt, J=6.9 Hz, 1H), 3.25-3.14 (m, 2H), 3.05-2.94 (m, 2H), 2.14-2.00 (m, 2H), 1.46 (d, J=6.8 Hz, 6H).

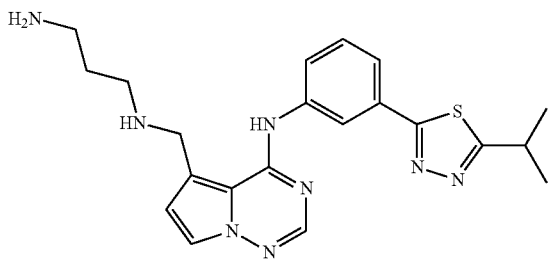 [SMILES: CC(C)c1nnc(-c2cccc(Nc3ncnn4ccc(CNCCCN)c34)c2)s1]

Part B: N1-((4-((3-(5-isopropyl-1,3,4-thiadiazol-2-yl)phenyl)amino)pyrrolo[2,1-f][1,2,4]triazin-5-yl)methyl)propane-1,3-diamine To a solution of N1-((7-bromo-4-(3-(5-isopropyl-1,3,4-thiadiazol-2-yl)phenylamino)pyrrolo[1,2-f][1,2,4]triazin-5-yl)methyl)propane-1,3-diamine, TFA (0.068 g, 0.110 mmol) in dry MeOH (30 mL) in a round bottom flask flushed with nitrogen was added Pd/C (0.032 g, 0.301 mmol) at room temperature. The flask was capped and the reaction mixture stirred under a balloon of hydrogen for 30 min. The reaction mixture was filtered through glass wool and concentrated under reduced pressure. The residue was redissolved in MeOH (2 mL) and purified by reverse phase preparative HPLC (water/Methanol/0.1% TFA) to obtain N1-((4-(3-(5-isopropyl-1,3,4-thiadiazol-2-yl)phenylamino)pyrrolo[1,2-f][1,2,4]triazin-5-yl)methyl)propane-1,3-diamine, TFA (0.0314 g, 0.058 mmol, 52% yield) as a pale brown oil. LCMS (ESI) m/e 423.3 [(M+H)$^+$, calcd for $C_{21}H_{27}N_8S$ 423.2]. $^1$H NMR (400 MHz, MeOD) δ 7.75 (t, J=1.6 Hz, 1H), 7.71 (dt, J=7.7, 1.3 Hz, 1H), 7.57 (t, J=7.9 Hz, 1H), 7.47 (s, 1H), 7.44 (d, J=2.8 Hz, 1H), 7.35-7.28 (m, 1H), 6.66 (d, J=2.8 Hz, 1H), 4.49 (s, 2H), 3.50 (spt, J=6.9 Hz, 1H), 3.24-3.16 (m, 2H), 3.02-2.97 (m, 2H), 2.13-2.01 (m, 2H), 1.46 (d, J=6.8 Hz, 6H); HPLC retention time (method C): $t_R$=5.08 min.

Example 70

N1-((4-((3-(5-isopropyl-1,3,4-thiadiazol-2-yl)phenyl)amino)pyrrolo[2,1-f][1,2,4]triazin-5-yl)methyl)-2-methylpropane-1,3-diamine

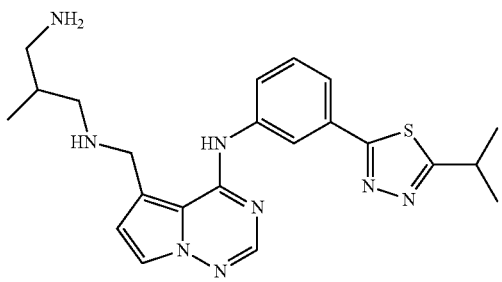 [SMILES: CC(CN)CNCc1ccn2ncnc(Nc3cccc(-c4nnc(C(C)C)s4)c3)c12]

Prepared as in Example 70 using 3-(5-isopropyl-1,3,4-thiadiazol-2-yl)aniline (0.052 g, 0.239 mmol) and tert-butyl 3-amino-2-methylpropylcarbamate (0.045 g, 0.239 mmol) to afford N1-((4-(3-(5-isopropyl-1,3,4-thiadiazol-2-yl)phenylamino)pyrrolo[1,2-f][1,2,4]triazin-5-yl)methyl)propane-1,3-diamine, TFA (0.0314 g, 0.058 mmol, 29% yield for 3 steps) as a pale brown oil. LCMS (ESI) m/e 437.3 [(M+H)$^+$, calcd for $C_{22}H_{29}N_8S$ 437.2]. $^1$H NMR (400 MHz, MeOD) δ 7.77-7.69 (m, 2H), 7.57 (t, J=8.2 Hz, 1H), 7.45 (s, 1H), 7.43 (d, J=2.8 Hz, 1H), 7.29 (d, J=8.6 Hz, 1H), 6.65 (d, J=2.8 Hz, 1H), 4.52-4.42 (m, 2H), 3.50 (spt, J=6.9 Hz, 1H), 3.21 (dd, J=12.8, 5.3 Hz, 1H), 3.07-2.97 (m, 2H), 2.86-2.74 (m, 1H), 2.34-2.17 (m, 1H), 1.46 (d, J=6.8 Hz, 6H), 1.05 (d, J=6.8 Hz, 3H); HPLC retention time (method C): $t_R$=4.95 min.

Example 71

5-((3-(aminomethyl)piperidin-1-yl)methyl)-N-(3-(5-isopropyl-1,3,4-thiadiazol-2-yl)phenyl)pyrrolo[2,1-f][1,2,4]triazin-4-amine

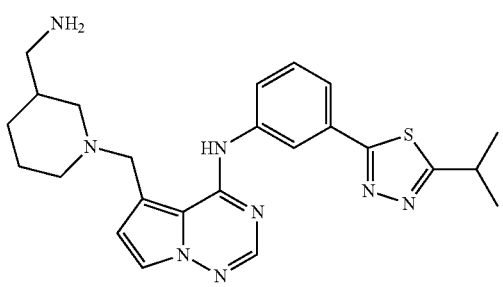 [SMILES: CC(C)c1nnc(-c2cccc(Nc3ncnn4ccc(CN5CCCC(CN)C5)c34)c2)s1]

Prepared as in Example 70 using 3-(5-isopropyl-1,3,4-thiadiazol-2-yl)aniline (0.057 g, 0.258 mmol) and tert-butyl piperidin-3-ylmethylcarbamate (0.055 g, 0.258 mmol) to afford 5-((3-(aminomethyl)piperidin-1-yl)methyl)-N-(3-(5-isopropyl-1,3,4-thiadiazol-2-yl)phenyl)pyrrolo[1,2-f][1,2,4]triazin-4-amine, TFA (0.0273 g, 0.047 mmol, 20% yield for 3 steps) as a pale brown oil. LCMS (ESI) m/e 463.4 [(M+H)⁺, calcd for $C_{24}H_{31}N_8S$ 463.2]. ¹H NMR (400 MHz, MeOD) δ 7.81-7.77 (m, 1H), 7.76-7.69 (m, 1H), 7.60 (t, J=7.8 Hz, 1H), 7.50 (s, 1H), 7.49 (d, J=2.8 Hz, 1H), 7.36 (dd, J=7.9, 1.1 Hz, 1H), 6.67 (d, J=2.8 Hz, 1H), 4.63-4.42 (m, 2H), 3.62 (br. s, 2H), 3.50 (dquin, J=13.8, 6.9 Hz, 1H), 3.02-2.81 (m, 3H), 2.75 (br. s, 1H), 2.20-1.87 (m, 3H), 1.63 (d, J=6.8 Hz, 1H), 1.47 (d, J=6.8 Hz, 6H), 1.38-1.20 (m, 1H); HPLC retention time (method C): $t_R$=5.73 min.

Example 72

5-((4-aminopiperidin-1-yl)methyl)-N-(3-(difluoromethyl)-5-(2-isopropyl-2H-tetrazol-5-yl)phenyl)pyrrolo[2,1-f][1,2,4]triazin-4-amine

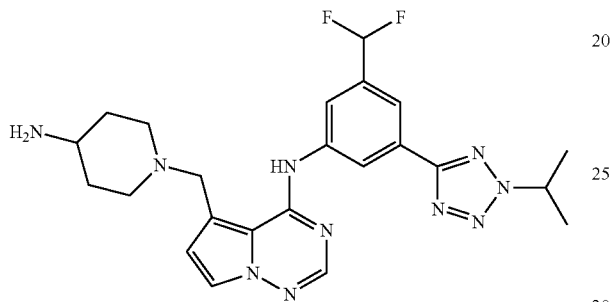

Prepared as in Example 1, Parts B and C using 3-(difluoromethyl)-5-(2-isopropyl-2H-tetrazol-5-yl)aniline (0.306 g, 1.208 mmol) and tert-butyl piperidin-4-ylcarbamate (0.266 g, 1.329 mmol) to afford 5-((4-aminopiperidin-1-yl)methyl)-N-(3-(difluoromethyl)-5-(2-isopropyl-2H-tetrazol-5-yl)phenyl)pyrrolo[1,2-f][1,2,4]triazin-4-amine, 2 TFA (0.345 g, 0.476 mmol, 39% yield for 3 steps) as an off-white solid. LCMS (ESI) m/e 483.4 [(M+H)⁺, calcd for $C_{23}H_{29}FN_{10}$ 483.3]. ¹H NMR (400 MHz, MeOD) δ 8.06 (d, J=11.1 Hz, 2H), 7.53 (s, 2H), 7.48 (d, J=2.5 Hz, 1H), 7.04-6.73 (m, 1H), 6.72 (d, J=2.5 Hz, 1H), 5.22-5.14 (m, 1H), 4.68 (s, 2H), 3.74 (br. s, 2H), 3.47 (br. s, 1H), 3.25-3.06 (m, 2H), 2.28 (d, J=11.8 Hz, 2H), 2.03-1.76 (m, 2H), 1.68 (d, J=6.8 Hz, 6H); HPLC retention time (method C): $t_R$=9.43 min.

Example 73

5-((4-aminopiperidin-1-yl)methyl)-N-(3-(5-cyclopentyl-1,2,4-oxadiazol-3-yl)phenyl)pyrrolo[2,1-f][1,2,4]triazin-4-amine

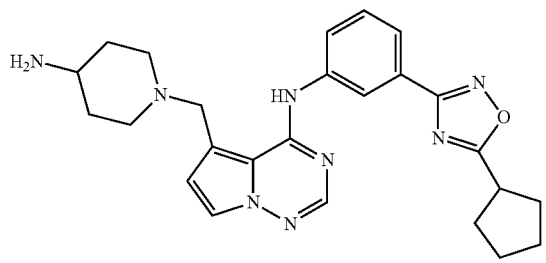 [SMILES: NC1CCN(Cc2ccn3ncnc(Nc4cccc(-c5noc(C6CCCC6)n5)c4)c23)CC1]

Prepared as in Example 1, Parts B and C using 3-(5-cyclopentyl-1,2,4-oxadiazol-3-yl)aniline (0.298 g, 1.300 mmol) and tert-butyl piperidin-4-ylcarbamate (0.260 g, 1.300 mmol) to afford 5-((4-aminopiperidin-1-yl)methyl)-N-(3-(5-cyclopentyl-1,2,4-oxadiazol-3-yl)phenyl)pyrrolo[1,2-f][1,2,4]triazin-4-amine, 2 TFA (0.274 g, 0.391 mmol, 33% yield for 3 steps) as an off-white solid. LCMS (ESI) m/e 459.3 [(M+H)⁺, calcd for $C_{25}H_{31}N_8O$ 495.3]. ¹H NMR (400 MHz, MeOD) δ 7.94-7.85 (m, 2H), 7.59 (t, J=7.8 Hz, 1H), 7.53 (s, 1H), 7.50 (d, J=2.8 Hz, 1H), 7.40 (d, J=7.8 Hz, 1H), 6.71 (d, J=2.8 Hz, 1H), 4.60 (s, 2H), 3.69 (br. s, 2H), 3.48-3.40 (m, 2H), 3.16 (br. s, 2H), 2.27 (d, J=11.8 Hz, 2H), 2.22-2.09 (m, 2H), 2.01-1.90 (m, 2H), 1.89-1.66 (m, 6H); HPLC retention time (method C): $t_R$=9.66 min.

Example 74

5-((4-aminopiperidin-1-yl)methyl)-N-(5-(2-isopropyl-2H-tetrazol-5-yl)-1H-indol-7-yl)pyrrolo[2,1-f][1,2,4]triazin-4-amine

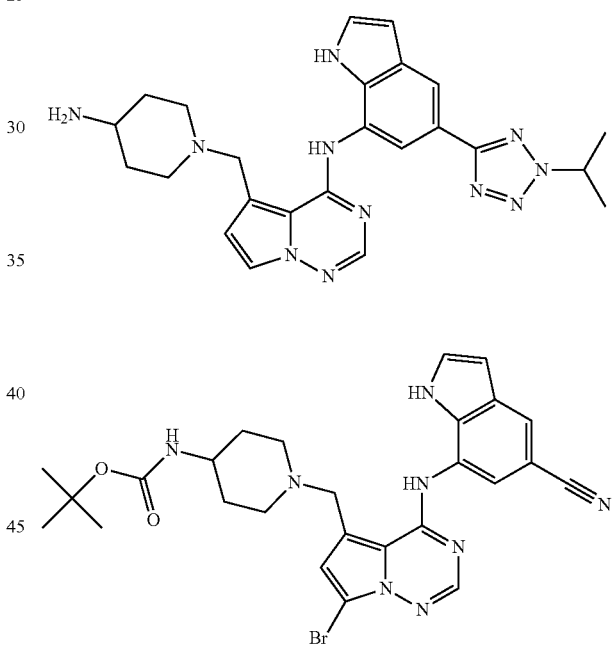

Part A: tert-butyl (1-((7-bromo-4-((5-cyano-1H-indol-7-yl)amino)pyrrolo[2,1-f][1,2,4]triazin-5-yl)methyl)piperidin-4-yl)carbamate Prepared as in Example 68 Part F using 7-amino-1H-indole-5-carbonitrile (73.7 mg, 0.469 mmol) and tert-butyl piperidin-4-ylcarbamate (94 mg, 0.469 mmol) to afford tert-butyl 1-((7-bromo-4-(5-cyano-1H-indol-7-ylamino)pyrrolo[1,2-f][1,2,4]triazin-5-yl)methyl)piperidin-4-ylcarbamate (61 mg, 0.076 mmol, 16% yield) as a yellow oil. LCMS (ESI) m/e 565.2, 568.2 Br pattern [(M+H)⁺, calcd for $C_{26}H_{30}N_8O_2$ 565.2].

115

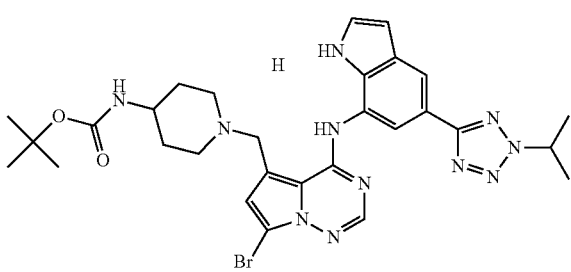

Chemical Formula: C₂₉H₃₇BrN₁₁O₂
Exact Mass: 650.23

Part B: tert-butyl (1-((7-bromo-4-((5-(2-isopropyl-2H-tetrazol-5-yl)-1H-indol-7-yl)amino)pyrrolo[2,1-f][1,2,4]triazin-5-yl)methyl)piperidin-4-yl)carbamate Prepared as in Example 49 Parts B-C using to afford tert-butyl 1-((7-bromo-4-(5-(2-isopropyl-2H-tetrazol-5-yl)-1H-indol-7-ylamino)pyrrolo[1,2-f][1,2,4]triazin-5-yl) methyl)piperidin-4-ylcarbamate, TFA (14 mg, 0.018 mmol, 24% yield for two steps) as a brown solid. LCMS (ESI) m/e 650.3, 652.3 Br pattern [(M+H)$^+$, calcd for C₂₉H₃₇BrN₁₁O₂ 650.2].

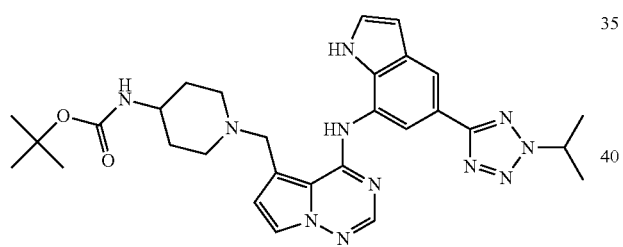

Part C: tert-butyl (1-((4-((5-(2-isopropyl-2H-tetrazol-5-yl)-1H-indol-7-yl)amino)pyrrolo[2,1-f][1,2,4]triazin-5-yl)methyl)piperidin-4-yl)carbamate To a solution of tert-butyl 1-((7-bromo-4-(5-(2-isopropyl-2H-tetrazol-5-yl)-1H-indol-7-ylamino)pyrrolo[1,2-f][1,2,4]triazin-5-yl)methyl)piperidin-4-ylcarbamate (0.012 g, 0.018 mmol) in MeOH (0.180 mL) in a round-bottomed flask flushed with nitrogen at room temperature was added Pd/C (0.019 g, 0.018 mmol). The flask was then flushed with hydrogen and the solution stirred under a balloon of hydrogen for 40 min. The solids were filtered off and the filtrate concentrated under reduced pressure. The material was carried on without further purification and assuming quantitative yield. LCMS (ESI) m/e 572.3 [(M+H)$^+$, calcd for C₂₉H₃₈N₁₁O₂ 572.3].

116

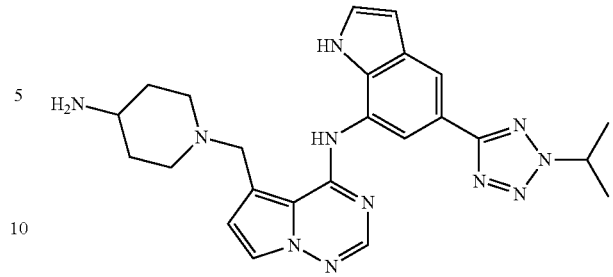

Part D: 5-((4-aminopiperidin-1-yl)methyl)-N-(5-(2-isopropyl-2H-tetrazol-5-yl)-1H-indol-7-yl)pyrrolo[2,1-f][1,2,4]triazin-4-amine A solution of tert-butyl 1-((4-(5-(2-isopropyl-2H-tetrazol-5-yl)-1H-indol-7-ylamino)pyrrolo[1,2-f][1,2,4]triazin-5-yl) methyl)piperidin-4-ylcarbamate (10.29 mg, 0.018 mmol) and TFA (0.18 mL, 2.336 mmol) in DCM (0.180 mL) was stirred at room temperature for 2 h. The reaction mixture was concentrated under reduced pressure. The residue was purified by reverse phase HPLC (10%-65% MeOH/H2O/0.1% TFA) to afford 5-((4-aminopiperidin-1-yl)methyl)-N-(5-(2-isopropyl-2H-tetrazol-5-yl)-1H-indol-7-yl)pyrrolo[1,2-f][1,2,4]triazin-4-amine, 2 TFA (7.9 mg, 0.011 mmol, 62% yield for 2 steps) as a pale yellow amorphous solid. LCMS (ESI) m/e 472.3 [(M+H)$^+$, calcd for C₂₄H₃₀N₁₁ 472.3]. $^1$H NMR (400 MHz, MeOD) δ ppm 8.27 (d, J=1.26 Hz, 1H), 7.67 (d, J=1.26 Hz, 1H), 7.54 (d, J=2.77 Hz, 1H), 7.46 (s, 1H), 7.37 (d, J=3.02 Hz, 1H), 6.71 (d, J=3.02 Hz, 1H), 6.68 (d, J=3.02 Hz, 1H), 5.16 (septet, J=6.80 Hz, 1H), 4.58 (s, 2H), 3.73 (d, J=8.56 Hz, 2H), 3.34-3.45 (m, 1H), 3.03-3.18 (m, 2H), 2.19 (d, J=11.83 Hz, 2H), 1.69 (d, J=6.80 Hz, 6H), 1.60-1.65 (m, 2H); HPLC retention time (method H): t$_R$=6.54 min; HPLC retention time (method I): t$_R$=7.54 min.

Example 75

5-((4-aminopiperidin-1-yl)methyl)-N-(4-(2-isopropyl-2H-tetrazol-5-yl)-1H-benzo[d]imidazol-6-yl)pyrrolo[2,1-f][1,2,4]triazin-4-amine

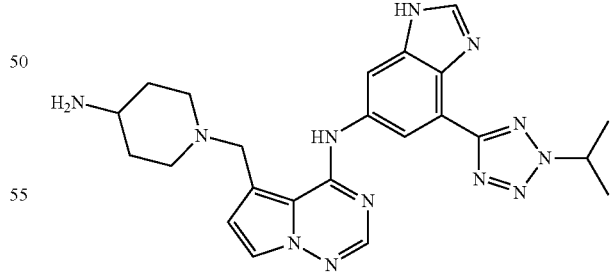

Prepared as in Example 74 to afford 5-((4-aminopiperidin-1-yl)methyl)-N-(4-(2-isopropyl-2H-tetrazol-5-yl)-1H-benzo[d]imidazol-6-yl)pyrrolo[1,2-f][1,2,4]triazin-4-amine, 2 TFA (19.4 mg, 0.027 mmol) as a pale yellow solid. LCMS (ESI) m/e 473.2 [(M+H)$^+$, calcd for C₂₃H₂₉N₁₂ 473.3]. $^1$H NMR (400 MHz, MeOD) δ ppm 9.44 (s, 1H), 8.16 (d, J=1.76 Hz, 1H), 7.91 (s, 1H), 7.56 (s, 1H), 7.52 (d, J=3.02 Hz, 1H), 6.71 (d, J=2.77 Hz, 1H), 5.28 (septet, J=6.55 Hz, 1H), 4.61 (s, 2H), 3.72 (d, J=11.33 Hz, 2H), 3.44 (t, J=11.08 Hz, 1H), 3.05-3.23 (m, 2H), 2.26 (d, J=12.84 Hz, 2H), 1.79-1.96 (m, 2H), 1.74 (d, J=6.55 Hz, 6H); HPLC retention time (method H): $t_R$=4.17 min; HPLC retention time (method I): $t_R$=4.73 min.

Example 76

N-(3-(2-isopropyl-2H-tetrazol-5-yl)phenyl)pyrrolo[2,1-f][1,2,4]triazin-4-amine

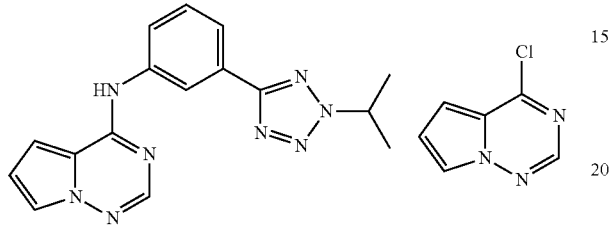

Part A: 4-chloropyrrolo[2,1-f][1,2,4]triazine

To a solution of pyrrolo[2,1-f][1,2,4]triazin-4(3H)-one (0.56 g, 4.14 mmol) [prepared as in S. A. Patil, B. A. Otter and R. S. Klein, *J. Het. Chem.*, 31, 781-786 (1994)] in dry toluene (50 mL) was added $POCl_3$ (3.09 mL, 33.2 mmol) and DIEA (0.724 mL, 4.14 mmol). The reaction mixture was heated to reflux overnight. The reaction mixture was cooled to room temperature and concentrated under reduced pressure. The residue was purified by silica gel chromatography (0-40% ethyl acetate in hexanes) to obtain 4-chloropyrrolo[2,1-f][1,2,4]triazine (0.462 g, 3.01 mmol, 73% yield) as a brown solid. LCMS (ESI) m/e 154.1 [(M+H)$^+$, calcd for $C_6H_5ClN_3$ 154.0].

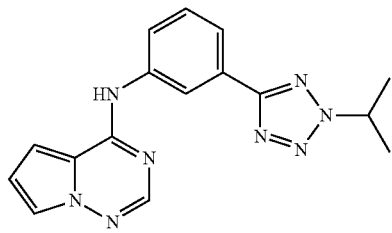 [SMILES: CC(C)n1nnc(-c2cccc(Nc3ncnn4cccc34)c2)n1]

Part B: N-(3-(2-isopropyl-2H-tetrazol-5-yl)phenyl)pyrrolo[1,2-f][1,2,4]triazin-4-amine To a solution of 4-chloropyrrolo[1,2-f][1,2,4]triazine (0.2 g, 1.302 mmol), in acetonitrile (10 mL) in a microwave vial was added 3-(2-isopropyl-2H-tetrazol-5-yl)aniline (0.265 g, 1.302 mmol). The reaction tube was flushed with nitrogen and capped then heated in a microwave for 45 min at 85° C. The reaction mixture was concentrated and residue purified by reverse phase preparative HPLC (water/methanol/0.1% TFA) to afford N-(3-(2-isopropyl-2H-tetrazol-5-yl)phenyl)pyrrolo[1,2-f][1,2,4]triazin-4-amine, TFA (0.2563 g, 0.578 mmol, 44% yield). LCMS (ESI) m/e 321.2 [(M+H)$^+$, calcd for $C_{16}H_{17}N_8$ 321.2]. $^1$H NMR (400 MHz, CHLOROFORM-d) δ ppm 8.30 (d, J=7.81 Hz, 1H), 8.21 (t, J=1.64 Hz, 1H), 7.84 (s, 1H), 7.68 (dd, J=2.52, 1.51 Hz, 1H), 7.63 (t, J=7.93 Hz, 1H), 7.52 (d, J=8.06 Hz, 1H), 6.55 (dd, J=4.78, 2.77 Hz, 1H), 5.93 (d, J=4.03 Hz, 1H), 5.10 (spt, J=6.71 Hz, 1H), 1.68 (d, J=6.80 Hz, 6H); HPLC retention time (method E): $t_R$=10.34 min; HPLC retention time (method F): $t_R$=8.34 min.

Example 77

N-(3-(5-isopropyl-1,2,4-oxadiazol-3-yl)phenyl)pyrrolo[2,1-f][1,2,4]triazin-4-amine

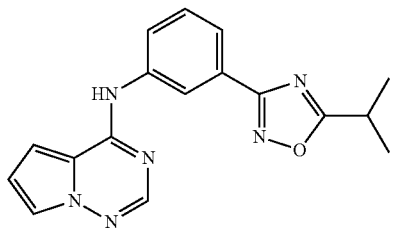 [SMILES: CC(C)c1nc(-c2cccc(Nc3ncnn4cccc34)c2)no1]

Prepared as in Example 76, Part B using 3-(5-isopropyl-1,2,4-oxadiazol-3-yl)aniline (132 mg, 0.651 mmol) to afford N-(3-(5-isopropyl-1,2,4-oxadiazol-3-yl)phenyl)pyrrolo[1,2-f][1,2,4]triazin-4-amine (67 mg, 0.203 mmol, 31% yield) as a yellow oil. LCMS (ESI) m/e 321.0 [(M+H)$^+$, calcd for $C_{17}H_{17}N_6O$ 321.2]. $^1$H NMR (400 MHz, CHLOROFORM-d) δ ppm 8.24 (t, J=1.76 Hz, 1H), 8.04-8.12 (m, 2H), 7.85-7.91 (m, 1H), 7.64 (dd, J=2.64, 1.38 Hz, 1H), 7.52 (t, J=7.93 Hz, 1H), 7.06 (br. s, 1H), 6.72 (dd, J=4.41, 2.64 Hz, 1H), 6.63 (dd, J=4.53, 1.51 Hz, 1H), 3.18-3.40 (m, J=7.18, 7.03, 7.03, 7.03, 7.03, 7.03 Hz, 1H), 1.46 (d, J=7.05 Hz, 6H); HPLC retention time (method H): $t_R$=18.70 min; HPLC retention time (method I): $t_R$=15.22 min.

Example 78

N-(3-(5-(1-chloro-2-methylpropan-2-yl)-1,2,4-oxadiazol-3-yl)phenyl)pyrrolo[2,1-f][1,2,4]triazin-4-amine

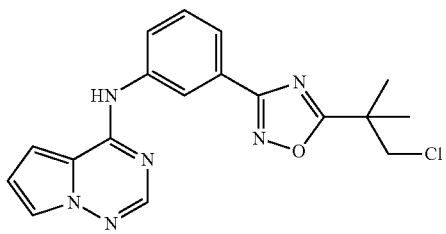 [SMILES: CC(C)(CCl)c1nc(-c2cccc(Nc3ncnn4cccc34)c2)no1]

Prepared as in Example 76, Part B using 3-(5-(1-chloro-2-methylpropan-2-yl)-1,2,4-oxadiazol-3-yl)aniline (525 mg, 2.084 mmol) to afford N-(3-(5-(1-chloro-2-methylpropan-2-yl)-1,2,4-oxadiazol-3-yl)phenyl)pyrrolo[1,2-f][1,2,4]triazin-4-amine (340 mg, 0.894 mmol, 43% yield) as a yellow oil. LCMS (ESI) m/e 369.0 [(M+H)$^+$, calcd for $C_{18}H_{18}ClN_6O$ 369.1]. $^1$H NMR (400 MHz, CHLOROFORM-d) δ ppm 8.25 (t, J=1.76 Hz, 1H), 8.04-8.11 (m, 2H), 7.89 (d, J=7.81 Hz, 1H), 7.64 (dd, J=2.64, 1.38 Hz, 1H), 7.52 (t, J=7.93 Hz, 1H), 7.08 (br. s, 1H), 6.73 (dd, J=4.41, 2.64 Hz, 1H), 6.65 (dd, J=4.53, 1.51 Hz, 1H), 3.84 (s, 2H), 1.59

Example 79

N-(3-(5-isopropyl-1, 3, 4-thiadiazol-2-yl)phenyl) pyrrolo[2,1-f][1,2,4]triazin-4-amine

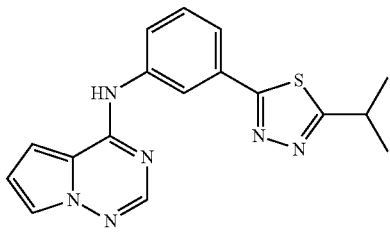

Prepared as in Example 76, Part B using 3-(5-isopropyl-1,3,4-thiadiazol-2-yl)aniline (143 mg, 0.651 mmol) to afford N-(3-(5-isopropyl-1,3,4-thiadiazol-2-yl)phenyl)pyrrolo[1,2-f][1,2,4]triazin-4-amine (91 mg, 0.265 mmol, 41% yield) as a yellow oil. LCMS (ESI) m/e 337.0 [(M+H)$^+$, calcd for $C_{17}H_{17}N_6S$ 337.1]. $^1$H NMR (400 MHz, CHLOROFORM-d) δ ppm 12.49 (br. s, 1H), 8.10 (s, 1H), 7.78-7.95 (m, 2H), 7.58-7.72 (m, 2H), 7.51 (t, J=7.81 Hz, 1H), 6.59 (dd, J=4.53, 2.52 Hz, 1H), 6.24 (br. s, 1H), 3.47 (spt, J=7.05 Hz, 1H), 1.44 (d, J=7.05 Hz, 6H); HPLC retention time (method H): $t_R$=14.58 min; HPLC retention time (method I): $t_R$=11.47 min.

Example 80

N-(3-(5-isopropyl-1,3,4-oxadiazol-2-yl)phenyl)pyrrolo[2,1-f][1,2,4]triazin-4-amine

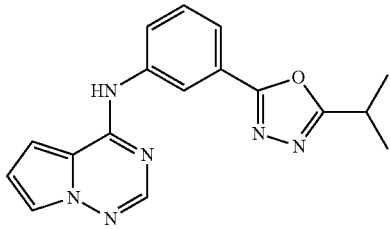 [SMILES: CC(C)c1nnc(-c2cccc(Nc3ncnn4cccc34)c2)o1]

Prepared as in Example 76, Part B using 3-(5-isopropyl-1,3,4-oxadiazol-2-yl)aniline (132 mg, 0.651 mmol) to afford N-(3-(5-isopropyl-1,3,4-oxadiazol-2-yl)phenyl)pyrrolo[1,2-f][1,2,4]triazin-4-amine (55 mg, 0.168 mmol, 26% yield) as a yellow oil. LCMS (ESI) m/e 321.0 [(M+H)$^+$, calcd for $C_{17}H_{17}N_6O$ 321.2]. $^1$H NMR (400 MHz, CHLOROFORM-d) δ ppm 13.79 (br. s, 1H), 8.21 (ddd, J=7.93, 1.38, 1.26 Hz, 1H), 8.08 (t, J=1.64 Hz, 1H), 7.86 (s, 1H), 7.70 (dd, 1H), 7.67 (t, J=7.93 Hz, 1H), 7.55-7.61 (m, 1H), 6.58 (dd, J=4.78, 2.52 Hz, 1H), 5.89 (dd, J=4.78, 1.26 Hz, 1H), 3.26 (spt, J=7.01 Hz, 1H), 1.44 (d, J=7.05 Hz, 6H); HPLC retention time (method H): $t_R$=13.18 min; HPLC retention time (method I): $t_R$=10.35 min.

Example 81

2-methyl-2-(3-(3-(pyrrolo[2,1-f][1,2,4]triazin-4-ylamino)phenyl)-1,2,4-oxadiazol-5-yl)propan-1-ol

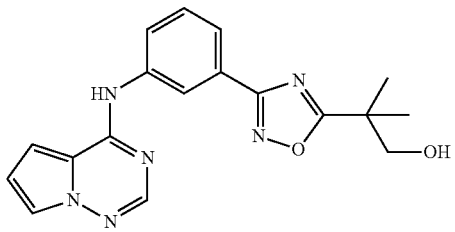 [SMILES: CC(C)(CO)c1nc(-c2cccc(Nc3ncnn4cccc34)c2)no1]

Prepared as in Example 76, Part B using 2-(3-(3-aminophenyl)-1,2,4-oxadiazol-5-yl)-2-methylpropan-1-ol (152 mg, 0.651 mmol) to afford 2-methyl-2-(3-(3-(pyrrolo[1,2-f][1,2,4]triazin-4-ylamino)phenyl)-1,2,4-oxadiazol-5-yl)propan-1-ol (88 mg, 0.246 mmol, 38% yield) as a yellow solid. LCMS (ESI) m/e 351.0 [(M+H)$^+$, calcd for $C_{18}H_{19}N_6O_2$ 351.2]. $^1$H NMR (400 MHz, CHLOROFORM-d) ppm 13.83 (s, 1H), 8.22 (d, J=7.81 Hz, 1H), 8.14 (t, J=1.64 Hz, 1H), 7.84 (s, 1H), 7.69 (dd, J=2.52, 1.51 Hz, 1H), 7.64 (t, J=7.81 Hz, 1H), 7.54-7.59 (m, 1H), 6.56 (dd, J=4.78, 2.52 Hz, 1H), 5.87 (d, J=4.78 Hz, 1H), 3.78 (s, 2H), 1.45 (s, 6H); HPLC retention time (method H): $t_R$=12.01 min; HPLC retention time (method I): $t_R$=9.65 min.

Example 82

N-(3-(5-(1-amino-2-methylpropan-2-yl)-1,2,4-oxadiazol-3-yl)phenyl)pyrrolo[2,1-f][1,2,4]triazin-4-amine

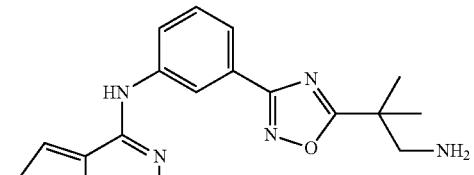

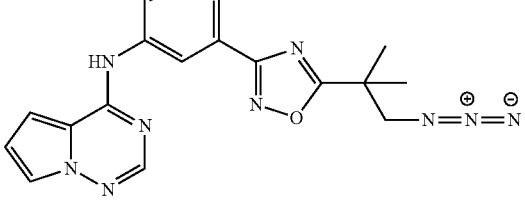

Part A: N-(3-(5-(1-azido-2-methylpropan-2-yl)-1,2,4-oxadiazol-3-yl)phenyl)pyrrolo[2,1-f][1,2,4]triazin-4-amine A solution of N-(3-(5-(1-chloro-2-methylpropan-2-yl)-1,2,4-oxadiazol-3-yl)phenyl)pyrrolo[1,2-f][1,2,4]triazin-4-amine (320 mg, 0.868 mmol) (prepared as described in Example 78) and sodium azide (85 mg, 1.301 mmol) in NMP (8676 μL) was heated in the microwave at 160° C. for 45 min. The reaction mixture was cooled to room temperature and concentrated. Water (15 mL) was added to the residue and the mixture was extracted with EtOAc (3×15 mL). The combined organic layers were washed with brine (4×10 mL), dried (MgSO$_4$), filtered and concentrated under reduced pressure. The crude material was carried on without further purification, assuming quantitative yield. LCMS (ESI) m/e 376.0 [(M+H)$^+$, calcd for $C_{18}H_{19}N_9O$ 376.2].

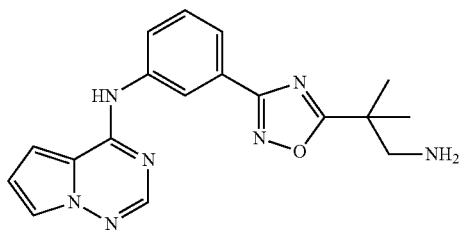 [SMILES: CC(C)(CN)c1nc(-c2cccc(Nc3ncnn4cccc34)c2)no1]

Part B: N-(3-(5-(1-amino-2-methylpropan-2-yl)-1,2,4-oxadiazol-3-yl)phenyl)pyrrolo[2,1-f][1,2,4]triazin-4-amine A solution of N-(3-(5-(1-azido-2-methylpropan-2-yl)-1,2,4-oxadiazol-3-yl)phenyl)pyrrolo[1,2-f][1,2,4]triazin-4-amine (326 mg, 0.868 mmol) in EtOH (2.17 mL) was shaken under 50 psi of hydrogen for 2 h. The mixture was filtered through Celite and concentrated under reduced pressure. The crude material was purified by reverse phase HPLC (10%-100% MeOH/H$_2$O/0.1% TFA) to afford N-(3-(5-(1-amino-2-methylpropan-2-yl)-1,2,4-oxadiazol-3-yl)phenyl)pyrrolo[1,2-f][1,2,4]triazin-4-amine, TFA (268 mg, 0.567 mmol, 65% yield for 2 steps) as a pale yellow oil.

LCMS (ESI) m/e 350.0 [(M+H)$^+$, calcd for $C_{18}H_{20}N_7O$ 350.2]. $^1$H NMR (400 MHz, MeOD) δ ppm 8.40 (t, J=1.76 Hz, 1H), 8.07 (d, J=7.81 Hz, 1H), 7.92 (s, 1H), 7.82 (dt, J=8.06, 1.13 Hz, 1H), 7.80 (dd, J=2.64, 1.38 Hz, 1H), 7.65 (t, J=7.93 Hz, 1H), 7.24 (d, J=3.27 Hz, 1H), 6.84 (dd, J=4.66, 2.64 Hz, 1H), 3.41 (s, 2H), 1.58 (s, 6H); HPLC retention time (method H): $t_R$=7.81 min; HPLC retention time (method I): $t_R$=7.38 min.

Example 83

(3-(2-isopropyl-2H-tetrazol-5-yl)-5-(pyrrolo[2,1-f][1,2,4]triazin-4-ylamino)phenyl)methanol

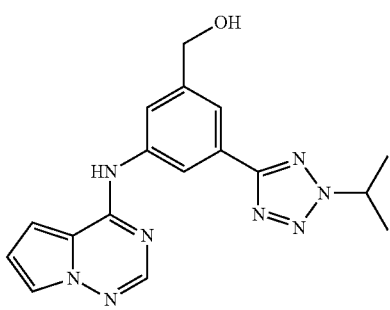 [SMILES: CC(C)n1nnc(-c2cc(CO)cc(Nc3ncnn4cccc34)c2)n1]

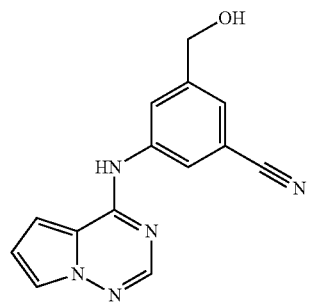 [SMILES: N#Cc1cc(CO)cc(Nc2ncnn3cccc23)c1]

Part A: 3-(hydroxymethyl)-5-(pyrrolo[2,1-f][1,2,4]triazin-4-ylamino)benzonitrile Prepared as in Example 76, Part B using 3-amino-5-(hydroxymethyl)benzonitrile, HCl (32.3 mg, 0.175 mmol) to afford 3-(hydroxymethyl)-5-(pyrrolo[1,2-f][1,2,4]triazin-4-ylamino)benzonitrile, TFA (6 mg, 0.013 mmol, 8% yield) as a yellow oil. LCMS (ESI) m/e 266.0 [(M+H)$^+$, calcd for $C_{14}H_{12}N_5O$ 266.1].

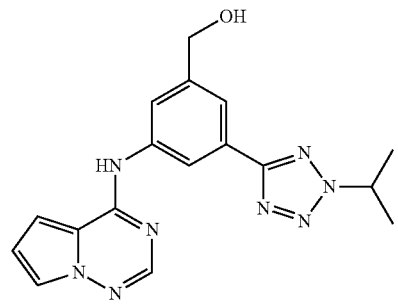 [SMILES: CC(C)n1nnc(-c2cc(CO)cc(Nc3ncnn4cccc34)c2)n1]

Part B: (3-(2-isopropyl-2H-tetrazol-5-yl)-5-(pyrrolo[2,1-f][1,2,4]triazin-4-ylamino)phenyl)methanol Prepared as described in Example 49, Parts B and C to afford (3-(2-isopropyl-2H-tetrazol-5-yl)-5-(pyrrolo[1,2-f][1,2,4]triazin-4-ylamino)phenyl)methanol, TFA (3 mg, 6.14 μmol, 11% yield for 2 steps) as a yellow oil. LCMS (ESI) m/e 351.1 [(MAI), calcd for $C_{17}H_{19}N_8O$ 351.2]. $^1$H NMR (400 MHz, MeOD) δ ppm 8.38-8.44 (m, 1H), 7.88-8.00 (m, 3H), 7.68 (dd, J=2.77, 1.51 Hz, 1H), 7.16 (dd, J=4.53, 1.51 Hz, 1H), 6.77 (dd, J=4.41, 2.64 Hz, 1H), 5.17 (septet, J=6.80 Hz, 1H), 4.72 (s, 2H), 1.69 (d, J=6.80 Hz, 6H).

Example 84

3-(2-isopropyl-2H-tetrazol-5-yl)-5-(pyrrolo[2,1-f][1,2,4]triazin-4-ylamino)phenol

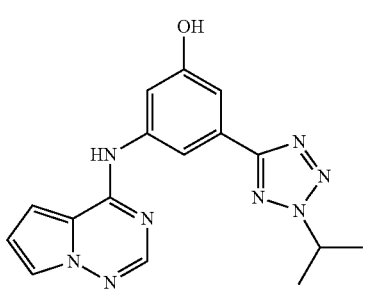 [SMILES: CC(C)n1nnc(-c2cc(O)cc(Nc3ncnn4cccc34)c2)n1]

Prepared as described in Example 83 to afford 3-(2-isopropyl-2H-tetrazol-5-yl)-5-(pyrrolo[1,2-f][1,2,4]triazin-4-ylamino)phenol, TFA (0.0663 g, 0.144 mmol) as a yellow solid. LCMS (ESI) m/e 337.1 [(M+H)+, calcd for $C_{16}H_{17}N_8O$ 337.2]; $^1$H NMR (400 MHz, MeOD) δ 7.88 (s, 1H), 7.78 (dd, J=2.5, 1.5 Hz, 1H), 7.76 (dd, J=1.9, 1.4 Hz, 1H), 7.51 (dd, J=2.3, 1.5 Hz, 1H), 7.27 (d, J=3.8 Hz, 1H), 7.23 (t, J=2.1 Hz, 1H), 6.83 (dd, J=4.7, 2.6 Hz, 1H), 5.13 (dquin, J=13.4, 6.7 Hz, 1H), 1.66 (d, J=6.5 Hz, 6H); HPLC retention time (method C): $t_R$=10.18 min.

Example 85

3-(5-isopropyl-1,2,4-oxadiazol-3-yl)-5-(pyrrolo[2,1-f][1,2,4]triazin-4-ylamino)phenol

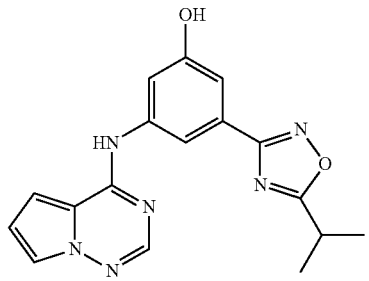 [SMILES: CC(C)c1nc(-c2cc(O)cc(Nc3ncnn4cccc34)c2)no1]

Prepared as described in Example 83 to afford 3-(5-isopropyl-1,2,4-oxadiazol-3-yl)-5-(pyrrolo[1,2-f][1,2,4]triazin-4-ylamino)phenol, TFA (0.0887 g, 0.193 mmol, 32% yield) as a brownish yellow solid. LCMS (ESI) m/e 337.1 [(M+H)+, calcd for $C_{17}H_{17}N_6O_2$ 337.1]. $^1$H NMR (400 MHz, MeOD) δ 7.88 (s, 1H), 7.80 (dd, J=2.4, 1.4 Hz, 1H), 7.70 (d, J=1.3 Hz, 1H), 7.49-7.43 (m, 1H), 7.32-7.22 (m, 2H), 6.84 (dd, J=4.4, 2.6 Hz, 1H), 3.30 (sept, J=7.1 Hz, 1H), 1.41 (d, J=7.1 Hz, 6H); HPLC retention time (method C): $t_R$=10.85 min.

Example 86

N-(3-(5-isopropyl-1,2,4-oxadiazol-3-yl)-5-methylpyrrolo[2,1-f][1,2,4]triazin-4-amine

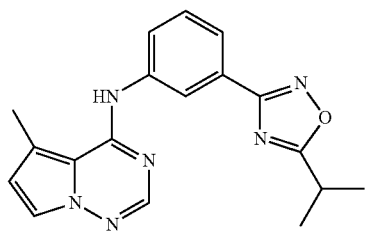 [SMILES: Cc1ccn2ncnc(Nc3cccc(-c4noc(C(C)C)n4)c3)c12]

To a solution of 4-chloro-5-methylpyrrolo[1,2-f][1,2,4]triazine (0.089 g, 0.531 mmol) [prepared as in Ref. WO 03/042172 A2] in acetonitrile (10 mL) in a microwave vial was added 3-(5-isopropyl-1,2,4-oxadiazol-3-yl)aniline (0.108 g, 0.531 mmol). The reaction tube was flushed with nitrogen and capped. The reaction mixture was heated in a microwave for 45 minutes at 85° C. The reaction mixture was concentrated under reduced pressure and the residue was purified by reverse phase preparative HPLC (water/Methanol/0.1% TFA). The required fractions were concentrated and dried under high vacuum to obtain N-(3-(5-isopropyl-1,2,4-oxadiazol-3-yl)phenyl)-5-methylpyrrolo[1,2-f][1,2,4]triazin-4-amine, TFA (0.0195 g, 0.039 mmol, 7% yield). LCMS (ESI) m/e 335.3 [(M+H)+, calcd for $C_{18}H_{19}N_6O$ 335.2]. $^1$H NMR (400 MHz, MeOD) δ 8.31-8.24 (m, 1H), 8.07 (dt, J=7.6, 1.4 Hz, 1H), 7.79-7.62 (m, 4H), 6.69 (d, J=2.5 Hz, 1H), 3.32 (sept, J=7.01 Hz, 1H), 2.69 (s, 3H), 1.43 (d, J=7.1 Hz, 6H); HPLC retention time (method C): $t_R$=12.16 min.

Example 87

N-(3-(5-isopropyl-1,3,4-thiadiazol-2-yl)phenyl)-5-methylpyrrolo[2,1-f][1,2,4]triazin-4-amine

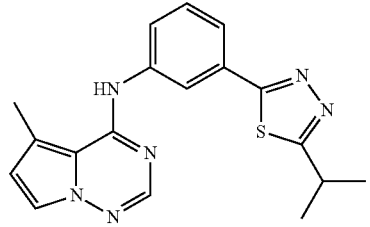 [SMILES: Cc1ccn2ncnc(Nc3cccc(-c4nnc(C(C)C)s4)c3)c12]

Prepared as described in Example 86 using 3-(5-isopropyl-1,3,4-thiadiazol-2-yl)aniline (0.116 g, 0.531 mmol) to afford N-(3-(5-isopropyl-1,3,4-thiadiazol-2-yl)phenyl)-5-methylpyrrolo[1,2-f][1,2,4]triazin-4-amine, TFA (0.1418 g, 0.299 mmol, 56% yield) as an off-white solid. LCMS (ESI) m/e 351.2 [(M+H)+, calcd for $C_{18}H_{19}N_6S$ 351.1]. $^1$H NMR (400 MHz, CHLOROFORM-d) δ 12.18 (t, J=1.8 Hz, 1H), 11.76-11.65 (m, 3H), 11.57-11.44 (m, 2H), 10.54 (d, J=2.3 Hz, 1H), 8.69 (br. s, 3H), 7.45 (spt, J=6.9 Hz, 1H), 5.43 (d, J=7.1 Hz, 6H); HPLC retention time (method C): $t_R$=11.71 min.

Example 88

N-(3-(2-isopropyl-2H-tetrazol-5-yl)phenyl)-5-methylpyrrolo[2,1-f][1,2,4]triazin-4-amine

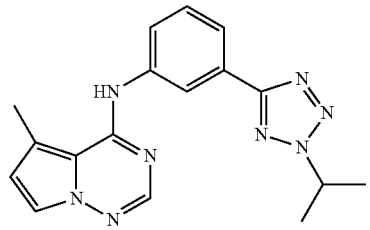 [SMILES: Cc1ccn2ncnc(Nc3cccc(-c4nnn(C(C)C)n4)c3)c12]

Prepared as described in Example 86 using 3-(2-isopropyl-2H-tetrazol-5-yl)aniline (0.108 g, 0.531 mmol) to afford N-(3-(2-isopropyl-2H-tetrazol-5-yl)phenyl)-5-methylpyrrolo[1,2-f][1,2,4]triazin-4-amine, TFA (0.0971 g, 0.212 mmol, 40% yield) as a pale yellow solid. LCMS (ESI) m/e 335.3 [(M+H)+, calcd for $C_{17}H_{19}N_8$ 335.2]. $^1$H NMR (400 MHz, MeOD) δ 8.31 (d, J=1.8 Hz, 1H), 8.12 (dt, J=7.0, 1.7 Hz, 1H), 7.75-7.62 (m, 4H), 6.68 (d, J=2.3 Hz, 1H), 5.15 (spt, J=6.7 Hz, 1H), 2.67 (s, 3H), 1.67 (d, J=6.8 Hz, 6H); HPLC retention time (method C): $t_R$=10.72 min.

Example 89

N-(3-(2-isopropyl-2H-tetrazol-5-yl)phenyl)-5-methylpyrrolo[2,1-f][1,2,4]triazin-4-amine

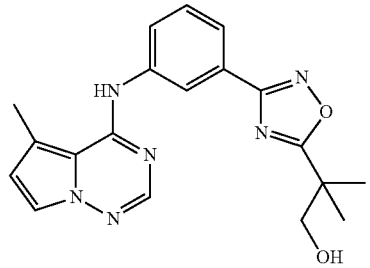 [SMILES: Cc1ccn2ncnc(Nc3cccc(-c4noc(C(C)(C)CO)n4)c3)c12]

Prepared as described in Example 86 using 2-(3-(3-aminophenyl)-1,2,4-oxadiazol-5-yl)-2-methylpropan-1-ol (0.124 g, 0.531 mmol) to afford 2-methyl-2-(3-(3-(5-methylpyrrolo[1,2-f][1,2,4]triazin-4-ylamino)phenyl)-1,2,4-oxadiazol-5-yl)propan-1-ol, TFA (0.100 g, 0.206 mmol, 39% yield) as a pale yellow solid. LCMS (ESI) m/e 365.2 [(M+H)$^+$, calcd for $C_{19}H_{21}N_6O_2$ 365.2]. $^1$H NMR (400 MHz, MeOD) δ 8.25 (d, J=1.5 Hz, 1H), 8.16-8.08 (m, 1H), 7.79-7.64 (m, 4H), 6.72 (d, J=2.0 Hz, 1H), 3.78-3.71 (m, 2H), 2.73-2.62 (m, 3H), 1.44 (s, 6H); HPLC retention time (method C): $t_R$=10.16 min.

Example 90

N-(3-(5-(1-chloro-2-methylpropan-2-yl)-1,2,4-oxadiazol-3-yl)phenyl)-5-methylpyrrolo[2,1-f][1,2,4]triazin-4-amine

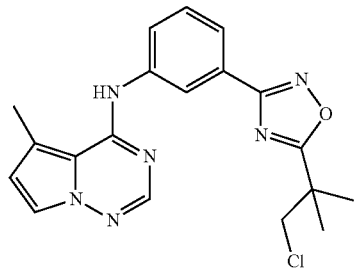 [SMILES: Cc1ccn2ncnc(Nc3cccc(-c4noc(C(C)(C)CCl)n4)c3)c12]

Prepared as described in Example 86 using 3-(5-(1-chloro-2-methylpropan-2-yl)-1,2,4-oxadiazol-3-yl)aniline (0.105 g, 0.416 mmol) to afford N-(3-(5-(1-chloro-2-methylpropan-2-yl)-1,2,4-oxadiazol-3-yl)phenyl)-5-methylpyrrolo[1,2-f][1,2,4]triazin-4-amine, TFA (0.040 g, 0.079 mmol, 19% yield) as a reddish oil. LCMS (ESI) m/e 383.2 [(M+H)$^+$, calcd for $C_{19}H_{20}ClN_6O_2$ 383.1]. $^1$H NMR (400 MHz, MeOD) δ 8.32-8.25 (m, 1H), 8.05 (dt, J=7.8, 1.3 Hz, 1H), 7.81-7.61 (m, 4H), 6.66 (d, J=2.5 Hz, 1H), 3.91 (s, 2H), 2.68 (s, 3H), 1.57 (s, 6H); HPLC retention time (method C): $t_R$=13.72 min.

Example 91

N-(3-(5-(1-amino-2-methylpropan-2-yl)-1,2,4-oxadiazol-3-yl)phenyl)-5-methylpyrrolo[2,1-f][1,2,4]triazin-4-amine

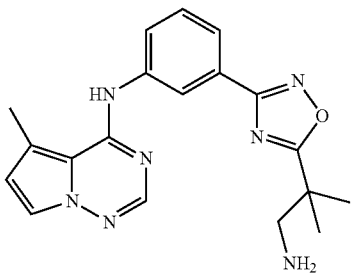 [SMILES: Cc1ccn2ncnc(Nc3cccc(-c4noc(C(C)(C)CN)n4)c3)c12]

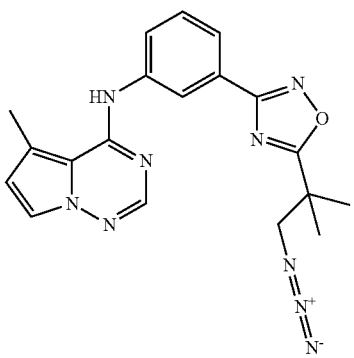 [SMILES: Cc1ccn2ncnc(Nc3cccc(-c4noc(C(C)(C)CN=[N+]=[N-])n4)c3)c12]

Part A: N-(3-(5-(1-azido-2-methylpropan-2-yl)-1,2,4-oxadiazol-3-yl)phenyl)-5-methylpyrrolo[2,1-f][1,2,4]triazin-4-amine To a solution of N-(3-(5-(1-chloro-2-methylpropan-2-yl)-1,2,4-oxadiazol-3-yl)phenyl)-5-methylpyrrolo[1,2-f][1,2,4]triazin-4-amine (0.215 g, 0.562 mmol) [prepared as described in Example 90] in dry N-Methyl-2-pyrrolidinone (10 mL) in a microwave vial under nitrogen was added sodium azide (0.073 g, 1.123 mmol) at room temperature. The reaction vial was capped and heated in the microwave at 120° C. for 20 minutes. The reaction mixture was filtered through a Buchner funnel using methanol as solvent. The filtrate was concentrated to remove the methanol. The residue was purified by reverse phase preparative HPLC (water/Methanol/0.1% TFA) to afford N-(3-(5-(1-azido-2-methylpropan-2-yl)-1,2,4-oxadiazol-3-yl)phenyl)-5-methylpyrrolo[1,2-f][1,2,4]triazin-4-amine (0.165 g, 0.424 mmol, 75% yield). LCMS (ESI) m/e 390.2 [(M)$^+$, calcd for $C_{19}H_{20}N_9O$ 390.2].

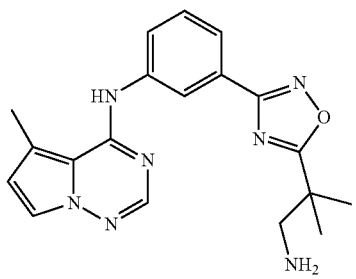 [SMILES: Cc1ccn2ncnc(Nc3cccc(-c4noc(C(C)(C)CN)n4)c3)c12]

Part B: N-(3-(5-(1-amino-2-methylpropan-2-yl)-1,2,4-oxadiazol-3-yl)phenyl)-5-methylpyrrolo[2,1-f][1,2,4]triazin-4-amine To a solution of N-(3-(5-(1-azido-2-methylpropan-2-yl)-1,2,4-oxadiazol-3-yl)phenyl)-5-methylpyrrolo[1,2-f][1,2,4]triazin-4-amine (0.165 g, 0.424 mmol) in dry MeOH (20 mL) in a Parr bottle under nitrogen at room temperature was added Pd/C (0.045 g, 0.424 mmol). The reaction mixture was shaken under hydrogen (50 psi) on a Parr shaker for 2 h. The reaction was filtered through a glass filter and the filtrate was concentrated under reduced pressure. The residue was purified by reverse phase preparative HPLC (water/Methanol/0.1% TFA) to afford N-(3-(5-(1-amino-2-methylpropan-2-yl)-1,2,4-oxadiazol-3-yl)phenyl)-5-methylpyrrolo[1,2-f][1,2,4]triazin-4-amine, 2 TFA (0.056 g, 0.095 mmol, 22% yield) as a colorless oil. LCMS (ESI) m/e 364.2 [(M+H)$^+$, calcd for $C_{19}H_{22}N_7O$ 364.2]. $^1$H NMR (500 MHz, MeOD) δ 8.36 (t, J=1.7 Hz, 1H), 8.17 (dt, J=7.8, 1.3 Hz, 1H), 7.82-7.76 (m, 3H), 7.75-7.69 (m, 1H), 6.74 (d, J=2.4 Hz, 1H), 3.45 (s, 2H), 2.73 (s, 3H), 1.62 (s, 6H); HPLC retention time (method C): $t_R$=6.95 min.

Example 92

N-(3-(5-isopropyl-1,2,4-oxadiazol-3-yl)-5-methoxyphenyl)-5-methylpyrrolo[2,1-f][1,2,4]triazin-4-amine

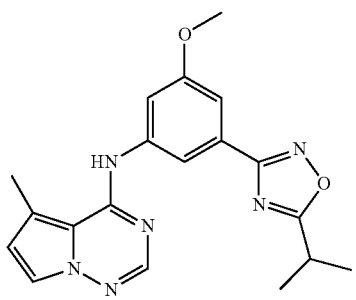 [SMILES: COc1cc(Nc2ncnn3ccc(C)c23)cc(-c2noc(C(C)C)n2)c1]

Prepared as described in Example 86 using 3-(5-isopropyl-1,2,4-oxadiazol-3-yl)-5-methoxyaniline (0.071 g, 0.304 mmol) to afford N-(3-(5-isopropyl-1,2,4-oxadiazol-3-yl)-5-methoxyphenyl)-5-methylpyrrolo[1,2-f][1,2,4]triazin-4-amine, TFA (0.0185 g, 0.038 mmol, 12% yield) as a reddish oil. LCMS (ESI) m/e 365.2 [(M+H)$^+$, calcd for $C_{19}H_{21}N_6O_2$ 365.2]. $^1$H NMR (400 MHz, MeOD) δ 7.85-7.80 (m, 1H), 7.73 (s, 1H), 7.67 (d, J=2.5 Hz, 1H), 7.54 (dd, J=2.4, 1.4 Hz, 1H), 7.43-7.38 (m, 1H), 6.65 (d, J=2.5 Hz, 1H), 3.89 (s, 3H), 3.31 (spt, J=7.1 Hz, 1H), 2.66 (s, 3H), 1.43 (d, J=7.1 Hz, 6H); HPLC retention time (method C): $t_R$=13.47 min.

Example 93

3-(5-isopropyl-1,2,4-oxadiazol-3-yl)-5-((5-methylpyrrolo[2,1-f][1,2,4]triazin-4-yl)amino)phenol

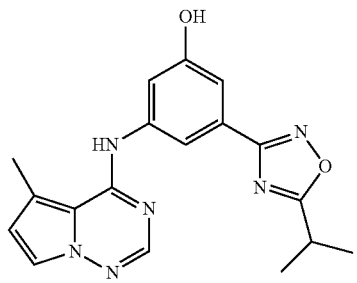 [SMILES: Cc1ccn2ncnc(Nc3cc(O)cc(-c4noc(C(C)C)n4)c3)c12]

Prepared as described in Example 86 using 3-amino-5-(5-isopropyl-1,2,4-oxadiazol-3-yl)phenol (0.085 g, 0.388 mmol) to afford 3-(5-isopropyl-1,2,4-oxadiazol-3-yl)-5-(5-methylpyrrolo[1,2-f][1,2,4]triazin-4-ylamino)phenol, TFA (0.083 g, 0.176 mmol, 45% yield) as a reddish oil. LCMS (ESI) m/e 351.1 [(M+H)$^+$, calcd for $C_{18}H_{19}N_6O_2$ 351.2]. $^1$H NMR (400 MHz, MeOD) δ 7.79 (d, J=2.5 Hz, 1H), 7.71 (s, 1H), 7.68-7.64 (m, 1H), 7.57 (dd, J=2.3, 1.3 Hz, 1H), 7.15 (t, J=2.1 Hz, 1H), 6.73 (d, J=2.3 Hz, 1H), 3.32 (spt, J=7.1 Hz, 1H), 2.67 (s, 3H), 1.42 (d, J=7.1 Hz, 6H); HPLC retention time (method C): $t_R$=10.92 min.

Example 94 ethyl 4-((3-(5-isopropyl-1,3,4-thiadiazol-2-yl)phenyl)amino)pyrrolo[2,1-f][1,2,4]triazine-5-carboxylate

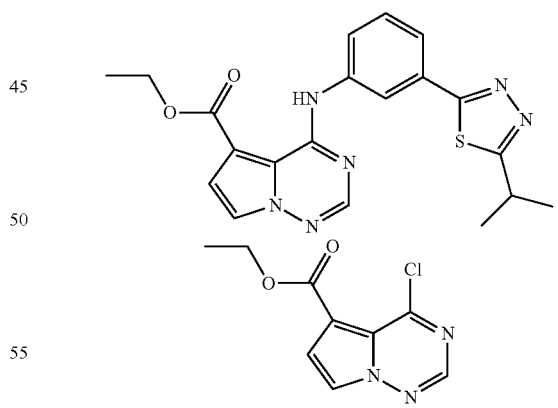

Part A: ethyl 4-chloropyrrolo[2,1-f][1,2,4]triazine-5-carboxylate

A solution of ethyl 4-oxo-3,4-dihydropyrrolo[1,2-f][1,2,4]triazine-5-carboxylate (500 mg, 2.413 mmol) [prepared as described in U.S. Pat. No. 7,514,435] in thionyl chloride (7046 µL, 97 mmol) with 1 drop DMF was heated to 80° C. for 2 h. The reaction mixture was cooled to room temperature and concentrated under reduced pressure. Added dry DCM to the residue and concentrated 3× to ensure removal of excess thionyl chloride. Obtained ethyl 4-chloropyrrolo [1,2-f][1,2,4]triazine-5-carboxylate (544 mg, 2.41 mmol, quantitative crude yield) as an orange-brown solid. Carried on without further purification. LCMS (ESI) m/e 226.0 [(M+H)+, calcd for C9H9ClN3O2 226.0]. 1H NMR (400 MHz, DMSO-d6) δ 8.58 (s, 1H), 8.24 (d, J=2.77 Hz, 1H), 7.47 (d, J=3.02 Hz, 1H), 4.31 (q, J=7.18 Hz, 2H), 1.32 (t, J=7.18 Hz, 3H).

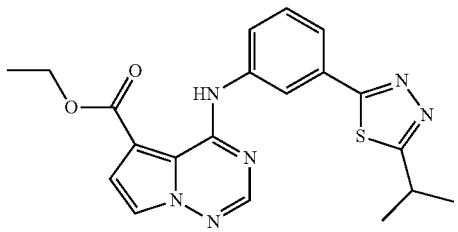 [SMILES: CCOC(=O)c1ccn2ncnc(Nc3cccc(-c4nnc(C(C)C)s4)c3)c12]

Part B: ethyl 4-((3-(5-isopropyl-1,3,4-thiadiazol-2-yl)phenyl)amino)pyrrolo[2,1-f][1,2,4]triazine-5-carboxylate To a solution of ethyl 4-chloropyrrolo[1,2-f][1,2,4]triazine-5-carboxylate (0.04 g, 0.177 mmol) in dry acetonitrile (7 mL) in a microwave tube flushed with nitrogen was added 3-(5-isopropyl-1,3,4-thiadiazol-2-yl)aniline (0.039 g, 0.177 mmol) and DIEA (0.037 mL, 0.213 mmol). The reaction tube was capped and heated in a microwave at 85° C. for 45 min. The reaction mixture was concentrated under reduced pressure and purified by reverse phase preparative HPLC (water/Methanol/0.1% TFA) to afford ethyl 4-(3-(5-isopropyl-1,3,4-thiadiazol-2-yl)phenylamino)pyrrolo[1,2-f][1,2,4]triazine-5-carboxylate, TFA (0.0236 g, 0.044 mmol, 25% yield) as a pale brown solid. LCMS (ESI) m/e 409.0 [(M+H)+, calcd for C20H21N6O2S 409.1]. 1H NMR (400 MHz, MeOD) δ 8.35 (t, J=1.8 Hz, 1H), 7.89 (s, 1H), 7.63 (dt, J=8.1, 1.0 Hz, 1H), 7.44 (dd, J=7.7, 0.9 Hz, 1H), 7.35 (d, J=3.0 Hz, 1H), 7.24 (t, J=7.8 Hz, 1H), 6.96 (d, J=3.0 Hz, 1H), 4.29 (q, J=7.2 Hz, 2H), 3.45 (spt, J=6.9 Hz, 1H), 1.46 (d, J=6.8 Hz, 6H), 1.36 (t, J=7.2 Hz, 3H); HPLC retention time (method C): $t_R$=18.79 min.

Example 95 ethyl 4-((3-hydroxy-5-(2-isopropyl-2H-tetrazol-5-yl)phenyl)amino)pyrrolo[2,1-f][1,2,4]triazine-5-carboxylate

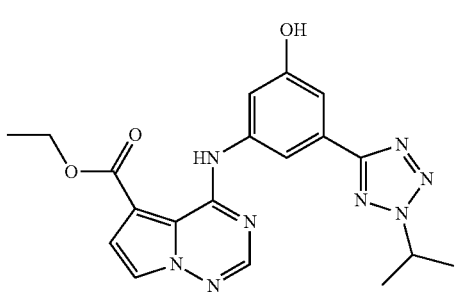 [SMILES: CCOC(=O)c1ccn2ncnc(Nc3cc(O)cc(-c4nnn(C(C)C)n4)c3)c12]

Prepared as described in Example 94 using 3-amino-5-(2-isopropyl-2H-tetrazol-5-yl)phenol (0.039 g, 0.177 mmol) to afford ethyl 4-(3-hydroxy-5-(2-isopropyl-2H-tetrazol-5-yl)phenylamino)pyrrolo[1,2-f][1,2,4]triazine-5-carboxylate, TFA (0.017 g, 0.032 mmol, 18% yield) as a brown solid. LCMS (ESI) m/e 409.0 [(M+H)+, calcd for C19H21N8O3 409.2]. 1H NMR (400 MHz, MeOD) δ 8.70 (d, J=2.0 Hz, 1H), 8.05 (s, 1H), 7.76 (dd, J=8.4, 2.1 Hz, 1H), 7.63 (d, J=3.0 Hz, 1H), 7.23 (d, J=3.0 Hz, 1H), 7.03 (d, J=8.3 Hz, 1H), 4.42 (q, J=7.1 Hz, 2H), 3.31 (spt, J=7.0 Hz, 1H), 1.43 (d, J=7.1 Hz, 6H), 1.40 (t, J=7.0 Hz, 3H); HPLC retention time (method C): $t_R$=16.88 min.

Example 96 ethyl 4-((3-(2-isopropyl-2H-tetrazol-5-yl)phenyl)amino)pyrrolo[2,1-f][1,2,4]triazine-5-carboxylate

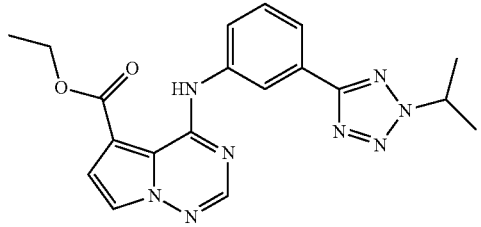 [SMILES: CCOC(=O)c1ccn2ncnc(Nc3cccc(-c4nnn(C(C)C)n4)c3)c12]

Prepared as described in Example 94 using 3-(2-isopropyl-2H-tetrazol-5-yl)aniline (20.81 mg, 0.102 mmol) to afford ethyl 4-((3-(2-isopropyl-2H-tetrazol-5-yl)phenyl)amino)pyrrolo[2,1-f][1,2,4]triazine-5-carboxylate, TFA (15 mg, 0.029 mmol, 31% yield) as a beige solid. LCMS (ESI) m/e 393.2 [(M+H)+, calcd for C19H21N8O2 393.2]. 1H NMR (400 MHz, MeOD) δ ppm 8.60 (t, J=1.8 Hz, 1H), 8.07 (s, 1H), 7.95 (dd, J=8.2, 1.4 Hz, 1H), 7.80 (d, J=7.6 Hz, 1H), 7.53 (d, J=3.0 Hz, 1H), 7.46 (t, J=7.9 Hz, 1H), 7.16 (d, J=3.0 Hz, 1H), 5.17 (spt, J=6.7 Hz, 1H), 4.41 (q, J=7.2 Hz, 2H), 1.70 (d, J=6.8 Hz, 6H), 1.41 (t, J=7.2 Hz, 3H); HPLC retention time (method E): $t_R$=20.05 min; HPLC retention time (method F): $t_R$=15.51 min.

Example 97 ethyl 4-((3-(5-isopropyl-1,2,4-oxadiazol-3-yl)phenyl)amino)pyrrolo[2,1-f][1,2,4]triazine-5-carboxylate

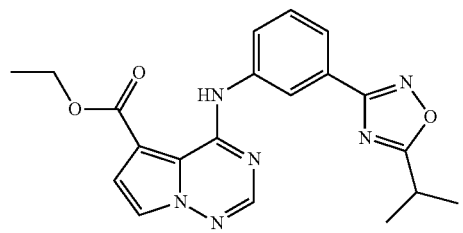 [SMILES: CCOC(=O)c1ccn2ncnc(Nc3cccc(-c4noc(C(C)C)n4)c3)c12]

Prepared as described in Example 94 using 3-(5-isopropyl-1,2,4-oxadiazol-3-yl)aniline (0.036 g, 0.177 mmol) to afford ethyl 4-(3-(5-isopropyl-1,2,4-oxadiazol-3-yl)phenylamino)pyrrolo[1,2-f][1,2,4]triazine-5-carboxylate, TFA (0.016 g, 0.031 mmol, 17% yield) as a yellow solid. LCMS (ESI) m/e 393.2 [(M+H)+, calcd for $C_{20}H_{21}N_6O_3$ 393.2]. $^1$H NMR (400 MHz, CHLOROFORM-d) δ 8.69-8.59 (m, 1H), 8.18 (s, 1H), 8.11-8.02 (m, 1H), 7.88 (dt, J=7.7, 1.2 Hz, 1H), 7.59-7.47 (m, 2H), 7.22 (d, J=3.0 Hz, 1H), 4.46 (q, J=7.2 Hz, 2H), 3.34 (spt, J=7.0 Hz, 1H), 1.50 (d, J=7.1 Hz, 6H), 1.46 (t, J=7.2 Hz, 3H); HPLC retention time (method C): $t_R$=19.03 min.

Example 98

(4-((3-(2-isopropyl-2H-tetrazol-5-yl)phenyl)amino)pyrrolo[2,1-f][1,2,4]triazin-5-yl)methanol

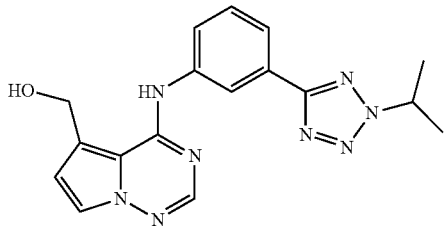 [SMILES: CC(C)n1nnc(-c2cccc(Nc3ncnn4ccc(CO)c34)c2)n1]

To a solution of ethyl 4-(3-(2-isopropyl-2H-tetrazol-5-yl)phenylamino)pyrrolo[1,2-f][1,2,4]triazine-5-carboxylate (114 mg, 0.291 mmol) [prepared as described in Example 96] in THF (1.453 mL) at 0° C. was added LAH (2M in THF) (0.291 mL, 0.581 mmol) dropwise. The resultant mixture was warmed to room temperature and stirred for 3 h. The mixture was filtered and the filtrate was extracted with EtOAc (3×10 mL). The combined organics were washed with brine (1×10 mL), dried (MgSO4), filtered and concentrated under reduced pressure. The crude material was purified by reverse phase HPLC (40%-100% MeOH/H$_2$O/0.1% TFA). The fractions were basified with saturated aqueous sodium bicarbonate and extracted with EtOAc (3×10 mL). The combined organics were washed with brine (1×10 mL), dried (MgSO4), filtered and concentrated under reduced pressure. Obtained (4-(3-(2-isopropyl-2H-tetrazol-5-yl)phenylamino)pyrrolo[1,2-f][1,2,4]triazin-5-yl)methanol (80 mg, 0.224 mmol, 77% yield) as a colorless oil. LCMS (ESI) m/e 351.2 [(M+H)+, calcd for $C_{17}H_{19}N_8O$ 351.2]. $^1$H NMR (400 MHz, CHLOROFORM-d) δ ppm 10.10 (br. s, 1H), 8.40 (t, J=1.9 Hz, 1H), 7.99 (s, 1H), 7.93 (ddd, J=8.1, 2.3, 1.0 Hz, 1H), 7.83 (ddd, J=7.9, 1.3, 1.1 Hz, 1H), 7.41-7.48 (m, 2H), 6.48 (d, J=2.5 Hz, 1H), 5.10 (spt, J=6.8 Hz, 1H), 3.03 (br. s, 1H), 1.70 (d, J=6.8 Hz, 6H); HPLC retention time (method E): $t_R$=11.05 min; HPLC retention time (method F): $t_R$=9.42 min.

Example 99

5-(aminomethyl)-N-(3-(2-isopropyl-2H-tetrazol-5-yl)phenyl)pyrrolo[2,1-f][1,2,4]triazin-4-amine

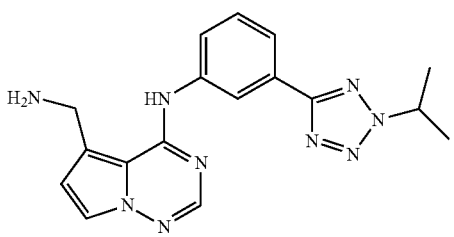 [SMILES: CC(C)n1nnc(-c2cccc(Nc3ncnn4ccc(CN)c34)c2)n1]

To a solution of (4-(3-(2-isopropyl-2H-tetrazol-5-yl)phenylamino)pyrrolo[1,2-f][1,2,4]triazin-5-yl)methanol (66 mg, 0.188 mmol) and DIEA (115 µL, 0.659 mmol) in NMP (435 µL, 4.52 mmol) cooled to −20° C. was added methanesulfonyl chloride (19.08 µL, 0.245 mmol) dropwise. The solution was stirred at −20° C. for 1 h, them warmed to 0° C. and stirred for 30 min. Added ammonia (2M in methanol) (942 µL, 1.884 mmol) and stirred at 0° C. for 2 h. LC/MS shows peaks corresponding to displacement of the intermediate chloride with NH2 as well as with OMe (from the methanol). The reaction mixture was concentrated under reduced pressure. The crude material was purified by reverse phase HPLC (30%-100% MeOH/H$_2$O/0.1% TFA). Isolated OMe derivative as a TFA salt (see Example 100) The product fractions were basified with saturated aqueous sodium bicarbonate and extracted with EtOAc (3×10 mL). The combined organics were washed with brine (1×10 mL), dried (MgSO$_4$), filtered and concentrated under reduced pressure. Obtained 5-(aminomethyl)-N-(3-(2-isopropyl-2H-tetrazol-5-yl)phenyl)pyrrolo[1,2-f][1,2,4]triazin-4-amine (9 mg, 0.024 mmol, 13% yield) as a colorless film. LCMS (ESI) m/e 350.2 [(M+H)+, calcd for $C_{17}H_{20}N_9$ 350.2]. $^1$H NMR (400 MHz, MeOD) δ ppm 8.46 (t, J=1.8 Hz, 1H), 7.83-7.87 (m, 1H), 7.76-7.81 (m, 2H), 7.46 (t, J=7.9 Hz, 1H), 7.44 (d, J=2.8 Hz, 1H), 6.56 (d, J=2.8 Hz, 1H), 5.15 (spt, J=6.7 Hz, 1H), 4.16 (s, 2H), 1.68 (d, J=6.8 Hz, 6H); HPLC retention time (method E): $t_R$=6.91 min; HPLC retention time (method F): $t_R$=7.22 min.

Example 100

N-(3-(2-isopropyl-2H-tetrazol-5-yl)phenyl)-5-(methoxymethyl)pyrrolo[2,1-f][1,2,4]triazin-4-amine

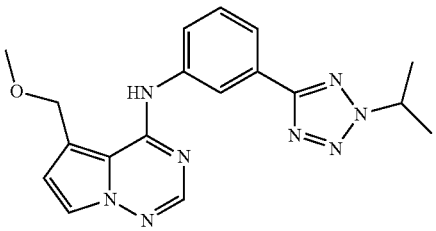 [SMILES: COCc1ccn2ncnc(Nc3cccc(-c4nnn(C(C)C)n4)c3)c12]

Isolated as side product from Example 99. Obtained N-(3-(2-isopropyl-2H-tetrazol-5-yl)phenyl)-5-(methoxymethyl)pyrrolo[1,2-f][1,2,4]triazin-4-amine, TFA (8 mg, 0.016 mmol, 9% yield) as a colorless film. LCMS (ESI) m/e 365.2 [(M+H)+, calcd for $C_{18}H_{21}N_8O$ 365.2]. $^1$H NMR (400 MHz, MeOD) δ ppm 8.45 (t, J=1.8 Hz, 1H), 7.97 (d, J=7.8 Hz, 1H), 7.92 (s, 1H), 7.79 (ddd, J=8.1, 2.2, 1.0 Hz, 1H), 7.67 (d, J=2.5 Hz, 1H), 7.59 (t, J=7.9 Hz, 1H), 6.75 (d, J=2.8 Hz, 1H), 5.17 (spt, J=6.5 Hz, 1H), 4.90 (s, 2H), 3.59 (s, 3H), 1.69 (d, J=6.5 Hz, 6H); HPLC retention time (method E): $t_R$=15.36 min; HPLC retention time (method F): $t_R$=12.54 min.

Example 101

4-((3-(2-isopropyl-2H-tetrazol-5-yl)phenyl)amino)-N,N-dimethylpyrrolo[2,1-f][1,2,4]triazine-5-carboxamide

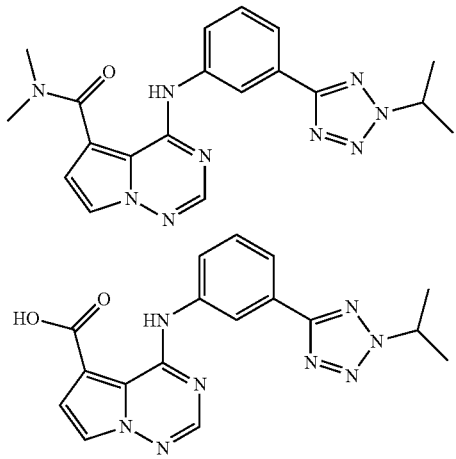

Part A: 4-((3-(2-isopropyl-2H-tetrazol-5-yl)phenyl)amino)pyrrolo[2,1-f][1,2,4]triazine-5-carboxylic acid To a solution of ethyl 4-(3-(2-isopropyl-2H-tetrazol-5-yl)phenylamino)pyrrolo[1,2-f][1,2,4]triazine-5-carboxylate (0.393 g, 1.001 mmol) [prepared as described in Example 96] in dry THF (100 mL) was added lithium hydroxide, H₂O (0.126 g, 3.00 mmol) and water (2.000 mL). The reaction mixture was heated to 40° C. for 4 hours. The reaction mixture was neutralized with 1N HCl and extracted with ethyl acetate (3×200 mL). The organic layers were combined and washed with water (1×100 mL), brine (1×100 mL), dried (MgSO4) and concentrated under reduced pressure to obtain 4-(3-(2-isopropyl-2H-tetrazol-5-yl)phenylamino)pyrrolo[1,2-f][1,2,4]triazine-5-carboxylic acid (0.289 g, 0.793 mmol, 79% yield). The product was carried on without further purification. LCMS (ESI) m/e 365.1 [(M+H)⁺, calcd for $C_{17}H_{17}N_8O_2$ 365.2].

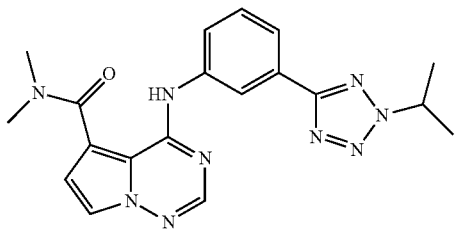 [SMILES: CC(C)n1nnc(-c2cccc(Nc3ncnn4ccc(C(=O)N(C)C)c34)c2)n1]

Part B: 4-((3-(2-isopropyl-2H-tetrazol-5-yl)phenyl)amino)-N,N-dimethylpyrrolo[2,1-f][1,2,4]triazine-5-carboxamide To a mixture of 4-(3-(2-isopropyl-2H-tetrazol-5-yl)phenylamino)pyrrolo[1,2-f][1,2,4]triazine-5-carboxylic acid (36 mg, 0.099 mmol) and HATU (56.4 mg, 0.148 mmol) in DMF (494 µL) was added dimethylamine hydrochloride (40.3 mg, 0.494 mmol) and DIEA (121 µL, 0.692 mmol). The reaction mixture was stirred at room temperature for 1 h. The crude material was concentrated under reduced pressure and purified by reverse phase HPLC (40%-100% MeOH/H₂O/0.1% TFA). The product fractions were basified with saturated aqueous sodium bicarbonate and extracted with EtOAc (3×10 mL). The combined organics were washed with brine (1×10 mL), dried (MgSO₄), filtered and concentrated under reduced pressure. Obtained 4-(3-(2-isopropyl-2H-tetrazol-5-yl)phenylamino)-N,N-dimethylpyrrolo[1,2-f][1,2,4]triazine-5-carboxamide (30.7 mg, 0.077 mmol, 78% yield) as a pale brown oil. LCMS (ESI) m/e 392.3 [(M+H)⁺, calcd for $C_{19}H_{22}N_9O$ 392.2]. ¹H NMR (400 MHz, CHLOROFORM-d) ppm 11.79 (s, 1H), 8.61 (t, J=1.9 Hz, 1H), 8.10 (s, 1H), 7.82-7.93 (m, 2H), 7.51 (d, 1H), 7.47 (t, J=7.9 Hz, 1H), 6.83 (d, J=3.0 Hz, 1H), 5.10 (spt, J=6.8 Hz, 1H), 3.25 (br. s, 6H), 1.69 (d, J=6.8 Hz, 6H); HPLC retention time (method E): $t_R$=16.16 min; HPLC retention time (method F): $t_R$=13.20 min.

Example 102

5-((dimethylamino)methyl)-N-(3-(2-isopropyl-2H-tetrazol-5-yl)phenyl)pyrrolo[2,1-f][1,2,4]triazin-4-amine

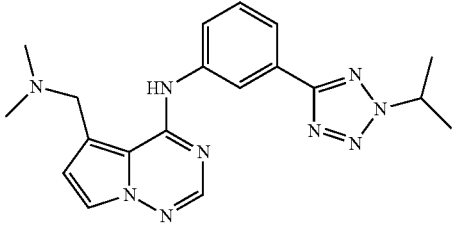 [SMILES: CC(C)n1nnc(-c2cccc(Nc3ncnn4ccc(CN(C)C)c34)c2)n1]

To a solution of 4-(3-(2-isopropyl-2H-tetrazol-5-yl)phenylamino)-N,N-dimethylpyrrolo[1,2-f][1,2,4]triazine-5-carboxamide (17.8 mg, 0.045 mmol) [prepared as described in Example 101] in THF (227 µL) 0° C. was added LAH (2M in THF) (45.5 µL, 0.091 mmol). The solution warmed to room temperature and stirred for 2.5 h. The reaction mixture was quenched with 20% aqueous Rochell's salt and filtered. The filtrate was extracted with EtOAc (3×10 mL). The combined organics were washed with brine (1×10 mL), dried (MgSO₄), filtered and concentrated under reduced pressure. The crude material was purified by reverse phase HPLC (30%-100% MeOH/H₂O/0.1% TFA). The product fractions were basified with saturated aqueous sodium bicarbonate and extracted with EtOAc (3×10 mL). The combined organics were washed with brine (1×10 mL), dried (MgSO₄), filtered and concentrated under reduced pressure. Obtained 5-((dimethylamino)methyl)-N-(3-(2-isopropyl-2H-tetrazol-5-yl)phenyl)pyrrolo[1,2-f][1,2,4]triazin-4-amine (9 mg, 0.024 mmol, 52% yield) as a colorless film. LCMS (ESI) m/e 378.2 [(M+H)⁺, calcd for $C_{19}H_{24}N_9$ 378.2]. ¹H NMR (400 MHz, CHLOROFORM-d) δ ppm 12.86 (br. s, 1H), 8.38 (t, J=1.9 Hz, 1H), 8.00 (ddd, J=8.1, 2.2, 1.0 Hz, 1H), 7.98 (s, 1H), 7.84 (d, J=7.8 Hz, 1H), 7.48 (d, J=8.06 Hz, 1H), 7.46 (d, J=2.5 Hz, 1H), 6.49 (d, J=2.5 Hz, 1H), 5.10 (spt, J=6.7 Hz, 1H), 3.75 (s, 2H), 2.47 (s, 6H), 1.70 (d, J=6.8 Hz, 6H); HPLC retention time (method E): $t_R$=7.06 min; HPLC retention time (method F): $t_R$=7.91 min.

Example 103

4-((3-(2-isopropyl-2H-tetrazol-5-yl)phenyl)amino)-N-methylpyrrolo[2,1-f][1,2,4]triazine-5-carboxamide

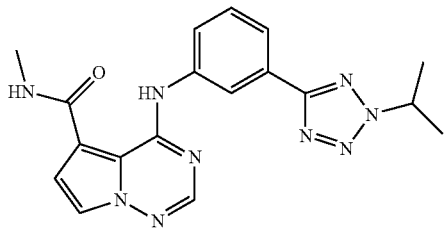 [SMILES: CNC(=O)c1ccn2ncnc(Nc3cccc(-c4nnn(C(C)C)n4)c3)c12]

Prepared as in Example 101 using methanamine hydrochloride (33.4 mg, 0.494 mmol) to afford 4-(3-(2-isopropyl-2H-tetrazol-5-yl)phenylamino)-N-methylpyrrolo[1,2-f][1,2,4]triazine-5-carboxamide (28.5 mg, 0.074 mmol, 75% yield) as a pale yellow solid. LCMS (ESI) m/e 378.2 [(M+H)$^+$, calcd for $C_{18}H_{20}N_9O$ 378.2]. $^1$H NMR (400 MHz, CHLOROFORM-d) δ ppm 13.18 (s, 1H), 8.70 (t, J=1.8 Hz, 1H), 8.07 (s, 1H), 7.95 (ddd, J=8.1, 2.3, 1.0 Hz, 1H), 7.88 (ddd, J=7.9, 1.3, 1.1 Hz, 1H), 7.47 (t, J=7.9 Hz, 1H), 7.44 (d, J=3.0 Hz, 1H), 6.79 (d, J=3.3 Hz, 1H), 6.49 (d, J=4.5 Hz, 1H), 5.11 (spt, J=6.8 Hz, 1H), 3.04 (d, J=4.8 Hz, 3H), 1.70 (d, J=6.8 Hz, 6H); HPLC retention time (method E): $t_R$=15.47 min; HPLC retention time (method F): $t_R$=12.41 min.

Example 104

N-ethyl-4-((3-(2-isopropyl-2H-tetrazol-5-yl)phenyl)amino)pyrrolo[2,1-f][1,2,4]triazine-5-carboxamide

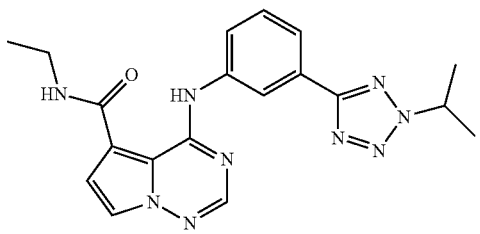 [SMILES: CCNC(=O)c1ccn2ncnc(Nc3cccc(-c4nnn(C(C)C)n4)c3)c12]

Prepared as in Example 101 using ethylamine (8.62 μL, 0.132 mmol) to afford N-ethyl-4-(3-(2-isopropyl-2H-tetrazol-5-yl)phenylamino)pyrrolo[1,2-f][1,2,4]triazine-5-carboxamide, TFA (0.0164 g, 0.032 mmol, 24% yield) as a colorless film. LCMS (ESI) m/e 392.1 [(M+H)$^+$, calcd for $C_{19}H_{22}N_9O$ 392.2]. $^1$H NMR (500 MHz, MeOD) δ 8.74-8.62 (m, 1H), 8.15-8.02 (m, 1H), 8.00-7.94 (m, 1H), 7.91-7.79 (m, 1H), 7.58 (dd, J=12.1, 2.9 Hz, 1H), 7.50 (dt, J=14.3, 7.9 Hz, 1H), 7.23 (dd, J=18.6, 3.1 Hz, 1H), 5.28-5.12 (m, 1H), 3.49 (q, J=7.1 Hz, 2H), 1.73 (d, J=6.6 Hz, 6H), 1.29 (t, J=7.2 Hz, 3H).

Example 105

N-(cyclopropylmethyl)-4-((3-(2-isopropyl-2H-tetrazol-5-yl)phenyl)amino)pyrrolo[2,1-f][1,2,4]triazine-5-carboxamide

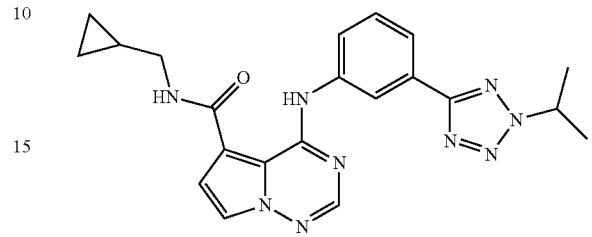

Prepared as in Example 101 using aminomethylcyclopropane (0.011 mL, 0.132 mmol) to afford N-(cyclopropylmethyl)-4-(3-(2-isopropyl-2H-tetrazol-5-yl)phenylamino)pyrrolo[1,2-f][1,2,4]triazine-5-carboxamide, TFA (0.018 g, 0.034 mmol, 26% yield) as a colorless solid. LCMS (ESI) m/e 418.1 [(M+H)$^+$, calcd for $C_{21}H_{24}N_9O$ 418.2]. $^1$H NMR (500 MHz, MeOD) δ 8.65 (t, J=1.7 Hz, 1H), 8.04 (s, 1H), 7.93 (d, J=1.8 Hz, 1H), 7.92 (d, J=1.8 Hz, 1H), 7.63 (d, J=3.1 Hz, 1H), 7.55 (t, J=7.9 Hz, 1H), 7.33 (d, J=3.1 Hz, 1H), 5.18 (spt, J=6.7 Hz, 1H), 3.36-3.32 (m, 2H), 1.73 (d, J=6.7 Hz, 6H), 1.22-1.12 (m, 1H), 0.61-0.52 (m, 2H), 0.38-0.29 (m, 2H); HPLC retention time (method C): $t_R$=16.07 min.

Example 106

N-isopropyl-4-((3-(2-isopropyl-2H-tetrazol-5-yl)phenyl)amino)pyrrolo[2,1-f][1,2,4]triazine-5-carboxamide

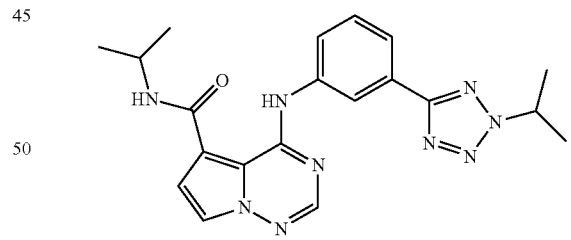

Prepared as in Example 101 using isopropylamine (0.011 mL, 0.132 mmol) to afford N-isopropyl-4-(3-(2-isopropyl-2H-tetrazol-5-yl)phenylamino)pyrrolo[1,2-f][1,2,4]triazine-5-carboxamide, TFA (0.0094 g, 0.018 mmol, 13% yield) as a colorless film. LCMS (ESI) m/e 406.1 [(M+H)$^+$, calcd for $C_{20}H_{24}N_9O$ 406.2]. $^1$H NMR (500 MHz, CHLOROFORM-d) δ 8.72 (t, J=1.8 Hz, 1H), 8.10 (s, 1H), 7.93 (dd, J=15.6, 7.9 Hz, 2H), 7.55-7.41 (m, 2H), 6.79 (d, J=3.1 Hz, 1H), 5.12 (spt, J=6.8 Hz, 1H), 4.45-4.21 (m, 1H), 1.71 (d, J=6.7 Hz, 6H), 1.31 (d, J=6.4 Hz, 6H); HPLC retention time (method C): $t_R$=15.68 min.

Example 107

N-(cyanomethyl)-4-((3-(2-isopropyl-2H-tetrazol-5-yl)phenyl)amino)pyrrolo[2,1-f][1,2,4]triazine-5-carboxamide

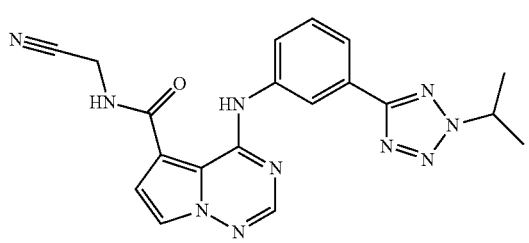 [SMILES: CC(C)n1nnc(-c2cccc(Nc3ncnn4ccc(C(=O)NCC#N)c34)c2)n1]

Prepared as in Example 101 using aminoacetonitrile (7.39 mg, 0.132 mmol) to afford N-(cyanomethyl)-4-(3-(2-isopropyl-2H-tetrazol-5-yl)phenylamino)pyrrolo[1,2-f][1,2,4]triazine-5-carboxamide, TFA (0.012 g, 0.023 mmol, 17% yield) as an off-white solid. LCMS (ESI) m/e 403.1 [(M+H)$^+$, calcd for $C_{19}H_{19}N_{10}O$ 403.2]. $^1$H NMR (500 MHz, CHLOROFORM-d) δ 8.59 (t, J=1.8 Hz, 1H), 8.03-7.97 (m, 1H), 7.91-7.75 (m, 2H), 7.47-7.38 (m, 2H), 7.04 (d, J=3.1 Hz, 1H), 5.04 (spt, J=6.7 Hz, 1H), 4.26 (s, 2H), 1.63 (d, J=6.7 Hz, 6H); HPLC retention time (method C): $t_R$=14.03 min.

Example 108

4-((3-(2-isopropyl-2H-tetrazol-5-yl)phenyl)amino)-N-(2-methoxyethyl)pyrrolo[2,1-f][1,2,4]triazine-5-carboxamide

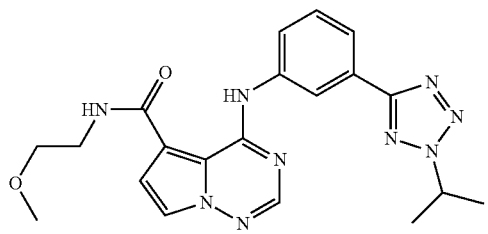 [SMILES: COCCNC(=O)c1ccn2ncnc(Nc3cccc(-c4nnn(C(C)C)n4)c3)c12]

Prepared as in Example 101 using 2-methoxyethylamine (0.011 mL, 0.132 mmol) to afford 4-(3-(2-isopropyl-2H-tetrazol-5-yl)phenylamino)-N-(2-methoxyethyl)pyrrolo[1,2-f][1,2,4]triazine-5-carboxamide, TFA (0.025 g, 0.046 mmol, 35% yield) as a colorless film. LCMS (ESI) m/e 422.1 [(M+H)$^+$, calcd for $C_{20}H_{24}N_9O_2$ 422.2]. $^1$H NMR (400 MHz, MeOD) δ 8.68 (t, J=1.8 Hz, 1H), 8.07 (s, 1H), 7.99 (ddd, J=8.1, 2.2, 1.0 Hz, 1H), 7.90 (dt, J=7.9, 1.2 Hz, 1H), 7.64 (d, J=3.0 Hz, 1H), 7.55 (t, J=7.9 Hz, 1H), 7.30 (d, J=3.0 Hz, 1H), 5.20 (spt, J=6.7 Hz, 1H), 3.71-3.60 (m, 4H), 3.42 (s, 3H), 1.73 (d, J=6.8 Hz, 6H); HPLC retention time (method C): $t_R$=14.70 min.

Example 109

(4-aminopiperidin-1-yl)(4-((3-(2-isopropyl-2H-tetrazol-5-yl)phenyl)amino)pyrrolo[2,1-f][1,2,4]triazin-5-yl)methanone

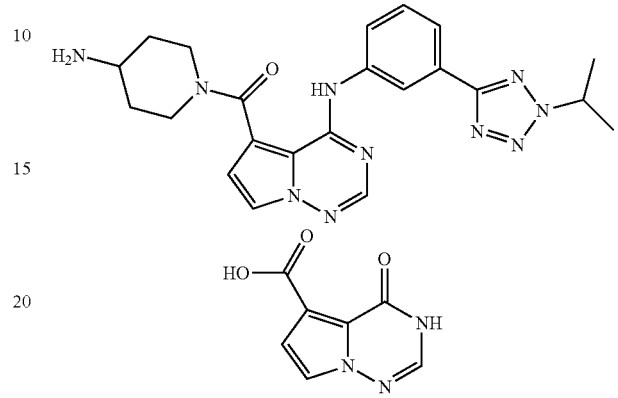

Part A: 4-oxo-3,4-dihydropyrrolo[2,1-f][1,2,4]triazine-5-carboxylic acid

To a partial suspension of ethyl 4-oxo-3,4-dihydropyrrolo[1,2-f][1,2,4]triazine-5-carboxylate (1 g, 4.83 mmol) [prepared as described in U.S. Pat. No. 7,514,435] in THF (10.17 mL) and MeOH (1.272 mL) was added lithium hydroxide (0.578 g, 24.13 mmol) in water (2.54 mL). The reaction was heated to 50° C. for 2 h then stirred at room temperature overnight. The mixture was concentrated under reduced pressure, diluted with water (10 mL) then acidified to pH-5 with glacial acetic acid (1.382 mL, 24.13 mmol). The off-white solid was collected by vacuum filtration and air dried for 2 h. Obtained 4-oxo-3,4-dihydropyrrolo[1,2-f][1,2,4]triazine-5-carboxylic acid (742 mg, 4.06 mmol, 84% yield) as an off-white amorphous solid. $^1$H NMR (400 MHz, DMSO-d$_6$) δ ppm 14.14 (br. s, 1H), 8.17 (s, 1H), 7.82 (d, J=3.0 Hz, 1H), 7.08 (d, J=3.0 Hz, 1H).

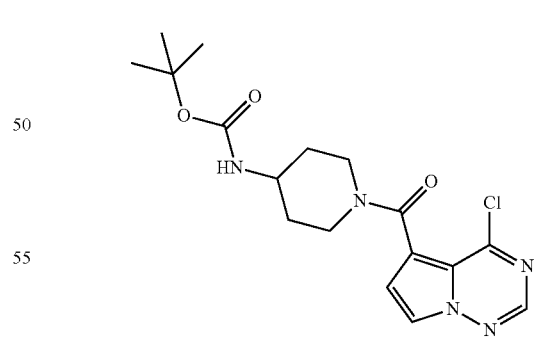

Part B: tert-butyl (1-(4-chloropyrrolo[2,1-f][1,2,4]triazine-5-carbonyl)piperidin-4-yl)carbamate To a solution of 4-oxo-3,4-dihydropyrrolo[2,1-f][1,2,4]triazine-5-carboxylic acid (0.371 g, 2.07 mmol) in thionyl chloride (3.78 mL, 51.8 mmol) was added DMF (8.01 µl, 0.104 mmol). The solution was heated to 80° C. for 1.25 h.

The solution was cooled to room temperature and concentrated under reduced pressure. DCM (10 mL) was added and the solution concentrated under reduced pressure (3×) to remove excess thionyl chloride. DCM (6.9 mL) was added followed by tert-butyl piperidin-4-ylcarbamate (415 mg, 2.070 mmol) and DIEA (723 µL, 4.14 mmol). The resultant mixture was stirred at room temperature overnight. The reaction mixture was diluted with water (10 mL) and extracted with DCM (3×20 mL). The combined organics were washed with brine (1×20 mL), dried (MgSO4), filtered and concentrated under reduced pressure. The residue was purified via silica gel chromatography (10%-100% EtOAc in hexanes) to afford tert-butyl 1-(4-chloropyrrolo[1,2-f][1,2,4]triazine-5-carbonyl)piperidin-4-ylcarbamate (195 mg, 0.359 mmol, 17% yield) as a yellow semi-solid. $^1$H NMR (400 MHz, CHLOROFORM-d) δ ppm 8.24 (s, 1H), 7.84 (d, J=2.5 Hz, 1H), 6.92 (d, J=2.8 Hz, 1H), 4.68 (br. s, 1H), 4.47 (br. s, 1H), 3.70 (br. s, 1H), 3.56 (d, J=14.9 Hz, 1H), 2.91-3.20 (m, 3H), 1.81-2.14 (m, 2H), 1.42 (s, 9H).

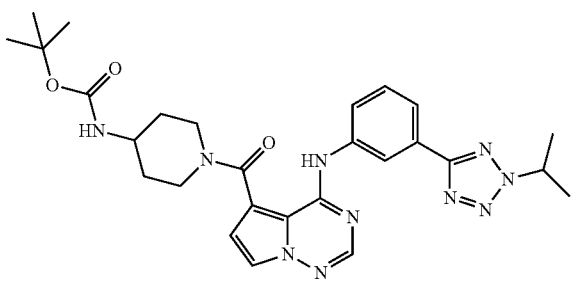 [SMILES: CC(C)n1nnc(-c2cccc(Nc3ncnn4ccc(C(=O)N5CCC(NC(=O)OC(C)(C)C)CC5)c34)c2)n1]

Part C: tert-butyl (1-(4-((3-(2-isopropyl-2H-tetrazol-S-yl)phenyl)amino)pyrrolo[2,1-f][1,2,4]triazine-5-carbonyl)piperidin-4-yl)carbamate A solution of tert-butyl 1-(4-chloropyrrolo[1,2-f][1,2,4]triazine-5-carbonyl)piperidin-4-ylcarbamate (50 mg, 0.132 mmol), 3-(2-isopropyl-2H-tetrazol-5-yl)aniline (53.5 mg, 0.263 mmol) and DIEA (46.0 µL, 0.263 mmol) in acetonitrile (600 µL) was stirred at room temperature for 1 h. The reaction mixture was concentrated under reduced pressure. The residue was purified by reverse phase HPLC (40%-100% MeOH/H$_2$O/0.1% TFA). Obtained tert-butyl 1-(4-(3-(2-isopropyl-2H-tetrazol-5-yl)phenylamino)pyrrolo[1,2-f][1,2,4]triazine-5-carbonyl)piperidin-4-ylcarbamate (56 mg, 0.102 mmol, 78% yield) as a yellow amorphous solid. LCMS (ESI) m/e 547.3 [(M+H)$^+$, calcd for C$_{27}$H$_{35}$N$_{10}$O$_3$ 547.3].

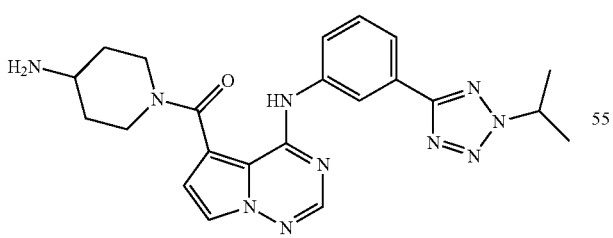

Part D: (4-aminopiperidin-1-yl)(4-((3-(2-isopropyl-2H-tetrazol-5-yl)phenyl)amino)pyrrolo[2,1-f][1,2,4]triazin-5-yl)methanone A solution of tert-butyl 1-(4-(3-(2-isopropyl-2H-tetrazol-5-yl)phenylamino)pyrrolo[1,2-f][1,2,4]triazine-5-carbonyl) piperidin-4-ylcarbamate (56 mg, 0.102 mmol) in hydrogen chloride (2M in diethyl ether) (2561 µL, 5.12 mmol) was stirred at room temperature for 2 h. The reaction mixture was concentrated under reduced pressure. The residue was purified by reverse phase HPLC (10%-100% MeOH/H$_2$O/0.1% TFA). Obtained (4-aminopiperidin-1-yl)(4-(3-(2-isopropyl-2H-tetrazol-5-yl)phenylamino)pyrrolo[1,2-f][1,2,4]triazin-5-yl)methanone, 2 TFA (33.4 mg, 0.047 mmol, 46% yield) as a colorless film. LCMS (ESI) m/e 447.2 [(M+H)$^+$, calcd for C$_{22}$H$_{27}$N$_{10}$O 447.3]. $^1$H NMR (400 MHz, MeOD) δ ppm 8.58 (t, J=1.6 Hz, 1H), 8.12 (s, 1H), 7.92 (ddd, J=8.2, 2.1, 1.0 Hz, 1H), 7.86 (dt, J=7.8, 1.3 Hz, 1H), 7.68 (d, J=3.0 Hz, 1H), 7.52 (t, J=7.9 Hz, 1H), 6.98 (d, 1H), 5.11-5.24 (m, J=6.7, 6.7, 6.7, 6.7, 6.5, 6.3 Hz, 1H), 4.68 (d, J=12.1 Hz, 2H), 3.39-3.54 (m, 1H), 3.15-3.27 (m, 2H), 2.11 (d, J=13.6 Hz, 2H), 1.70 (d, J=6.8 Hz, 6H), 1.58-1.68 (m, 2H); HPLC retention time (method E): t$_R$=9.13 min; HPLC retention time (method F): t$_R$=9.40 min.

Example 110

(R)-2-amino-N-(3-((5-(4-aminopiperidine-1-carbonyl)pyrrolo[2,1-f][1,2,4]triazin-4-yl)amino)phenyl)-4-methylpentanamide

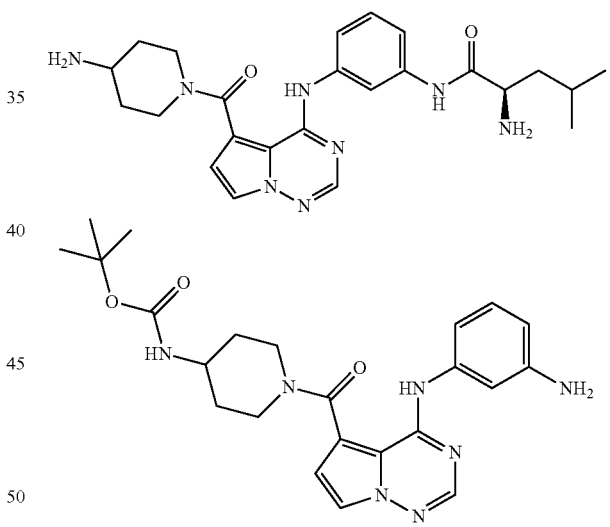

Part A: tert-butyl (1-(4-((3-aminophenyl)amino) pyrrolo[2,1-f][1,2,4]triazine-5-carbonyl)piperidin-4-yl)carbamate Prepared as described in Example 109, Parts A-C using tert-butyl piperidin-4-ylcarbamate (415 mg, 2.070 mmol) in Part B and benzene-1,3-diamine (71.2 mg, 0.658 mmol) in Part C to afford tert-butyl 1-(4-(3-aminophenylamino)pyrrolo[1,2-f][1,2,4]triazine-5-carbonyl)piperididn-4-ylcarbamate, TFA (75 mg, 0.126 mmol, 96% yield) as a yellow oil. LCMS (ESI) m/e 452.3 [(M+H)$^+$, calcd for C$_{23}$H$_{30}$N$_7$O$_3$ 452.2].

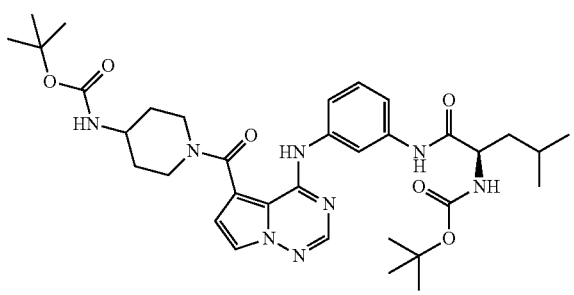 [SMILES: CC(C)C[C@@H](NC(=O)OC(C)(C)C)C(=O)Nc1cccc(Nc2ncnn3ccc(C(=O)N4CCC(NC(=O)OC(C)(C)C)CC4)c23)c1]

Part B: (R)-tert-butyl (4-methyl-1-oxo-1-((3-((5-(4-(tert-butoxycarbonylamino)piperidine-1-carbonyl)pyrrolo[2,1-f][1,2,4]triazin-4-yl)amino)phenyl)amino)pentan-2-yl)carbamate To a solution of (R)-2-(tert-butoxycarbonylamino)-4-methylpentanoic acid (19.47 mg, 0.084 mmol), DCC (17.36 mg, 0.084 mmol) and DMAP (1.028 mg, 8.42 µmol) in DCM (842 µL) which was stirred for 5 min was added tert-butyl 1-(4-(3-aminophenylamino)pyrrolo[1,2-f][1,2,4]triazine-5-carbonyl)piperidin-4-ylcarbamate (38 mg, 0.084 mmol) and DIEA (29.4 µL, 0.168 mmol). The reaction mixture was stirred at room temperature overnight. The crude material was concentrated under reduced pressure and carried on into next reaction without purification. LCMS (ESI) m/e 665.3 [(M+H)+, calcd for $C_{34}H_{49}N_8O_6$ 665.4].

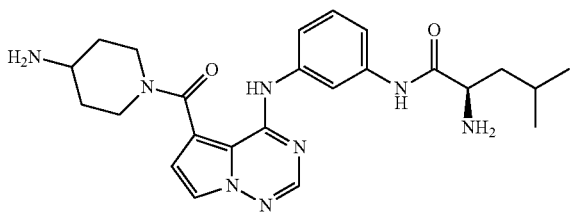 [SMILES: CC(C)C[C@@H](N)C(=O)Nc1cccc(Nc2ncnn3ccc(C(=O)N4CCC(N)CC4)c23)c1]

Part C: (R)-2-amino-N-(3-((5-(4-aminopiperidine-1-carbonyl)pyrrolo[2,1-f][1,2,4]triazin-4-yl)amino)phenyl)-4-methylpentanamide A solution of (R)-tert-butyl (4-methyl-1-oxo-1-((3-((5-(4-(tert-butoxycarbonylamino)piperidine-1-carbonyl)pyrrolo[2,1-f][1,2,4]triazin-4-yl)amino)phenyl)amino)pentan-2-yl)carbamate (55.8 mg, 0.084 mmol) in hydrogen chloride (2M in diethyl ether) (2100 µL, 4.20 mmol) was stirred at room temperature for 4 h. The reaction mixture was concentrated under reduced pressure and purified by reverse phase HPLC (10%-100% MeOH/H2O/0.1% TFA) to afford (R)-2-amino-N-(3-(5-(4-aminopiperidine-1-carbonyl)pyrrolo[1,2-f][1,2,4]triazin-4-ylamino)phenyl)-4-methylpentanamide, 2 TFA (11 mg, 0.015 mmol, 18% yield) as a brown oil. LCMS (ESI) m/e 465.3 [(M+H)+, calcd for $C_{24}H_{33}N_8O_2$ 465.3]. $^1$H NMR (400 MHz, MeOD) δ ppm 8.26 (t, J=2.0 Hz, 1H), 8.10 (s, 1H), 7.68 (d, J=3.0 Hz, 1H), 7.56 (dd, J=7.8, 1.5 Hz, 1H), 7.46 (t, J=8.1 Hz, 1H), 7.04 (dd, J=7.4, 1.6 Hz, 1H), 6.99 (d, J=2.8 Hz, 1H), 4.51 (d, J=8.3 Hz, 2H), 4.35-4.43 (m, 1H), 3.96-4.12 (m, 1H), 3.69 (s, 2H), 2.02 (d, J=10.6 Hz, 2H), 1.82-1.96 (m, 2H), 1.43-1.68 (m, 3H), 1.13-1.33 (m, 2H), 1.04 (d, J=7.1 Hz, 2H), 1.01 (d, J=6.8 Hz, 2H); HPLC retention time (method E): $t_R$=5.14 min; HPLC retention time (method F): $t_R$=5.54 min.

Example 111 methyl 5-((4-aminopiperidin-1-yl)methyl)-4-((3-(2-isopropyl-2H-tetrazol-5-yl)phenyl)amino)pyrrolo[2,1-f][1,2,4]triazine-6-carboxylate

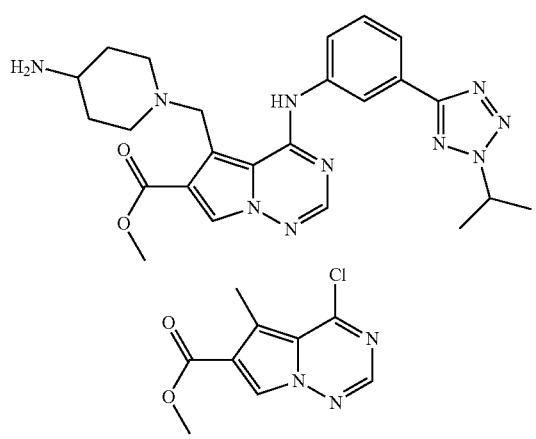

Part A: methyl 4-chloro-5-methylpyrrolo[2,1-f][1,2,4]triazine-6-carboxylate

To a solution of methyl 5-methyl-4-oxo-3,4-dihydropyrrolo[1,2-f][1,2,4]triazine-6-carboxylate (4 g, 19.31 mmol) [prepared as described in WO 2002040486] in dry toluene (50 mL) was added phosphorus oxychloride (3.24 mL, 34.8 mmol) and DIEA (8.43 mL, 48.3 mmol). The reaction mixture was heated to reflux overnight. The reaction mixture was cooled to room temperature and concentrated under reduced pressure. The residue was purified via silica gel chromatography (0-40% EtOAc in hexanes) to afford methyl 4-chloro-5-methylpyrrolo[1,2-f][1,2,4]triazine-6-carboxylate (3.1 g, 13.74 mmol, 71% yield) as yellow solid. LCMS (ESI) m/e 226.0 [(M+H)+, calcd for $C_9H_9ClN_3O_2$ 226.0].

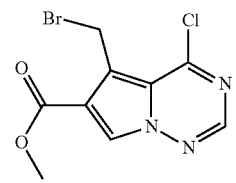 [SMILES: COC(=O)c1cn2ncnc(Cl)c2c1CBr]

Part B: methyl 5-(bromomethyl)-4-chloropyrrolo[2,1-f][1,2,4]triazine-6-carboxylate To a solution of methyl 4-chloro-5-methylpyrrolo[1,2-f][1,2,4]triazine-6-carboxylate (3.1 g, 13.74 mmol) in dry CCl4 (100 mL) under nitrogen atmosphere at room temperature was added NBS (2.445 g, 13.74 mmol) and AIBN (0.226 g, 1.374 mmol). The reaction mixture was heated to reflux for 90 min. The reaction mixture was cooled to room temperature and then washed with cold saturated aqueous NaHCO3. The organic layer was separated and washed with brine (1×50 mL), dried (MgSO4), and concentrated under reduced pressure to obtain methyl 5-(bromomethyl)-4-chloropyrrolo[1,2-f][1,2,4]triazine-6-carboxylate (3.86 g, 12.68 mmol, 92% yield) as a brown solid. The product was used as such without further purification. LCMS (ESI) m/e 304.0, 306.0 Br pattern [(M+H)+, calcd for $C_9H_8BrClN_3O_2$ 304.0].

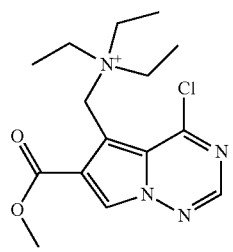 [SMILES: CC[N+](CC)(CC)Cc1c(C(=O)OC)cn2ncnc(Cl)c12]

Part C: N-((4-chloro-6-(methoxycarbonyl)pyrrolo[2,1-f][1,2,4]triazin-5-yl)methyl)-N,N-diethylethanaminium To a solution of the methyl 5-(bromomethyl)-4-chloropyrrolo[1,2-f][1,2,4]triazine-6-carboxylate (3.86 g, 12.68 mmol) in dry THF (50 mL) at room temperature under nitrogen was added TEA (3.53 mL, 25.4 mmol). The reaction mixture was stirred overnight. The light brown precipitate was collected by vacuum filtration and washed with cold THF then dried under vacuum. Obtained N-((4-chloro-6-(methoxycarbonyl)pyrrolo[1,2-f][1,2,4]triazin-5-yl)methyl)-N,N-diethylethanaminium (3.91 g, 12.00 mmol, 95% yield) as a light brown solid. The material was stored under nitrogen in a dry dessicator until needed. LCMS (ESI) m/e 325.2 [(M)+, calcd for $C_{15}H_{22}ClN_4O_2$ 325.1].

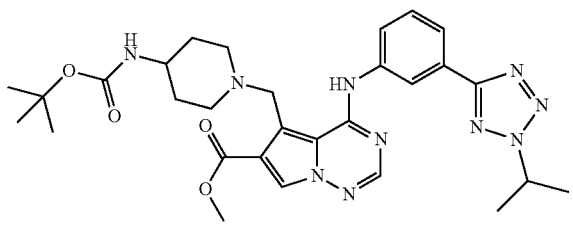 [SMILES: COC(=O)c1cn2ncnc(Nc3cccc(-c4nnn(C(C)C)n4)c3)c2c1CN1CCC(NC(=O)OC(C)(C)C)CC1]

Part D: methyl 5-((4-((tert-butoxycarbonyl)amino)piperidin-1-yl)methyl)-4-((3-(2-isopropyl-2H-tetrazol-5-yl)phenyl)amino)pyrrolo[2,1-f][1,2,4]triazine-6-carboxylate To a solution of N-((4-chloro-6-(methoxycarbonyl)pyrrolo[1,2-f][1,2,4]triazin-5-yl)methyl)-N,N-diethylethanaminium, bromide salt (0.2 g, 0.493 mmol) in dry acetonitrile (12 mL) in a microwave tube flushed with nitrogen was added 3-(2-isopropyl-2H-tetrazol-5-yl)aniline (0.100 g, 0.493 mmol). The reaction tube was capped and heated in a microwave at 85° C. for 45 min. To the reaction mixture was added tert-butyl piperidin-4-ylcarbamate (0.099 g, 0.493 mmol) and DIEA (0.181 mL, 1.035 mmol) and the reaction tube was capped again and heated in a microwave at 85° C. for 45 min. The reaction mixture was concentrated and the residue purified by silica gel chromatography 0-40% EtOAc in hexanes). Required fractions were concentrated to obtain methyl 5-((4-(tert-butoxycarbonylamino)piperidin-1-yl)methyl)-4-(3-(2-isopropyl-2H-tetrazol-5-yl)phenylamino)pyrrolo[1,2-f][1,2,4]triazine-6-carboxylate (0.169 g, 0.286 mmol, 58% yield) as a brown solid. LCMS (ESI) m/e 591.3 [(M+H)+, calcd for $C_{29}H_{39}N_{10}O_4$ 591.3].

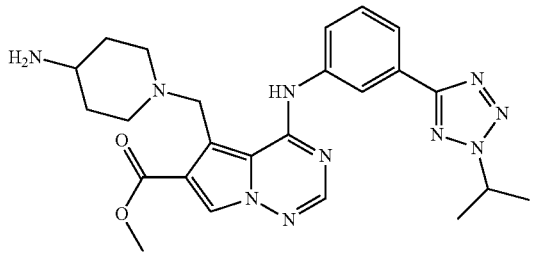 [SMILES: COC(=O)c1cn2ncnc(Nc3cccc(-c4nnn(C(C)C)n4)c3)c2c1CN1CCC(N)CC1]

Part E: methyl 5-((4-aminopiperidin-1-yl)methyl)-4-((3-(2-isopropyl-2H-tetrazol-5-yl)phenyl)amino)pyrrolo[2,1-f][1,2,4]triazine-6-carboxylate To a solution of methyl 5-((4-(tert-butoxycarbonylamino)piperidin-1-yl)methyl)-4-(3-(2-isopropyl-2H-tetrazol-5-yl)phenylamino)pyrrolo[1,2-f][1,2,4]triazine-6-carboxylate (0.169 g, 0.286 mmol) in dry $CH_2Cl_2$ (20 mL) at room temperature under nitrogen was added TFA (0.132 mL, 1.717 mmol). The reaction mixture was stirred at room temperature for 3 h. The reaction mixture was concentrated and purified by reverse phase preparative HPLC (water/Methanol/0.1% TFA) to afford methyl 5-((4-aminopiperidin-1-yl)methyl)-4-(3-(2-isopropyl-2H-tetrazol-5-yl)phenylamino)pyrrolo[1,2-f][1,2,4]triazine-6-carboxylate, 2 TFA (0.0872 g, 0.119 mmol, 42% yield) as a pale yellow oil. LCMS (ESI) m/e 491.3 [(M+H)+, calcd for $C_{24}H_{31}N_{10}O_2$ 491.3]. $^1$H NMR (400 MHz, MeOD) δ 7.96 (s, 1H), 7.92 (d, J=7.8 Hz, 1H), 7.83 (br. s, 1H), 7.59 (t, J=7.8 Hz, 1H), 7.53 (s, 1H), 7.27 (d, J=5.3 Hz, 1H), 5.16 (sept, J=6.7 Hz, 1H), 5.00 (br. s, 2H), 3.89 (s, 3H), 3.77 (br. s, 2H), 3.47 (br. s, 2H), 3.35-3.32 (m, 1H), 2.25 (d, J=11.1 Hz, 2H), 2.02-1.78 (m, 2H), 1.67 (d, J=6.8 Hz, 6H); HPLC retention time (method C): $t_R$=7.59 min.

Biological Data

Methods
AAK1 Kinase Assay

The assays were performed in U-bottom 384-well plates. The final assay volume was 30 μl prepared from 15 μl additions of enzyme and substrates (fluoresceinated peptide (5-FAM)-Aha-KEEQSQITSQVTGQIGWR-NH2 and ATP) and test compounds in assay buffer (10 mM Tris-HCL pH 7.4, 10 mM $MgCl_2$, 0.01% Tween-20 and 1.0 mM DTT). The reactions were initiated by the combination of bacterially expressed, GST-Xa-hAAK1 with substrates and test compounds. The reactions were incubated at room temperature for 3 hours and terminated by adding 60 μl of 35 mM EDTA buffer to each sample. The reactions were analyzed on the Caliper LabChip 3000 (Caliper, Hopkinton, Mass.) by electrophoretic separation of the fluorescent substrate and phosphorylated product. Inhibition data were calculated by comparison to EDTA quenched control reactions for 100% inhibition and vehicle-only reactions for 0% inhibition. The final concentration of reagents in the assays are ATP, 22 μM; (5-FAM)-Aha-KEEQSQITSQVTGQIGWR-$NH_2$, 1.5 μM; GST-Xa-hAAK1, 3.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis. Results are shown in Table 2. Functional potency for select compounds is listed as $IC_{50}$ ranges where a=1-10 nM; b=10.01-100 nM; c=100.01-1000 nM; d=1000.01-5000 nM.

TABLE 2

| Example Number | AAK1 $IC_{50}$ (nM) |
|---|---|
| 1 | c |
| 2 | b |
| 3 | b |
| 4 | c |
| 5 | b |
| 6 | b |
| 7 | c |
| 8 | 7.3 |
| 9 | b |
| 10 | b |
| 11 | c |
| 12 | 446 |
| 13 | c |
| 14 | c |
| 15 | b |
| 16 | c |
| 17 | c |
| 18 | c |
| 19 | 2119 |
| 20 | d |
| 21 | b |
| 22 | 14 |
| 23 | c |
| 24 | b |
| 25 | c |
| 26 | c |
| 27 | c |
| 28 | c |
| 29 | c |
| 30 | c |
| 31 | c |
| 32 | c |
| 33 | b |
| 34 | b |
| 35 | c |
| 36 | 3.3 |
| 37 | a |
| 38 | a |
| 39 | b |
| 40 | b |
| 41 | b |
| 42 | b |
| 43 | 265 |
| 44 | 10 |
| 45 | b |
| 46 | b |
| 47 | b |
| 48 | b |
| 49 | 21 |
| 50 | c |
| 51 | a |
| 52 | c |
| 53 | b |
| 54 | c |
| 55 | c |
| 56 | d |
| 57 | b |
| 58 | d |
| 59 | 128 |
| 60 | c |
| 61 | 2575 |
| 62 | c |
| 63 | c |
| 64 | c |
| 65 | 72 |
| 66 | 1102 |
| 67 | c |
| 68 | d |
| 69 | c |
| 70 | c |
| 71 | d |
| 72 | b |
| 73 | 16 |
| 74 | b |
| 75 | c |
| 76 | 220 |
| 77 | 291 |
| 78 | 112 |
| 79 | 269 |
| 80 | 384 |
| 81 | 413 |
| 82 | 67 |
| 83 | 406 |
| 84 | 75 |
| 85 | 82 |
| 86 | 123 |
| 87 | 325 |
| 88 | 22 |
| 89 | 207 |
| 90 | 52 |
| 91 | 63 |
| 92 | 1173 |
| 93 | 73 |
| 94 | 474 |
| 95 | 2528 |
| 96 | 624 |
| 97 | 883 |
| 98 | 92 |
| 99 | 217 |
| 100 | 54 |
| 101 | 687 |
| 102 | 49 |
| 103 | 26 |
| 104 | 195 |
| 105 | 785 |
| 106 | 2347 |
| 107 | 469 |
| 108 | 289 |
| 109 | 4772 |
| 110 | 7713 |
| 111 | 16 |

AAK1 Knockout Mice

Mice homozygous (−/−) for the disruption of the AAK1 gene were prepared by two methods; gene trapping and homologous recombination.

Gene trapping is a method of random insertional mutagenesis that uses a fragment of DNA coding for a reporter or selectable marker gene as a mutagen. Gene trap vectors have been designed to integrate into introns or genes in a manner that allows the cellular splicing machinery to splice vector encoded exons to cellular mRNAs. Commonly, gene trap vectors contain selectable marker sequences that are preceded by strong splice acceptor sequences and are not preceded by a promoter. Thus, when such vectors integrate into a gene, the cellular splicing machinery splices exons from the trapped gene onto the 5' end of the selectable marker sequence. Typically, such selectable marker genes can only be expressed if the vector encoding the gene has integrated into an intron. The resulting gene trap events are subsequently identified by selecting for cells that can survive selective culture.

Embryonic stem cells (Lex-1 cells from derived murine strain A129), were mutated by a process involving the insertion of at least a portion of a genetically engineered vector sequence into the gene of interest, the mutated embryonic stem cells were microinjected into blastocysts which were subsequently introduced into pseudopregnant female hosts and carried to term using established methods. See, e.g., "Mouse Mutagenesis", 1998, Zambrowicz et al., eds., Lexicon Press, The Woodlands, Tex. The resulting chimeric animals were subsequently bred to produce offspring capable of germline transmission of an allele containing the engineered mutation in the gene of interest.

AAK1-gene disrupted mice were also made by homologous recombination. In this case, the second coding exon of the murine AAK1 gene (see GenBank Accession Number NM_177762) was removed by methods known in the art. See, e.g., U.S. Pat. Nos. 5,487,992, 5,627,059, and 5,789,215.

Mice homozygous (−/−) for the disruption of the AAK1 gene were studied in conjunction with mice heterozygous (+/−) for the disruption of the AAK1 gene, and wild-type (+/+) litter mates. During this analysis, the mice were subject to a medical work-up using an integrated suite of medical diagnostic procedures designed to assess the function of the major organ systems in a mammalian subject. Homozygous (−/−) "knockout" mice were studied in conjunction with their heterozygous (+/−) and wild-type (+/+) litter mates. Disruption of the AAK1 gene was confirmed by Southern analysis. Expression of the murine homolog of AAK1 was detected by RT-PCR in murine brain; spinal cord; eye; thymus; spleen; lung; kidney; liver; skeletal muscle; bone; stomach, small intestine and colon; heart; adipose; asthmatic lung; LPS liver; blood; banded heart; aortic tree; prostate; and mammary gland (5 week virgin, mature virgin, 12 DPC, 3 day post-partum (lactating), 3 day post-weaning (early involution), and 7 day post-weaning (late involution)).

AAK1 homozygous (−/−) and their wild-type (+/+) littermates were tested using the formalin paw test in order to assess their acute and tonic nociceptive responses. For these tests, Automatic Nociception Analyzers (purchased from the Ozaki lab at University of California, San Diego) were used. A metal band was placed around the left hind paw of each mouse 30 minutes prior to testing. After the 30-minute acclimation period, 20 µl of 5% formalin is subcutaneously injected in the dorsal surface of the left hind paw. Mice were individually housed in cylindrical chambers for 45 minutes. Fresh 5% formalin solution was prepared by diluting formaldehyde (Formalde-fresh 20%, Fisher Scientific, Fair Lawn, N.J.) with distilled water. Investigatory compounds were administered 30 minutes prior to formalin injection.

A computer recorded flinches per minute, total flinches for phase I (acute phase=first 8 minutes), and total flinches for phase II (tonic phase=time between minutes 20-40 or 10-60 minutes for drug studies) through an electromagnetic field. See Yaksh T L, Ozaki G, McCumber D, Rathbun M, Svensson C, Malkmus S, Yaksh M C. *An automated flinch detecting system for use in the formalin nociceptive bioassay.* J Appl Physiol., 2001; 90:2386-402. As shown in FIG. 1, phase 1 and phase 2 data were obtained using homozygous (−/−) mice females (n=16), wild-type females (n=15), homozygous (−/−) mice males (n=9), and wild-type males (n=18). In all groups and in both phases, the AAK1 homozygous (−/−) mice exhibited significantly less recorded paw flinching than their wild-type (+/+) littermates.

Studies of AAK1 knockout mice showed that disruption of the AAK1 gene affects pain response as measured using the formalin paw test described above. The same test was used to confirm that the administration of an AAK1 inhibitor can also affect pain response.

A compound of the disclosure was tested in this assay at different doses. Gabapentin and pregabalin were used as positive controls. Results are shown below in Table 3, wherein the effect of gabapentin at 200 mg/kg is considered a 100% response, the % response for the other compounds is relative to the 200 mg/kg dose of gabapentin, "sc" means subcutaneous administration; "po" means oral administration.

TABLE 3

| Compound | Dose (mg/kg) | Response |
|---|---|---|
| Gabapentin | 200 sc | 73% |
| Example 1: 6-(((1R,4R)-4-aminocyclohexyl)amino)-N-(3-(5-isopropyl-1,2,4-oxadiazol-3-yl)phenyl)imidazo[1,2-b]pyridazine-3-carboxamide | 60 sc | 59% |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The invention claimed is:

1. A method for treating or managing a disease or a disorder mediated by adaptor associated kinase 1 activity, wherein the disease or disorder is pain, Parkinson's disease, or schizophrenia; the method comprising administering to a patient in need thereof a therapeutically effective amount of a compound of formula (I)

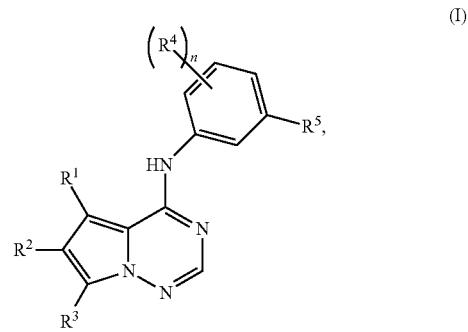

or a pharmaceutically acceptable salt thereof, wherein:

n is 0, 1, or 2;

$R^1$ is $CH_2NR^aR^b$, $-C(O)NR^aR^b$, $-CH_2OR^6$, or $-CO_2R^6$;

$R^2$ is hydrogen and or $-CO_2R^6$;

$R^3$ is hydrogen or Br;

when n is 1, $R^4$ is halo, haloalkyl, hydroxy$C_1$-$C_3$alkyl, or $-OR^6$; or, when n is 2, the two $R^4$ groups are on adjacent carbon atoms, and together with the atoms to which they are attached, form a five-membered ring which is

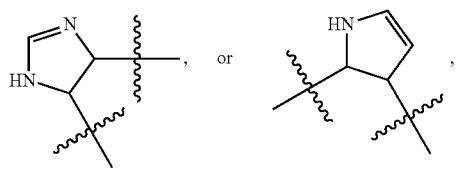

wherein "⌇" indicates the point of attachment to the six-membered aromatic ring;

$R^5$ is $C_2$alkenyl, —NHC(O)$R^7$, —C(O)NH$R^7$,

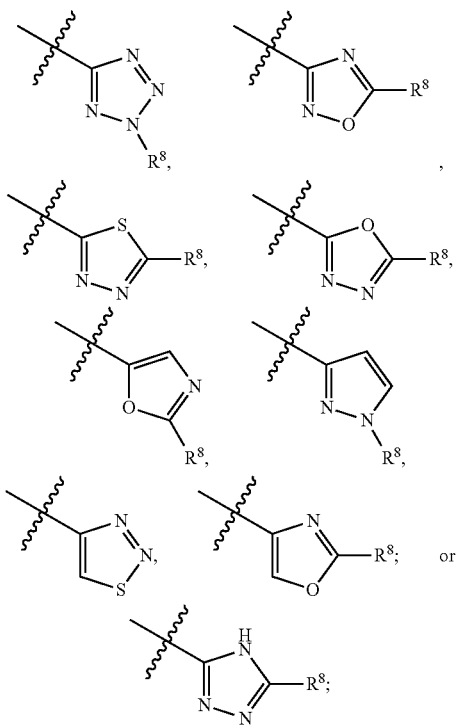

each $R^6$ is independently hydrogen or $C_1$-$C_6$ alkyl;
$R^7$ is $C_1$-$C_6$alkyl, or amino$C_1$-$C_6$alkyl;
$R^8$ is amino$C_1$-$C_6$alkyl, $C_1$-$C_6$alkyl, $C_3$-$C_6$cycloalkyl, halo$C_1$-$C_6$alkyl, hydroxy$C_1$-$C_6$alkyl, or phenyl; and
$R^a$ and $R^b$ are independently hydrogen, $C_1$-$C_3$alkoxy$C_1$-$C_3$alkyl, $C_1$-$C_3$alkyl, amino$C_2$-$C_6$alkyl, cyano$C_1$-$C_3$alkyl, $C_3$-$C_6$cycloalkyl$C_1$-$C_3$alkyl,

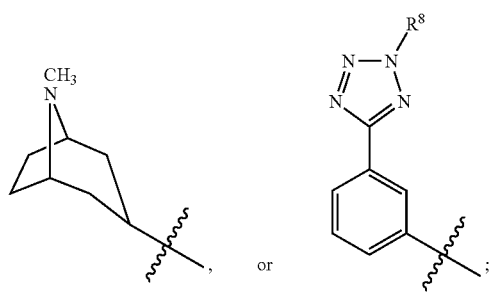

or $R^a$ and $R^b$, together with the nitrogen atom to which they are attached, form a ring which is azetidinyl, morpholinyl, piperazinyl, piperidinyl, pyrrolidinyl,

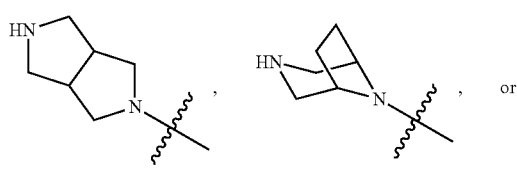

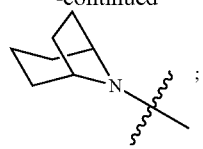

wherein the ring is optionally substituted with one or two substituents independently selected from the group consisting of $C_1$-$C_3$acylamino, $C_1$-$C_3$alkyl, amino, amino$C_1$-$C_3$alkyl, hydroxy, and methylamino.

2. The method of claim 1, wherein $R^a$ and $R^b$, together with the nitrogen atom to which they are attached, form a piperidinyl or piperazinyl ring optionally substituted with one or two substituents independently selected from the group consisting of $C_1$-$C_3$acylamino, $C_1$-$C_3$alkyl, amino, amino$C_1$-$C_3$alkyl, hydroxy, and methylamino.

3. The method of claim 1 wherein the pain is neuropathic pain.

4. The method of claim 3 wherein the neuropathic pain is fibromyalgia or peripheral neuropathy.

5. The method of claim 1 wherein the compound of formula (I) is
  5-((4-aminopiperidin-1-yl)methyl)-N-(3-(oxazol-5-yl)phenyl)pyrrolo[2,1-f][1,2,4]triazin-4-amine;
  5-((4-aminopiperidin-1-yl)methyl)-N-(3-(5-isopropyl-1,2,4-oxadiazol-3-yl)phenyl)pyrrolo[2,1-f][1,2,4]triazin-4-amine;
  2-((5-((4-aminopiperidin-1-yl)methyl)pyrrolo[2,1-f][1,2,4]triazin-4-yl)amino)-4-(5-isopropyl-1,2,4-oxadiazol-3-yl)phenol;
  5-((4-aminopiperidin-1-yl)methyl)-N-(3-vinylphenyl)pyrrolo[2,1-f][1,2,4]triazin-4-amine;
  5-((4-aminopiperidin-1-yl)methyl)-N-(3-(5-(tert-butyl)-1,2,4-oxadiazol-3-yl)phenyl)pyrrolo[2,1-f][1,2,4]triazin-4-amine;
  5-((4-aminopiperidin-1-yl)methyl)-N-(3-(5-(tert-pentyl)-1,2,4-oxadiazol-3-yl)phenyl)pyrrolo[2,1-f][1,2,4]triazin-4-amine;
  3-((5-((4-aminopiperidin-1-yl)methyl)pyrrolo[2,1-f][1,2,4]triazin-4-yl)amino)-5-(oxazol-2-yl)phenol;
  5-((4-aminopiperidin-1-yl)methyl)-N-(3-(2-isopropyl-2H-tetrazol-5-yl)phenyl)pyrrolo[2,1-f][1,2,4]triazin-4-amine;
  5-((4-aminopiperidin-1-yl)methyl)-N-(3-(5-isopropyl-1,3,4-thiadiazol-2-yl)phenyl)pyrrolo[2,1-f][1,2,4]triazin-4-amine;
  2-(3-(3-((5-((4-aminopiperidin-1-yl)methyl)pyrrolo[2,1-f][1,2,4]triazin-4-yl)amino)phenyl)-1,2,4-oxadiazol-5-yl)-2-methylpropan-1-ol;
  5-((4-aminopiperidin-1-yl)methyl)-N-(3-(5-(chloromethyl)-1,2,4-oxadiazol-3-yl)phenyl)pyrrolo[2,1-f][1,2,4]triazin-4-amine;
  5-((4-aminopiperidin-1-yl)methyl)-N-(3-(1-methyl-1H-pyrazol-3-yl)phenyl)pyrrolo[2,1-f][1,2,4]triazin-4-amine;
  5-((4-aminopiperidin-1-yl)methyl)-N-(3-(5-methyl-1,2,4-oxadiazol-3-yl)phenyl)pyrrolo[2,1-f][1,2,4]triazin-4-amine;
  N-(3-(1,2,3-thiadiazol-4-yl)phenyl)-5-((4-aminopiperidin-1-yl)methyl)pyrrolo[2,1-f][1,2,4]triazin-4-amine;
  5-((4-aminopiperidin-1-yl)methyl)-N-(3-(5-ethyl-4H-1,2,4-triazol-3-yl)phenyl)pyrrolo[2,1-f][1,2,4]triazin-4-amine;

5-((4-aminopiperidin-1-yl)methyl)-N-(3-(3-phenyl-1,2,4-oxadiazol-5-yl)phenyl)pyrrolo[2, 1-f][1,2,4]triazin-4-amine;

5-((4-aminopiperidin-1-yl)methyl)-N-(3-(5-methyl-1,3,4-thiadiazol-2-yl)phenyl)pyrrolo[2,1-f][1,2,4]triazin-4-amine;

N-(3-(5-methyl-1,3,4-thiadiazol-2-yl)phenyl)-5-((4-(methylamino)piperidin-1-yl)methyl)pyrrolo[2,1-f][1,2,4]triazin-4-amine;

5-((3-aminoazetidin-1-yl)methyl)-N-(3-(5-methyl-1,3,4-thiadiazol-2-yl)phenyl)pyrrolo[2,1-f][1,2,4]triazin-4-amine;

5-((hexahydropyrrolo[3,4-c]pyrrol-2(1H)-yl)methyl)-N-(3-(5-methyl-1,3,4-thiadiazol-2-yl)phenyl)pyrrolo[2,1-f][1,2,4]triazin-4-amine;

5-((4-aminopiperidin-1-yl)methyl)-N-(3-(5-propyl-1,3,4-thiadiazol-2-yl)phenyl)pyrrolo[2,1-f][1,2,4]triazin-4-amine;

5-((4-aminopiperidin-1-yl)methyl)-N-(3-(5-cyclohexyl-1,2,4-oxadiazol-3-yl)phenyl)pyrrolo[2,1-f][1,2,4]triazin-4-amine;

5-((4-aminopiperidin-1-yl)methyl)-N-(3-(5-cyclopropyl-1,3,4-thiadiazol-2-yl)phenyl)pyrrolo[2,1-f][1,2,4]triazin-4-amine;

N-(3-(5-cyclopropyl-1,3,4-thiadiazol-2-yl)phenyl)-5-((4-(methylamino)piperidin-1-yl)methyl)pyrrolo[2,1-f][1,2,4]triazin-4-amine;

5-((3-aminoazetidin-1-yl)methyl)-N-(3-(5-cyclopropyl-1,3,4-thiadiazol-2-yl)phenyl)pyrrolo[2,1-f][1,2,4]triazin-4-amine;

N-(3-(5-cyclopropyl-1,3,4-thiadiazol-2-yl)phenyl)-5-((hexahydropyrrolo[3,4-c]pyrrol-2(1H)-yl)methyl)pyrrolo[2,1-f][1,2,4]triazin-4-amine;

N-(3-(5-isopropyl-1,3,4-thiadiazol-2-yl)phenyl)-5-((4-(methylamino)piperidin-1-yl)methyl)pyrrolo[2,1-f][1,2,4]triazin-4-amine;

5-((3-aminoazetidin-1-yl)methyl)-N-(3-(5-isopropyl-1,3,4-thiadiazol-2-yl)phenyl)pyrrolo[2,1-f][1,2,4]triazin-4-amine;

5-((hexahydropyrrolo[3,4-c]pyrrol-2(1H)-yl)methyl)-N-(3-(5-isopropyl-1,3,4-thiadiazol-2-yl)phenyl)pyrrolo[2,1-f][1,2,4]triazin-4-amine;

N-(3-(5-isopropyl-1,3,4-thiadiazol-2-yl)phenyl)-5-((3-(methylamino)pyrrolidin-1-yl)methyl)pyrrolo[2,1-f][1,2,4]triazin-4-amine;

5-((3-(aminomethyl)pyrrolidin-1-yl)methyl)-N-(3-(5-isopropyl-1,3,4-thiadiazol-2-yl)phenyl)pyrrolo[2,1-f][1,2,4]triazin-4-amine;

5-((3-aminopyrrolidin-1-yl)methyl)-N-(3-(5-isopropyl-1,3,4-thiadiazol-2-yl)phenyl)pyrrolo[2,1-f][1,2,4]triazin-4-amine;

3-((5-((4-aminopiperidin-1-yl)methyl)pyrrolo[2,1-f][1,2,4]triazin-4-yl)amino)-N-isobutylbenzamide;

N-(3-(2-isopropyl-2H-tetrazol-5-yl)phenyl)-5-(piperazin-1-ylmethyl)pyrrolo[2, 1-f][1,2,4]triazin-4-amine;

N-(3-(5-isopropyl-1,3,4-thiadiazol-2-yl)phenyl)-5-(piperazin-1-ylmethyl)pyrrolo[2, 1-f][1,2,4]triazin-4-amine;

3-((5-((4-aminopiperidin-1-yl)methyl)pyrrolo[2,1-f][1,2,4]triazin-4-yl)amino)-5-(2-isopropyl-2H-tetrazol-5-yl)phenol;

3-((5-((4-aminopiperidin-1-yl)methyl)pyrrolo[2,1-f][1,2,4]triazin-4-yl)amino)-5-(5-isopropyl-1,2,4-oxadiazol-3-yl)phenol;

2-((5-((4-aminopiperidin-1-yl)methyl)pyrrolo[2,1-f][1,2,4]triazin-4-yl)amino)-4-(2-isopropyl-2H-tetrazol-5-yl)phenol;

N-(3-(5-isopropyl-1,2,4-oxadiazol-3-yl)phenyl)-5-((4-(methylamino)piperidin-1-yl)methyl)pyrrolo[2,1-f][1,2,4]triazin-4-amine;

N-(3-(5-isopropyl-1,3,4-oxadiazol-2-yl)phenyl)-5-((4-(methylamino)piperidin-1-yl)methyl)pyrrolo[2,1-f][1,2,4]triazin-4-amine;

N-(3-(5-(tert-butyl)-1,2,4-oxadiazol-3-yl)phenyl)-5-((4-(methylamino)piperidin-1-yl)methyl)pyrrolo[2,1-f][1,2,4]triazin-4-amine;

N-(3-(2-isopropyl-2H-tetrazol-5-yl)phenyl)-5-((4-(methylamino)piperidin-1-yl)methyl)pyrrolo[2,1-f][1,2,4]triazin-4-amine 5-((4-aminopiperidin-1-yl)methyl)-N-(2-chloro-5-(5-isopropyl-1,2,4-oxadiazol-3-yl)phenyl)pyrrolo[2,1-f][1,2,4]triazin-4-amine;

N-(3-fluoro-5-(5-isopropyl-1,2,4-oxadiazol-3-yl)phenyl)-5-((4-(methylamino)piperidin-1-yl)methyl)pyrrolo[2, 1-f][1,2,4]triazin-4-amine;

5-((4-aminopiperidin-1-yl)methyl)-N-(3-chloro-5-(5-isopropyl-1,2,4-oxadiazol-3-yl)phenyl)pyrrolo[2,1-f][1,2,4]triazin-4-amine;

5-((4-aminopiperidin-1-yl)methyl)-N-(3-fluoro-5-(5-isopropyl-1,2,4-oxadiazol-3-yl)phenyl)pyrrolo[2,1-f][1,2,4]triazin-4-amine;

5-((4-aminopiperidin-1-yl)methyl)-N-(3-(5-cyclopropyl-1,2,4-oxadiazol-3-yl)phenyl)pyrrolo[2,1-f][1,2,4]triazin-4-amine;

(3R,4R)-4-amino-1-((4-((3-(5-isopropyl-1,3,4-thiadiazol-2-yl)phenyl)amino)pyrrolo[2,1-f][1,2,4]triazin-5-yl)methyl)piperidin-3-ol;

5-((4-aminopiperidin-1-yl)methyl)-N-(4-fluoro-3-(2-isopropyl-2H-tetrazol-5-yl)phenyl)pyrrolo[2,1-f][1,2,4]triazin-4-amine;

5-((4-aminopiperidin-1-yl)methyl)-N-(2-fluoro-5-(2-isopropyl-2H-tetrazol-5-yl)phenyl)pyrrolo[2,1-f][1,2,4]triazin-4-amine;

5-((4-aminopiperidin-1-yl)methyl)-N-(3-fluoro-5-(2-isopropyl-2H-tetrazol-5-yl)phenyl)pyrrolo[2,1-f][1,2,4]triazin-4-amine;

5-((4-aminopiperidin-1-yl)methyl)-N-(2-fluoro-5-(5-isopropyl-1,2,4-oxadiazol-3-yl)phenyl)pyrrolo[2,1-f][1,2,4]triazin-4-amine;

N-(1-((4-((3-(5-isopropyl-1,3,4-thiadiazol-2-yl)phenyl)amino)pyrrolo[2,1-f][1,2,4]triazin-5-yl)methyl)piperidin-4-yl)acetamide;

N-(3-(2-isopropyl-2H-tetrazol-5-yl)phenyl)-5-((4-methylpiperazin-1-yl)methyl)pyrrolo[2, 1-f][1,2,4]triazin-4-amine;

N-(3-(5-isopropyl-1,3,4-thiadiazol-2-yl)phenyl)-5-((4-methylpiperazin-1-yl)methyl)pyrrolo[2,1-f][1,2,4]triazin-4-amine;

N-(3-(5-isopropyl-1,3,4-thiadiazol-2-yl)phenyl)-5-(morpholinomethyl)pyrrolo[2, 1-f][1,2,4]triazin-4-amine;

N-(3-(2-isopropyl-2H-tetrazol-5-yl)phenyl)-5-(morpholinomethyl)pyrrolo[2,1-f][1,2,4]triazin-4-amine;

N-(3-(2-isopropyl-2H-tetrazol-5-yl)phenyl)-5-((8-methyl-8-azabicyclo[3.2.1]octan-3-ylamino)methyl)pyrrolo[1,2-f][1,2,4]triazin-4-amine;

(1R,5S)-8-((4-((3-(2-isopropyl-2H-tetrazol-5-yl)phenyl)amino)pyrrolo[2,1-f][1,2,4]triazin-5-yl)methyl)-8-azabicyclo[3.2.1]octan-3-ol;

N-(3-(2-isopropyl-2H-tetrazol-5-yl)phenyl)-5-(((1R,5S)-3-methyl-3,8-diazabicyclo[3.2.1]octan-8-yl)methyl)pyrrolo[2,1-f][1,2,4]triazin-4-amine;

N-(3-(2-isopropyl-2H-tetrazol-5-yl)phenyl)-5-(((3-(2-isopropyl-2H-tetrazol-5-yl)phenyl)amino)methyl)pyrrolo[2,1-f][1,2,4]triazin-4-amine;

5-((4-aminopiperidin-1-yl)methyl)-N-(3-isopropoxy-5-(2-isopropyl-2H-tetrazol-5-yl)phenyl)pyrrolo[2,1-f][1,2,4]triazin-4-amine;

N-(3-(2-isopropyl-2H-tetrazol-5-yl)phenyl)-5-((methylamino)methyl)pyrrolo[2,1-f][1,2,4]triazin-4-amine;

1-((4-((3-(2-isopropyl-2H-tetrazol-5-yl)phenyl)amino)pyrrolo[2,1-f][1,2,4]triazin-5-yl)methyl)azetidine-3-carbonitrile;

1-((4-((3-(2-isopropyl-2H-tetrazol-5-yl)phenyl)amino)pyrrolo[2,1-f][1,2,4]triazin-5-yl)methyl)piperidine-4-carbonitrile;

2-(((4-((3-(2-isopropyl-2H-tetrazol-5-yl)phenyl)amino)pyrrolo[2,1-f][1,2,4]triazin-5-yl)methyl)amino)acetonitrile;

(R)-2-amino-N-(3-((5-((4-aminopiperidin-1-yl)methyl)pyrrolo[2,1-f][1,2,4]triazin-4-yl)amino)phenyl)-4-methylpentanamide;

5-((4-aminopiperidin-1-yl)methyl)-7-bromo-N-(3-(oxazol-5-yl)phenyl)pyrrolo[2, 1-f][1,2,4]triazin-4-amine;

N1-((4-((3-(5-isopropyl-1,3,4-thiadiazol-2-yl)phenyl)amino)pyrrolo[2,1-f][1,2,4]triazin-5-yl)methyl)propane-1,3-diamine;

N1-((4-((3-(5-isopropyl-1,3,4-thiadiazol-2-yl)phenyl)amino)pyrrolo[2,1-f][1,2,4]triazin-5-yl)methyl)-2-methylpropane-1,3-diamine;

5-((3-(aminomethyl)piperidin-1-yl)methyl)-N-(3-(5-isopropyl-1,3,4-thiadiazol-2-yl)phenyl)pyrrolo[2,1-f][1,2,4]triazin-4-amine;

5-((4-aminopiperidin-1-yl)methyl)-N-(3-(difluoromethyl)-5-(2-isopropyl-2H-tetrazol-5-yl)phenyl)pyrrolo[2,1-f][1,2,4]triazin-4-amine;

5-((4-aminopiperidin-1-yl)methyl)-N-(3-(5-cyclopentyl-1,2,4-oxadiazol-3-yl)phenyl)pyrrolo[2,1-f][1,2,4]triazin-4-amine;

5-((4-aminopiperidin-1-yl)methyl)-N-(5-(2-isopropyl-2H-tetrazol-5-yl)-1H-indol-7-yl)pyrrolo[2,1-f][1,2,4]triazin-4-amine;

5-((4-aminopiperidin-1-yl)methyl)-N-(4-(2-isopropyl-2H-tetrazol-5-yl)-1H-benzo[d]imidazol-6-yl)pyrrolo[2,1-f][1,2,4]triazin-4-amine;

N-(3-(2-isopropyl-2H-tetrazol-5-yl)phenyl)pyrrolo[2,1-f][1,2,4]triazin-4-amine;

N-(3-(5-isopropyl-1,2,4-oxadiazol-3-yl)phenyl)pyrrolo[2,1-f][1,2,4]triazin-4-amine;

N-(3-(5-(1-chloro-2-methylpropan-2-yl)-1,2,4-oxadiazol-3-yl)phenyl)pyrrolo[2, 1-f][1,2,4]triazin-4-amine;

N-(3-(5-isopropyl-1,3,4-thiadiazol-2-yl)phenyl)pyrrolo[2,1-f][1,2,4]triazin-4-amine;

N-(3-(5-isopropyl-1,3,4-oxadiazol-2-yl)phenyl)pyrrolo[2,1-f][1,2,4]triazin-4-amine;

2-methyl-2-(3-(3-(pyrrolo[2,1-f][1,2,4]triazin-4-ylamino)phenyl)-1,2,4-oxadiazol-5-yl)propan-1-ol;

N-(3-(5-(1-amino-2-methylpropan-2-yl)-1,2,4-oxadiazol-3-yl)phenyl)pyrrolo[2,1-f][1,2,4]triazin-4-amine;

(3-(2-isopropyl-2H-tetrazol-5-yl)-5-(pyrrolo[2,1-f][1,2,4]triazin-4-ylamino)phenyl)methanol;

3-(2-isopropyl-2H-tetrazol-5-yl)-5-(pyrrolo[2,1-f][1,2,4]triazin-4-ylamino)phenol 3-(5-isopropyl-1,2,4-oxadiazol-3-yl)-5-(pyrrolo[2,1-f][1,2,4]triazin-4-ylamino)phenol;

N-(3-(5-isopropyl-1,2,4-oxadiazol-3-yl)phenyl)-5-methylpyrrolo[2,1-f][1,2,4]triazin-4-amine;

N-(3-(5-isopropyl-1,3,4-thiadiazol-2-yl)phenyl)-5-methylpyrrolo[2,1-f][1,2,4]triazin-4-amine;

N-(3-(2-isopropyl-2H-tetrazol-5-yl)phenyl)-5-methypyrrolo[2-f][1,2,4]triazin-4-amine;

N-(3-(2-isopropyl-2H-tetrazol-5-yl)phenyl)-5-methypyrrolo[2-f][1,2,4]triazin-4-amine;

N-(3-(5-(1-chloro-2-methylpropan-2-yl)-1,2,4-oxadiazol-3-yl)phenyl)-5-methylpyrrolo[2,1-f][1,2,4]triazin-4-amine;

N-(3-(5-(1-amino-2-methylpropan-2-yl)-1,2,4-oxadiazol-3-yl)phenyl)-5-methylpyrrolo[2,1-f][1,2,4]triazin-4-amine;

N-(3-(5-isopropyl-1,2,4-oxadiazol-3-yl)-5-methoxyphenyl)-5-methylpyrrolo[2,1-f][1,2,4]triazin-4-amine;

3-(5-isopropyl-1,2,4-oxadiazol-3-yl)-5-((5-methylpyrrolo[2,1-f][1,2,4]triazin-4-yl)amino)phenol;

ethyl 4-((3-(5-isopropyl-1,3,4-thiadiazol-2-yl)phenyl)amino)pyrrolo[2,1-f][1,2,4]triazine-5-carboxylate;

ethyl 4-((3-hydroxy-5-(2-isopropyl-2H-tetrazol-5-yl)phenyl)amino)pyrrolo[2, 1-f][1,2,4]triazine-5-carboxylate;

ethyl 4-((3-(2-isopropyl-2H-tetrazol-5-yl)phenyl)amino)pyrrolo[2,1-f][1,2,4]triazine-5-carboxylate;

ethyl 4-((3-(5-isopropyl-1,2,4-oxadiazol-3-yl)phenyl)amino)pyrrolo[2,1-f][1,2,4]triazine-5-carboxylate;

(4-((3-(2-isopropyl-2H-tetrazol-5-yl)phenyl)amino)pyrrolo[2,1-f][1,2,4]triazin-5-yl)methanol;

5-(aminomethyl)-N-(3-(2-isopropyl-2H-tetrazol-5-yl)phenyl)pyrrolo[2,1-f][1,2,4]triazin-4-amine;

N-(3-(2-isopropyl-2H-tetrazol-5-yl)phenyl)-5-(methoxymethyl)pyrrolo[2,1-f][1,2,4]triazin-4-amine;

4-((3-(2-isopropyl-2H-tetrazol-5-yl)phenyl)amino)-N,N-dimethylpyrrolo[2,1-f][1,2,4]triazine-5-carboxamide;

5-((dimethylamino)methyl)-N-(3-(2-isopropyl-2H-tetrazol-5-yl)phenyl)pyrrolo[2,1-f][1,2,4]triazin-4-amine;

4-((3-(2-isopropyl-2H-tetrazol-5-yl)phenyl)amino)-N-methylpyrrolo[2,1-f][1,2,4]triazine-5-carboxamide;

N-ethyl-4-((3-(2-isopropyl-2H-tetrazol-5-yl)phenyl)amino)pyrrolo[2,1-f][1,2,4]triazine-5-carboxamide;

N-(cyclopropylmethyl)-4-((3-(2-isopropyl-2H-tetrazol-5-yl)phenyl)amino)pyrrolo[2,1-f][1,2,4]triazine-5-carboxamide;

N-isopropyl-4-((3-(2-isopropyl-2H-tetrazol-5-yl)phenyl)amino)pyrrolo[2,1-f][1,2,4]triazine-5-carboxamide;

N-(cyanomethyl)-4-((3-(2-isopropyl-2H-tetrazol-5-yl)phenyl)amino)pyrrolo[2,1-f][1,2,4]triazine-5-carboxamide;

4-((3-(2-isopropyl-2H-tetrazol-5-yl)phenyl)amino)-N-(2-methoxyethyl)pyrrolo[2,1-f][1,2,4]triazine-5-carboxamide;

(4-aminopiperidin-1-yl)(4-((3-(2-isopropyl-2H-tetrazol-5-yl)phenyl)amino)pyrrolo[2,1-f][1,2,4]triazin-5-yl)methanone;

(R)-2-amino-N-(3-((5-(4-aminopiperidine-1-carbonyl)pyrrolo[2,1-f][1,2,4]triazin-4-yl)amino)phenyl)-4-methylpentanamide; or methyl 5-((4-aminopiperidin-1-yl)methyl)-4-((3-(2-isopropyl-2H-tetrazol-5-yl)phenyl)amino)pyrrolo[2,1-f][1,2,4]triazine-6-carboxylate;

or a pharmaceutically acceptable salt thereof.

6. A method of inhibiting adaptor associated kinase 1 (AAK1) activity, comprising contacting AAK1 with a compound of formula (I)

(I)

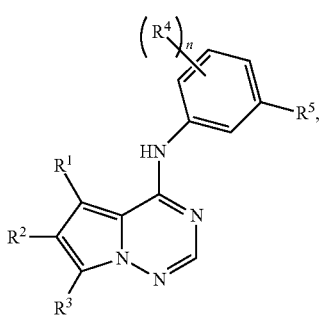

or a pharmaceutically acceptable salt thereof, wherein:

n is 0, 1, or 2;

$R^1$ is $CH_2NR^aR^b$, $-C(O)NR^aR^b$, $-CH_2OR^6$, or $-CO_2R^6$ $R^2$ is hydrogen or $-CO_2R^6$;

$R^3$ is hydrogen or Br;

when n is 1, $R^4$ is halo, haloalkyl, hydroxy$C_1$-$C_3$alkyl, or $-OR^6$; or, when n is 2, the two $R^4$ groups are on adjacent carbon atoms, and together with the atoms to which they are attached, form a five-membered ring which is

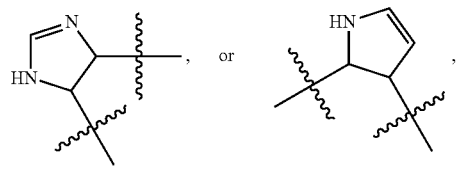 [SMILES: *C1N=CNC1* ; *C1C=CNC1*]

wherein "⌇" indicates the point of attachment to the six-membered aromatic ring;

$R^5$ is $C_2$alkenyl, $-NHC(O)R^7$, $-C(O)NHR^7$,

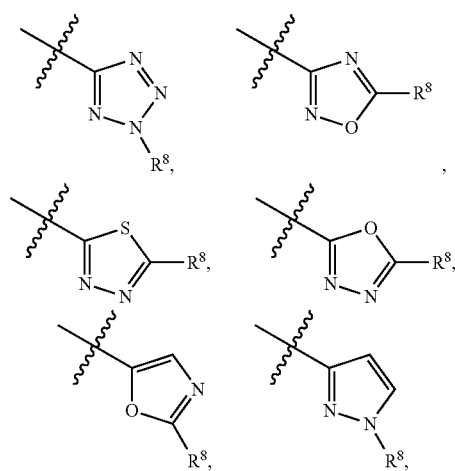

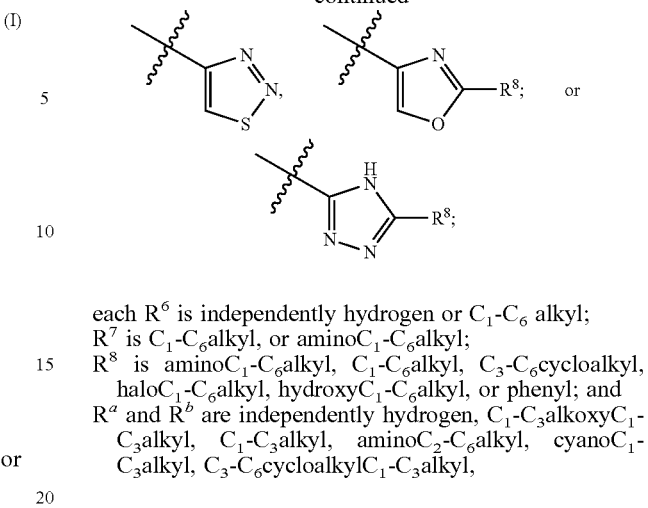

each $R^6$ is independently hydrogen or $C_1$-$C_6$ alkyl;
$R^7$ is $C_1$-$C_6$alkyl, or amino$C_1$-$C_6$alkyl;
$R^8$ is amino$C_1$-$C_6$alkyl, $C_1$-$C_6$alkyl, $C_3$-$C_6$cycloalkyl, halo$C_1$-$C_6$alkyl, hydroxy$C_1$-$C_6$alkyl, or phenyl; and
$R^a$ and $R^b$ are independently hydrogen, $C_1$-$C_3$alkoxy$C_1$-$C_3$alkyl, $C_1$-$C_3$alkyl, amino$C_2$-$C_6$alkyl, cyano$C_1$-$C_3$alkyl, $C_3$-$C_6$cycloalkyl$C_1$-$C_3$alkyl,

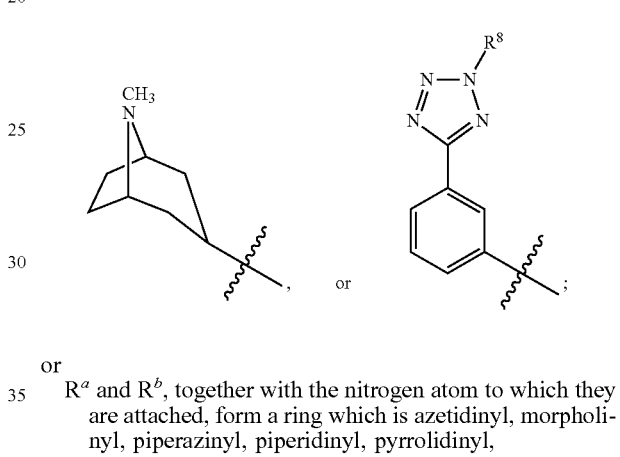

or $R^a$ and $R^b$, together with the nitrogen atom to which they are attached, form a ring which is azetidinyl, morpholinyl, piperazinyl, piperidinyl, pyrrolidinyl,

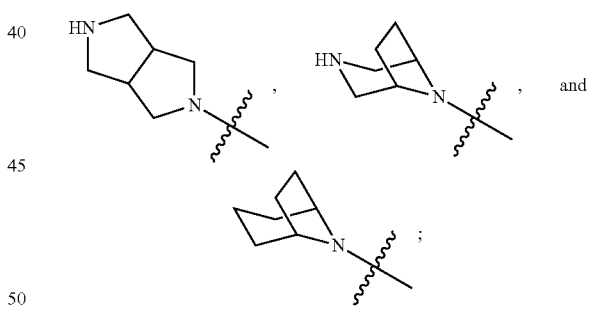

wherein the ring is optionally substituted with one or two substituents independently selected from the group consisting of $C_1$-$C_3$acylamino, $C_1$-$C_3$alkyl, amino, amino$C_1$-$C_3$alkyl, hydroxy, and methylamino.

7. The method of claim 6, wherein $R^a$ and $R^b$, together with the nitrogen atom to which they are attached, form a piperidinyl or piperazinyl ring optionally substituted with one or two substituents independently selected from the group consisting of $C_1$-$C_3$acylamino, $C_1$-$C_3$alkyl, amino, amino$C_1$-$C_3$alkyl, hydroxy, and methylamino.

* * * * *

UNITED STATES PATENT AND TRADEMARK OFFICE
CERTIFICATE OF CORRECTION

PATENT NO.        : 9,737,542 B2
APPLICATION NO.   : 15/027585
DATED             : August 22, 2017
INVENTOR(S)       : Dzierba et al.

Page 1 of 1

It is certified that error appears in the above-identified patent and that said Letters Patent is hereby corrected as shown below:

In the Claims

Claim 1, Column 148, Line 49:
Before "or" delete "and".

Signed and Sealed this
First Day of January, 2019

Andrei Iancu
*Director of the United States Patent and Trademark Office*